US010041058B2

(12) United States Patent
Gready et al.

(10) Patent No.: US 10,041,058 B2
(45) Date of Patent: Aug. 7, 2018

(54) PROCESS FOR GENERATION OF PROTEIN AND USES THEREOF

(71) Applicant: The Australian National University, Canberra, ACT (AU)

(72) Inventors: Jill E. Gready, Curtin (AU); Babu Kannappan, Hawker (AU)

(73) Assignee: The Australian National University, Canberra (AU)

( * ) Notice: Subject to any disclaimer, the term of this patent is extended or adjusted under 35 U.S.C. 154(b) by 0 days.

(21) Appl. No.: 15/424,513

(22) Filed: Feb. 3, 2017

(65) Prior Publication Data
US 2017/0152499 A1 Jun. 1, 2017

Related U.S. Application Data

(60) Division of application No. 12/422,190, filed on Apr. 10, 2009, now Pat. No. 9,598,688, which is a continuation-in-part of application No. PCT/AU2007/001542, filed on Oct. 10, 2007.

(60) Provisional application No. 61/045,552, filed on Apr. 16, 2008.

(30) Foreign Application Priority Data

Oct. 10, 2006 (AU) ............................... 2006905622

(51) Int. Cl.
*C12N 9/88* (2006.01)
(52) U.S. Cl.
CPC ........ *C12N 9/88* (2013.01); *C12Y 401/01039* (2013.01)
(58) Field of Classification Search
None
See application file for complete search history.

(56) References Cited

U.S. PATENT DOCUMENTS

| 7,314,975 | B2 | 1/2008 | Kurek et al. |
| 8,129,512 | B2 | 3/2012 | Zhu et al. |
| 2003/0073135 | A1 | 4/2003 | Zhu |
| 2004/0038262 | A1 | 2/2004 | Chatterjee et al. |
| 2006/0075522 | A1 | 4/2006 | Cleveland et al. |

FOREIGN PATENT DOCUMENTS

| WO | 2000/028008 A1 | 5/2000 |
| WO | 2000/028017 A1 | 5/2000 |
| WO | 2003/091420 A2 | 11/2003 |

OTHER PUBLICATIONS

PNAS, vol. 80, No. 13, [Part 1: Biological Sciences] (Jul. 1, 1983), pp. 4050-4054).*

Altschul et al., "Gapped BLAST and PSI-BLAST: A New Generation of Protein Database Search Programs", Nucleic Acids Research, vol. 25, No. 17, 1997, pp. 3389-3402.
Alvizo et al., "Computational Protein Design Promises to Revolutionize Protein Engineering", BioTechniques, vol. 42, No. 1, 2007, pp. 31-39.
Andrews et al., "Manipulating Ribulose Bisphosphate Carboxylase/Oxygenase in the Chloroplasts of Higher Plants", Archives of Biochemistry and Biophysics, vol. 414, 2003, pp. 159-169.
Andrews, J. T., "Catalysis by Cyanobacterial Ribulose-Bisphosphate Carboxylase Large Subunits in the Complete Absence of Small Subunit", Journal of Biological Chemistry, vol. 263, No. 25, Sep. 5, 1988, pp. 12213-12219.
Baker et al., "Using Deubiquitylating Enzymes as Research Tools", Methods in Enzymology, vol. 398, 2005, pp. 540-554.
"Biomolecular Engineering", Wikipedia the free Encyclopedia, Last Modified on Jan. 15, 2014, and retrieved on Jan. 23, 2014, available online at <http://en.wikipedia.org/wiki/Biomolecular_engineering>, 18 pages.
Bloom et al., "Evolving Strategies for Enzyme Engineering", Current Opinion in Structural Biology, vol. 15, 2005, pp. 447-452.
Ciniglia et al., "Hidden biodiversity of the Extremophilic *Cyanidiales* Red Algae", Molecular Ecology, vol. 13, 2004, pp. 1827-1838.
Corneille et al., "Efficient Elimination of Selectable Marker Genes from the Plastid Genome by the CRE-Lox Site-Specific Recombination System", Plant Journal, vol. 27, No. 2, 2001, pp. 171-178.
Cummins et al., "Calculation of a Complete Enzymic Reaction Surface: Reaction and Activation Free Energies for Hydride-Ion Transfer in Dihydrofolate Reductase", Journal of Chemical Theory and Computation, vol. 3, No. 3, 2007, pp. 1203-1211.
Cummins et al., "Computational Methods for the Study of Enzymic Reaction Mechanisms III: A Perturbation Plus QM/MM Approach for Calculating Relative Free Energies of Protonation", Journal of Computational Chemistry, vol. 26, 2005, pp. 561-568.

(Continued)

*Primary Examiner* — Jeanette M Lieb
(74) *Attorney, Agent, or Firm* — Morrison & Foerster LLP

(57) ABSTRACT

A method of generating a protein with an improved functional property, the method comprising:
(a) identifying at least one Target amino acid Residue in a first protein, wherein said Target amino acid Residue is associated with said functional property;
(b) comparing at least one homologous second protein from the same or a different phylogenetic branch as the first protein with the first protein and identifying at least one Variant amino acid Residue between the first protein and the second protein;
(c) selecting at least one Candidate amino acid Residue from the Variant amino acid Residue identified in (b) on the basis of said Candidate amino acid Residue affecting said Target amino acid Residue with respect to said functional property;
(d) forming at least one Candidate Mutant protein in silico or producing at least one Candidate Mutant protein in vitro in which said at least one Candidate amino acid Residue from the second protein substitutes a corresponding residue in the first protein; and
(e) screening said at least one Candidate Mutant protein produced in (d) to identify a protein having said improved functional property; a Rubisco protein and its large subunit polypeptide produced by the method; and polynucleotides encoding the same.

16 Claims, 41 Drawing Sheets

(56) References Cited

OTHER PUBLICATIONS

Figure 1:
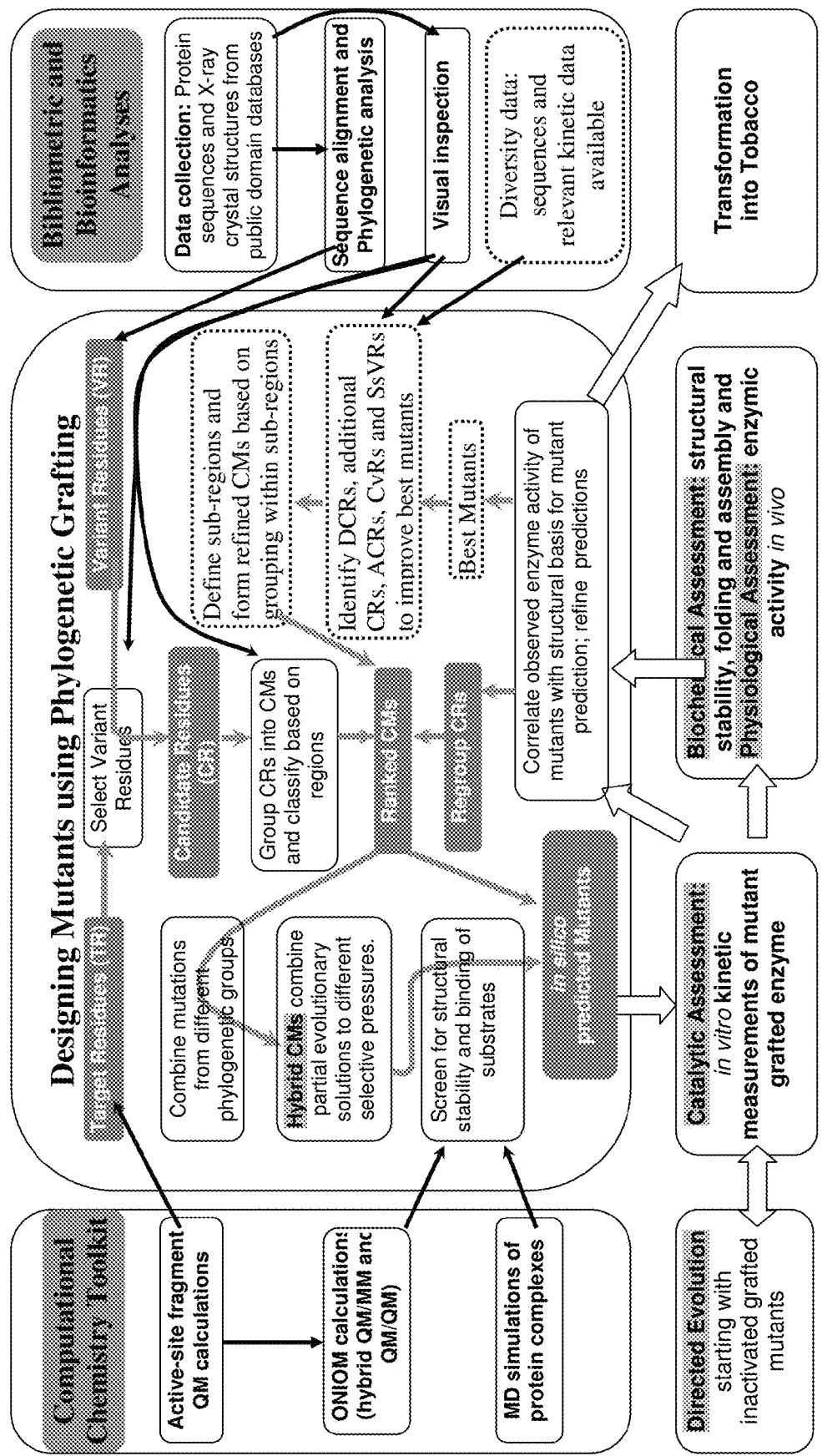
Figure 2:
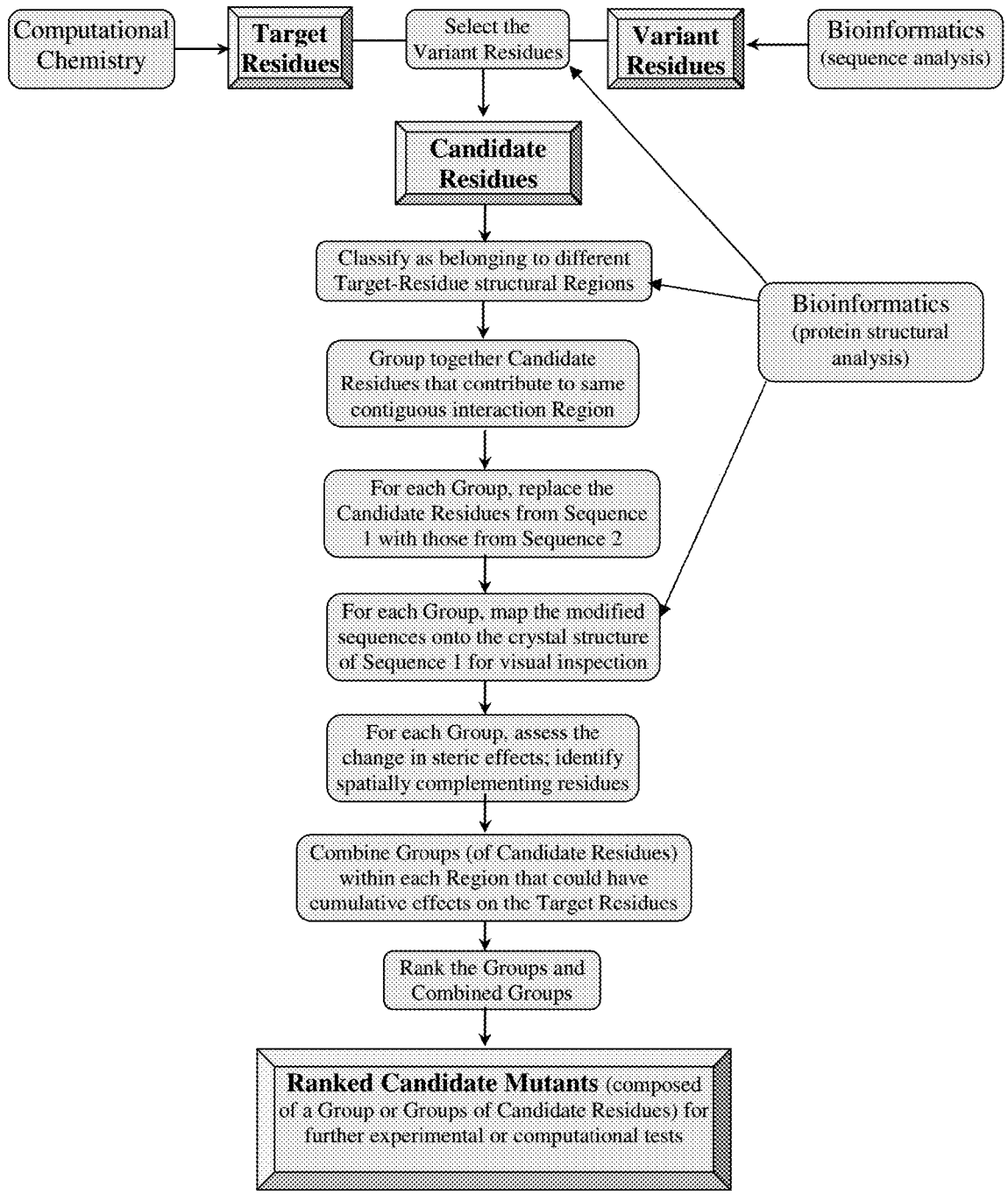

Cummins et al., "Coupled Semiempirical Molecular Orbital and Molecular Mechanics Model (QM/MM) for Organic Molecules in Aqueous Solution", Journal of Computational Chemistry, vol. 18, No. 12, 1997, pp. 1496-1512.

Cummins et al., "Coupled Semiempirical Quantum Mechanics and Molecular Mechanics (QM/MM) Calculations on the Aqueous Solvation Free Energies of Ionized Molecules", Journal of Computational Chemistry, vol. 20, No. 10, 1999, pp. 1028-1038.

Cummins et al., "Molecular Dynamics and Free Energy Perturbation Study of Hydride-Ion Transfer Step in Dihydrofolate Reductase Using Combined Quantum and Molecular Mechanical Model", Journal of Computational Chemistry, vol. 19, No. 8, 1998, pp. 977-988.

Database UNIPROT, "RecName: Full=Ribulose Bisphosphate Carboxylase Large Chain; Short=RuBisCO Large Subunit; EC=4.1.1.39", retrieved from EBI Accession No. UNIPROT: 098949, May 1, 1999.

Database UNIPROT, "SubName: Full=Ribulose 1.5-Bisphosphate Carboxylase Large Subunit; Flags: Fragment", retrieved from EBI Accession No. UNIPROT: 019874, Jan. 1, 1998.

Database UNIPROT, "SubName: Full=Ribulose-1.5-Bisphosphate Carboxylase/Oxygenase Large Subunit; Flags: Fragment", retrieved from EBI Accession No. UNIPROT: Q8MAS2, Oct. 1, 2002.

Database UNIPROT, "SubName: Full=Rubisco Large Subunit; Flags: Fragment", retrieved from EBI Accession No. UNIPROT: Q33525, Nov. 1, 1996.

Du et al., "Suppressor Mutations in the Chloroplast-Encoded Large Subunit Improve the Thermal Stability of Wild-Type Ribulose-1,5-Bisphosphate Carboxylase/Oxygenase", The Journal of Biological Chemistry, vol. 275, No. 26, Jun. 30, 2000, pp. 19844-19847.

Eckardt et al., "Heat Denaturation Profiles of Ribulose-I,5-Bisphosphate Carboxylase/Oxygenase (Rubisco) and Rubisco Activase and the Inability of Rubisco Activase to Restore Activity of Heat-Denatured Rubisco1", Plant Physiology, vol. 113, 1997, pp. 243-248.

Emlyn-Jones et al., "RbcX Can Function as a Rubisco Chaperonin, But is Non-Essential in Synechococcus PCC7942", Plant Cell Physiology, vol. 47, No. 12, 2006, pp. 1630-1640.

Evans et al., "The Specific Activity of Ribulose-1,5-Bisphosphate Carboxylase in Relation to Genotype in Wheat", Planta, vol. 167, 1986, pp. 344-350.

Extended European Search report and Search Opinion received for European Patent Application No. 07815347.5, dated Sep. 21, 2010, 17 pages.

Extended European Search report and Search Opinion received for European Patent Application No. 13168432.6, dated Mar. 7, 2014, 34 pages.

Farquhar et al., "A Biochemical Model of Photosynthetic $CO_2$ Assimilation in Leaves of $C_3$ Species", Planta, vol. 149, 1980, pp. 78-90.

Final Office Action received for U.S. Appl. No. 12/422,190, dated Mar. 1, 2013, 12 pages.

Freshwater et al., "A Gene Phylogeny of the Red Algae (*Rhodophyta*) based on Plastid rbcL", Proceedings of the National Academy of Sciences, vol. 91, Jul. 1994, pp. 7281-7285.

Galmes et al., "Rubisco Specificity Factor Tends to be Larger in Plant Species from Drier Habitats and in Species with Persistent Leaves", Plant, Cell and Environment, vol. 28, 2005, pp. 571-579.

Gready et al., "Simulations of Enzyme Reaction Mechanism in Active Sites: Accounting for an Environment which is much more than a Solvent Perturbation", Modeling Molecular Structure and Reactivity in Biological Systems, 2006, pp. 101-118.

Gready, Jill E.., "Defining the Inefficiencies in the Chemical Mechanism of the Photosynthetic Enzyme Rubisco by Computational Simulation", Artificial Photosynthesis: From Basic Biology to Industrial Application, 2006, pp. 263-282.

Gready, Jill, "Simulation of Enzyme Mechanisms, and Protein Dynamics, Structures and Properties; Definition of the Chemical Mechanism of the Photosynthetic Enzyme Rubisco; Simulation of Protein Properties; Conformations of Disordered Peptides", available at <http://nf.nci.org.au/annualJeports/2005/data/projectJeports/Gready_J_E_x04.html>, Aug. 8, 2011, 4 pages.

Gutteridge et al., "Details of the Reactions Catalysed by Mutant Forms of Rubisco", Plant Physiology and Biochemistry, vol. 26, No. 6, 1988, pp. 675-682.

Hall et al., "BioEdit: a User-Friendly Biological Sequence Alignment Editor and Analysis Program for Windows 95/98/NT", Nucleic Acids Symposium Series, vol. 41, 1999, pp. 95-98.

International Preliminary Report on Patentability received for PCT Patent Application No. PCT/AU2007/001542, completed on Aug. 29, 2008, 5 pages.

International Search Report received for PCT Patent Application No. PCT/AU2007/001542, dated Jan. 7, 2008, 3 pages.

International Written Opinion received for PCT Patent Application No. PCT/AU2007/001542, dated Jan. 7, 2008, 6 pages.

Kane et al., "An Improved Method for Measuring the $CO_2/O_2$ Specificity of Ribulosebisphosphate Carboxylase-Oxygenase", Australian Journal of Plant Physiology, vol. 21, 1994, pp. 449-461.

Kane et al., "Potent Inhibition of Ribulose-Bisphosphate Carboxylase by an Oxidized Impurity in Ribulose-1,5-Bisphosphate", Plant Physiology, vol. 117, 1998, pp. 1059-1069.

Kannapan et al., "Redefinition of Rubisco Carboxylase Reaction Reveals Origin of Water for Hydration and New Roles for Active-Site Residues", Journal of the American Chemical Society, vol. 30, No. 45, 2008, pp. 15063-15080.

King et al., "Quantum Chemical Analysis of the Enolization of Ribulose Bisphosphate: The First Hurdle in the Fixation of $CO_2$ by Rubisco", Biochemistry, vol. 37, 1998, pp. 15414-15422.

Koop et al., "The Genetic Transformation of Plastids", Topics in Current Genetics, 2007, 54 pages.

Looger et al., "Computational Design of Receptor and Sensor Proteins with Novel Functions", Nature, vol. 423, May 8, 2003, pp. 185-190.

Marin-Navarro et al., "Cysteines 449 and 459 Modulate the Reduction-Oxidation Conformational Changes of Ribulose 1.5-Bisphosphate Carboxylase/Oxygenase and the Translocation of the Enzyme to Membranes During Stress", Plant, Cell and Environment, vol. 29, 2006, pp. 898-908.

Martin et al., "Ribulose 1,5-Bisphosphate Carboxylase Large Subunit", UniProt Accession No. Q32689, Nov. 1, 1996, 1 page.

Mueller-Cajar et al., "Directed Evolution of Rubisco in *Escherichia coli* Reveals a Specificity-Determining Hydrogen Bond in the Form II Enzyme", Biochemistry, vol. 46, 2007, pp. 14067-14074.

Nixon et al., "Hybrid Enzymes: Manipulating Enzyme Design", Trends in Biotechnology, vol. 16, Jun. 1998, pp. 258-264.

Non-Final Office Action received for U.S. Appl. No. 12/422,190, dated Apr. 22, 2016, 12 pages.

Non-Final Office Action received for U.S. Appl. No. 12/422,190, dated Apr. 27, 2012, 18 pages.

Notice of Allowance received for U.S. Appl. No. 12/422,190, dated Nov. 3, 2016, 7 pages.

Office Action received for European Patent Application No. 07815347.5, dated Jan. 20, 2012, 14 pages.

Office Action received for European Patent Application No. 07815347.5, dated Mar. 12, 2015, 4 pages.

Office Action received for European Patent Application No. 07815347.5, dated May 8, 2013, 10 pages.

Office Action received for European Patent Application No. 07815347.5, dated May 9, 2011, 6 pages.

Office Action received for European Patent Application No. 13168432.6, dated Apr. 14, 2015, 5 pages.

Parikh et al., "Directed Evolution of RuBisCO Hypermorphs Through Genetic Selection in Engineered *E.Coli*", Protein Engineering, Design & Selection, vol. 19, No. 3, 2006, pp. 113-119.

Parry et al., "Manipulation of Rubisco: the Amount, Activity, Function and Regulation", Journal of Experimental Botany, vol. 54, No. 386, 2003, pp. 1321-1333.

Parry et al., "Prospects for Crop Production under Drought: Research Priorities and Future Directions", Annals of Applied Biology, vol. 147, 2005, pp. 211-226.

(56) References Cited

OTHER PUBLICATIONS

Parry et al., "Prospects for Increasing Photosynthesis by Overcoming the Limitations of Rubisco", Journal of Agricultural Science, vol. 145, 2007, pp. 31-43.
Partial European Search Report received for European Patent Application No. 13168432.6, dated Sep. 11, 2013, 16 pages.
Pearce et al., "The Relationship Between Side Reactions and Slow Inhibition of Ribulose-Bisphosphate Carboxylase Revealed by a Loop 6 Mutant of the Tobacco Enzyme", The Journal of Biological Chemistry, vol. 278, No. 35, Aug. 29, 2003, pp. 32526-32536.
Price et al., "Analysis of a Genomic DNA Region from the Cyanobacterium *Synechococcus* sp. Strain PCC7942 Involved in Carboxysome Assembly and Function", Journal of Bacteriology, vol. 175, No. 10, May 1993, pp. 2871-2879.
"Protein Engineering", Wikipedia the free Encyclopedia, available at <http://en.wikipedia.org/wiki/Protein_engineering>, Jan. 23, 2014, 4 pages.
Read et al., "High Substrate Specificity Factor Ribulose Bisphosphate Carboxylase/Oxygenase from Eukaryotic Marine Algae and Properties of Recombinant Cyanobacterial Rubisco Containing "Algal" Residue Modifications[1]", Archives of Biochemistry and Biophysics, vol. 312, No. 1, Jul. 1994, pp. 210-218.
Restriction Requirement received for U.S. Appl. No. 12/422,190, dated Jan. 20, 2012, 8 pages.
Richardson et al., "Ribulose Bisphosphate Carboxylase Oxygenase", UniProt Accession No. Q9GG60, Mar. 1, 2001, 1 page.
Ruuska, S., "The Interplay between Limiting Processes in C3 Photosynthesis Studied by Rapid-Response Gas Exchange using Transgenic Tobacco Impaired in Photosynthesis", American Journal of Plant Physiology, vol. 25, 1998, pp. 859-870.
Sharwood et al., "The Catalytic Properties of Hybrid Rubisco Comprising Tobacco Small and Sunflower Large Subunits Mirror the Kinetically Equivalent Source Rubiscos and Can Support Tobacco Growth", Plant Physiology, vol. 146, Jan. 2008, pp. 83-96.
Spreitzer et al., "Phylogenetic Engineering at an Interface Between Large and Small Subunits Imparts Land-Plant Kinetic Properties to Algal Rubisco", Proceedings of the National Academy of Sciences of the United States of America, vol. 102, No. 47, Nov. 22, 2005, pp. 17225-17230.
Spreitzer, R. J., "Rubisco: Structure, Regulatory Interactions, and Possibilities for a Better Enzyme", Annual Review of Plant Biology, vol. 53, 2002, pp. 449-475.
Supplementary European Search Report received for European Patent Application No. 07815347.5, dated Oct. 8, 2010, 18 pages.
Svab et al., "High-Frequency Plastid Transformation in Tobacco by Selection for a Chimeric aadA gene", Proceedings of the National Academy of Sciences, vol. 90, Feb. 1993, pp. 913-917.
Thompson et al., "Clustal W: Improving the Sensitivity of Progressive Multiple Sequence Alignment through Sequence Weighting, Position-Specific Gap Penalties and Weight Matrix Choice", Nucleic Acids Research, vol. 22, No. 22, 1994, pp. 4673-4680.
Tsou et al., "Ribulose 1,5-Bisphosphate Carboxylase Large Subunit", UniProt Accession No. Q9GFP6, Mar. 1, 2001, 1 page.
Wei-Wen et al., "Molecular Modelling of Rice Rubisco", Chinese Journal of Chemistry, vol. 15, No. 4, 1997, pp. 353-360.
Whitney et al., "Construction of a Tobacco Master Line to Improve Rubisco Engineering in Chloroplasts", Journal of Experimental Botany Advance Access, Feb. 3, 2008, pp. 1-13.
Whitney et al., "Directed Mutation of the Rubisco Large Subunit of Tobacco Influences Photorespiration and Growth", Plant Physiology, vol. 121, Oct. 1999, pp. 579-588.
Whitney et al., "Form I Rubiscos from Non-Green Algae are Expressed Abundantly but not Assembled in Tobacco Chloroplasts", Plant Journal, vol. 26, No. 5, 2001, pp. 535-547.
Whitney et al., "Linked Rubisco Subunits Can Assemble into Functional Oligomers without Impeding Catalytic Performance", Journal of Biological Chemistry, vol. 282, No. 6, Feb. 9, 2007, pp. 3809-3818.
Whitney et al., "Plastome-Encoded Bacterial Ribulose-1,5-Bisphosphate Carboxylase/Oxygenase (RubisCO) Supports Photosynthesis and Growth in Tobacco", Proceedings of the National Academy of Sciences of the United States of America, vol. 98, No. 25, Dec. 4, 2001, pp. 14738-14743.
Yu et al., "An Evolution-Based Analysis Scheme to Identify CO2/O2 Specificity—Determining Factors for Ribulose 1,5-Bisphosphate Carboxylase/Oxygenase", Protein Engineering, Design & Selection, vol. 18, No. 12, 2005, pp. 589-596.
Yukawa et al., "Ribulose-1,5-Bisphosphate Carboxylase/Oxygenase Large Subunit", Accession No. YP_358684, 2006, 1 page.
Yukawa et al., "The Chloroplast Genome of Nicotiana Sylvestris and Nicotiana Tomentosiformis: Complete Sequencing Confirms that the Nicotiana Sylvestris Progenitor is the Maternal Genome Donor of Nicotiana Tabacum", Molecular Genetics and Genomics, vol. 275, 2006, pp. 367-373.
Zhu et al., "Would Transformation of C3 Crop Plants with Foreign Rubisco Increase Productivity? A Computational Analysis Extrapolating from Kinetic Properties to Canopy Photosynthesis", Plant, Cell and Environment, vol. 27, 2004, pp. 155-165.
Intention to Grant received for European Patent Application No. 07815347.5, dated Nov. 10, 2016, 8 pages.
Intention to Grant received for European Patent Application No. 07815347.5, dated May 9, 2017, 10 pages.
Decision to Grant received for European Patent Application No. 07815347.5, dated Aug. 3, 2017, 2 pages.
Office Action received for European Patent Application No. 13168432.6, dated Aug. 8, 2017, 4 pages.

\* cited by examiner

Figure 7A:
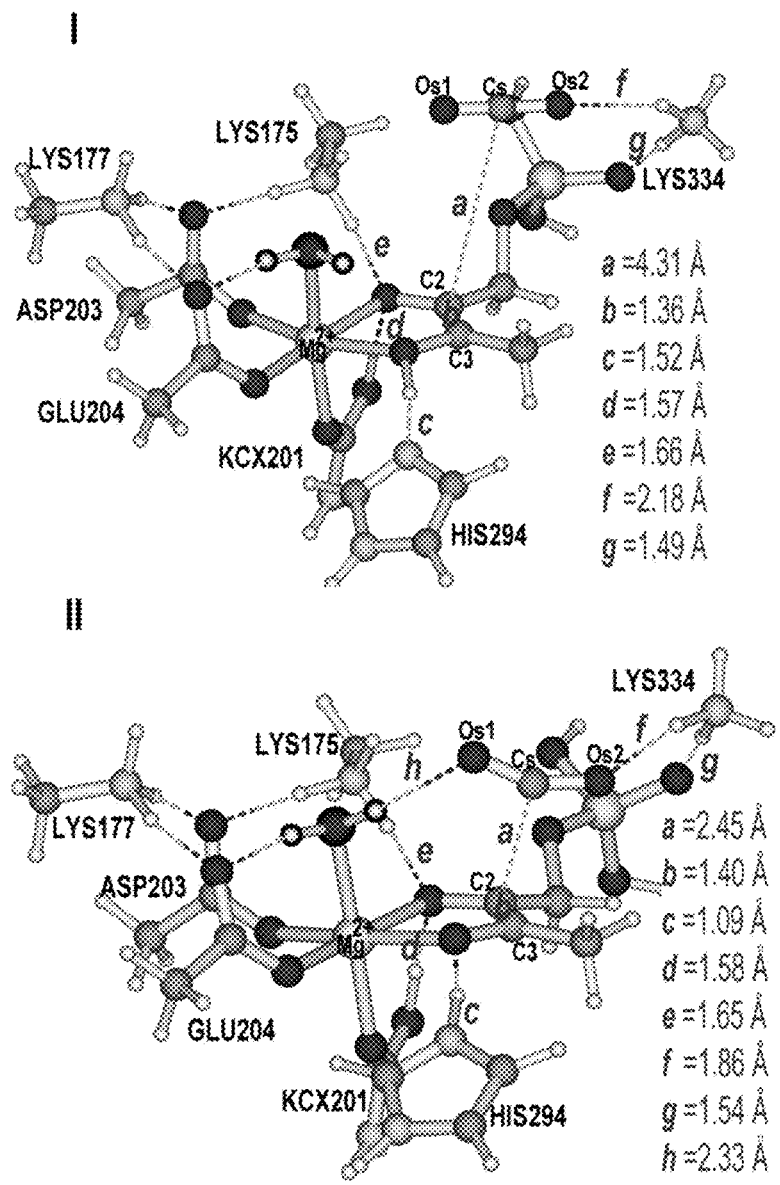
Figure 7B:
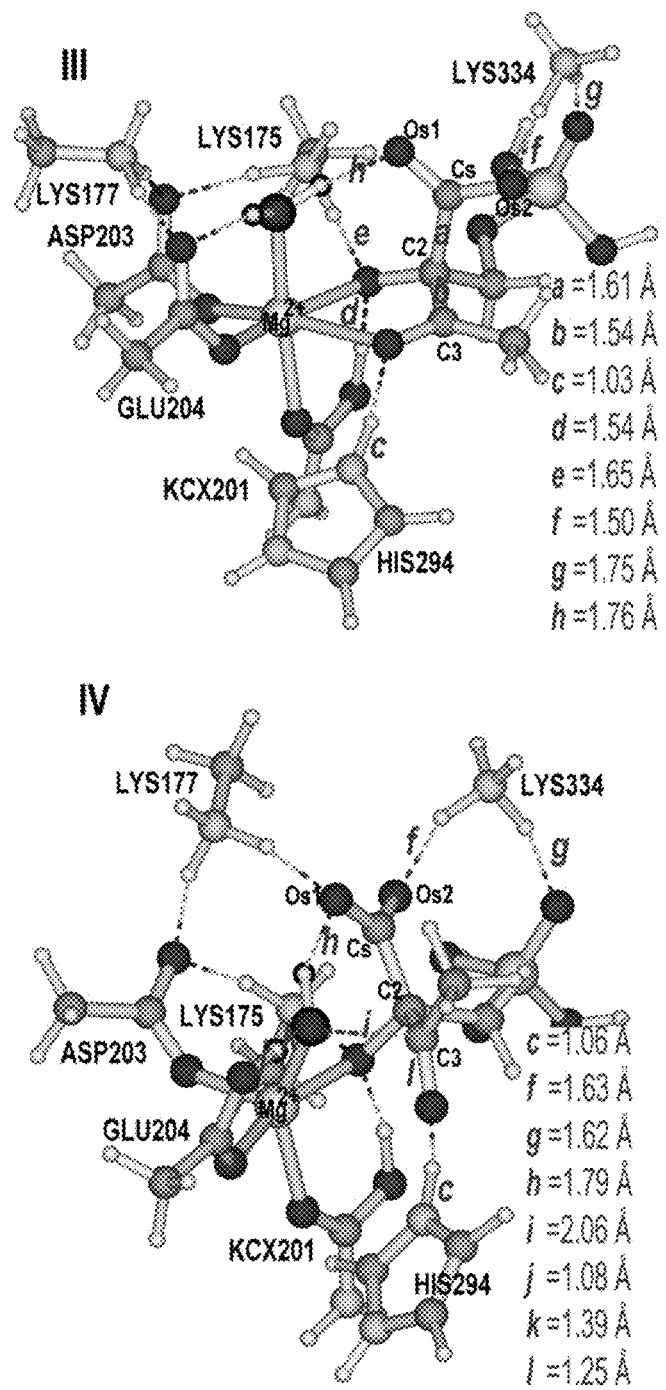
Figure 7D:
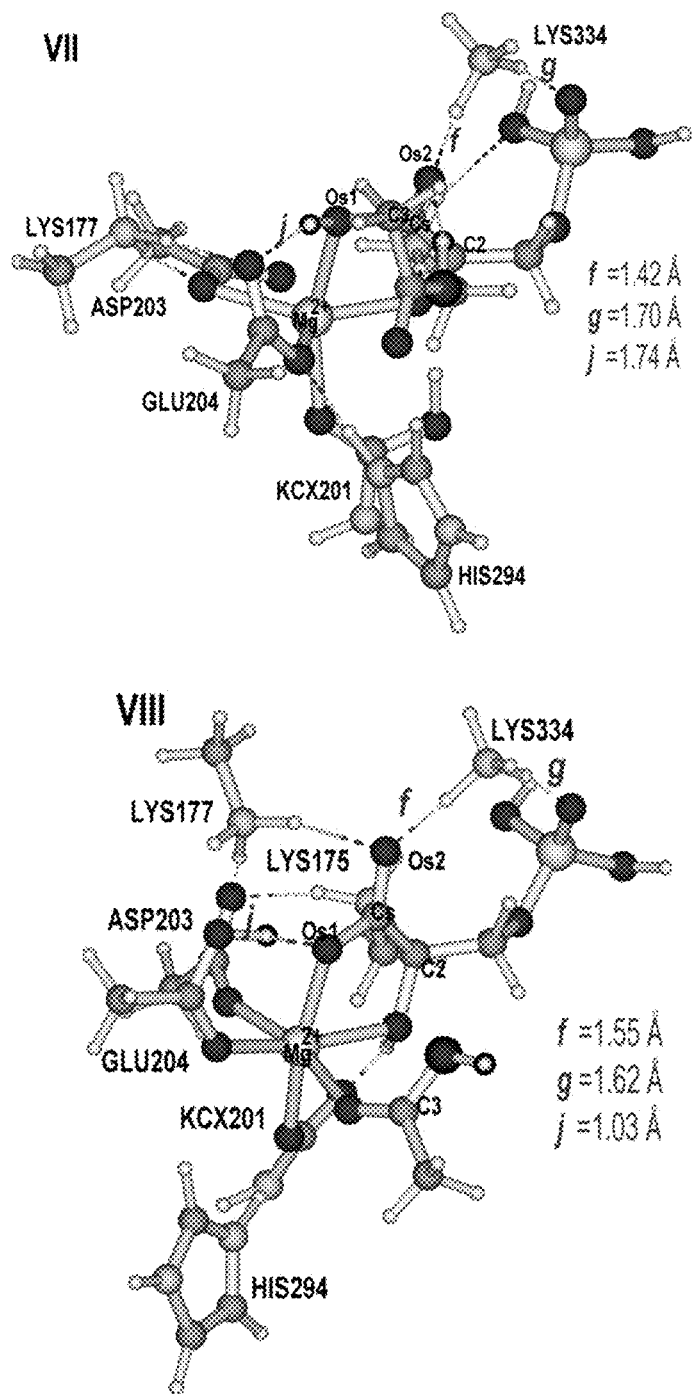
Figure 7E:
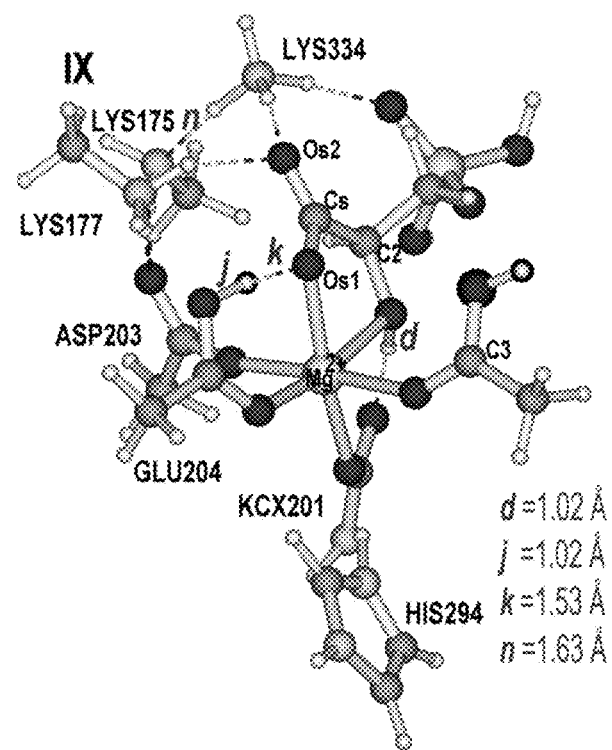

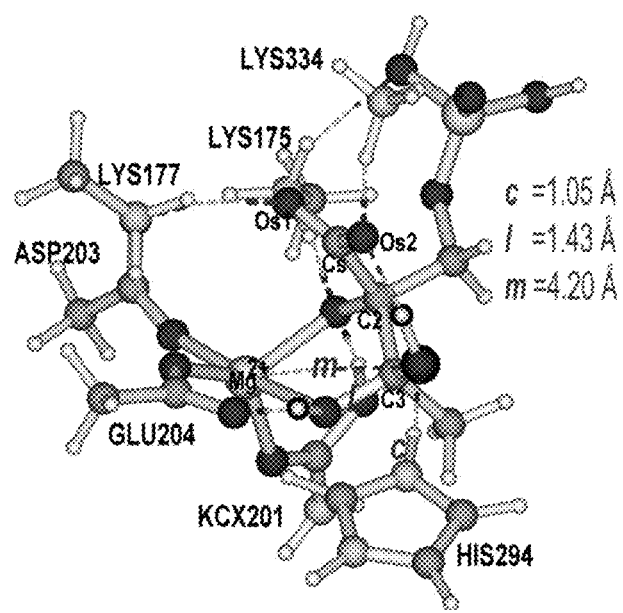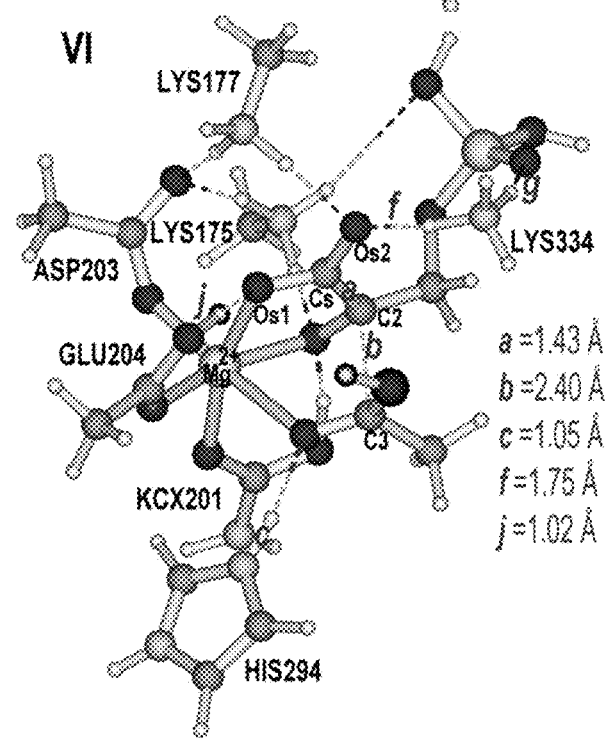
FIGURE 7C

FIGURE 9A

```
                                         130           136                150       156                 170       176
                                          ....|....    ....|....|    ....|....|    ....|....|    ....|....|    ....|....|
                                                        140                         160                           180
protista glaucophyta                 117 LTSIVGNVFG    FKALRALRLE    DLRIPVGYSK    TFQGPPHGIT    VERDKLMKYG    KRLLGCTIKP  176
cns50%(9) protista rhodophyta        121 YASIIGNVFG    FKAVKALRLE    DMRLPVAYLK    TFQGPAYGLI    VEREMDKFG     RPFLGAYVKP  180
cns50%(11) eubacteria cyanobacteria  118 LTSIVGNVFG    FKALRALRLE    DIRFPVAaIK    TFQGPPSGIQ    VERDKLMKYG    RPLLGCTIKP  177
plantae anthocerotophyta             117 FTSIVGNVFG    FKALRALRLE    DLRIPPAYSK    TFQGPPHGIQ    VERDKLMKYG    RPLLGCTIKP  176
cns50%(28) plantae bryophyta         117 FTSIVGNVFG    FKALRALRLE    DLRIPPAYSK    TFQGPPHGIQ    VERDKIMKYG    RPLLGCTIKP  176
cns50%(4) plantae charophyta         117 FTSIVGNVFG    FKALRALRLE    DLRIPPAYVK    TFQGPPHGIQ    VERRKLMKYG    RGLLGCTIKP  176
cns50%(4) plantae chlorophyta        117 FTSIVGNVFG    FKALRALRLE    DLRIPPSYSK    TFQGPPHGIQ    VERDKLMKYG    RPLLGCTIKP  176
plantae coniferophyta                117 FTSIVGNVFG    FKALRALRLE    DLRIPPAYSK    TFIGPPHGIQ    VERDKLMKYG    RPLLGCTIKP  176
plantae equisetophyta                117 FTSIVGNVFG    FKALRALRLE    DLRIPYSYIK    TFQGPPHGIQ    VERSKLMKYG    RPLLGCTIKP  176
plantae gnetophyta                   117 FTSIVGNVFG    FKALRALRLE    DLRIPsAYVK    TFQGPPHGIQ    VERDKLMKYG    RPLLGCTIKP  176
cns50%(134) plantae magnoliophyta    117 FTSIVGNVFG    FKALRALRLE    DLRIPAYSK     TFQGPPHGIQ    VERDKLMKYG    RPLLGCTIKP  176
cns50%(2) plantae pinophyta          117 FTSIVGNVFG    FKALRALRLE    DLRIPAYSK     TFQGPPHGIQ    VERDKLMKYG    RPLLGCTIKP  176
cns50%(2) plantae pteridophyta       117 LTSIVGKNVFG   FKALRALRLE    DLRILPAYSK    TFIGPPHGIQ    VERDKLMKYG    RPLLGCTIKP  176

190           196                210       216                 230       236
                                          ....|....    ....|....|    ....|....|    ....|....|    ....|....|    ....|....|
                                                        200                         220                           240
protista glaucophyta                 177 KLGLSAKNYG    RAVYECLRGG    LDFTKDDENV    NSQPFMRMRD    RFLYMDAIK     KSQAETGEIK  236
cns50%(9) protista rhodophyta        181 KIGLSGKNYG    RVVYEGLKGG    LDFLKGDEMI    NSQPFMRM+E    RYLXSMEGVN    RApAAoGEIK  240
cns50%(11) eubacteria cyanobacteria  178 KLGLSAKNYG    RAVYECLRGG    LDFTKDEMI     NSQFFQRMRS    RFLFVAEAIc    KRQAETGEIK  237
plantae anthocerotophyta             177 KLGLSAKNYG    RAVYECLRGG    LDFTKDDENV    NSQPFMRMRD    RFLFVAEAIF    KSQAETGEIK  236
cns50%(28) plantae bryophyta         177 KLGLSAKNYG    RAVYECLRGG    LDFTKDDENV    NSQPFMRMRD    RFLFVAEAIY    KSQAETGEIK  236
cns50%(4) plantae charophyta         177 KLGLSAKNYG    RAVYECLRGG    LDFTKDGENV    NSQPFMRMRD    RFLFVAEAIF    KAQAETGEIK  236
cns50%(4) plantae chlorophyta        177 KLGLSAKNYG    RAVYECLRGG    LDFTKDGENV    NSQPFMRMRD    RFLFVAEAIY    KAQAETGEVK  236
plantae coniferophyta                177 KLGLSAKNYG    RAVYECLRGG    LDFTKDDENV    NSQPFMRMRD    RFLFVAEALM    KAQAETGEIK  236
plantae equisetophyta                177 KLGLSAKNYG    RAVYECLRGG    LDFTKDDENV    NSQPFMRMRD    RFVFCAEALN    KAQAETGEIK  236
plantae gnetophyta                   177 KLGLSAKNYG    RAVYECLRGG    LDFTKDDENV    NSQPFMRMRD    RFVFCAEAIY    KAQAETGEIK  236
cns50%(134) plantae magnoliophyta    177 KLGLCAKNYG    RAVYECLRGG    LDFTKDDENV    NSQPFMRMRD    RFLFCAEAIY    KAQAETGEIK  236
cns50%(2) plantae pinophyta          177 KLGLSAKNYG    RAVYECLRGG    LDFTKDDENV    NSQPFMRMRD    RFVFCAEAIN    KAQAETGEIK  236
cns50%(2) plantae pteridophyta       177 KLGLSAKNYG    RAVYECLRGG    LDFTKDDENV    NSQPFMRMRD    RFLFVAEALF    KAQAETGEIK  236
```

```
cns50%(9) protista rhodophyta       1   ..........  ..........  ..........  ..........  ..........  ..........
cns50%(11) eubacteria cyanobacteria 1   MspSVpERTR  IKNERYESGV  IPYAKmGYwD  PDYVVKDTDV  LAnFRhTPQP  GVDPYEASAA   60
cns50%(134) plantae magnoliophyta   1   MSYAQhKoQo  KuGYp~~AGV  KDYRL~~YYT  PDYTPKDTDL  LAAFRhTPQP  GVPsEEAGAA   57
                                        MSPQTETKAS  V~GFK~~AGV  KDYKL~~YYT  PDYETKDTDI  LAAFRVTPQP  GVPPEAGAA    56
                                                                                                            116
                                                10          20          30          40          50          60

120
cns50%(9) protista rhodophyta      61   VAQESSTATW  TFVWTDLLTA  QDIYRAKAYK  YDuVPNoSDQ  YFAVIAYDID  LFEEGSTANL  120
cns50%(11) eubacteria cyanobacteria 58  VAAESSTGTW  TFVWTDLLTD  ADRYAKGRGYD  IEPVPGEDNQ  YaAFIAYPID  LFEEGSVTNV  117
cns50%(134) plantae magnoliophyta  57   VAAESSTGTW  TFVWTDGLTS  LDRYKGRCYH  IEPVAGGENQ  FIAVVAYPID  LFEEGSVTNM  116
                                                                                                            176
                                                70          80          90         100         110         120

180
cns50%(9) protista rhodophyta     121   TNSIIGNVFG  FKAUKALRLE  DMRLPVAYLK  TFQGPAtGlI  VERREMDKFG  RPELGATIKP  180
cns50%(11) eubacteria cyanobacteria 118 LDSIVGNVFG  FKAIRALRLE  DIRFPVAaIK  TFQGPRHGIQ  VERDKLNKYG  RPELGCTIKP  177
cns50%(134) plantae magnoliophyta 117   FISIVGNVFG  FKAIRALRLE  DLRIPsAYVK  TFQGPRHGIQ  VERSKENKYG  RPELGCTIKP  176
                                                                                                            236
                                               130         140         150         160         170         180

240
cns50%(9) protista rhodophyta     181   KLGLSQKNYG  RVVYEGLRGG  LDFLKDDENI  NSQPFMRW+E  RILKSMEGTN  RApAkoGEIK  240
cns50%(11) eubacteria cyanobacteria 178 KLGLSAKNYG  RAVYECLRGG  LDFTKDDENI  NSQPFQRWRD  RELFVAEAIc  KAQAETGEIK  237
cns50%(134) plantae magnoliophyta 177   KLGLSAKNYG  RAVYECLRGG  LDFTKDDENV  NSQPFMRWRD  RELECAEAIY  KAQAETGEIK  236
                                                                                                            296
                                               190         200         210         220         230         240 cns50%(9) protista rhodophyta     241   GHYLNVTAAT  NE-MYBRAEF  AKELGSWIIM  ID-LVYGYTA  IQTMAIWARK  NDMQIHIHRA  298
cns50%(11) eubacteria cyanobacteria 238 GHYLNVTAsT  CEEMhKRAEF  AKELGPHIIM  HDFLNGGETA  NTTEAKWCRD  NGILLHIHRA  297
cns50%(134) plantae magnoliophyta 237   GHYLNATAGT  CEEMIKRAVF  ARELGVPIVM  HDYLRGGETA  NISAHYCRD  NGLLLHIHRA  296
                                               250         260         270         280         290         300
```

FIGURE 10A

FIGURE 10B

```
                                    17              26                    46
                           10       20       30       40       50       60
                           ....|....|....|....|....|....|....|....|....|....|....|....|
cns50%(9) protista rhodophyta      1  MspSVpERTR IKNERYESGV TPYAKMGYtD PDYVVKDTDy LALFRVTPQP GVDPvEASAA    60
cns50%(11) eubacteria cyanobacteria 1  .SYAQhKoQo KuGYp~~A. KD.RL~T.MT .TP...L.. .A..h.... .PsE.G...    57
cns50%(134) plantae magnoliophyta   1  .S.QTETKAS V~GFK~~A. ...K.~... .ET...... ........ ........    56

....|....|....|....|....|....|....|....|....|....|....|....|
                           70       80       90       100      110      120
cns50%(9) protista rhodophyta     61  VAgESSTAtW TVWTDLLTA CDLYRAKIY VDuVPNoSDQ YFAYIAvDID LFEEGSIAN   120
cns50%(11) eubacteria cyanobacteria 58  ..A..G.... ....H.... .D.L.R.KGRc.B TEP..GEDN. .a.F..PL. .....VT.V.   117
cns50%(134) plantae magnoliophyta  57  .......... .......G..S ......B.. P.A.EE .FI.V... ........N   116

....|....|....|....|....|....|....|....|....|....|....|....|
                           130      140      150      160      170      180
cns50%(9) protista rhodophyta    121  tASIgGNVFG FKAVKALRLE DMRiPVAYLK TFQGPATGLI VERERMDKFG RPFLGATVKP  180
cns50%(11) eubacteria cyanobacteria 118  .T..V..... .LR....... ...aI..... .PH.IQ.... .DKLN.Y... .L.C.I...   177
cns50%(134) plantae magnoliophyta 117  .E........ .......... ..s..V.... .......I.. .......... ........   176

....|....|....|....|....|....|....|....|....|....|....|....|
                           190      200      210      220      230      240
cns50%(9) protista rhodophyta    181  KLGLSGKNYG RVVYEGLKGG LDFLKDDENI NSQPFMRW+E RYLYSMEGVN RApAAoGElK  240
cns50%(11) eubacteria cyanobacteria 178  ..A....... .A...C.R.. ...T...... ......Q.RD .F.FVA.AIc K.Q.ET..I.   237
cns50%(134) plantae magnoliophyta 177  .......... .......... ......V... ........ ..R..C... YK.Q.T..I.   236

....|....|....|....|....|....|....|....|....|....|....|....|
                           250      260      270      280      290      300
cns50%(9) protista rhodophyta    241  GHYLNVTAAT ME-MYERAEF AKELGSVIIM ID~LvIGYTA IQTMAIWARK NDMILHLHRA  298
cns50%(11) eubacteria cyanobacteria 238  .....s. C.E.hK... ..pP.I. .H.F. NG.F. .NT.L.K.C.D .GIL..I...   297
cns50%(134) plantae magnoliophyta 237  .....A.G.. .E.l..V. .R..V.V. .Y...... .S.HY... .L......   296
```

FIGURE 11A

```
                                      310       316       336              356
                                       |    .    |    .    |    .    |    .    |
cns50%(9) protista rhodophyta      299 CNSFYSRQKs HGMNFRVICK WMRMAGVDHI HAGTVVGKLE GDPlMI+GFY NTLLLoHL-1 357
cns50%(11) eubacteria cyanobacteria 298 MHAVID...N ..IH...LA. CL.LS.G..L .T........ .ERuITM..V DL.RE-aVEc 356
cns50%(134) plantae magnoliophyta  297 ......N... .......... .......A.. .......... .......... . DDFIEK   356
                                           320       330       340       350       360
                                                                                          416
                                           370       376       390       396        410       420
                                       |    .    |    .    |    .    |    .    |    .    |    .    |
cns50%(9) protista rhodophyta      358 NLPQGIFFEQ DWASLRKVTP VASGGIHCGQ MHQLLDYLGD DVVLQFGGGT IGHPDGIQAG 417
cns50%(11) eubacteria cyanobacteria 357 DRSR....T. ...MPG.MA. .......... .VWH.PA.VEIF.. .S........ .L...W.NAP. 416
cns50%(134) plantae magnoliophyta  357 .....Y....  ...V...L.. .......... .......T.. .......... .......... 415
                                           430       436       450       456       470       480
                                       |    .    |    .    |    .    |    .    |    .    |    .    |
cns50%(9) protista rhodophyta      418 ATANRVALES MVIARNEGRD YVAEGPQILR DAAKTCGPLQ TALDLWKDIT FNYTSTDTAD 477
cns50%(11) eubacteria cyanobacteria 417 ......A C.Q....... .c LtR..sD.I. E...WSPE.A l.CE...E.K .EFEAM..L.  475
cns50%(134) plantae magnoliophyta  417 .V........ .......... .A ..NE....  .S........ .A. V..... .......... 475
```

FIGURE 11B

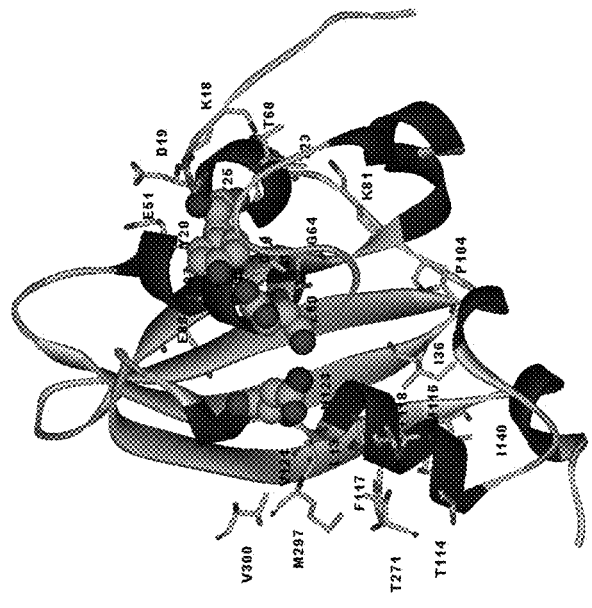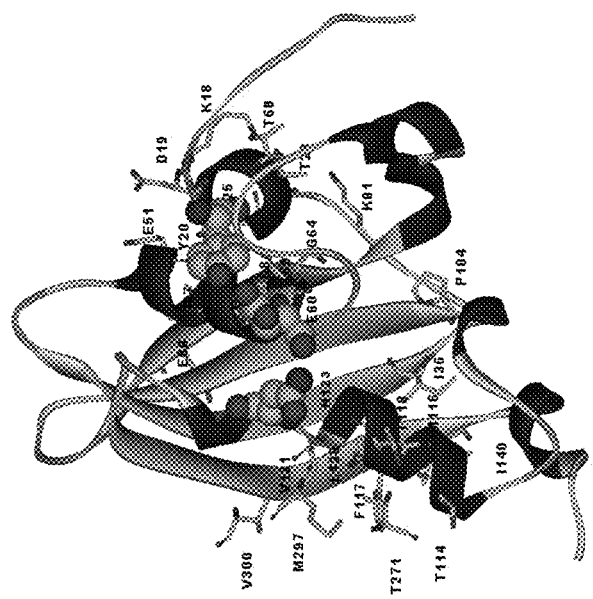
FIGURE 17

FIGURE 18B

SEQUENCE LISTING

```
<160> NUMBER OF SEQ ID NOS: 80

<210> SEQ ID NO 1
<211> LENGTH: 475
<212> TYPE: PRT
<213> ORGANISM: Cyanophora paradoxa

<400> SEQUENCE: 1

Met Ser Ser Gln Ala Arg Thr Gln Thr Arg Ala Gly Phe Lys Ala Gly
1               5                   10                  15

Val Lys Asp Tyr Arg Leu Thr Tyr Tyr Thr Pro Glu Tyr Thr Pro Lys
            20                  25                  30

Glu Thr Asp Ile Leu Ala Ala Phe Arg Met Thr Pro Gln Pro Gly Val
        35                  40                  45

Pro Pro Glu Glu Cys Ala Ala Val Ala Ala Glu Ser Ser Thr Gly
    50                  55                  60

Thr Trp Thr Thr Val Trp Thr Asp Gly Leu Thr Ser Leu Asp Arg Tyr
65                  70                  75                  80

Lys Gly Arg Ser Tyr Gly Phe Glu Pro Val Pro Gly Glu Glu Asn Gln
                85                  90                  95

Tyr Ile Cys Tyr Val Ala Tyr Pro Leu Asp Leu Phe Glu Glu Gly Ser
            100                 105                 110

Val Thr Asn Met Leu Thr Ser Ile Val Gly Asn Val Phe Gly Phe Lys
        115                 120                 125

Ala Leu Arg Ala Leu Arg Leu Glu Asp Leu Arg Ile Pro Val Gly Tyr
    130                 135                 140

Ser Lys Thr Phe Gln Gly Pro Pro His Gly Ile Thr Val Glu Arg Asp
145                 150                 155                 160

Lys Leu Asn Lys Tyr Gly Arg Ala Leu Leu Gly Cys Thr Ile Lys Pro
                165                 170                 175

Lys Leu Gly Leu Ser Ala Lys Asn Tyr Gly Arg Ala Val Tyr Glu Cys
            180                 185                 190

Leu Arg Gly Gly Leu Asp Phe Thr Lys Asp Asp Glu Asn Val Asn Ser
        195                 200                 205

Gln Pro Phe Met Arg Trp Arg Asp Arg Phe Leu Tyr Val Met Asp Ala
    210                 215                 220

Ile Lys Lys Ser Gln Ala Glu Thr Gly Glu Ile Lys Gly His Tyr Leu
225                 230                 235                 240

Asn Ala Thr Ala Pro Thr Thr Glu Glu Met Ile Lys Arg Ala Glu Phe
                245                 250                 255

Ala Ala Glu Leu Asp Ala Pro Ile Ile Met His Asp Tyr Ile Thr Ala
            260                 265                 270

Gly Phe Thr Ser Asn Thr Thr Leu Ala Arg Trp Cys Arg Asp Asn Gly
        275                 280                 285

Pro Leu Leu His Ile His Arg Ala Met His Ala Val Ile Asp Arg Gln
    290                 295                 300

Lys Asn His Gly Ile His Phe Arg Val Leu Ala Lys Thr Leu Arg Met
305                 310                 315                 320

Ser Gly Gly Asp His Leu His Ser Gly Thr Val Val Gly Lys Leu Glu
                325                 330                 335
```

-continued

Gly Asp Arg Ala Gly Thr Leu Gly Phe Val Asp Leu Met Arg Asp Asp
                340                 345                 350

His Ile Glu Gln Asp Arg Ser Arg Gly Ile Phe Phe Thr Gln Asp Trp
            355                 360                 365

Ala Ser Met Pro Gly Val Met Pro Val Ala Ser Gly Gly Ile His Ile
370                 375                 380

Trp His Met Pro Ala Leu Val Asp Ile Phe Gly Asp Asp Ser Cys Leu
385                 390                 395                 400

Gln Phe Gly Gly Gly Thr Leu Gly His Pro Trp Gly Asn Ala Pro Gly
                405                 410                 415

Ala Val Ala Asn Arg Val Ala Leu Glu Ala Cys Val Gln Ala Arg Asn
            420                 425                 430

Glu Gly Arg Asn Leu Ala Arg Glu Gly Asn Glu Ile Ile Arg Glu Ala
        435                 440                 445

Ala Arg Phe Ser Pro Glu Leu Ala Ala Ala Cys Glu Val Trp Lys Glu
    450                 455                 460

Ile Lys Phe Glu Phe Glu Thr Ile Asp Thr Ile
465                 470                 475

<210> SEQ ID NO 2
<211> LENGTH: 488
<212> TYPE: PRT
<213> ORGANISM: Artificial
<220> FEATURE:
<223> OTHER INFORMATION: 50% consensus sequence for rhodophyta (9
      species) Rubisco LSU
<220> FEATURE:
<221> NAME/KEY: MISC_FEATURE
<222> LOCATION: (2)..(2)
<223> OTHER INFORMATION: residue is one of A, C, D, G, N, P, S, T or V
<220> FEATURE:
<221> NAME/KEY: MISC_FEATURE
<222> LOCATION: (3)..(3)
<223> OTHER INFORMATION: residue is one of C, D, E, H, K, N, Q, R, S or
      T
<220> FEATURE:
<221> NAME/KEY: MISC_FEATURE
<222> LOCATION: (6)..(6)
<223> OTHER INFORMATION: residue is one of C, D, E, H, K, N, Q, R, S or
      T
<220> FEATURE:
<221> NAME/KEY: MISC_FEATURE
<222> LOCATION: (93)..(93)
<223> OTHER INFORMATION: residue is one of A, G or S
<220> FEATURE:
<221> NAME/KEY: MISC_FEATURE
<222> LOCATION: (97)..(97)
<223> OTHER INFORMATION: residue is one of S or T
<220> FEATURE:
<221> NAME/KEY: MISC_FEATURE
<222> LOCATION: (159)..(159)
<223> OTHER INFORMATION: residue is one of I, L or V
<220> FEATURE:
<221> NAME/KEY: MISC_FEATURE
<222> LOCATION: (219)..(219)
<223> OTHER INFORMATION: residue is one of H, K or R
<220> FEATURE:
<221> NAME/KEY: MISC_FEATURE
<222> LOCATION: (233)..(233)
<223> OTHER INFORMATION: residue is one of C, D, E, H, K, N, Q, R, S or
      T
<220> FEATURE:
<221> NAME/KEY: MISC_FEATURE
<222> LOCATION: (236)..(236)
<223> OTHER INFORMATION: residue is one of S or T
<220> FEATURE:
<221> NAME/KEY: MISC_FEATURE
<222> LOCATION: (239)..(239)
<223> OTHER INFORMATION: residue is one of I, L or V

```
<220> FEATURE:
<221> NAME/KEY: MISC_FEATURE
<222> LOCATION: (253)..(253)
<223> OTHER INFORMATION: residue is one of D or E
<220> FEATURE:
<221> NAME/KEY: MISC_FEATURE
<222> LOCATION: (269)..(269)
<223> OTHER INFORMATION: residue is one of I, L or V
<220> FEATURE:
<221> NAME/KEY: MISC_FEATURE
<222> LOCATION: (309)..(309)
<223> OTHER INFORMATION: residue is one of A, C, D, G, N, P, S, T or V
<220> FEATURE:
<221> NAME/KEY: MISC_FEATURE
<222> LOCATION: (343)..(343)
<223> OTHER INFORMATION: residue is one of I, L or  V
<220> FEATURE:
<221> NAME/KEY: MISC_FEATURE
<222> LOCATION: (346)..(346)
<223> OTHER INFORMATION: residue is one of H, K or R
<220> FEATURE:
<221> NAME/KEY: MISC_FEATURE
<222> LOCATION: (355)..(355)
<223> OTHER INFORMATION: residue is one of S or T
<220> FEATURE:
<221> NAME/KEY: MISC_FEATURE
<222> LOCATION: (358)..(358)
<223> OTHER INFORMATION: residue is one of D or E
<220> FEATURE:
<221> NAME/KEY: MISC_FEATURE
<222> LOCATION: (359)..(359)
<223> OTHER INFORMATION: residue is one of I, L or V

<400> SEQUENCE: 2

Met Xaa Xaa Ser Val Xaa Glu Arg Thr Arg Ile Lys Asn Glu Arg Tyr
1               5                   10                  15

Glu Ser Gly Val Ile Pro Tyr Ala Lys Met Gly Tyr Trp Asp Pro Asp
            20                  25                  30

Tyr Val Val Lys Asp Thr Asp Val Leu Ala Leu Phe Arg Val Thr Pro
        35                  40                  45

Gln Pro Gly Val Asp Pro Val Glu Ala Ser Ala Ala Val Ala Gly Glu
    50                  55                  60

Ser Ser Thr Ala Thr Trp Thr Val Val Trp Thr Asp Leu Leu Thr Ala
65                  70                  75                  80

Cys Asp Leu Tyr Arg Ala Lys Ala Tyr Lys Val Asp Xaa Val Pro Asn
                85                  90                  95

Xaa Ser Asp Gln Tyr Phe Ala Tyr Ile Ala Tyr Asp Ile Asp Leu Phe
            100                 105                 110

Glu Glu Gly Ser Ile Ala Asn Leu Thr Ala Ser Ile Ile Gly Asn Val
        115                 120                 125

Phe Gly Phe Lys Ala Val Lys Ala Leu Arg Leu Glu Asp Met Arg Leu
    130                 135                 140

Pro Val Ala Tyr Leu Lys Thr Phe Gln Gly Pro Ala Thr Gly Xaa Ile
145                 150                 155                 160

Val Glu Arg Glu Arg Met Asp Lys Phe Gly Arg Pro Phe Leu Gly Ala
                165                 170                 175

Thr Val Lys Pro Lys Leu Gly Leu Ser Gly Lys Asn Tyr Gly Arg Val
            180                 185                 190

Val Tyr Glu Gly Leu Lys Gly Gly Leu Asp Phe Leu Lys Asp Asp Glu
        195                 200                 205

Asn Ile Asn Ser Gln Pro Phe Met Arg Trp Xaa Glu Arg Tyr Leu Tyr
    210                 215                 220

Ser Met Glu Gly Val Asn Arg Ala Xaa Ala Ala Xaa Gly Glu Xaa Lys
225                 230                 235                 240
```

```
Gly His Tyr Leu Asn Val Thr Ala Ala Thr Met Glu Xaa Met Tyr Glu
                245                 250                 255

Arg Ala Glu Phe Ala Lys Glu Leu Gly Ser Val Ile Xaa Met Ile Asp
            260                 265                 270

Leu Val Ile Gly Tyr Thr Ala Ile Gln Thr Met Ala Ile Trp Ala Arg
        275                 280                 285

Lys Asn Asp Met Ile Leu His Leu His Arg Ala Gly Asn Ser Thr Tyr
    290                 295                 300

Ser Arg Gln Lys Xaa His Gly Met Asn Phe Arg Val Ile Cys Lys Trp
305                 310                 315                 320

Met Arg Met Ala Gly Val Asp His Ile His Ala Gly Thr Val Val Gly
                325                 330                 335

Lys Leu Glu Gly Asp Pro Xaa Met Ile Xaa Gly Phe Tyr Asn Thr Leu
            340                 345                 350

Leu Leu Xaa His Leu Xaa Xaa Asn Leu Pro Gln Gly Ile Phe Phe Glu
        355                 360                 365

Gln Asp Trp Ala Ser Leu Arg Lys Val Thr Pro Val Ala Ser Gly Gly
    370                 375                 380

Ile His Cys Gly Gln Met His Gln Leu Leu Asp Tyr Leu Gly Asp Asp
385                 390                 395                 400

Val Val Leu Gln Phe Gly Gly Gly Thr Ile Gly His Pro Asp Gly Ile
                405                 410                 415

Gln Ala Gly Ala Thr Ala Asn Arg Val Ala Leu Glu Ser Met Val Ile
            420                 425                 430

Ala Arg Asn Glu Gly Arg Asp Tyr Val Ala Glu Gly Pro Gln Ile Leu
        435                 440                 445

Arg Asp Ala Ala Lys Thr Cys Gly Pro Leu Gln Thr Ala Leu Asp Leu
    450                 455                 460

Trp Lys Asp Ile Thr Phe Asn Tyr Thr Ser Thr Asp Thr Ala Asp Phe
465                 470                 475                 480

Val Glu Thr Pro Thr Ala Asn Val
                485
```

```
<210> SEQ ID NO 3
<211> LENGTH: 476
<212> TYPE: PRT
<213> ORGANISM: Artificial
<220> FEATURE:
<223> OTHER INFORMATION: 50% consensus sequence for cyanobacteria
      Rubisco
<220> FEATURE:
<221> NAME/KEY: MISC_FEATURE
<222> LOCATION: (6)..(6)
<223> OTHER INFORMATION: Residue is one of A, C, F, G, H, I, K, L, M, R,
      T, V, W or Y
<220> FEATURE:
<221> NAME/KEY: MISC_FEATURE
<222> LOCATION: (8)..(8)
<223> OTHER INFORMATION: Residue is one of S or T
<220> FEATURE:
<221> NAME/KEY: MISC_FEATURE
<222> LOCATION: (10)..(10)
<223> OTHER INFORMATION: Residue is one of S or T
<220> FEATURE:
<221> NAME/KEY: MISC_FEATURE
<222> LOCATION: (12)..(12)
<223> OTHER INFORMATION: Residue is one of A, G or S
<220> FEATURE:
<221> NAME/KEY: MISC_FEATURE
<222> LOCATION: (15)..(15)
<223> OTHER INFORMATION: Residue is one of C, D, E, H, K, N, Q, R, S or
      T
```

```
<220> FEATURE:
<221> NAME/KEY: MISC_FEATURE
<222> LOCATION: (43)..(43)
<223> OTHER INFORMATION: Residue is one of A, C, F, G, H, I, K, L, M, R,
      T, V, W or Y
<220> FEATURE:
<221> NAME/KEY: MISC_FEATURE
<222> LOCATION: (51)..(51)
<223> OTHER INFORMATION: Residue is one of A, C, D, G, N, P, S, T or V
<220> FEATURE:
<221> NAME/KEY: MISC_FEATURE
<222> LOCATION: (99)..(99)
<223> OTHER INFORMATION: Residue is one of F, H, W or Y
<220> FEATURE:
<221> NAME/KEY: MISC_FEATURE
<222> LOCATION: (145)..(145)
<223> OTHER INFORMATION: Residue is one of F, H, W or Y
<220> FEATURE:
<221> NAME/KEY: MISC_FEATURE
<222> LOCATION: (227)..(227)
<223> OTHER INFORMATION: Residue is one of D, E, H, K or R
<220> FEATURE:
<221> NAME/KEY: MISC_FEATURE
<222> LOCATION: (246)..(246)
<223> OTHER INFORMATION: Residue is one of A, C, D, G, N, P, S, T or V
<220> FEATURE:
<221> NAME/KEY: MISC_FEATURE
<222> LOCATION: (252)..(252)
<223> OTHER INFORMATION: Residue is one of A, C, F, G, H, I, K, L, M, R,
      T, V, W or Y
<220> FEATURE:
<221> NAME/KEY: MISC_FEATURE
<222> LOCATION: (263)..(263)
<223> OTHER INFORMATION: Residue is one of C, D, E, H, K, N, Q, R, S or
      T
<220> FEATURE:
<221> NAME/KEY: MISC_FEATURE
<222> LOCATION: (290)..(290)
<223> OTHER INFORMATION: Residue is one of I, L or V
<220> FEATURE:
<221> NAME/KEY: MISC_FEATURE
<222> LOCATION: (341)..(341)
<223> OTHER INFORMATION: Residue is one of A, G or S
<220> FEATURE:
<221> NAME/KEY: MISC_FEATURE
<222> LOCATION: (353)..(353)
<223> OTHER INFORMATION: Residue is one of D or E
<220> FEATURE:
<221> NAME/KEY: MISC_FEATURE
<222> LOCATION: (354)..(354)
<223> OTHER INFORMATION: Residue is one of F, H, W or Y
<220> FEATURE:
<221> NAME/KEY: MISC_FEATURE
<222> LOCATION: (357)..(357)
<223> OTHER INFORMATION: Residue is one of D, E, H, K or R
<220> FEATURE:
<221> NAME/KEY: MISC_FEATURE
<222> LOCATION: (437)..(437)
<223> OTHER INFORMATION: Residue is one of D, E, H, K, R
<220> FEATURE:
<221> NAME/KEY: MISC_FEATURE
<222> LOCATION: (439)..(439)
<223> OTHER INFORMATION: Residue is one of A, C, D, E, G, H, K, N, Q, R,
      S, T
<220> FEATURE:
<221> NAME/KEY: MISC_FEATURE
<222> LOCATION: (443)..(443)
<223> OTHER INFORMATION: Residue is one of A, C, D, G, N, P, S, T or V
<220> FEATURE:
<221> NAME/KEY: MISC_FEATURE
<222> LOCATION: (458)..(458)
<223> OTHER INFORMATION: Residue is one of I, L or V

<400> SEQUENCE: 3

Met Ser Tyr Ala Gln Xaa Lys Xaa Gln Xaa Lys Xaa Gly Tyr Xaa Ala
1               5                   10                  15

Gly Val Lys Asp Tyr Arg Leu Thr Tyr Tyr Thr Pro Asp Tyr Thr Pro
```

```
                20                  25                  30
Lys Asp Thr Asp Leu Leu Ala Ala Phe Arg Xaa Thr Pro Gln Pro Gly
            35                  40                  45

Val Pro Xaa Glu Glu Ala Gly Ala Ala Val Ala Ala Glu Ser Ser Thr
50                  55                  60

Gly Thr Trp Thr Thr Val Trp Thr Asp Leu Leu Thr Asp Leu Asp Arg
65                  70                  75                  80

Tyr Lys Gly Arg Cys Tyr Asp Ile Glu Pro Val Pro Gly Glu Asp Asn
                85                  90                  95

Gln Tyr Xaa Ala Phe Ile Ala Tyr Pro Leu Asp Leu Phe Glu Glu Gly
            100                 105                 110

Ser Val Thr Asn Val Leu Thr Ser Ile Val Gly Asn Val Phe Gly Phe
            115                 120                 125

Lys Ala Leu Arg Ala Leu Arg Leu Glu Asp Ile Arg Phe Pro Val Ala
            130                 135                 140

Xaa Ile Lys Thr Phe Gln Gly Pro Pro His Gly Ile Gln Val Glu Arg
145                 150                 155                 160

Asp Lys Leu Asn Lys Tyr Gly Arg Pro Leu Leu Gly Cys Thr Ile Lys
                165                 170                 175

Pro Lys Leu Gly Leu Ser Ala Lys Asn Tyr Gly Arg Ala Val Tyr Glu
            180                 185                 190

Cys Leu Arg Gly Gly Leu Asp Phe Thr Lys Asp Asp Glu Asn Ile Asn
            195                 200                 205

Ser Gln Pro Phe Gln Arg Trp Arg Asp Arg Phe Leu Phe Val Ala Glu
            210                 215                 220

Ala Ile Xaa Lys Ala Gln Ala Glu Thr Gly Glu Ile Lys Gly His Tyr
225                 230                 235                 240

Leu Asn Val Thr Ala Xaa Thr Cys Glu Glu Met Xaa Lys Arg Ala Glu
                245                 250                 255

Phe Ala Lys Glu Leu Gly Xaa Pro Ile Ile Met His Asp Phe Leu Thr
            260                 265                 270

Gly Gly Phe Thr Ala Asn Thr Thr Leu Ala Lys Trp Cys Arg Asp Asn
            275                 280                 285

Gly Xaa Leu Leu His Ile His Arg Ala Met His Ala Val Ile Asp Arg
            290                 295                 300

Gln Lys Asn His Gly Ile His Phe Arg Val Leu Ala Lys Cys Leu Arg
305                 310                 315                 320

Leu Ser Gly Gly Asp His Leu His Thr Gly Thr Val Val Gly Lys Leu
                325                 330                 335

Glu Gly Glu Arg Xaa Ile Thr Met Gly Phe Val Asp Leu Leu Arg Glu
            340                 345                 350

Xaa Xaa Val Glu Xaa Asp Arg Ser Arg Gly Ile Phe Phe Thr Gln Asp
            355                 360                 365

Trp Ala Ser Met Pro Gly Val Met Ala Val Ala Ser Gly Gly Ile His
            370                 375                 380

Val Trp His Met Pro Ala Leu Val Glu Ile Phe Gly Asp Asp Ser Val
385                 390                 395                 400

Leu Gln Phe Gly Gly Gly Thr Leu Gly His Pro Trp Gly Asn Ala Pro
                405                 410                 415

Gly Ala Thr Ala Asn Arg Val Ala Leu Glu Ala Cys Val Gln Ala Arg
            420                 425                 430

Asn Glu Gly Arg Xaa Leu Xaa Arg Glu Gly Xaa Asp Ile Ile Arg Glu
            435                 440                 445
```

```
Ala Ala Lys Trp Ser Pro Glu Leu Ala Xaa Ala Cys Glu Leu Trp Lys
    450                 455                 460

Glu Ile Lys Phe Glu Phe Glu Ala Met Asp Thr Leu
465                 470                 475

<210> SEQ ID NO 4
<211> LENGTH: 475
<212> TYPE: PRT
<213> ORGANISM: Anthoceros formosae

<400> SEQUENCE: 4

Met Ser Pro Gln Thr Glu Thr Lys Ala Gly Val Gly Phe Lys Ala Gly
1               5                   10                  15

Val Lys Asp Tyr Arg Leu Thr Tyr Tyr Thr Pro Asp Tyr Glu Thr Lys
                20                  25                  30

Asp Thr Asp Ile Leu Ala Ala Phe Arg Met Thr Pro Gln Pro Gly Val
            35                  40                  45

Pro Pro Glu Glu Ala Gly Ala Ala Val Ala Ala Glu Ser Ser Thr Gly
        50                  55                  60

Thr Trp Thr Thr Val Trp Thr Asp Gly Leu Thr Ser Leu Asp Arg Tyr
65                  70                  75                  80

Lys Gly Arg Cys Tyr Asp Ile Glu Pro Val Ala Gly Glu Glu Asn Gln
                85                  90                  95

Tyr Ile Ala Tyr Val Ala Tyr Pro Leu Asp Leu Phe Glu Glu Gly Ser
            100                 105                 110

Val Thr Asn Met Phe Thr Ser Ile Val Gly Asn Val Phe Gly Phe Lys
        115                 120                 125

Ala Leu Arg Ala Leu Arg Leu Glu Asp Leu Arg Ile Pro Pro Ala Tyr
    130                 135                 140

Ser Lys Thr Phe Gln Gly Pro Pro His Gly Ile Gln Val Glu Arg Asp
145                 150                 155                 160

Lys Leu Asn Lys Tyr Gly Arg Pro Leu Leu Gly Cys Thr Ile Lys Pro
                165                 170                 175

Lys Leu Gly Leu Ser Ala Lys Asn Tyr Gly Arg Ala Val Tyr Glu Cys
            180                 185                 190

Leu Arg Gly Gly Leu Asp Phe Thr Lys Asp Asp Glu Asn Val Asn Ser
        195                 200                 205

Gln Pro Phe Met Arg Trp Arg Asp Arg Phe Leu Phe Val Ala Glu Ala
    210                 215                 220

Ile Phe Lys Ser Gln Ala Glu Thr Gly Glu Ile Lys Gly His Tyr Leu
225                 230                 235                 240

Asn Ala Thr Ala Gly Thr Cys Glu Glu Met Met Lys Arg Ala His Phe
                245                 250                 255

Ala Arg Glu Leu Gly Met Pro Ile Val Met His Asp Tyr Leu Thr Gly
            260                 265                 270

Gly Phe Thr Ala Asn Thr Thr Leu Ala Arg Tyr Cys Arg Asp Asn Gly
        275                 280                 285

Leu Leu Leu His Ile His Arg Ala Met His Ala Val Ile Asp Arg Gln
    290                 295                 300

Arg Asn His Gly Ile His Phe Arg Val Leu Ala Lys Ala Leu Arg Met
305                 310                 315                 320

Ser Gly Gly Asp His Ile His Ser Gly Thr Val Val Gly Lys Leu Glu
                325                 330                 335

Gly Glu Arg Glu Val Thr Leu Gly Phe Val Asp Leu Leu Arg Asp Asp
```

```
                    340                 345                 350
Tyr Ile Glu Lys Asp Arg Ser Arg Gly Ile Tyr Phe Thr Gln Asp Trp
                355                 360                 365

Val Ser Met Pro Gly Val Leu Pro Val Ala Ser Gly Gly Ile His Val
            370                 375                 380

Trp His Met Ser Ala Leu Thr Glu Ile Phe Gly Asp Asp Ser Val Leu
385                 390                 395                 400

Gln Phe Gly Gly Gly Thr Leu Gly His Pro Trp Gly Asn Ala Pro Gly
                405                 410                 415

Ala Val Ala Asn Arg Val Ala Leu Glu Ala Cys Val Gln Ala Arg Asn
                420                 425                 430

Glu Gly Arg Asp Leu Ala Arg Glu Gly Asn Asp Ile Ile Arg Glu Ala
                435                 440                 445

Ser Lys Trp Ser Pro Glu Leu Ala Ala Ala Cys Glu Val Trp Lys Glu
                450                 455                 460

Ile Lys Phe Val Phe Glu Thr Ile Asp Thr Leu
465                 470                 475

<210> SEQ ID NO 5
<211> LENGTH: 475
<212> TYPE: PRT
<213> ORGANISM: Artificial
<220> FEATURE:
<223> OTHER INFORMATION: 50% consensus sequence for bryophyta (28
      species)

<400> SEQUENCE: 5

Met Ser Pro Gln Thr Glu Thr Lys Ala Gly Val Gly Phe Lys Ala Gly
1               5                   10                  15

Val Lys Asp Tyr Arg Leu Thr Tyr Tyr Thr Pro Asp Tyr Gln Thr Lys
                20                  25                  30

Glu Thr Asp Ile Leu Ala Ala Phe Arg Met Thr Pro Gln Pro Gly Val
            35                  40                  45

Pro Ala Glu Glu Ala Gly Ala Ala Val Ala Ala Glu Ser Ser Thr Gly
        50                  55                  60

Thr Trp Thr Thr Val Trp Thr Asp Gly Leu Thr Ser Leu Asp Arg Tyr
65                  70                  75                  80

Lys Gly Arg Cys Tyr Asp Ile Glu Ala Val Pro Gly Glu Glu Asn Gln
                85                  90                  95

Tyr Ile Ala Tyr Val Ala Tyr Pro Leu Asp Leu Phe Glu Glu Gly Ser
                100                 105                 110

Val Thr Asn Leu Phe Thr Ser Ile Val Gly Asn Val Phe Gly Phe Lys
            115                 120                 125

Ala Leu Arg Ala Leu Arg Leu Glu Asp Leu Arg Ile Pro Pro Ala Tyr
        130                 135                 140

Ser Lys Thr Phe Gln Gly Pro Pro His Gly Ile Gln Val Glu Arg Asp
145                 150                 155                 160

Lys Leu Asn Lys Tyr Gly Arg Pro Leu Leu Gly Cys Thr Ile Lys Pro
                165                 170                 175

Lys Leu Gly Leu Ser Ala Lys Asn Tyr Gly Arg Ala Val Tyr Glu Cys
                180                 185                 190

Leu Arg Gly Gly Leu Asp Phe Thr Lys Asp Asp Glu Asn Val Asn Ser
            195                 200                 205

Gln Pro Phe Met Arg Trp Arg Asp Arg Phe Leu Phe Val Ala Glu Ala
        210                 215                 220
```

Ile Tyr Lys Ser Gln Ala Glu Thr Gly Glu Ile Lys Gly His Tyr Leu
225                 230                 235                 240

Asn Ala Thr Ala Gly Thr Cys Glu Glu Met Leu Lys Arg Ala Gln Phe
            245                 250                 255

Ala Arg Glu Leu Gly Met Pro Ile Val Met His Asp Tyr Leu Thr Gly
            260                 265                 270

Gly Phe Thr Ala Asn Thr Ser Leu Ala His Tyr Cys Arg Asp Asn Gly
        275                 280                 285

Leu Leu Leu His Ile His Arg Ala Met His Ala Val Ile Asp Arg Gln
        290                 295                 300

Lys Asn His Gly Met His Phe Arg Val Leu Ala Lys Ala Leu Arg Leu
305                 310                 315                 320

Ser Gly Gly Asp His Ile His Ala Gly Thr Val Val Gly Lys Leu Glu
                325                 330                 335

Gly Glu Arg Gln Val Thr Leu Gly Phe Val Asp Leu Leu Arg Asp Asp
            340                 345                 350

Tyr Ile Glu Lys Asp Arg Ser Arg Gly Ile Tyr Phe Thr Gln Asp Trp
            355                 360                 365

Val Ser Leu Pro Gly Val Leu Pro Val Ala Ser Gly Gly Ile His Val
        370                 375                 380

Trp His Met Pro Ala Leu Thr Glu Ile Phe Gly Asp Asp Ser Val Leu
385                 390                 395                 400

Gln Phe Gly Gly Gly Thr Leu Gly His Pro Trp Gly Asn Ala Pro Gly
                405                 410                 415

Ala Val Ala Asn Arg Val Ala Leu Glu Ala Cys Val Gln Ala Arg Asn
            420                 425                 430

Glu Gly Arg Asp Leu Ala Arg Glu Gly Asn Glu Val Ile Arg Glu Ala
            435                 440                 445

Ala Lys Trp Ser Pro Glu Leu Ala Ala Ala Cys Glu Val Trp Lys Glu
        450                 455                 460

Ile Lys Phe Glu Phe Glu Thr Ile Asp Thr Val
465                 470                 475

<210> SEQ ID NO 6
<211> LENGTH: 475
<212> TYPE: PRT
<213> ORGANISM: Artificial
<220> FEATURE:
<223> OTHER INFORMATION: 50% consensus sequence charophyta (4 species)

<400> SEQUENCE: 6

Met Ser Pro Gln Thr Glu Thr Lys Ala Gly Ala Gly Phe Lys Ala Gly
1               5                   10                  15

Val Lys Asp Tyr Arg Leu Thr Tyr Tyr Thr Pro Asp Tyr Glu Thr Lys
            20                  25                  30

Glu Thr Asp Ile Leu Ala Ala Phe Arg Met Thr Pro Gln Ala Gly Val
        35                  40                  45

Pro Pro Glu Glu Ala Gly Ala Ala Val Ala Ala Glu Ser Ser Thr Gly
    50                  55                  60

Thr Trp Thr Thr Val Trp Thr Asp Gly Leu Thr Ser Leu Asp Arg Tyr
65                  70                  75                  80

Lys Gly Arg Cys Tyr Asp Ile Glu Pro Val Ala Gly Glu Glu Asn Gln
                85                  90                  95

Tyr Ile Ala Tyr Val Ala Tyr Pro Leu Asp Leu Phe Glu Glu Gly Ser
            100                 105                 110

```
Val Thr Asn Leu Phe Thr Ser Ile Val Gly Asn Val Phe Gly Phe Lys
            115                 120                 125

Ala Leu Arg Ala Leu Arg Leu Glu Asp Leu Arg Ile Pro Pro Ala Tyr
        130                 135                 140

Ser Lys Thr Phe Gln Gly Pro Pro His Gly Ile Gln Val Glu Arg Asp
145                 150                 155                 160

Lys Ile Asn Lys Tyr Gly Arg Pro Leu Leu Gly Cys Thr Ile Lys Pro
                165                 170                 175

Lys Leu Gly Leu Ser Ala Lys Asn Tyr Gly Arg Ala Val Tyr Glu Cys
            180                 185                 190

Leu Arg Gly Gly Leu Asp Phe Thr Lys Asp Asp Glu Asn Val Asn Ser
        195                 200                 205

Gln Pro Phe Met Arg Trp Arg Asp Arg Phe Leu Phe Val Ala Glu Ala
        210                 215                 220

Ile Phe Lys Ala Gln Ala Glu Thr Gly Glu Ile Lys Gly His Tyr Leu
225                 230                 235                 240

Asn Ala Thr Ala Gly Thr Cys Glu Glu Met Leu Lys Arg Ala Ala Tyr
                245                 250                 255

Ala Lys Glu Leu Gly Val Pro Ile Ile Met His Asp Tyr Leu Thr Gly
            260                 265                 270

Gly Phe Thr Ala Asn Thr Ser Leu Ala His Tyr Cys Arg Asp Asn Gly
        275                 280                 285

Leu Leu Leu His Ile His Arg Ala Met His Ala Val Ile Asp Arg Gln
        290                 295                 300

Lys Asn His Gly Ile His Phe Arg Val Leu Ala Lys Ala Leu Arg Met
305                 310                 315                 320

Ser Gly Gly Asp His Ile His Ser Gly Thr Val Val Gly Lys Leu Glu
                325                 330                 335

Gly Glu Arg Glu Val Thr Leu Gly Phe Val Asp Leu Leu Arg Asp Asp
            340                 345                 350

Tyr Ile Glu Lys Asp Arg Ser Arg Gly Ile Tyr Phe Thr Gln Asp Trp
        355                 360                 365

Val Ser Met Pro Gly Val Leu Pro Val Ala Ser Gly Gly Ile His Val
        370                 375                 380

Trp His Met Pro Ala Leu Thr Glu Ile Phe Gly Asp Asp Ser Val Leu
385                 390                 395                 400

Gln Phe Gly Gly Gly Thr Leu Gly His Pro Trp Gly Asn Ala Pro Gly
                405                 410                 415

Ala Val Ala Asn Arg Val Ala Leu Glu Ala Cys Val Gln Ala Arg Asn
            420                 425                 430

Glu Gly Arg Asp Leu Ala Arg Glu Gly Asn Asp Val Ile Arg Glu Ala
        435                 440                 445

Cys Lys Trp Ser Pro Glu Leu Ala Ala Ala Cys Glu Val Trp Lys Glu
        450                 455                 460

Ile Lys Phe Glu Phe Asp Thr Ile Asp Thr Leu
465                 470                 475

<210> SEQ ID NO 7
<211> LENGTH: 475
<212> TYPE: PRT
<213> ORGANISM: Artificial
<220> FEATURE:
<223> OTHER INFORMATION: 50% consensus sequence for chlorophyta (4
      species)
<220> FEATURE:
<221> NAME/KEY: MISC_FEATURE
```

<222> LOCATION: (282)..(282)
<223> OTHER INFORMATION: Residue is one of A, C, D, G, N, P, S, T or V

<400> SEQUENCE: 7

Met Val Pro Gln Thr Glu Thr Lys Ala Gly Ala Gly Phe Lys Ala Gly
1               5                   10                  15

Val Lys Asp Tyr Arg Leu Thr Tyr Thr Pro Asp Tyr Val Val Lys
            20                  25                  30

Asp Thr Asp Ile Leu Ala Ala Phe Arg Met Thr Pro Gln Pro Gly Val
            35                  40                  45

Pro Pro Glu Glu Cys Gly Ala Ala Val Ala Ala Glu Ser Ser Thr Gly
        50                  55                  60

Thr Trp Thr Thr Val Trp Thr Asp Gly Leu Thr Ser Leu Asp Arg Tyr
65                  70                  75                  80

Lys Gly Arg Cys Tyr Asp Ile Glu Pro Val Pro Gly Glu Asp Asn Gln
                85                  90                  95

Tyr Ile Ala Tyr Val Ala Tyr Pro Ile Asp Leu Phe Glu Glu Gly Ser
            100                 105                 110

Val Thr Asn Leu Phe Thr Ser Ile Val Gly Asn Val Phe Gly Phe Lys
        115                 120                 125

Ala Leu Arg Ala Leu Arg Leu Glu Asp Leu Arg Ile Pro Pro Ala Tyr
    130                 135                 140

Val Lys Thr Phe Gln Gly Pro Pro His Gly Ile Gln Val Glu Arg Asp
145                 150                 155                 160

Lys Leu Asn Lys Tyr Gly Arg Gly Leu Leu Gly Cys Thr Ile Lys Pro
                165                 170                 175

Lys Leu Gly Leu Ser Ala Lys Asn Tyr Gly Arg Ala Val Tyr Glu Cys
            180                 185                 190

Leu Arg Gly Gly Leu Asp Phe Thr Lys Asp Asp Glu Asn Val Asn Ser
        195                 200                 205

Gln Pro Phe Met Arg Trp Arg Asp Arg Phe Leu Phe Val Ala Glu Ala
    210                 215                 220

Ile Tyr Lys Ala Gln Ala Glu Thr Gly Glu Val Lys Gly His Tyr Leu
225                 230                 235                 240

Asn Ala Thr Ala Ala Thr Cys Glu Glu Met Leu Lys Arg Ala Val Cys
                245                 250                 255

Ala Lys Glu Leu Gly Val Pro Ile Ile Met His Asp Tyr Leu Thr Gly
            260                 265                 270

Gly Phe Thr Ala Asn Thr Ser Leu Ala Xaa Tyr Cys Arg Asp Asn Gly
        275                 280                 285

Leu Leu Leu His Ile His Arg Ala Met His Ala Val Ile Asp Arg Gln
    290                 295                 300

Arg Asn His Gly Ile His Phe Arg Val Leu Ala Lys Ala Leu Arg Leu
305                 310                 315                 320

Ser Gly Gly Asp His Leu His Ser Gly Thr Val Val Gly Lys Leu Glu
                325                 330                 335

Gly Glu Arg Glu Val Thr Leu Gly Phe Val Asp Leu Met Arg Asp Asp
            340                 345                 350

Tyr Ile Glu Lys Asp Arg Ser Arg Gly Ile Tyr Phe Thr Gln Asp Trp
        355                 360                 365

Cys Ser Met Pro Gly Val Met Pro Val Ala Ser Gly Gly Ile His Val
    370                 375                 380

Trp His Met Pro Ala Leu Val Glu Ile Phe Gly Asp Asp Ala Cys Leu
385                 390                 395                 400

```
Gln Phe Gly Gly Gly Thr Leu Gly His Pro Trp Asn Ala Pro Gly
            405                 410                 415

Ala Ala Ala Asn Arg Val Ala Leu Glu Ala Cys Thr Gln Ala Arg Asn
        420                 425                 430

Glu Gly Arg Asp Leu Ala Arg Glu Gly Gly Asp Val Ile Arg Ser Ala
        435                 440                 445

Cys Lys Trp Ser Pro Glu Leu Ala Ala Ala Cys Glu Val Trp Lys Glu
450                 455                 460

Ile Lys Phe Glu Phe Asp Thr Ile Asp Lys Leu
465                 470                 475

<210> SEQ ID NO 8
<211> LENGTH: 475
<212> TYPE: PRT
<213> ORGANISM: Pinus thunbergii

<400> SEQUENCE: 8

Met Ser Pro Lys Thr Glu Thr Lys Ala Ser Val Gly Phe Lys Ala Gly
1               5                   10                  15

Val Lys Asp Tyr Arg Leu Thr Tyr Tyr Thr Pro Glu Tyr Gln Thr Lys
            20                  25                  30

Asp Thr Asp Ile Leu Ala Ala Phe Arg Val Thr Pro Gln Pro Gly Val
        35                  40                  45

Pro Pro Glu Glu Ala Gly Ala Ala Val Ala Ala Glu Ser Ser Thr Gly
    50                  55                  60

Thr Trp Thr Thr Val Trp Thr Asp Gly Leu Thr Ser Leu Asp Arg Tyr
65                  70                  75                  80

Lys Gly Arg Cys Tyr Asp Ile Glu Pro Val Pro Gly Glu Glu Thr Gln
                85                  90                  95

Phe Ile Ala Tyr Val Ala Tyr Pro Leu Asp Leu Phe Glu Glu Gly Ser
            100                 105                 110

Val Thr Asn Leu Phe Thr Ser Ile Val Gly Asn Val Phe Gly Phe Lys
        115                 120                 125

Ala Leu Arg Ala Leu Arg Leu Glu Asp Leu Arg Ile Pro Pro Ser Tyr
    130                 135                 140

Ser Lys Thr Phe Gln Gly Pro Pro His Gly Ile Gln Val Glu Arg Asp
145                 150                 155                 160

Lys Leu Asn Lys Tyr Gly Arg Pro Leu Leu Gly Cys Thr Ile Lys Pro
                165                 170                 175

Lys Leu Gly Leu Ser Ala Lys Asn Tyr Gly Arg Ala Val Tyr Glu Cys
            180                 185                 190

Leu Arg Gly Gly Leu Asp Phe Thr Lys Asp Asp Glu Asn Val Asn Ser
        195                 200                 205

Gln Pro Phe Met Arg Trp Arg Asp Arg Phe Val Phe Cys Ala Glu Ala
    210                 215                 220

Leu Asn Lys Ala Gln Ala Glu Thr Gly Glu Ile Lys Gly His Tyr Leu
225                 230                 235                 240

Asn Ala Thr Ala Gly Thr Cys Glu Glu Met Met Lys Arg Ala Ile Phe
                245                 250                 255

Ala Arg Glu Leu Gly Val Pro Ile Val Met His Asp Tyr Leu Thr Gly
            260                 265                 270

Gly Phe Thr Ala Asn Thr Ser Leu Ala His Tyr Cys Arg Asp Asn Gly
        275                 280                 285

Leu Leu Leu His Ile His Arg Ala Met His Ala Val Ile Asp Arg Gln
```

```
                290                 295                 300

Arg Asn His Gly Met His Phe Arg Val Leu Ala Lys Ala Leu Arg Met
305                 310                 315                 320

Ser Gly Gly Asp His Ile His Ala Gly Thr Val Val Gly Lys Leu Glu
                325                 330                 335

Gly Glu Arg Asp Val Thr Leu Gly Phe Val Asp Leu Leu Arg Asp Asp
                340                 345                 350

Phe Ile Glu Lys Asp Arg Ser Arg Gly Ile Tyr Phe Thr Gln Asp Trp
                355                 360                 365

Val Ser Met Pro Gly Val Leu Pro Val Ala Ser Gly Gly Ile His Val
                370                 375                 380

Trp His Met Pro Ala Leu Thr Glu Ile Phe Gly Asp Asp Ser Val Leu
385                 390                 395                 400

Gln Phe Gly Gly Gly Thr Leu Gly His Pro Trp Gly Asn Ala Pro Gly
                405                 410                 415

Ala Val Ala Asn Arg Val Ala Leu Glu Ala Cys Val Gln Ala Arg Asn
                420                 425                 430

Glu Gly Arg Asp Leu Ala Arg Glu Gly Asn Glu Val Ile Arg Glu Ala
                435                 440                 445

Cys Lys Trp Ser Pro Glu Leu Ala Ala Ala Cys Glu Ile Trp Lys Glu
                450                 455                 460

Ile Lys Phe Glu Phe Asp Val Ile Asp Arg Leu
465                 470                 475

<210> SEQ ID NO 9
<211> LENGTH: 475
<212> TYPE: PRT
<213> ORGANISM: Equisetum arvense

<400> SEQUENCE: 9

Met Ser Pro Gln Thr Glu Thr Lys Ala Gly Val Gly Phe Lys Ala Gly
1               5                   10                  15

Val Lys Asp Tyr Arg Leu Thr Tyr Phe Thr Pro Asp Tyr Glu Thr Lys
                20                  25                  30

Asp Thr Asp Ile Leu Ala Ala Phe Arg Met Thr Pro Gln Pro Gly Val
                35                  40                  45

Pro Pro Glu Glu Ala Gly Ala Ala Val Ala Ala Glu Ser Ser Thr Gly
                50                  55                  60

Thr Trp Thr Thr Val Trp Thr Asp Gly Leu Thr Ser Leu Asp Arg Tyr
65                  70                  75                  80

Lys Gly Arg Cys Tyr Asn Ile Glu Pro Val Ala Gly Glu Asp Asn Gln
                85                  90                  95

Phe Ile Ala Tyr Val Ala Tyr Pro Leu Asp Leu Phe Glu Glu Gly Ser
                100                 105                 110

Val Thr Asn Leu Phe Thr Ser Ile Val Gly Asn Val Phe Gly Phe Lys
                115                 120                 125

Ala Leu Arg Ala Leu Arg Leu Glu Asp Leu Arg Ile Pro Pro Ala Tyr
                130                 135                 140

Ser Lys Thr Phe Ile Gly Pro Pro His Gly Ile Gln Val Glu Arg Asp
145                 150                 155                 160

Lys Leu Asn Lys Tyr Gly Arg Pro Leu Leu Gly Cys Thr Ile Lys Pro
                165                 170                 175

Lys Leu Gly Leu Ser Ala Lys Asn Tyr Gly Arg Ala Val Tyr Glu Cys
                180                 185                 190
```

```
Leu Arg Gly Gly Leu Asp Phe Thr Lys Asp Asp Glu Asn Val Asn Ser
            195                 200                 205
Gln Pro Phe Met Arg Trp Arg Asp Arg Phe Leu Phe Val Ala Glu Ala
        210                 215                 220
Leu Phe Lys Ser Gln Ala Glu Thr Gly Glu Ile Lys Gly His Tyr Leu
225                 230                 235                 240
Asn Ala Thr Ala Gly Thr Cys Glu Glu Met Leu Lys Arg Ala Val Phe
                245                 250                 255
Ala Arg Glu Leu Gly Ala Pro Ile Val Met His Asp Tyr Leu Thr Gly
            260                 265                 270
Gly Phe Thr Ala Asn Thr Ser Leu Ala Phe Tyr Cys Arg Asp Asn Gly
        275                 280                 285
Leu Leu Leu His Ile His Arg Ala Met His Ala Val Ile Asp Arg Gln
290                 295                 300
Lys Asn His Gly Ile His Phe Arg Val Leu Ala Lys Ala Leu Arg Met
305                 310                 315                 320
Ser Gly Gly Asp His Ile His Thr Gly Thr Val Val Gly Lys Leu Glu
                325                 330                 335
Gly Glu Arg Asp Leu Thr Leu Gly Phe Val Asp Leu Leu Arg Asp Asp
            340                 345                 350
Phe Ile Glu Lys Asp Arg Ser Arg Gly Ile Tyr Phe Thr Gln Asp Trp
        355                 360                 365
Val Ser Met Pro Gly Val Leu Pro Val Ala Ser Gly Gly Ile His Val
370                 375                 380
Trp His Met Pro Ala Leu Thr Glu Ile Phe Gly Asp Asp Ser Val Leu
385                 390                 395                 400
Gln Phe Gly Gly Gly Thr Leu Gly His Pro Trp Gly Asn Ala Pro Gly
                405                 410                 415
Ala Val Ala Asn Arg Val Ala Val Glu Ala Cys Val Gln Ala Arg Asn
            420                 425                 430
Glu Gly Arg Asp Leu Ala Thr Glu Gly Asn Asp Ile Ile Arg Glu Ala
        435                 440                 445
Ala Lys Trp Ser Pro Glu Leu Ala Ala Ala Cys Glu Val Trp Lys Glu
450                 455                 460
Ile Lys Phe Glu Tyr Glu Ala Met Asp Thr Leu
465                 470                 475

<210> SEQ ID NO 10
<211> LENGTH: 475
<212> TYPE: PRT
<213> ORGANISM: Welwitschia mirabilis

<400> SEQUENCE: 10

Met Ser Pro Lys Thr Glu Thr Lys Ala Ser Val Gly Phe Gln Ala Gly
1               5                   10                  15
Val Lys Asp Tyr Arg Leu Thr Tyr Tyr Thr Pro Glu Tyr Gln Thr Lys
            20                  25                  30
Asp Thr Asp Ile Leu Ala Ala Phe Arg Val Thr Pro Gln Pro Gly Val
        35                  40                  45
Pro Pro Glu Glu Ala Gly Ala Ala Val Ala Ala Glu Ser Ser Thr Gly
    50                  55                  60
Thr Trp Thr Thr Val Trp Thr Asp Gly Leu Thr Ser Leu Asp Arg Tyr
65                  70                  75                  80
Lys Gly Arg Cys Tyr Asp Leu Glu Pro Val Pro Gly Glu Asp Asn Gln
                85                  90                  95
```

Tyr Ile Ala Tyr Val Ala Tyr Pro Leu Asp Leu Phe Glu Glu Gly Ser
            100                 105                 110

Val Thr Asn Met Phe Thr Ser Ile Val Gly Asn Val Phe Gly Phe Lys
            115                 120                 125

Ala Leu Arg Ala Leu Arg Leu Glu Asp Leu Arg Ile Pro Thr Ser Tyr
    130                 135                 140

Ile Lys Thr Phe Gln Gly Pro Pro His Gly Ile Gln Val Glu Arg Asp
145                 150                 155                 160

Lys Leu Asn Lys Tyr Gly Arg Pro Leu Leu Gly Cys Thr Ile Lys Pro
                165                 170                 175

Lys Leu Gly Leu Ser Ala Lys Asn Tyr Gly Arg Ala Val Tyr Glu Cys
            180                 185                 190

Leu Arg Gly Gly Leu Asp Phe Thr Lys Asp Asp Glu Asn Val Asn Ser
            195                 200                 205

Gln Pro Phe Met Arg Trp Arg Asp Arg Phe Val Phe Cys Ala Glu Ala
    210                 215                 220

Ile Tyr Lys Ala Gln Ala Glu Thr Gly Glu Ile Lys Gly His Tyr Leu
225                 230                 235                 240

Asn Ala Thr Ala Gly Thr Cys Glu Glu Met Ile Lys Arg Ala Val Phe
                245                 250                 255

Ala Arg Glu Leu Gly Val Pro Ile Val Met His Asp Tyr Leu Thr Gly
            260                 265                 270

Gly Phe Thr Ala Asn Thr Thr Leu Ala His Tyr Cys Arg Asp Asn Gly
            275                 280                 285

Leu Leu Leu His Ile His Arg Ala Met His Ala Val Ile Asp Arg Gln
    290                 295                 300

Lys Asn His Gly Met His Phe Arg Val Leu Ala Lys Ala Leu Arg Met
305                 310                 315                 320

Ser Gly Gly Asp His Ile His Ala Gly Thr Val Val Gly Lys Leu Glu
                325                 330                 335

Gly Glu Arg Glu Ile Thr Leu Gly Phe Val Asp Leu Leu Arg Asp Asp
            340                 345                 350

Phe Ile Glu Lys Asp Arg Ser Arg Gly Ile Tyr Phe Thr Gln Asp Trp
    355                 360                 365

Val Ser Met Pro Gly Val Met Pro Val Ala Ser Gly Gly Ile His Val
370                 375                 380

Trp His Met Pro Ala Leu Thr Asp Ile Phe Gly Asp Asp Ala Val Leu
385                 390                 395                 400

Gln Phe Gly Gly Gly Thr Leu Gly His Pro Trp Gly Asn Ala Pro Gly
                405                 410                 415

Ala Val Ala Asn Arg Val Ala Leu Glu Ala Cys Val Gln Ala Arg Asn
            420                 425                 430

Glu Gly Arg Asp Leu Ala Arg Glu Gly Asn Glu Val Ile Arg Glu Ala
            435                 440                 445

Ala Lys Trp Ser Pro Glu Leu Ala Ala Ala Cys Glu Val Trp Lys Glu
    450                 455                 460

Ile Lys Phe Glu Phe Glu Ser Val Asp Thr Leu
465                 470                 475

<210> SEQ ID NO 11
<211> LENGTH: 475
<212> TYPE: PRT
<213> ORGANISM: Artificial
<220> FEATURE:

```
<223> OTHER INFORMATION: 50% consensus sequence for magnoliophyta (134
      species)
<220> FEATURE:
<221> NAME/KEY: MISC_FEATURE
<222> LOCATION: (142)..(142)
<223> OTHER INFORMATION: Residue is one of A, C, D, G, N, P, S, T or V
<220> FEATURE:
<221> NAME/KEY: MISC_FEATURE
<222> LOCATION: (251)..(251)
<223> OTHER INFORMATION: Residue is one of I, L or V

<400> SEQUENCE: 11

Met Ser Pro Gln Thr Glu Thr Lys Ala Ser Val Gly Phe Lys Ala Gly
1               5                   10                  15

Val Lys Asp Tyr Lys Leu Thr Tyr Tyr Thr Pro Asp Tyr Glu Thr Lys
            20                  25                  30

Asp Thr Asp Ile Leu Ala Ala Phe Arg Val Thr Pro Gln Pro Gly Val
        35                  40                  45

Pro Pro Glu Glu Ala Gly Ala Ala Val Ala Ala Glu Ser Ser Thr Gly
    50                  55                  60

Thr Trp Thr Thr Val Trp Thr Asp Gly Leu Thr Ser Leu Asp Arg Tyr
65                  70                  75                  80

Lys Gly Arg Cys Tyr His Ile Glu Pro Val Ala Gly Glu Glu Asn Gln
                85                  90                  95

Phe Ile Ala Tyr Val Ala Tyr Pro Leu Asp Leu Phe Glu Glu Gly Ser
            100                 105                 110

Val Thr Asn Met Phe Thr Ser Ile Val Gly Asn Val Phe Gly Phe Lys
        115                 120                 125

Ala Leu Arg Ala Leu Arg Leu Glu Asp Leu Arg Ile Pro Xaa Ala Tyr
    130                 135                 140

Val Lys Thr Phe Gln Gly Pro Pro His Gly Ile Gln Val Glu Arg Asp
145                 150                 155                 160

Lys Leu Asn Lys Tyr Gly Arg Pro Leu Leu Gly Cys Thr Ile Lys Pro
                165                 170                 175

Lys Leu Gly Leu Ser Ala Lys Asn Tyr Gly Arg Ala Val Tyr Glu Cys
            180                 185                 190

Leu Arg Gly Gly Leu Asp Phe Thr Lys Asp Asp Glu Asn Val Asn Ser
        195                 200                 205

Gln Pro Phe Met Arg Trp Arg Asp Arg Phe Leu Phe Cys Ala Glu Ala
    210                 215                 220

Ile Tyr Lys Ala Gln Ala Glu Thr Gly Glu Ile Lys Gly His Tyr Leu
225                 230                 235                 240

Asn Ala Thr Ala Gly Thr Cys Glu Glu Met Xaa Lys Arg Ala Val Phe
                245                 250                 255

Ala Arg Glu Leu Gly Val Pro Ile Val Met His Asp Tyr Leu Thr Gly
            260                 265                 270

Gly Phe Thr Ala Asn Thr Ser Leu Ala His Tyr Cys Arg Asp Asn Gly
        275                 280                 285

Leu Leu Leu His Ile His Arg Ala Met His Ala Val Ile Asp Arg Gln
    290                 295                 300

Lys Asn His Gly Met His Phe Arg Val Leu Ala Lys Ala Leu Arg Met
305                 310                 315                 320

Ser Gly Gly Asp His Ile His Ala Gly Thr Val Val Gly Lys Leu Glu
                325                 330                 335

Gly Glu Arg Glu Ile Thr Leu Gly Phe Val Asp Leu Leu Arg Asp Asp
            340                 345                 350
```

```
Phe Ile Glu Lys Asp Arg Ser Arg Gly Ile Tyr Phe Thr Gln Asp Trp
            355                 360                 365

Val Ser Leu Pro Gly Val Leu Pro Val Ala Ser Gly Gly Ile His Val
370                 375                 380

Trp His Met Pro Ala Leu Thr Glu Ile Phe Gly Asp Asp Ser Val Leu
385                 390                 395                 400

Gln Phe Gly Gly Gly Thr Leu Gly His Pro Trp Gly Asn Ala Pro Gly
                405                 410                 415

Ala Val Ala Asn Arg Val Ala Leu Glu Ala Cys Val Gln Ala Arg Asn
            420                 425                 430

Glu Gly Arg Asp Leu Ala Arg Glu Gly Asn Glu Ile Ile Arg Glu Ala
        435                 440                 445

Ser Lys Trp Ser Pro Glu Leu Ala Ala Ala Cys Glu Val Trp Lys Glu
450                 455                 460

Ile Lys Phe Glu Phe Glu Ala Met Asp Thr Leu
465                 470                 475

<210> SEQ ID NO 12
<211> LENGTH: 475
<212> TYPE: PRT
<213> ORGANISM: Artificial
<220> FEATURE:
<223> OTHER INFORMATION: 50% consensus sequence for pinophyta (2
      species)

<400> SEQUENCE: 12

Met Ser Pro Lys Thr Glu Thr Lys Ala Ser Val Gly Phe Lys Ala Gly
1               5                   10                  15

Val Lys Asp Tyr Arg Leu Thr Tyr Tyr Thr Pro Glu Tyr Gln Thr Lys
            20                  25                  30

Asp Thr Asp Ile Leu Ala Ala Phe Arg Val Thr Pro Gln Pro Gly Val
        35                  40                  45

Pro Ala Glu Glu Ala Gly Ala Ala Val Ala Ala Glu Ser Ser Thr Gly
    50                  55                  60

Thr Trp Thr Thr Val Trp Thr Asp Gly Leu Thr Ser Leu Asp Arg Tyr
65                  70                  75                  80

Lys Gly Arg Cys Tyr Asp Ile Glu Pro Val Pro Gly Glu Glu Asn Gln
                85                  90                  95

Phe Ile Ala Tyr Val Ala Tyr Pro Leu Asp Leu Phe Glu Glu Gly Ser
            100                 105                 110

Val Thr Asn Leu Phe Thr Ser Ile Val Gly Asn Val Phe Gly Phe Lys
        115                 120                 125

Ala Leu Arg Ala Leu Arg Leu Glu Asp Leu Arg Ile Pro Pro Ala Tyr
    130                 135                 140

Ser Lys Thr Phe Gln Gly Pro Pro His Gly Ile Gln Val Glu Arg Asp
145                 150                 155                 160

Lys Leu Asn Lys Tyr Gly Arg Pro Leu Leu Gly Cys Thr Ile Lys Pro
                165                 170                 175

Lys Leu Gly Leu Ser Ala Lys Asn Tyr Gly Arg Ala Val Tyr Glu Cys
            180                 185                 190

Leu Arg Gly Gly Leu Asp Phe Thr Lys Asp Asp Glu Asn Val Asn Ser
        195                 200                 205

Gln Pro Phe Met Arg Trp Arg Asp Arg Phe Val Phe Cys Ala Glu Ala
    210                 215                 220

Ile Asn Lys Ala Gln Ala Glu Thr Gly Glu Ile Lys Gly His Tyr Leu
225                 230                 235                 240
```

```
Asn Ala Thr Ala Gly Thr Cys Glu Glu Met Met Lys Arg Ala Ile Phe
                245                 250                 255

Ala Arg Glu Leu Gly Val Pro Ile Val Met His Asp Tyr Leu Thr Gly
            260                 265                 270

Gly Phe Thr Ala Asn Thr Ser Leu Ala His Tyr Cys Arg Asp Asn Gly
            275                 280                 285

Leu Leu Leu His Ile His Arg Ala Met His Ala Val Ile Asp Arg Gln
            290                 295                 300

Lys Asn His Gly Met His Phe Arg Val Leu Ala Lys Ala Leu Arg Met
305                 310                 315                 320

Ser Gly Gly Asp His Ile His Ala Gly Thr Val Val Gly Lys Leu Glu
                325                 330                 335

Gly Glu Arg Asp Val Thr Leu Gly Phe Val Asp Leu Leu Arg Asp Asp
            340                 345                 350

Phe Ile Glu Lys Asp Arg Ser Arg Gly Ile Tyr Phe Thr Gln Asp Trp
            355                 360                 365

Val Ser Met Pro Gly Val Leu Pro Val Ala Ser Gly Gly Ile His Val
            370                 375                 380

Trp His Met Pro Ala Leu Thr Glu Ile Phe Gly Asp Asp Ser Val Leu
385                 390                 395                 400

Gln Phe Gly Gly Gly Thr Leu Gly His Pro Trp Gly Asn Ala Pro Gly
                405                 410                 415

Ala Val Ala Asn Arg Val Ala Leu Glu Ala Cys Val Gln Ala Arg Asn
            420                 425                 430

Glu Gly Arg Asp Leu Ala Arg Glu Gly Asn Glu Val Ile Arg Glu Ala
            435                 440                 445

Cys Lys Trp Ser Pro Glu Leu Ala Ala Ala Cys Glu Ile Trp Lys Glu
            450                 455                 460

Ile Lys Phe Glu Phe Asp Ala Ile Asp Arg Leu
465                 470                 475

<210> SEQ ID NO 13
<211> LENGTH: 475
<212> TYPE: PRT
<213> ORGANISM: Artificial
<220> FEATURE:
<223> OTHER INFORMATION: 50% consensus sequence for pteridophyta (2
      species)

<400> SEQUENCE: 13

Met Ser Pro Gln Thr Glu Thr Lys Thr Gly Ile Gly Phe Lys Ala Gly
1               5                   10                  15

Val Lys Asp Tyr Arg Leu Thr Tyr Tyr Thr Pro Asp Tyr Glu Thr Lys
            20                  25                  30

Asp Thr Asp Ile Leu Ala Ala Phe Arg Met Thr Pro Gln Pro Gly Val
        35                  40                  45

Pro Ala Glu Glu Ala Gly Ala Ala Val Ala Ala Glu Ser Ser Thr Gly
    50                  55                  60

Thr Trp Thr Thr Val Trp Thr Asp Gly Leu Thr Ser Leu Asp Arg Tyr
65                  70                  75                  80

Lys Gly Arg Cys Tyr Asp Ile Glu Pro Val Ala Gly Glu Glu Asn Gln
                85                  90                  95

Tyr Ile Ala Tyr Val Ala Tyr Pro Leu Asp Leu Phe Glu Glu Gly Ser
            100                 105                 110

Val Thr Asn Met Leu Thr Ser Ile Val Gly Asn Val Phe Gly Phe Lys
```

```
                       115                 120                 125
Ala Leu Arg Ala Leu Arg Leu Glu Asp Leu Arg Ile Leu Pro Ala Tyr
        130                 135                 140

Ser Lys Thr Phe Ile Gly Pro Pro His Gly Ile Gln Val Glu Arg Asp
145                 150                 155                 160

Lys Leu Asn Lys Tyr Gly Arg Pro Leu Leu Gly Cys Thr Ile Lys Pro
                165                 170                 175

Lys Leu Gly Leu Cys Ala Lys Asn Tyr Gly Arg Ala Val Tyr Glu Cys
            180                 185                 190

Leu Arg Gly Gly Leu Asp Phe Thr Lys Asp Asp Glu Asn Val Asn Ser
        195                 200                 205

Gln Pro Phe Met Arg Trp Arg Asp Arg Phe Leu Phe Val Ala Glu Ala
    210                 215                 220

Leu Phe Lys Ala Gln Ala Glu Thr Gly Glu Ile Lys Gly His Tyr Leu
225                 230                 235                 240

Asn Ala Thr Ala Ala Thr Cys Glu Glu Met Ile Lys Arg Ala Ile Phe
                245                 250                 255

Ala Arg Glu Leu Gly Ala Pro Ile Val Met His Asp Tyr Leu Thr Gly
            260                 265                 270

Gly Phe Thr Ala Asn Thr Ser Leu Ala Phe Tyr Cys Arg Asp Asn Gly
        275                 280                 285

Leu Leu Leu His Ile His Arg Ala Met His Ala Val Ile Asp Arg Gln
    290                 295                 300

Lys Asn His Gly Met His Phe Arg Val Leu Ala Lys Ala Leu Arg Met
305                 310                 315                 320

Ser Gly Gly Asp His Ile His Ala Gly Thr Val Val Gly Lys Leu Glu
                325                 330                 335

Gly Glu Arg Glu Val Thr Leu Gly Phe Val Asp Leu Leu Arg Asp Asp
            340                 345                 350

Tyr Ile Glu Lys Asp Arg Ser Arg Gly Ile Tyr Phe Thr Gln Asp Trp
        355                 360                 365

Val Ser Met Pro Gly Val Phe Pro Val Ala Ser Gly Gly Ile His Val
    370                 375                 380

Trp His Met Pro Ala Leu Thr Glu Ile Phe Gly Asp Asp Ser Val Leu
385                 390                 395                 400

Gln Phe Gly Gly Gly Thr Leu Gly His Pro Trp Gly Asn Ala Pro Gly
                405                 410                 415

Ala Val Ala Asn Arg Val Ala Leu Glu Ala Cys Val Gln Ala Arg Asn
            420                 425                 430

Glu Gly Arg Asp Leu Ala Arg Glu Gly Asn Glu Ile Ile Arg Glu Ala
        435                 440                 445

Ser Lys Trp Ser Pro Glu Leu Ala Ala Ala Cys Glu Val Trp Lys Glu
    450                 455                 460

Ile Lys Phe Glu Phe Glu Thr Ile Asp Thr Val
465                 470                 475

<210> SEQ ID NO 14
<211> LENGTH: 493
<212> TYPE: PRT
<213> ORGANISM: Galdieria partita

<400> SEQUENCE: 14

Met Ser Gln Ser Ile Glu Glu Lys Ser Val Gln Glu Arg Thr Arg Ile
1               5                   10                  15
```

-continued

Lys Asn Ser Arg Tyr Glu Ser Gly Val Ile Pro Tyr Ala Lys Met Gly
            20                  25                  30

Tyr Trp Asn Pro Asp Tyr Gln Val Lys Asp Thr Asp Val Leu Ala Leu
        35                  40                  45

Phe Arg Val Thr Pro Gln Pro Gly Val Asp Pro Ile Glu Ala Ala Ala
    50                  55                  60

Ala Val Ala Gly Glu Ser Ser Thr Ala Thr Trp Thr Val Val Trp Thr
65                  70                  75                  80

Asp Leu Leu Thr Ala Ala Asp Leu Tyr Arg Ala Lys Ala Tyr Lys Val
                85                  90                  95

Asp Gln Val Pro Asn Asn Pro Glu Gln Tyr Phe Ala Tyr Ile Ala Tyr
            100                 105                 110

Glu Leu Asp Leu Phe Glu Gly Ser Ile Ala Asn Leu Thr Ala Ser
        115                 120                 125

Ile Ile Gly Asn Val Phe Gly Phe Lys Ala Val Lys Ala Leu Arg Leu
    130                 135                 140

Glu Asp Met Arg Leu Pro Leu Ala Tyr Leu Lys Thr Phe Gln Gly Pro
145                 150                 155                 160

Ala Thr Gly Val Ile Leu Glu Arg Glu Arg Leu Asp Lys Phe Gly Arg
                165                 170                 175

Pro Leu Leu Gly Cys Thr Thr Lys Pro Lys Leu Gly Leu Ser Gly Lys
            180                 185                 190

Asn Tyr Gly Arg Val Val Tyr Glu Ala Leu Lys Gly Leu Asp Phe
        195                 200                 205

Val Lys Asp Asp Glu Asn Ile Asn Ser Gln Pro Phe Met Arg Trp Arg
210                 215                 220

Glu Arg Tyr Leu Phe Thr Met Glu Ala Val Asn Lys Ala Ser Ala Ala
225                 230                 235                 240

Thr Gly Glu Val Lys Gly His Tyr Leu Asn Val Thr Ala Ala Thr Met
                245                 250                 255

Glu Glu Met Tyr Ala Arg Ala Asn Phe Ala Lys Glu Leu Gly Ser Val
            260                 265                 270

Ile Ile Met Ile Asp Leu Val Ile Gly Tyr Thr Ala Ile Gln Thr Met
        275                 280                 285

Ala Lys Trp Ala Arg Asp Asn Asp Met Ile Leu His Leu His Arg Ala
    290                 295                 300

Gly Asn Ser Thr Tyr Ser Arg Gln Lys Asn His Gly Met Asn Phe Arg
305                 310                 315                 320

Val Ile Cys Lys Trp Met Arg Met Ala Gly Val Asp His Ile His Ala
                325                 330                 335

Gly Thr Val Val Gly Lys Leu Glu Gly Asp Pro Ile Ile Thr Arg Gly
            340                 345                 350

Phe Tyr Lys Thr Leu Leu Leu Pro Lys Leu Glu Arg Asn Leu Gln Glu
        355                 360                 365

Gly Leu Phe Phe Asp Met Glu Trp Ala Ser Leu Arg Lys Val Met Pro
    370                 375                 380

Val Ala Ser Gly Gly Ile His Ala Gly Gln Met His Gln Leu Ile His
385                 390                 395                 400

Tyr Leu Gly Glu Asp Val Val Leu Gln Phe Gly Gly Gly Thr Ile Gly
                405                 410                 415

His Pro Asp Gly Ile Gln Ala Gly Ala Thr Ala Asn Arg Val Ala Leu
            420                 425                 430

Glu Ala Met Ile Leu Ala Arg Asn Glu Asn Arg Asp Tyr Leu Thr Glu

```
                435                 440                 445
Gly Pro Glu Ile Leu Arg Glu Ala Ala Lys Thr Cys Gly Ala Leu Arg
    450                 455                 460

Thr Ala Leu Asp Leu Trp Lys Asp Ile Thr Phe Asn Tyr Thr Ser Thr
465                 470                 475                 480

Asp Thr Ser Asp Phe Val Glu Pro Thr Ala Asn Ile
                485                 490

<210> SEQ ID NO 15
<211> LENGTH: 488
<212> TYPE: PRT
<213> ORGANISM: Griffithsia monolis

<400> SEQUENCE: 15

Met Ser Asn Ser Val Glu Glu Arg Thr Arg Ile Lys Asn Glu Arg Tyr
1               5                   10                  15

Glu Ser Gly Val Ile Pro Tyr Ala Lys Met Gly Tyr Trp Asp Pro Asn
                20                  25                  30

Tyr Ala Val Lys Asp Thr Asp Ile Leu Ala Leu Phe Arg Val Ser Pro
            35                  40                  45

Gln Pro Gly Val Asp Pro Val Glu Ala Ser Ala Ala Val Ala Gly Glu
    50                  55                  60

Ser Ser Thr Ala Thr Trp Thr Val Val Trp Thr Asp Leu Leu Thr Ala
65                  70                  75                  80

Cys Asp Leu Tyr Arg Ala Lys Ala Tyr Lys Val Glu Ser Val Pro Asn
                85                  90                  95

Thr Ser Asp Gln Tyr Phe Ala Tyr Ile Ser Tyr Asp Ile Asp Leu Phe
            100                 105                 110

Glu Glu Gly Ser Ile Ala Asn Leu Thr Ala Ser Ile Ile Gly Asn Val
    115                 120                 125

Phe Gly Phe Lys Ala Val Lys Ala Leu Arg Leu Glu Asp Met Arg Ile
130                 135                 140

Pro Val Ala Tyr Leu Lys Thr Phe Gln Gly Pro Ala Thr Gly Ile Val
145                 150                 155                 160

Val Glu Arg Glu Arg Met Asp Lys Phe Gly Arg Pro Phe Leu Gly Ala
                165                 170                 175

Thr Val Lys Pro Lys Leu Gly Leu Ser Gly Lys Asn Tyr Gly Arg Val
            180                 185                 190

Val Tyr Glu Gly Leu Arg Gly Gly Leu Asp Phe Leu Lys Asp Asp Glu
    195                 200                 205

Asn Ile Asn Ser Gln Pro Phe Met Arg Trp Lys Glu Arg Phe Leu Tyr
210                 215                 220

Ser Ile Glu Ala Val Asn Arg Ser Ile Ala Ala Thr Gly Glu Val Lys
225                 230                 235                 240

Gly His Tyr Met Asn Val Thr Ala Ala Thr Met Glu Glu Met Tyr Glu
                245                 250                 255

Arg Ala Glu Phe Ala Lys Gln Leu Gly Thr Val Ile Ile Met Ile Asp
            260                 265                 270

Leu Val Ile Gly Tyr Thr Ala Ile Gln Thr Met Gly Ile Trp Ala Arg
    275                 280                 285

Lys Asn Asp Met Ile Leu His Leu His Arg Ala Gly Asn Ser Thr Tyr
290                 295                 300

Ser Arg Gln Lys Ile His Gly Met Asn Phe Arg Val Ile Cys Lys Trp
305                 310                 315                 320
```

```
Met Arg Met Ala Gly Val Asp His Ile His Ala Gly Thr Val Val Gly
            325                 330                 335

Lys Leu Glu Gly Asp Pro Leu Met Ile Arg Gly Phe Tyr Asn Thr Leu
        340                 345                 350

Leu Leu Pro Tyr Leu Glu Val Asn Leu Pro Gln Gly Ile Phe Phe Gln
    355                 360                 365

Gln Asp Trp Ala Ser Leu Arg Lys Val Thr Pro Val Ala Ser Gly Gly
370                 375                 380

Ile His Cys Gly Gln Met His Gln Leu Leu Asp Tyr Leu Gly Asn Asp
385                 390                 395                 400

Val Val Leu Gln Phe Gly Gly Thr Ile Gly His Pro Asp Gly Ile
                405                 410                 415

Gln Ala Gly Ala Thr Ala Asn Arg Val Ala Leu Glu Ser Met Val Ile
            420                 425                 430

Ala Arg Asn Glu Gly Arg Asp Tyr Val Ala Glu Gly Pro Gln Ile Leu
        435                 440                 445

Arg Asp Ala Ala Lys Thr Cys Gly Pro Leu Gln Thr Ala Leu Asp Leu
    450                 455                 460

Trp Lys Asp Ile Thr Phe Asn Tyr Thr Ser Thr Asp Thr Ala Asp Phe
465                 470                 475                 480

Val Glu Thr Pro Thr Ala Asn Val
                485

<210> SEQ ID NO 16
<211> LENGTH: 472
<212> TYPE: PRT
<213> ORGANISM: Synechococcus elongatus PCC6301

<400> SEQUENCE: 16

Met Pro Lys Thr Gln Ser Ala Ala Gly Tyr Lys Ala Gly Val Lys Asp
1               5                   10                  15

Tyr Lys Leu Thr Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Gly Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
65                  70                  75                  80

Cys Tyr His Ile Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205
```

Gln Arg Trp Arg Asp Arg Phe Leu Phe Val Ala Asp Ala Ile His Lys
    210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
                260                 265                 270

Ala Asn Thr Thr Leu Ala Lys Trp Cys Arg Asp Asn Gly Val Leu Leu
            275                 280                 285

His Ile His Arg Ala Met His Ala Val Ile Asp Arg Gln Arg Asn His
    290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
                325                 330                 335

Ala Ser Thr Leu Gly Phe Val Asp Leu Met Arg Glu Asp His Ile Glu
                340                 345                 350

Ala Asp Arg Ser Arg Gly Val Phe Phe Thr Gln Asp Trp Ala Ser Met
            355                 360                 365

Pro Gly Val Leu Pro Val Ala Ser Gly Gly Ile His Val Trp His Met
370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
                405                 410                 415

Asn Arg Val Ala Leu Glu Ala Cys Val Gln Ala Arg Asn Glu Gly Arg
            420                 425                 430

Asp Leu Tyr Arg Glu Gly Gly Asp Ile Leu Arg Glu Ala Gly Lys Trp
            435                 440                 445

Ser Pro Glu Leu Ala Ala Ala Leu Asp Leu Trp Lys Glu Ile Lys Phe
    450                 455                 460

Glu Phe Glu Thr Met Asp Lys Leu
465                 470

<210> SEQ ID NO 17
<211> LENGTH: 475
<212> TYPE: PRT
<213> ORGANISM: Spinacia oleracea

<400> SEQUENCE: 17

Met Ser Pro Gln Thr Glu Thr Lys Ala Ser Val Gly Phe Lys Ala Gly
1               5                   10                  15

Val Lys Asp Tyr Lys Leu Thr Tyr Tyr Thr Pro Glu Tyr Glu Thr Leu
            20                  25                  30

Asp Thr Asp Ile Leu Ala Ala Phe Arg Val Ser Pro Gln Pro Gly Val
        35                  40                  45

Pro Pro Glu Glu Ala Gly Ala Ala Val Ala Ala Glu Ser Ser Thr Gly
50                  55                  60

Thr Trp Thr Thr Val Trp Thr Asp Gly Leu Thr Asn Leu Asp Arg Tyr
65                  70                  75                  80

Lys Gly Arg Cys Tyr His Ile Glu Pro Val Ala Gly Glu Glu Asn Gln
                85                  90                  95

Tyr Ile Cys Tyr Val Ala Tyr Pro Leu Asp Leu Phe Glu Glu Gly Ser

```
            100                 105                 110
Val Thr Asn Met Phe Thr Ser Ile Val Gly Asn Val Phe Gly Phe Lys
            115                 120                 125

Ala Leu Arg Ala Leu Arg Leu Glu Asp Leu Arg Ile Pro Val Ala Tyr
            130                 135             140

Val Lys Thr Phe Gln Gly Pro Pro His Gly Ile Gln Val Glu Arg Asp
145                 150                 155                 160

Lys Leu Asn Lys Tyr Gly Arg Pro Leu Leu Gly Cys Thr Ile Lys Pro
                    165                 170                 175

Lys Leu Gly Leu Ser Ala Lys Asn Tyr Gly Arg Ala Val Tyr Glu Cys
                180                 185                 190

Leu Arg Gly Gly Leu Asp Phe Thr Lys Asp Asp Glu Asn Val Asn Ser
            195                 200                 205

Gln Pro Phe Met Arg Trp Arg Asp Arg Phe Leu Phe Cys Ala Glu Ala
            210                 215                 220

Leu Tyr Lys Ala Gln Ala Glu Thr Gly Glu Ile Lys Gly His Tyr Leu
225                 230                 235                 240

Asn Ala Thr Ala Gly Thr Cys Glu Asp Met Met Lys Arg Ala Val Phe
                    245                 250                 255

Ala Arg Glu Leu Gly Val Pro Ile Val Met His Asp Tyr Leu Thr Gly
                260                 265                 270

Gly Phe Thr Ala Asn Thr Thr Leu Ser His Tyr Cys Arg Asp Asn Gly
            275                 280                 285

Leu Leu Leu His Ile His Arg Ala Met His Ala Val Ile Asp Arg Gln
            290                 295                 300

Lys Asn His Gly Met His Phe Arg Val Leu Ala Lys Ala Leu Arg Leu
305                 310                 315                 320

Ser Gly Gly Asp His Ile His Ser Gly Thr Val Val Gly Lys Leu Glu
                    325                 330                 335

Gly Glu Arg Asp Ile Thr Leu Gly Phe Val Asp Leu Leu Arg Asp Asp
                340                 345                 350

Tyr Thr Glu Lys Asp Arg Ser Arg Gly Ile Tyr Phe Thr Gln Ser Trp
            355                 360                 365

Val Ser Thr Pro Gly Val Leu Pro Val Ala Ser Gly Gly Ile His Val
            370                 375                 380

Trp His Met Pro Ala Leu Thr Glu Ile Phe Gly Asp Asp Ser Val Leu
385                 390                 395                 400

Gln Phe Gly Gly Gly Thr Leu Gly His Pro Trp Gly Asn Ala Pro Gly
                    405                 410                 415

Ala Val Ala Asn Arg Val Ala Leu Glu Ala Cys Val Gln Ala Arg Asn
                420                 425                 430

Glu Gly Arg Asp Leu Ala Arg Glu Gly Asn Thr Ile Ile Arg Glu Ala
            435                 440                 445

Thr Lys Trp Ser Pro Glu Leu Ala Ala Ala Cys Glu Val Trp Lys Glu
450                 455                 460

Ile Lys Phe Glu Phe Pro Ala Met Asp Thr Val
465                 470                 475

<210> SEQ ID NO 18
<211> LENGTH: 475
<212> TYPE: PRT
<213> ORGANISM: Nicotiana tabacum

<400> SEQUENCE: 18
```

```
Met Ser Pro Gln Thr Glu Thr Lys Ala Ser Val Gly Phe Lys Ala Gly
1               5                   10                  15

Val Lys Asp Tyr Lys Leu Thr Tyr Tyr Thr Pro Asp Tyr Glu Thr Lys
            20                  25                  30

Asp Thr Asp Ile Leu Ala Ala Phe Arg Val Thr Pro Gln Pro Gly Val
            35                  40                  45

Pro Pro Glu Glu Ala Gly Ala Ala Val Ala Ala Glu Ser Ser Thr Gly
        50                  55                  60

Thr Trp Thr Thr Val Trp Thr Asp Gly Leu Thr Ser Leu Asp Arg Tyr
65                      70                  75                  80

Lys Gly Arg Cys Tyr His Ile Glu Pro Val Ala Gly Asp Glu Asn Gln
                85                  90                  95

Phe Ile Ala Tyr Val Ala Tyr Pro Leu Asp Leu Phe Glu Glu Gly Ser
                100                 105                 110

Val Thr Asn Met Phe Thr Ser Ile Val Gly Asn Val Phe Gly Phe Lys
            115                 120                 125

Ala Leu Arg Ala Leu Arg Leu Glu Asp Leu Arg Ile Pro Pro Ala Tyr
            130                 135                 140

Ala Lys Thr Phe Gln Gly Pro Pro His Gly Ile Gln Val Glu Arg Asp
145                 150                 155                 160

Lys Leu Asn Lys Tyr Gly Arg Pro Leu Leu Gly Cys Thr Ile Lys Pro
                165                 170                 175

Lys Leu Gly Leu Ser Ala Lys Asn Tyr Gly Arg Ala Val Tyr Glu Cys
                180                 185                 190

Leu Arg Gly Gly Leu Asp Phe Thr Lys Asp Asp Glu Asn Val Asn Ser
            195                 200                 205

Gln Pro Phe Met Arg Trp Arg Asp Arg Phe Leu Phe Cys Ala Glu Ala
            210                 215                 220

Ile Tyr Lys Ala Gln Ala Glu Thr Gly Glu Ile Lys Gly His Tyr Leu
225                 230                 235                 240

Asn Ala Thr Ala Gly Thr Cys Glu Glu Met Ile Lys Arg Ala Val Phe
                245                 250                 255

Ala Arg Glu Leu Gly Val Pro Ile Val Met His Asp Tyr Ile Thr Gly
            260                 265                 270

Gly Phe Thr Ala Asn Thr Ser Leu Ala His Tyr Cys Arg Asp Asn Gly
            275                 280                 285

Leu Leu Leu His Ile His Arg Ala Met His Ala Val Ile Asp Arg Gln
            290                 295                 300

Lys Asn His Gly Ile His Phe Arg Val Leu Ala Lys Ala Leu Arg Met
305                 310                 315                 320

Ser Gly Gly Asp His Ile His Ser Gly Thr Val Val Gly Lys Leu Glu
                325                 330                 335

Gly Glu Arg Asp Ile Thr Leu Gly Phe Val Asp Leu Leu Arg Asp Asp
            340                 345                 350

Phe Ile Glu Lys Asp Arg Ser Arg Gly Ile Tyr Phe Thr Gln Asp Trp
            355                 360                 365

Val Ser Leu Pro Gly Val Leu Pro Val Ala Ser Gly Gly Ile His Val
        370                 375                 380

Trp His Met Pro Ala Leu Thr Glu Ile Phe Gly Asp Asp Ser Val Leu
385                 390                 395                 400

Gln Phe Gly Gly Gly Thr Leu Gly His Pro Trp Gly Asn Ala Pro Gly
            405                 410                 415

Ala Val Ala Asn Arg Val Ala Leu Glu Ala Cys Val Gln Ala Arg Asn
```

-continued

```
                420                 425                 430
Glu Gly Arg Asp Leu Ala Arg Glu Gly Asn Glu Ile Ile Arg Glu Ala
            435                 440                 445
Ser Lys Trp Ser Pro Glu Leu Ala Ala Ala Cys Glu Val Trp Lys Glu
450                 455                 460
Ile Lys Phe Glu Phe Glu Ala Met Asp Thr Leu
465                 470                 475

<210> SEQ ID NO 19
<211> LENGTH: 477
<212> TYPE: PRT
<213> ORGANISM: Oriza sativa

<400> SEQUENCE: 19

Met Ser Pro Gln Thr Glu Thr Lys Ala Ser Val Gly Phe Lys Ala Gly
1               5                   10                  15
Val Lys Asp Tyr Lys Leu Thr Tyr Tyr Thr Pro Glu Tyr Glu Thr Lys
                20                  25                  30
Asp Thr Asp Ile Leu Ala Ala Phe Arg Val Thr Pro Gln Pro Gly Val
            35                  40                  45
Pro Pro Glu Glu Ala Gly Ala Ala Val Ala Ala Glu Ser Ser Thr Gly
        50                  55                  60
Thr Trp Thr Thr Val Trp Thr Asp Gly Leu Thr Ser Leu Asp Arg Tyr
65                  70                  75                  80
Lys Gly Arg Cys Tyr His Ile Glu Pro Val Val Gly Glu Asp Asn Gln
                85                  90                  95
Tyr Ile Ala Tyr Val Ala Tyr Pro Leu Asp Leu Phe Glu Glu Gly Ser
            100                 105                 110
Val Thr Asn Met Phe Thr Ser Ile Val Gly Asn Val Phe Gly Phe Lys
        115                 120                 125
Ala Leu Arg Ala Leu Arg Leu Glu Asp Leu Arg Ile Pro Pro Thr Tyr
130                 135                 140
Ser Lys Thr Phe Gln Gly Pro Pro His Gly Ile Gln Val Glu Arg Asp
145                 150                 155                 160
Lys Leu Asn Lys Tyr Gly Arg Pro Leu Leu Gly Cys Thr Ile Lys Pro
                165                 170                 175
Lys Leu Gly Leu Ser Ala Lys Asn Tyr Gly Arg Ala Cys Tyr Glu Cys
            180                 185                 190
Leu Arg Gly Gly Leu Asp Phe Thr Lys Asp Asp Glu Asn Val Asn Ser
        195                 200                 205
Gln Pro Phe Met Arg Trp Arg Asp Arg Phe Val Phe Cys Ala Glu Ala
210                 215                 220
Ile Tyr Lys Ser Gln Ala Glu Thr Gly Glu Ile Lys Gly His Tyr Leu
225                 230                 235                 240
Asn Ala Thr Ala Gly Thr Cys Glu Glu Met Ile Lys Arg Ala Val Phe
                245                 250                 255
Ala Arg Glu Leu Gly Val Pro Ile Val Met His Asp Tyr Leu Thr Gly
            260                 265                 270
Gly Phe Thr Ala Asn Thr Ser Leu Ala His Tyr Cys Arg Asp Asn Gly
        275                 280                 285
Leu Leu Leu His Ile His Arg Ala Met His Ala Val Ile Asp Arg Gln
290                 295                 300
Lys Asn His Gly Met His Phe Arg Val Leu Ala Lys Ala Leu Arg Met
305                 310                 315                 320
```

-continued

```
Ser Gly Gly Asp His Ile His Ala Gly Thr Val Val Gly Lys Leu Glu
            325                 330                 335

Gly Glu Arg Glu Met Thr Leu Gly Phe Val Asp Leu Leu Arg Asp Asp
        340                 345                 350

Phe Ile Glu Lys Asp Arg Ala Arg Gly Ile Phe Phe Thr Gln Asp Trp
            355                 360                 365

Val Ser Met Pro Gly Val Ile Pro Val Ala Ser Gly Gly Ile His Val
370                 375                 380

Trp His Met Pro Ala Leu Thr Glu Ile Phe Gly Asp Asp Ser Val Leu
385                 390                 395                 400

Gln Phe Gly Gly Gly Thr Leu Gly His Pro Trp Gly Asn Ala Pro Gly
            405                 410                 415

Ala Ala Ala Asn Arg Val Ala Leu Glu Ala Cys Val Gln Ala Arg Asn
            420                 425                 430

Glu Gly Arg Asp Leu Ala Arg Glu Gly Asn Glu Ile Ile Arg Ser Ala
        435                 440                 445

Cys Lys Trp Ser Pro Glu Leu Ala Ala Ala Cys Glu Ile Trp Lys Ala
    450                 455                 460

Ile Lys Phe Glu Phe Glu Pro Val Asp Lys Leu Asp Ser
465                 470                 475

<210> SEQ ID NO 20
<211> LENGTH: 475
<212> TYPE: PRT
<213> ORGANISM: Glycine max

<400> SEQUENCE: 20

Met Ser Pro Gln Thr Glu Thr Lys Ala Ser Val Gly Phe Lys Ala Gly
1               5                   10                  15

Val Lys Asp Tyr Lys Leu Thr Tyr Tyr Thr Pro Asp Tyr Glu Thr Lys
            20                  25                  30

Asp Thr Asp Ile Leu Ala Ala Phe Arg Val Thr Pro Gln Pro Gly Val
        35                  40                  45

Pro Pro Glu Glu Ala Gly Ala Ala Val Ala Ala Glu Ser Ser Thr Gly
    50                  55                  60

Thr Trp Thr Thr Val Trp Thr Asp Gly Leu Thr Ser Leu Asp Arg Tyr
65                  70                  75                  80

Lys Gly Arg Cys Tyr Gly Leu Glu Pro Val Ala Gly Glu Glu Asn Gln
                85                  90                  95

Tyr Ile Ala Tyr Val Ala Tyr Pro Leu Asp Leu Phe Glu Glu Gly Ser
            100                 105                 110

Val Thr Asn Met Phe Thr Ser Ile Val Gly Asn Val Phe Gly Phe Lys
        115                 120                 125

Ala Leu Arg Ala Leu Arg Leu Glu Asp Leu Arg Ile Pro Thr Ala Tyr
    130                 135                 140

Ile Lys Thr Phe Gln Gly Pro Pro His Gly Ile Gln Val Glu Arg Asp
145                 150                 155                 160

Lys Leu Asn Lys Tyr Gly Arg Pro Leu Leu Gly Cys Thr Ile Lys Pro
                165                 170                 175

Lys Leu Gly Leu Ser Ala Lys Asn Tyr Gly Arg Ala Val Tyr Glu Cys
            180                 185                 190

Leu Arg Gly Gly Leu Asp Phe Thr Lys Asp Asp Glu Asn Val Asn Ser
        195                 200                 205

Gln Pro Phe Met Arg Trp Arg Asp Arg Phe Leu Phe Cys Ala Glu Ala
    210                 215                 220
```

```
Ile Phe Lys Ser Gln Ala Glu Thr Gly Glu Ile Lys Gly His Tyr Leu
225                 230                 235                 240

Asn Ala Thr Ala Gly Thr Cys Glu Glu Met Met Lys Arg Ala Val Phe
            245                 250                 255

Ala Arg Glu Leu Gly Val Pro Ile Val Met His Asp Tyr Leu Thr Gly
        260                 265                 270

Gly Phe Thr Ala Asn Thr Ser Leu Ala His Tyr Cys Arg Asp Asn Gly
    275                 280                 285

Leu Leu Leu His Ile His Arg Ala Met His Ala Val Ile Asp Arg Gln
290                 295                 300

Lys Asn His Gly Met His Phe Arg Val Leu Ala Lys Ala Leu Arg Leu
305                 310                 315                 320

Ser Gly Gly Asp His Val His Ala Gly Thr Val Val Gly Lys Leu Glu
            325                 330                 335

Gly Glu Arg Glu Ile Thr Leu Gly Phe Val Asp Leu Leu Arg Asp Asp
        340                 345                 350

Phe Val Glu Lys Asp Arg Ser Arg Gly Ile Tyr Phe Thr Gln Asp Trp
    355                 360                 365

Val Ser Leu Pro Gly Val Leu Pro Val Ala Ser Gly Gly Ile His Val
370                 375                 380

Trp His Met Pro Ala Leu Thr Glu Ile Phe Gly Asp Asp Ser Val Leu
385                 390                 395                 400

Gln Phe Gly Gly Gly Thr Leu Gly His Pro Trp Gly Asn Ala Pro Gly
            405                 410                 415

Ala Val Ala Asn Arg Val Ala Leu Glu Ala Cys Val Gln Ala Arg Asn
        420                 425                 430

Glu Gly Arg Asp Leu Ala Arg Glu Gly Asn Glu Ile Ile Arg Glu Ala
    435                 440                 445

Ser Lys Trp Ser Pro Glu Leu Ala Ala Ala Cys Glu Val Trp Lys Glu
450                 455                 460

Ile Lys Phe Glu Phe Glu Ala Met Asp Thr Leu
465                 470                 475

<210> SEQ ID NO 21
<211> LENGTH: 476
<212> TYPE: PRT
<213> ORGANISM: Saccharum officinarum

<400> SEQUENCE: 21

Met Ser Pro Gln Thr Glu Thr Lys Ala Ser Val Gly Phe Lys Ala Gly
1               5                   10                  15

Val Lys Asp Tyr Lys Leu Thr Tyr Tyr Thr Pro Glu Tyr Glu Thr Lys
            20                  25                  30

Asp Thr Asp Ile Leu Ala Ala Phe Arg Val Thr Pro Gln Leu Gly Val
        35                  40                  45

Pro Pro Glu Glu Ala Gly Ala Ala Val Ala Ala Glu Ser Ser Thr Gly
    50                  55                  60

Thr Trp Thr Thr Val Trp Thr Asp Gly Leu Thr Ser Leu Asp Arg Tyr
65              70                  75                  80

Lys Gly Arg Cys Tyr His Ile Glu Pro Val Pro Gly Asp Pro Asp Gln
            85                  90                  95

Tyr Ile Cys Tyr Val Ala Tyr Pro Leu Asp Leu Phe Glu Glu Gly Ser
        100                 105                 110

Val Thr Asn Met Phe Thr Ser Ile Val Gly Asn Val Phe Gly Phe Lys
```

```
            115                 120                 125
Ala Leu Arg Ala Leu Arg Leu Glu Asp Leu Arg Ile Pro Pro Ala Tyr
        130                 135                 140

Val Lys Thr Phe Gln Gly Pro Pro His Gly Ile Gln Val Glu Arg Asp
145                 150                 155                 160

Lys Leu Asn Lys Tyr Gly Arg Pro Leu Leu Gly Cys Thr Ile Lys Pro
                165                 170                 175

Lys Leu Gly Leu Ser Ala Lys Asn Tyr Gly Arg Ala Cys Tyr Glu Cys
            180                 185                 190

Leu Arg Gly Gly Leu Asp Phe Thr Lys Asp Asp Glu Asn Val Asn Ser
        195                 200                 205

Gln Pro Phe Met Arg Trp Arg Asp Arg Phe Val Phe Cys Ala Glu Ala
    210                 215                 220

Ile Tyr Lys Ala Gln Ala Glu Thr Gly Glu Ile Lys Gly His Tyr Leu
225                 230                 235                 240

Asn Ala Thr Ala Gly Thr Cys Glu Glu Met Ile Lys Arg Ala Val Phe
                245                 250                 255

Ala Lys Glu Leu Gly Val Pro Ile Val Met His Asp Tyr Leu Thr Gly
            260                 265                 270

Gly Phe Thr Ala Asn Thr Thr Leu Ser His Tyr Cys Arg Asp Asn Gly
        275                 280                 285

Leu Leu Leu His Ile His Arg Ala Met His Ala Val Ile Asp Arg Gln
    290                 295                 300

Lys Asn His Gly Met His Phe Arg Val Leu Ala Lys Ala Leu Arg Met
305                 310                 315                 320

Ser Gly Gly Asp His Ile His Ser Gly Thr Val Val Gly Lys Leu Glu
                325                 330                 335

Gly Glu Arg Glu Ile Thr Leu Gly Phe Val Asp Leu Leu Arg Asp Asp
            340                 345                 350

Phe Ile Glu Lys Asp Arg Ser Arg Gly Ile Phe Phe Thr Gln Asp Trp
        355                 360                 365

Val Ser Met Pro Gly Val Ile Pro Val Ala Ser Gly Gly Ile His Val
    370                 375                 380

Trp His Met Pro Ala Leu Thr Glu Ile Phe Gly Asp Asp Ser Val Leu
385                 390                 395                 400

Gln Phe Gly Gly Gly Thr Leu Gly His Pro Trp Gly Asn Ala Pro Gly
                405                 410                 415

Ala Ala Ala Asn Arg Val Ala Leu Glu Ala Cys Val Gln Ala Arg Asn
            420                 425                 430

Glu Gly Arg Asp Leu Ala Arg Glu Gly Asn Glu Ile Ile Lys Ala Ala
        435                 440                 445

Cys Lys Trp Ser Ala Glu Leu Ala Ala Ala Cys Glu Ile Trp Lys Glu
    450                 455                 460

Ile Lys Phe Asp Thr Phe Lys Ala Met Asp Thr Leu
465                 470                 475

<210> SEQ ID NO 22
<211> LENGTH: 1845
<212> TYPE: DNA
<213> ORGANISM: Synechococcus PCC6301

<400> SEQUENCE: 22
atggccaaga cgcaatctgc cgcaggctat aaggccgggg tgaaggacta caaactcacc      60
tattcacccc ccgattacac cccccaaagac actgacctgc tggcggcttt ccgcttcagc     120
```

```
cctcagccgg gtgtccctgc tgacgaagct ggtgcggcga tcgcggctga atcttcgacc    180
ggtacctgga ccaccgtgtg gaccgacttg ctgaccgaca tggatcggta caaaggcaag    240
tgctaccaca tcgagccggt gcaaggcgaa gagaactcct actttgcgtt catcgcttac    300
ccgctcgacc tgtttgaaga agggtcggtc accaacatcc tgacctcgat cgtcggtaac    360
gtgtttggct tcaaagctat ccgttcgctg cgtctggaag acatccgctt ccccgtcgcc    420
ttggtcaaaa ccttccaagg tcctccccac ggtatccaag tcgagcgcga cctgctgaac    480
aagtacggcc gtccgatgct gggttgcacg atcaaaccaa aactcggtct gtcggcgaaa    540
aactacggtc gtgccgtcta cgaatgtctg cgcggcggtc tggacttcac caaagacgac    600
gaaaacatca actcgcagcc gttccaacgc tggcgcgatc gcttcctgtt tgtggctgat    660
gcaatccaca atcgcaagc agaaaccggt gaaatcaaag tcactacct gaacgtgacc    720 gcgccgacct gcgaagaaat gatgaaacgg gctgagttcg ctaaagaact cggcatgccg    780
atcatcatgc atgacttctt gacggctggt ttcaccgcca acaccacctt ggcaaaatgg    840
tgccgcgaca acggcgtcct gctgcacatc caccgtgcaa tgcacgcggt gatcgaccgt    900
cagcgtaacc acgggattca cttccgtgtc ttggccaagt gtttgcgtct gtccggtggt    960
gaccacctcc actccggcac cgtcgtcggc aaactggaag cgacaaagc ttcgaccttg   1020 ggctttgttg acttgatgcg cgaagaccac atcgaagctg accgcagccg tggggtcttc   1080
ttcacccaag attgggcgtc gatgccgggc gtgctgccgg ttgcttccgg tggtatccac   1140
gtgtggcaca tgcccgcact ggtggaaatc ttcggtgatg actccgttct ccagttcggt   1200
ggcggcacct tgggtcaccc ctgggtaat gctcctggtg caaccgcgaa ccgtgttgcc   1260
ttggaagctt gcgtccaagc tcggaacgaa ggtcgcgacc tctaccgtga aggcggcgac   1320
atccttcgtg aagctggcaa gtggtcgcct gaactggctg ctgccctcga cctctggaaa   1380
gagatcaagt cgaattcga acgatggac aagctctaag gagcctctga ctatcgctgg   1440
gggagtgagc gttgctgcgt aaagctttct ccccagcctt tcgacttaac ctttcaggat   1500
ttctgaatca tgagcatgaa actctgcccc aaagagcgtc gtttcgagac tttctcgtac   1560
ctgcctcccc tcagcgatcg ccaaatcgct gcacaaatcg agtacatgat cgagcaaggc   1620
ttccacccct tgatcgagtt caacgagcac tcgaatccgg aagagttcta ctggacgatg   1680
tggaagctcc ccctgtttga ctgcaagagc cctcagcaag tcctcgatga agtgcgtgag   1740
tgccgcagcg aatacggtga ttgctacatc cgtgtcgctg gcttcgacaa catcaagcag   1800
tgccaaaccg tgagcttcat cgttcatcgt cccggccgat actaa                   1845
```

<210> SEQ ID NO 23
<211> LENGTH: 111
<212> TYPE: PRT
<213> ORGANISM: Synechococcus PCC6301

<400> SEQUENCE: 23

Met Ser Met Lys Thr Leu Pro Lys Glu Arg Arg Phe Glu Thr Phe Ser
1               5                   10                  15

Tyr Leu Pro Pro Leu Ser Asp Arg Gln Ile Ala Ala Gln Ile Glu Tyr
            20                  25                  30

Met Ile Glu Gln Gly Phe His Pro Leu Ile Glu Phe Asn Glu His Ser
        35                  40                  45

Asn Pro Glu Glu Phe Tyr Trp Thr Met Trp Lys Leu Pro Leu Phe Asp
    50                  55                  60

Cys Lys Ser Pro Gln Gln Val Leu Asp Glu Val Arg Glu Cys Arg Ser
65                  70                  75                  80

Glu Tyr Gly Asp Cys Tyr Ile Arg Val Ala Gly Phe Asp Asn Ile Lys
            85                  90                  95

Gln Cys Gln Thr Val Ser Phe Ile Val His Arg Pro Gly Arg Tyr
        100                 105                 110

<210> SEQ ID NO 24
<211> LENGTH: 472
<212> TYPE: PRT
<213> ORGANISM: Synechococcus PCC6301

<400> SEQUENCE: 24

Met Ala Lys Thr Gln Ser Ala Ala Gly Tyr Lys Ala Gly Val Lys Asp
1               5                   10                  15

Tyr Lys Leu Thr Tyr Tyr Thr Pro Asp Tyr Thr Pro Lys Asp Thr Asp
                20                  25                  30

Leu Leu Ala Ala Phe Arg Phe Ser Pro Gln Pro Gly Val Pro Ala Asp
            35                  40                  45

Glu Ala Gly Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
65                  70                  75                  80

Cys Tyr His Ile Glu Pro Val Gln Gly Glu Glu Asn Ser Tyr Phe Ala
            85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
            115                 120                 125

Ser Leu Arg Leu Glu Asp Ile Arg Phe Pro Val Ala Leu Val Lys Thr
        130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
    210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
            260                 265                 270

Ala Asn Thr Thr Leu Ala Lys Trp Cys Arg Asp Asn Gly Val Leu Leu
        275                 280                 285

His Ile His Arg Ala Met His Ala Val Ile Asp Arg Gln Arg Asn His
    290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
                325                 330                 335

```
Ala Ser Thr Leu Gly Phe Val Asp Leu Met Arg Glu Asp His Ile Glu
            340                 345                 350
Ala Asp Arg Ser Arg Gly Val Phe Phe Thr Gln Asp Trp Ala Ser Met
            355                 360                 365
Pro Gly Val Leu Pro Val Ala Ser Gly Gly Ile His Val Trp His Met
            370                 375                 380
Pro Ala Leu Val Glu Ile Phe Gly Asp Asp Ser Val Leu Gln Phe Gly
385                 390                 395                 400
Gly Gly Thr Leu Gly His Pro Trp Gly Asn Ala Pro Gly Ala Thr Ala
                405                 410                 415
Asn Arg Val Ala Leu Glu Ala Cys Val Gln Ala Arg Asn Glu Gly Arg
            420                 425                 430
Asp Leu Tyr Arg Glu Gly Gly Asp Ile Leu Arg Glu Ala Gly Lys Trp
            435                 440                 445
Ser Pro Glu Leu Ala Ala Ala Leu Asp Leu Trp Lys Glu Ile Lys Phe
        450                 455                 460
Glu Phe Glu Thr Met Asp Lys Leu
465                 470

<210> SEQ ID NO 25
<211> LENGTH: 1845
<212> TYPE: DNA
<213> ORGANISM: Artificial
<220> FEATURE:
<223> OTHER INFORMATION: Based on wild-type Synechococcus sp. PCC6301
      rbcLS nucleotide sequence

<400> SEQUENCE: 25
atggccaaga cgcaatctgc cgcaggctat aaggccgggg tgaaggacta caaactcacc        60
tattggaccc ccgattacac ccccaaagac actgacctgc tggcggcttt ccgcttcagc      120
cctcagccgg gtgtccctgc tatcgaagct ggtgcggcga tcgcggctga atcttcgacc      180
ggtacctgga ccaccgtgtg gaccgacttg ctgaccgaca tggatcggta caaaggcaag      240
tgctaccaca tcgagccggt gcaaggcgaa gagaactcct actttgcgtt catcgcttac      300
ccgctcgacc tgtttgaaga agggtcggtc accaacatcc tgacctcgat cgtcggtaac      360
gtgtttggct tcaaagctat ccgttcgctg cgtctggaag acatccgctt ccccgtcgcc      420
ttggtcaaaa ccttccaagg tcctccccac ggtatccaag tcgagcgcga cctgctgaac      480
aagtacggcc gtccgatgct gggttgcacg atcaaaccaa aactcggtct gtcggcgaaa      540
aactacggtc gtgccgtcta cgaatgtctg cgcggcggtc tggacttcac caaagacgac      600
gaaaacatca actcgcagcc gttccaacgc tggcgcgatc gcttcctgtt tgtggctgat      660
gcaatccaca atcgcaagc agaaaccggt gaaatcaaag tcactacct gaacgtgacc      720 gcgccgacct gcgaagaaat gatgaaacgg gctgagttcg ctaaagaact cggcatgccg      780
atcatcatgc atgacttctt gacggctggt ttcaccgcca acaccacctt ggcaaaatgg      840
tgccgcgaca acggcgtcct gctgcacatc accgtgcaa tgcacgcggt gatcgaccgt      900
cagcgtaacc acgggattca cttccgtgtc ttggccaagt gtttgcgtct gtccggtggt      960
gaccacctcc actccggcac cgtcgtcggc aaactggaag cgacaaagc ttcgaccttg     1020 ggctttgttg acttgatgcg cgaagaccac atcgaagctg accgcagccg tggggtcttc     1080
ttcacccaag attgggcgtc gatgccgggc gtgctgccgg ttgcttccgg tggtatccac     1140
gtgtggcaca tgcccgcact ggtggaaatc ttcggtgatg actccgttct ccagttcggt     1200
```

```
ggcggcacct tgggtcaccc ctggggtaat gctcctggtg caaccgcgaa ccgtgttgcc    1260
ttggaagctt gcgtccaagc tcggaacgaa ggtcgcgacc tctaccgtga aggcggcgac    1320
atccttcgtg aagctggcaa gtggtcgcct gaactggctg ctgccctcga cctctggaaa    1380
gagatcaagt tcgaattcga acgatggaca agctctaag gagcctctga ctatcgctgg     1440
gggagtgagc gttgctgcgt aaagctttct ccccagcctt tcgacttaac cttcaggat    1500 ttctgaatca tgagcatgaa actctgccc aaagagcgtc gtttcgagac tttctcgtac     1560
ctgcctcccc tcagcgatcg ccaaatcgct gcacaaatcg agtacatgat cgagcaaggc    1620
ttccacccct tgatcgagtt caacgagcac tcgaatccgg aagagttcta ctggacgatg    1680
tggaagctcc ccctgtttga ctgcaagagc cctcagcaag tcctcgatga agtgcgtgag    1740
tgccgcagcg aataccggtga ttgctacatc cgtgtcgctg gcttcgacaa catcaagcag    1800
tgccaaaccg tgagcttcat cgttcatcgt cccggccgat actaa                   1845
```

<210> SEQ ID NO 26
<211> LENGTH: 472
<212> TYPE: PRT
<213> ORGANISM: Artificial
<220> FEATURE:
<223> OTHER INFORMATION: Based on wild-type Synechococcus sp. PCC6301
      rbcLS translated sequence

<400> SEQUENCE: 26

```
Met Ala Lys Thr Gln Ser Ala Ala Gly Tyr Lys Ala Gly Val Lys Asp
1               5                   10                  15

Tyr Lys Leu Thr Tyr Trp Thr Pro Asp Tyr Thr Pro Lys Asp Thr Asp
            20                  25                  30

Leu Leu Ala Ala Phe Arg Phe Ser Pro Gln Pro Gly Val Pro Ala Ile
        35                  40                  45

Glu Ala Gly Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
65                  70                  75                  80

Cys Tyr His Ile Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
    210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
```

245                 250                 255
Leu Gly Met Pro Ile Ile Met His Asp Phe Leu Thr Ala Gly Phe Thr
                260                 265                 270

Ala Asn Thr Thr Leu Ala Lys Trp Cys Arg Asp Asn Gly Val Leu Leu
            275                 280                 285

His Ile His Arg Ala Met His Ala Val Ile Asp Arg Gln Arg Asn His
        290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
                325                 330                 335

Ala Ser Thr Leu Gly Phe Val Asp Leu Met Arg Glu Asp His Ile Glu
            340                 345                 350

Ala Asp Arg Ser Arg Gly Val Phe Phe Thr Gln Asp Trp Ala Ser Met
        355                 360                 365

Pro Gly Val Leu Pro Val Ala Ser Gly Gly Ile His Val Trp His Met
370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
                405                 410                 415

Asn Arg Val Ala Leu Glu Ala Cys Val Gln Ala Arg Asn Glu Gly Arg
            420                 425                 430

Asp Leu Tyr Arg Glu Gly Gly Asp Ile Leu Arg Glu Ala Gly Lys Trp
        435                 440                 445

Ser Pro Glu Leu Ala Ala Ala Leu Asp Leu Trp Lys Glu Ile Lys Phe
    450                 455                 460

Glu Phe Glu Thr Met Asp Lys Leu
465                 470

<210> SEQ ID NO 27
<211> LENGTH: 1845
<212> TYPE: DNA
<213> ORGANISM: Artificial
<220> FEATURE:
<223> OTHER INFORMATION: Based on wild-type Synechococcus sp. PCC6301
      rbcLS nucleotide sequence

<400> SEQUENCE: 27
atggccaaga cgcaatctgc cgcaggctat aaggccgggg tgaaggacta caaactcacc      60
tattggaccc ccgattacac ccccaaagac actgacctgc tggcggcttt ccgcttcagc     120
cctcagccgg tgtccctgc tgtcgaagct ggtgcggcga tcgcggctga atcttcgacc      180
ggtacctgga ccaccgtgtg gaccgacttg ctgaccgaca tggatcggta caaaggcaag     240
tgctaccaca tcgagccggt gcaaggcgaa gagaactcct actttgcgtt catcgcttac     300
ccgctcgacc tgtttgaaga agggtcggtc accaacatcc tgacctcgat cgtcggtaac     360
gtgtttggct tcaaagctat ccgttcgctg cgtctggaag acatccgctt ccccgtcgcc     420
ttggtcaaaa ccttccaagg tcctccccac ggtatccaag tcgagcgcga cctgctgaac     480
aagtacggcc gtccgatgct gggttgcacg atcaaaccaa actcggtct gtcggcgaaa     540 aactacggtc gtgccgtcta cgaatgtctg cgcggcggtc tggacttcac caaagacgac     600
gaaaacatca actcgcagcc gttccaacgc tggcgcgatc gcttcctgtt tgtggctgat     660
gcaatccaca atcgcaagc agaaaccggt gaaatcaaag gtcactacct gaacgtgacc     720

-continued

```
gcgccgacct gcgaagaaat gatgaaacgg gctgagttcg ctaaagaact cggcatgccg    780
atcatcatgc atgacttctt gacggctggt tcaccgcca acaccacctt ggcaaaatgg    840
tgccgcgaca acggcgtcct gctgcacatc caccgtgcaa tgcacgcggt gatcgaccgt    900
cagcgtaacc acgggattca cttccgtgtc ttggccaagt gtttgcgtct gtccggtggt    960
gaccacctcc actccggcac cgtcgtcggc aaactggaag gcgacaaagc ttcgaccttg   1020
ggctttgttg acttgatgcg cgaagaccac atcgaagctg accgcagccg tggggtcttc   1080
ttcacccaag attgggcgtc gatgccgggc gtgctgccgg ttgcttccgg tggtatccac   1140
gtgtggcaca tgcccgcact ggtggaaatc ttcggtgatg actccgttct ccagttcggt   1200
ggcggcacct tgggtcaccc ctggggtaat gctcctggtg caaccgcgaa ccgtgttgcc   1260
ttggaagctt gcgtccaagc tcggaacgaa ggtcgcgacc tctaccgtga aggcggcgac   1320
atccttcgtg aagctggcaa gtggtcgcct gaactggctg ctgccctcga cctctggaaa   1380
gagatcaagt tcgaattcga aacgatggac aagctctaag gagcctctga ctatcgctgg   1440
gggagtgagc gttgctgcgt aaagctttct ccccagcctt tcgacttaac ctttcaggat   1500
ttctgaatca tgagcatgaa aactctgccc aaagagcgtc gtttcgagac tttctcgtac   1560
ctgcctcccc tcagcgatcg ccaaatcgct gcacaaatcg agtacatgat cgagcaaggc   1620
ttccaccccct tgatcgagtt caacgagcac tcgaatccgg aagagttcta ctggacgatg   1680
tggaagctcc ccctgtttga ctgcaagagc cctcagcaag tcctcgatga agtgcgtgag   1740
tgccgcagcg aatacggtga ttgctacatc cgtgtcgctg gcttcgacaa catcaagcag   1800
tgccaaaccg tgagcttcat cgttcatcgt cccggccgat actaa                   1845
```

<210> SEQ ID NO 28
<211> LENGTH: 472
<212> TYPE: PRT
<213> ORGANISM: Artificial
<220> FEATURE:
<223> OTHER INFORMATION: Based on wild-type Synechococcus sp. PCC6301
      rbcLS translated sequence

<400> SEQUENCE: 28

```
Met Ala Lys Thr Gln Ser Ala Ala Gly Tyr Lys Ala Gly Val Lys Asp
1               5                   10                  15

Tyr Lys Leu Thr Tyr Trp Thr Pro Asp Tyr Thr Pro Lys Asp Thr Asp
            20                  25                  30

Leu Leu Ala Ala Phe Arg Phe Ser Pro Gln Pro Gly Val Pro Ala Val
        35                  40                  45

Glu Ala Gly Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
65                  70                  75                  80

Cys Tyr His Ile Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140

Phe Gln Gly Pro Pro His Gly Ile Gln Val Glu Arg Asp Leu Leu Asn
145                 150                 155                 160
```

```
Lys Tyr Gly Arg Pro Met Leu Gly Cys Thr Ile Lys Pro Lys Leu Gly
                165                 170                 175
Leu Ser Ala Lys Asn Tyr Gly Arg Ala Val Tyr Glu Cys Leu Arg Gly
            180                 185                 190
Gly Leu Asp Phe Thr Lys Asp Asp Glu Asn Ile Asn Ser Gln Pro Phe
        195                 200                 205
Gln Arg Trp Arg Asp Arg Phe Leu Phe Val Ala Asp Ala Ile His Lys
    210                 215                 220
Ser Gln Ala Glu Thr Gly Glu Ile Lys Gly His Tyr Leu Asn Val Thr
225                 230                 235                 240
Ala Pro Thr Cys Glu Glu Met Met Lys Arg Ala Glu Phe Ala Lys Glu
                245                 250                 255
Leu Gly Met Pro Ile Ile Met His Asp Phe Leu Thr Ala Gly Phe Thr
            260                 265                 270
Ala Asn Thr Thr Leu Ala Lys Trp Cys Arg Asp Asn Gly Val Leu Leu
        275                 280                 285
His Ile His Arg Ala Met His Ala Val Ile Asp Arg Gln Arg Asn His
    290                 295                 300
Gly Ile His Phe Arg Val Leu Ala Lys Cys Leu Arg Leu Ser Gly Gly
305                 310                 315                 320
Asp His Leu His Ser Gly Thr Val Val Gly Lys Leu Glu Gly Asp Lys
                325                 330                 335
Ala Ser Thr Leu Gly Phe Val Asp Leu Met Arg Glu Asp His Ile Glu
            340                 345                 350
Ala Asp Arg Ser Arg Gly Val Phe Phe Thr Gln Asp Trp Ala Ser Met
        355                 360                 365
Pro Gly Val Leu Pro Val Ala Ser Gly Gly Ile His Val Trp His Met
    370                 375                 380
Pro Ala Leu Val Glu Ile Phe Gly Asp Asp Ser Val Leu Gln Phe Gly
385                 390                 395                 400
Gly Gly Thr Leu Gly His Pro Trp Gly Asn Ala Pro Gly Ala Thr Ala
                405                 410                 415
Asn Arg Val Ala Leu Glu Ala Cys Val Gln Ala Arg Asn Glu Gly Arg
            420                 425                 430
Asp Leu Tyr Arg Glu Gly Gly Asp Ile Leu Arg Glu Ala Gly Lys Trp
        435                 440                 445
Ser Pro Glu Leu Ala Ala Ala Leu Asp Leu Trp Lys Glu Ile Lys Phe
    450                 455                 460
Glu Phe Glu Thr Met Asp Lys Leu
465                 470

<210> SEQ ID NO 29
<211> LENGTH: 1845
<212> TYPE: DNA
<213> ORGANISM: Artificial
<220> FEATURE:
<223> OTHER INFORMATION: Based on wild-type Synechococcus sp. PCC6301
      rbcLS nucleotide sequence

<400> SEQUENCE: 29
atggccaaga cgcaatctgc cgcaggctat aaggccgggg tgaaggacta caaactcggc      60
tattcacccc ccgattacac ccccaaagac actgacctgc tggcggcttt ccgcttcagc     120
cctcagccgg gtgtccctgc tgacgaagct ggtgcggcga tcgcggctga atcttcgacc     180
ggtacctgga ccaccgtgtg gaccgacttg ctgaccgaca tggatcggta ccgcggcaag     240
```

-continued

```
tgctaccaca tcgagccggt gcaaggcgaa gagaactcct actttgcgtt catcgcttac      300
ccgctcgacc tgtttgaaga agggtcggtc accaacatcc tgacctcgat cgtcggtaac      360
gtgtttggct tcaaagctat ccgttcgctg cgtctggaag acatccgctt ccccgtcgcc      420
ttggtcaaaa ccttccaagg tcctccccac ggtatccaag tcgagcgcga cctgctgaac      480
aagtacggcc gtccgatgct gggttgcacg atcaaaccaa aactcggtct gtcggcgaaa      540
aactacggtc gtgccgtcta cgaatgtctg cgcggcggtc tggacttcac caaagacgac      600
gaaaacatca actcgcagcc gttccaacgc tggcgcgatc gcttcctgtt tgtggctgat      660
gcaatccaca atcgcaagc agaaaccggt gaaatcaaag tcactacct gaacgtgacc         720
gcgccgacct gcgaagaaat gatgaaacgg gctgagttcg ctaaagaact cggcatgccg      780
atcatcatgc atgacttctt gacggctggt tcaccgccca acaccacctt ggcaaaatgg      840
tgccgcgaca cggcgtcct gctgcacatc accgtgcaa tgcacgcggt gatcgaccgt         900
cagcgtaacc acgggattca cttccgtgtc ttggccaagt gttttgcgtct gtccggtggt     960
gaccacctcc actccggcac cgtcgtcggc aaactggaag cgacaaagc ttcgaccttg      1020
ggctttgttg acttgatgcg cgaagaccac atcgaagctg accgcagccg tggggtcttc     1080
ttcacccaag attgggcgtc gatgccgggc gtgctgccgg ttgcttccgg tggtatccac     1140
gtgtggcaca tgcccgcact ggtggaaatc ttcggtgatg actccgttct ccagttcggt     1200
ggcggcacct gggtcaccc ctggggtaat gctcctggtg caaccgcgaa ccgtgttgcc      1260
ttggaagctt gcgtccaagc tcggaacgaa ggtcgcgacc tctaccgtga aggcggcgac     1320
atccttcgtg aagctggcaa gtggtcgcct gaactggctg ctgccctcga cctctggaaa     1380
gagatcaagt tcgaattcga acgatggac aagctctaag gagcctctga ctatcgctgg      1440
gggagtgagc gttgctgcgt aaagctttct ccccagcctt tcgacttaac ctttcaggat     1500
ttctgaatca tgagcatgaa actctgccc aaagagcgtc gtttcgagac tttctcgtac      1560
ctgcctcccc tcagcgatcg ccaaatcgct gcacaaatcg agtacatgat cgagcaaggc     1620
ttccaccct tgatcgagtt caacgagcac tcgaatccgg aagagttcta ctggacgatg      1680
tggaagctcc ccctgtttga ctgcaagagc cctcagcaag tcctcgatga agtgcgtgag     1740
tgccgcagcg aatacggtga ttgctacatc cgtgtcgctg gcttcgacaa catcaagcag     1800
tgccaaaccg tgagcttcat cgttcatcgt cccggccgat actaa                     1845
```

<210> SEQ ID NO 30
<211> LENGTH: 472
<212> TYPE: PRT
<213> ORGANISM: Artificial
<220> FEATURE:
<223> OTHER INFORMATION: Based on wild-type Synechococcus sp. PCC6301
      rbcLS translated sequence

<400> SEQUENCE: 30

Met Ala Lys Thr Gln Ser Ala Ala Gly Tyr Lys Ala Gly Val Lys Asp
1               5                   10                  15

Tyr Lys Leu Gly Tyr Tyr Thr Pro Asp Tyr Thr Pro Lys Asp Thr Asp
                20                  25                  30

Leu Leu Ala Ala Phe Arg Phe Ser Pro Gln Pro Gly Val Pro Ala Asp
            35                  40                  45

Glu Ala Gly Ala Ala Ile Ala Ala Glu Ser Ser Thr Gly Thr Trp Thr
        50                  55                  60

Thr Val Trp Thr Asp Leu Leu Thr Asp Met Asp Arg Tyr Arg Gly Lys
65                  70                  75                  80

```
Cys Tyr His Ile Glu Pro Val Gln Gly Glu Asn Ser Tyr Phe Ala
             85                  90                  95
Phe Ile Ala Tyr Pro Leu Asp Leu Phe Glu Gly Ser Val Thr Asn
            100                 105                 110
Ile Leu Thr Ser Ile Val Gly Asn Val Phe Gly Phe Lys Ala Ile Arg
        115                 120                 125
Ser Leu Arg Leu Glu Asp Ile Arg Phe Pro Val Ala Leu Val Lys Thr
130                 135                 140
Phe Gln Gly Pro Pro His Gly Ile Gln Val Glu Arg Asp Leu Leu Asn
145                 150                 155                 160
Lys Tyr Gly Arg Pro Met Leu Gly Cys Thr Ile Lys Pro Lys Leu Gly
                165                 170                 175
Leu Ser Ala Lys Asn Tyr Gly Arg Ala Val Tyr Glu Cys Leu Arg Gly
            180                 185                 190
Gly Leu Asp Phe Thr Lys Asp Asp Glu Asn Ile Asn Ser Gln Pro Phe
        195                 200                 205
Gln Arg Trp Arg Asp Arg Phe Leu Phe Val Ala Asp Ala Ile His Lys
    210                 215                 220
Ser Gln Ala Glu Thr Gly Glu Ile Lys Gly His Tyr Leu Asn Val Thr
225                 230                 235                 240
Ala Pro Thr Cys Glu Glu Met Met Lys Arg Ala Glu Phe Ala Lys Glu
                245                 250                 255
Leu Gly Met Pro Ile Ile Met His Asp Phe Leu Thr Ala Gly Phe Thr
            260                 265                 270
Ala Asn Thr Thr Leu Ala Lys Trp Cys Arg Asp Asn Gly Val Leu Leu
        275                 280                 285
His Ile His Arg Ala Met His Ala Val Ile Asp Arg Gln Arg Asn His
    290                 295                 300
Gly Ile His Phe Arg Val Leu Ala Lys Cys Leu Arg Leu Ser Gly Gly
305                 310                 315                 320
Asp His Leu His Ser Gly Thr Val Val Gly Lys Leu Glu Gly Asp Lys
                325                 330                 335
Ala Ser Thr Leu Gly Phe Val Asp Leu Met Arg Glu Asp His Ile Glu
            340                 345                 350
Ala Asp Arg Ser Arg Gly Val Phe Phe Thr Gln Asp Trp Ala Ser Met
        355                 360                 365
Pro Gly Val Leu Pro Val Ala Ser Gly Gly Ile His Val Trp His Met
370                 375                 380
Pro Ala Leu Val Glu Ile Phe Gly Asp Asp Ser Val Leu Gln Phe Gly
385                 390                 395                 400
Gly Gly Thr Leu Gly His Pro Trp Gly Asn Ala Pro Gly Ala Thr Ala
                405                 410                 415
Asn Arg Val Ala Leu Glu Ala Cys Val Gln Ala Arg Asn Glu Gly Arg
            420                 425                 430
Asp Leu Tyr Arg Glu Gly Gly Asp Ile Leu Arg Glu Ala Gly Lys Trp
        435                 440                 445
Ser Pro Glu Leu Ala Ala Ala Leu Asp Leu Trp Lys Glu Ile Lys Phe
450                 455                 460
Glu Phe Glu Thr Met Asp Lys Leu
465                 470

<210> SEQ ID NO 31
<211> LENGTH: 1845
```

<212> TYPE: DNA
<213> ORGANISM: Artificial
<220> FEATURE:
<223> OTHER INFORMATION: Based on wild-type Synechococcus sp. PCC6301
    rbcLS nucleotide sequence

<400> SEQUENCE: 31

```
atggccaaga cgcaatctgc cgcaggctat aaggccgggg tgaaggacta caaactcacc      60
tattacaccc ccgattacac ccccaaagac actgacctgc tggcggcttt ccgcttcagc     120
cctcagccgg gtgtccctgc tgacgaagct gcggcggcga tcgcggctga atcttcgacc     180
ggtacctgga ccaccgtgtg gaccgacttg ctgaccgaca tggatcggta caaaggcaag     240
gcctaccacg tggagccggt gcaaggcgaa gagaactcct actttgcgtt catcgcttac     300
ccgctcgacc tgtttgaaga agggtcggtc accaacatcc tgacctcgat cgtcggtaac     360
gtgtttggct tcaaagctat ccgttcgctg cgtctggaag acatccgctt ccccgtcgcc     420
ttggtcaaaa ccttccaagg tcctccccac ggtatccaag tcgagcgcga cctgctgaac     480
aagtacggcc gtccgatgct gggttgcacg atcaaaccaa aactcggtct gtcggcgaaa     540
aactacggtc gtgccgtcta cgaatgtctg cgcggcggtc tggacttcac caaagacgac     600
gaaaacatca actcgcagcc gttccaacgc tggcgcgatc gcttcctgtt tgtggctgat     660
gcaatccaca atcgcaagc agaaaccggt gaaatcaaag gtcactacct gaacgtgacc     720
gcgccgacct gcgaagaaat gatgaaacgg gctgagttcg ctaaagaact cggcatgccg     780
atcatcatgc atgacttctt gacggctggt ttcaccgcca acaccacctt ggcaaaatgg     840
tgccgcgaca acgcgtcct gctgcacatc accgtgcaa tgcacgcggt gatcgaccgt     900
cagcgtaacc acgggattca cttccgtgtc ttggccaagt gtttgcgtct gtccggtggt     960
gaccacctcc actccggcac cgtcgtcggc aaactggaag cgacaaagc ttcgaccttg    1020
ggctttgttg acttgatgcg cgaagaccac atcgaagctg accgcagccg tggggtcttc    1080
ttcacccaag attgggcgtc gatgccggc gtgctgccgg ttgcttccgg tggtatccac    1140
gtgtggcaca tgcccgcact ggtggaaatc ttcggtgatg actccgttct ccagttcggt    1200
ggcggcacct tgggtcaccc ctggggtaat gctcctggtg caaccgcgaa ccgtgttgcc    1260
ttggaagctt gcgtccaagc tcggaacgaa ggtcgcgacc tctaccgtga aggcggcgac    1320
atccttcgtg aagctggcaa gtggtcgcct gaactggctg ctgccctcga cctctggaaa    1380
gagatcaagt tcgaattcga aacgatggac aagctctaag gagcctctga ctatcgctgg    1440
gggagtgagc gttgctgcgt aaagctttct ccccagcctt tcgacttaac ctttcaggat    1500
ttctgaatca tgagcatgaa aactctgccc aaagagcgtc gtttcgagac tttctcgtac    1560
ctgcctcccc tcagcgatcg ccaaatcgct gcacaaatcg agtacatgat cgagcaaggc    1620
ttccaccct tgatcgagtt caacgagcac tcgaatccgg aagagttcta ctggacgatg    1680
tggaagctcc ccctgtttga ctgcaagagc cctcagcaag tcctcgatga agtgcgtgag    1740
tgccgcagcg aatacggtga ttgctacatc cgtgtcgctg gcttcgacaa catcaagcag    1800
tgccaaaccg tgagcttcat cgttcatcgt cccggccgat actaa                    1845
```

<210> SEQ ID NO 32
<211> LENGTH: 472
<212> TYPE: PRT
<213> ORGANISM: Artificial
<220> FEATURE:
<223> OTHER INFORMATION: Based on wild-type Synechococcus sp. PCC6301
    rbcLS translated sequence

```
<400> SEQUENCE: 32

Met Ala Lys Thr Gln Ser Ala Ala Gly Tyr Lys Ala Gly Val Lys Asp
1               5                   10                  15

Tyr Lys Leu Thr Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
65              70                  75                  80

Ala Tyr His Val Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
    210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
            260                 265                 270

Ala Asn Thr Thr Leu Ala Lys Trp Cys Arg Asp Asn Gly Val Leu Leu
        275                 280                 285

His Ile His Arg Ala Met His Ala Val Ile Asp Arg Gln Arg Asn His
    290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
                325                 330                 335

Ala Ser Thr Leu Gly Phe Val Asp Leu Met Arg Glu Asp His Ile Glu
            340                 345                 350

Ala Asp Arg Ser Arg Gly Val Phe Phe Thr Gln Asp Trp Ala Ser Met
        355                 360                 365

Pro Gly Val Leu Pro Val Ala Ser Gly Gly Ile His Val Trp His Met
    370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
                405                 410                 415
```

Asn Arg Val Ala Leu Glu Ala Cys Val Gln Ala Arg Asn Glu Gly Arg
            420                 425                 430

Asp Leu Tyr Arg Glu Gly Gly Asp Ile Leu Arg Glu Ala Gly Lys Trp
            435                 440                 445

Ser Pro Glu Leu Ala Ala Ala Leu Asp Leu Trp Lys Glu Ile Lys Phe
        450                 455                 460

Glu Phe Glu Thr Met Asp Lys Leu
465                 470

<210> SEQ ID NO 33
<211> LENGTH: 1845
<212> TYPE: DNA
<213> ORGANISM: Artificial
<220> FEATURE:
<223> OTHER INFORMATION: Based on wild-type Synechococcus sp. PCC6301
      rbcLS nucleotide sequence

<400> SEQUENCE: 33

| | | | |
|---|---|---|---|
| atggccaaga cgcaatctgc cgcaggctat aaggccgggg tgaaggacta caaactcacc | 60 |
| tattacaccc ccgattacac ccccaaagac actgacctgc tggcggcttt ccgcttcagc | 120 |
| cctcagccgg gtgtccctgc tgacgaagct agcgcggcga tcgcggctga atcttcgacc | 180 |
| ggtacctgga ccaccgtgtg gaccgacttg ctgaccgaca tggatcggta caaaggcaag | 240 |
| gcctaccacg tggagccggt gcaaggcgaa gagaactcct actttgcgtt catcgcttac | 300 |
| ccgctcgacc tgtttgaaga agggtcggtc accaacatcc tgacctcgat cgtcggtaac | 360 |
| gtgtttggct tcaaagctat ccgttcgctg cgtctggaag acatccgctt ccccgtcgcc | 420 |
| ttggtcaaaa ccttccaagg tcctccccac ggtatccaag tcgagcgcga cctgctgaac | 480 |
| aagtacggcc gtccgatgct gggttgcacg atcaaaccaa aactcggtct gtcggcgaaa | 540 |
| aactacggtc gtgccgtcta cgaatgtctg cgcggcggtc tggacttcac caaagacgac | 600 |
| gaaaacatca actcgcagcc gttccaacgc tggcgcgatc gcttcctgtt tgtggctgat | 660 |
| gcaatccaca atcgcaagc agaaaccggt gaaatcaaag tcactacct gaacgtgacc | 720 |
| gcgccgacct gcgaagaaat gatgaaacgg ctgagttcg ctaaagaact cggcatgccg | 780 |
| atcatcatgc atgacttctt gacggctggt ttcaccgcca acaccacctt ggcaaaatgg | 840 |
| tgccgcgaca acgcgtcct gctgcacatc accgtgcaa tgcacgcggt gatcgaccgt | 900 |
| cagcgtaacc acgggattca cttccgtgtc ttggccaagt gtttgcgtct gtccggtggt | 960 |
| gaccacctcc actccggcac cgtcgtcggc aaactggaag cgacaaagc ttcgaccttg | 1020 |
| ggctttgttg acttgatgcg cgaagaccac atcgaagctg accgcagccg tggggtcttc | 1080 |
| ttcacccaag attgggcgtc gatgccgggc gtgctgccgg ttgcttccgg tggtatccac | 1140 |
| gtgtggcaca tgcccgcact ggtggaaatc ttcggtgatg actccgttct ccagttcggt | 1200 |
| ggcggcacct gggtcacccc tgggggtaat gctcctggtg caaccgcgaa ccgtgttgcc | 1260 |
| ttggaagctt gcgtccaagc tcggaacgaa ggtcgcgacc tctaccgtga aggcggcgac | 1320 |
| atccttcgtg aagctggcaa gtggtcgcct gaactggctg ctgccctcga cctctggaaa | 1380 |
| gagatcaagt tcgaattcga aacgatggac aagctctaag gagcctctga ctatcgctgg | 1440 |
| gggagtgagc gttgctgcgt aaagctttct ccccagcctt cgacttaac ctttcaggat | 1500 |
| ttctgaatca tgagcatgaa aactctgccc aaagagcgtc gtttcgagac tttctcgtac | 1560 |
| ctgcctcccc tcagcgatcg ccaaatcgct gcacaaatcg agtacatgat cgagcaaggc | 1620 |
| ttccaccct tgatcgagtt caacgagcac tcgaatccgg aagagttcta ctggacgatg | 1680 |

-continued

```
tggaagctcc ccctgtttga ctgcaagagc cctcagcaag tcctcgatga agtgcgtgag    1740
tgccgcagcg aatacggtga ttgctacatc cgtgtcgctg gcttcgacaa catcaagcag    1800
tgccaaaccg tgagcttcat cgttcatcgt cccggccgat actaa                    1845
```

<210> SEQ ID NO 34
<211> LENGTH: 472
<212> TYPE: PRT
<213> ORGANISM: Artificial
<220> FEATURE:
<223> OTHER INFORMATION: Based on wild-type Synechococcus sp. PCC6301
      rbcLS translated sequence

<400> SEQUENCE: 34

```
Met Ala Lys Thr Gln Ser Ala Ala Gly Tyr Lys Ala Gly Val Lys Asp
1               5                   10                  15

Tyr Lys Leu Thr Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Ser Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
65                  70                  75                  80

Ala Tyr His Val Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
    210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
            260                 265                 270

Ala Asn Thr Thr Leu Ala Lys Trp Cys Arg Asp Asn Gly Val Leu Leu
        275                 280                 285

His Ile His Arg Ala Met His Ala Val Ile Asp Arg Gln Arg Asn His
    290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
```

```
                   325               330                335
Ala Ser Thr Leu Gly Phe Val Asp Leu Met Arg Glu Asp His Ile Glu
            340                345                350

Ala Asp Arg Ser Arg Gly Val Phe Phe Thr Gln Asp Trp Ala Ser Met
            355                360                365

Pro Gly Val Leu Pro Val Ala Ser Gly Gly Ile His Val Trp His Met
        370                375                380

Pro Ala Leu Val Glu Ile Phe Gly Asp Asp Ser Val Leu Gln Phe Gly
385                390                395                400

Gly Gly Thr Leu Gly His Pro Trp Gly Asn Ala Pro Gly Ala Thr Ala
                405                410                415

Asn Arg Val Ala Leu Glu Ala Cys Val Gln Ala Arg Asn Glu Gly Arg
                420                425                430

Asp Leu Tyr Arg Glu Gly Gly Asp Ile Leu Arg Glu Ala Gly Lys Trp
            435                440                445

Ser Pro Glu Leu Ala Ala Ala Leu Asp Leu Trp Lys Glu Ile Lys Phe
    450                455                460

Glu Phe Glu Thr Met Asp Lys Leu
465                470
```

<210> SEQ ID NO 35
<211> LENGTH: 1845
<212> TYPE: DNA
<213> ORGANISM: Artificial
<220> FEATURE:
<223> OTHER INFORMATION: Based on wild-type Synechococcus sp. PCC6301
      rbcLS nucleotide sequence

<400> SEQUENCE: 35

```
atggccaaga cgcaatctgc cgcaggctat aaggccgggg tgaaggacta caaactcggc     60
tattggaccc ccgattacac ccccaaagac actgacctgc tggcggcttt ccgcttcagc    120
cctcagccgg tgtccctgc tatcgaagct ggtgcggcga tcgcggctga atcttcgacc    180
ggtacctgga ccaccgtgtg gaccgacttg ctgaccgaca tggatcggta ccgcggcaag    240
tgctaccaca tcgagccggt gcaaggcgaa gagaactcct actttgcgtt catcgcttac    300
ccgctcgacc tgtttgaaga agggtcggtc accaacatcc tgacctcgat cgtcggtaac    360
gtgtttggct tcaaagctat ccgttcgctg cgtctggaag acatccgctt ccccgtcgcc    420
ttggtcaaaa ccttccaagg tcctcccac ggtatccaag tcgagcgcga cctgctgaac    480
aagtacggcc gtccgatgct gggttgcacg atcaaaccaa aactcggtct gtcggcgaaa    540
aactacggtc gtgccgtcta cgaatgtctg cgcggcggtc tggacttcac caaagacgac    600
gaaaacatca ctcgcagcc gttccaacgc tggcgcgatc gcttcctgtt tgtggctgat    660
gcaatccaca atcgcaagc agaaaccggt gaaatcaaag gtcactacct gaacgtgacc    720
gcgccgacct gcgaagaaat gatgaaacgg gctgagttcg ctaaagaact cggcatgccg    780
atcatcatgc atgacttctt gacggctggt ttcaccgcca acaccacctt ggcaaaatgg    840
tgccgcgaca cggcgtcct gctgcacatc accgtgcaa tgcacgcggt gatcgaccgt    900
cagcgtaacc acgggattca cttccgtgtc ttggccaagt gtttgcgtct gtccggtggt    960
gaccacctcc actccggcac cgtcgtcggc aaactggaag gcgacaaagc ttcgaccttg   1020
ggctttgttg acttgatgcg cgaagaccac atcgaagctg accgcagccg tgggtcttc   1080 ttcacccaag attgggcgtc gatgccgggc gtgctgccgg ttgcttccgg tggtatccac   1140
gtgtggcaca tgcccgcact ggtggaaatc ttcggtgatg actccgttct ccagttcggt   1200
```

```
ggcggcacct tgggtcaccc ctggggtaat gctcctggtg caaccgcgaa ccgtgttgcc    1260
ttggaagctt gcgtccaagc tcggaacgaa ggtcgcgacc tctaccgtga aggcggcgac    1320
atccttcgtg aagctggcaa gtggtcgcct gaactggctg ctgccctcga cctctggaaa    1380
gagatcaagt tcgaattcga acgatggaca agctctaag gagcctctga ctatcgctgg     1440
gggagtgagc gttgctgcgt aaagctttct ccccagcctt tcgacttaac ctttcaggat    1500
ttctgaatca tgagcatgaa aactctgccc aaagagcgtc gtttcgagac tttctcgtac    1560
ctgcctcccc tcagcgatcg ccaaatcgct gcacaaatcg agtacatgat cgagcaaggc    1620
ttccacccct tgatcgagtt caacgagcac tcgaatccgg aagagttcta ctggacgatg    1680
tggaagctcc ccctgtttga ctgcaagagc cctcagcaag tcctcgatga agtgcgtgag    1740
tgccgcagcg aataccggtga ttgctacatc cgtgtcgctg gcttcgacaa catcaagcag    1800
tgccaaaccg tgagcttcat cgttcatcgt cccggccgat actaa                    1845
```

<210> SEQ ID NO 36
<211> LENGTH: 472
<212> TYPE: PRT
<213> ORGANISM: Artificial
<220> FEATURE:
<223> OTHER INFORMATION: Based on wild-type Synechococcus sp. PCC6301
      rbcLS translated sequence

<400> SEQUENCE: 36

```
Met Ala Lys Thr Gln Ser Ala Ala Gly Tyr Lys Ala Gly Val Lys Asp
1               5                   10                  15

Tyr Lys Leu Gly Tyr Trp Thr Pro Asp Tyr Thr Pro Lys Asp Thr Asp
            20                  25                  30

Leu Leu Ala Ala Phe Arg Phe Ser Pro Gln Pro Gly Val Pro Ala Ile
        35                  40                  45

Glu Ala Gly Ala Ala Ile Ala Ala Glu Ser Ser Thr Gly Thr Trp Thr
    50                  55                  60

Thr Val Trp Thr Asp Leu Leu Thr Asp Met Asp Arg Tyr Arg Gly Lys
65                  70                  75                  80

Cys Tyr His Ile Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
    210                 215                 220

Ser Gln Ala Glu Thr Gly Glu Ile Lys Gly His Tyr Leu Asn Val Thr
225                 230                 235                 240
```

```
Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
            260                 265                 270

Ala Asn Thr Thr Leu Ala Lys Trp Cys Arg Asp Asn Gly Val Leu Leu
        275                 280                 285

His Ile His Arg Ala Met His Ala Val Ile Asp Arg Gln Arg Asn His
    290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
                325                 330                 335

Ala Ser Thr Leu Gly Phe Val Asp Leu Met Arg Glu Asp His Ile Glu
            340                 345                 350

Ala Asp Arg Ser Arg Gly Val Phe Phe Thr Gln Asp Trp Ala Ser Met
        355                 360                 365

Pro Gly Val Leu Pro Val Ala Ser Gly Gly Ile His Val Trp His Met
    370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
                405                 410                 415

Asn Arg Val Ala Leu Glu Ala Cys Val Gln Ala Arg Asn Glu Gly Arg
            420                 425                 430

Asp Leu Tyr Arg Glu Gly Gly Asp Ile Leu Arg Glu Ala Gly Lys Trp
        435                 440                 445

Ser Pro Glu Leu Ala Ala Ala Leu Asp Leu Trp Lys Glu Ile Lys Phe
    450                 455                 460

Glu Phe Glu Thr Met Asp Lys Leu
465                 470

<210> SEQ ID NO 37
<211> LENGTH: 1845
<212> TYPE: DNA
<213> ORGANISM: Artificial
<220> FEATURE:
<223> OTHER INFORMATION: Based on wild-type Synechococcus sp. PCC6301
      rbcLS nucleotide sequence

<400> SEQUENCE: 37
atggccaaga cgcaatctgc cgcaggctat aaggccgggg tgaaggacta caaactcacc      60
tattggaccc ccgattacac ccccaaagac actgacctgc tggcggcttt ccgcttcagc     120
cctcagccgg tgtccctgc tatcgaagct gcggcggcga tcgcggctga atcttcgacc      180
ggtacctgga ccaccgtgtg gaccgacttg ctgaccgaca tggatcggta caaaggcaag     240
gcctaccacg tggagccggt gcaaggcgaa gagaactcct actttgcgtt catcgcttac     300
ccgctcgacc tgtttgaaga agggtcggtc accaacatcc tgacctcgat cgtcggtaac     360
gtgtttggct tcaaagctat ccgttcgctg cgtctggaag acatccgctt ccccgtcgcc     420
ttggtcaaaa ccttccaagg tcctccccac ggtatccaag tcgagcgcga cctgctgaac     480
aagtacggcc gtccgatgct gggttgcacg atcaaaccaa aactcggtct gtcggcgaaa     540
aactacggtc gtgccgtcta cgaatgtctg cgcggcggtc tggacttcac caaagacgac     600
gaaaacatca actcgcagcc gttccaacgc tggcgcgatc gcttcctgtt tgtggctgat     660
gcaatccaca atcgcaagc agaaaccggt gaaatcaaag gtcactacct gaacgtgacc     720
```

-continued

```
gcgccgacct gcgaagaaat gatgaaacgg gctgagttcg ctaaagaact cggcatgccg      780
atcatcatgc atgacttctt gacggctggt ttcaccgcca acaccacctt ggcaaaatgg      840
tgccgcgaca acggcgtcct gctgcacatc caccgtgcaa tgcacgcggt gatcgaccgt      900
cagcgtaacc acgggattca cttccgtgtc ttggccaagt gtttgcgtct gtccggtggt      960
gaccacctcc actccggcac cgtcgtcggc aaactggaag cgacaaagc ttcgaccttg      1020 ggctttgttg acttgatgcg cgaagaccac atcgaagctg accgcagccg tggggtcttc      1080
ttcacccaag attgggcgtc gatgccgggc gtgctgccgg ttgcttccgg tggtatccac      1140
gtgtggcaca tgcccgcact ggtggaaatc ttcggtgatg actccgttct ccagttcggt      1200
ggcggcacct tgggtcaccc ctggggtaat gctcctggtg caaccgcgaa ccgtgttgcc      1260
ttggaagctt gcgtccaagc tcggaacgaa ggtcgcgacc tctaccgtga aggcggcgac      1320
atccttcgtg aagctggcaa gtggtcgcct gaactggctg ctgccctcga cctctggaaa      1380
gagatcaagt tcgaattcga aacgatggac aagctctaag gagcctctga ctatcgctgg      1440
gggagtgagc gttgctgcgt aaagctttct ccccagcctt tcgacttaac cttcaggat      1500 ttctgaatca tgagcatgaa aactctgccc aaagagcgtc gtttcgagac tttctcgtac      1560
ctgcctcccc tcagcgatcg ccaaatcgct gcacaaatcg agtacatgat cgagcaaggc      1620
ttccacccct tgatcgagtt caacgagcac tcgaatccgg aagagttcta ctggacgatg      1680
tggaagctcc ccctgtttga ctgcaagagc cctcagcaag tcctcgatga agtgcgtgag      1740
tgccgcagcg aatacggtga ttgctacatc cgtgtcgctg gcttcgacaa catcaagcag      1800
tgccaaaccg tgagcttcat cgttcatcgt cccggccgat actaa                      1845
```

<210> SEQ ID NO 38
<211> LENGTH: 472
<212> TYPE: PRT
<213> ORGANISM: Artificial
<220> FEATURE:
<223> OTHER INFORMATION: Based on wild-type Synechococcus sp. PCC6301
   rbcLS translated sequence

<400> SEQUENCE: 38

```
Met Ala Lys Thr Gln Ser Ala Ala Gly Tyr Lys Ala Gly Val Lys Asp
1               5                   10                  15

Tyr Lys Leu Thr Tyr Trp Thr Pro Asp Tyr Thr Pro Lys Asp Thr Asp
            20                  25                  30

Leu Leu Ala Ala Phe Arg Phe Ser Pro Gln Pro Gly Val Pro Ala Ile
        35                  40                  45

Glu Ala Ala Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
65                  70                  75                  80

Ala Tyr His Val Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140

Phe Gln Gly Pro Pro His Gly Ile Gln Val Glu Arg Asp Leu Leu Asn
145                 150                 155                 160
```

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
    210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
            260                 265                 270

Ala Asn Thr Thr Leu Ala Lys Trp Cys Arg Asp Asn Gly Val Leu Leu
        275                 280                 285

His Ile His Arg Ala Met His Ala Val Ile Asp Arg Gln Arg Asn His
    290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
                325                 330                 335

Ala Ser Thr Leu Gly Phe Val Asp Leu Met Arg Glu Asp His Ile Glu
            340                 345                 350

Ala Asp Arg Ser Arg Gly Val Phe Phe Thr Gln Asp Trp Ala Ser Met
        355                 360                 365

Pro Gly Val Leu Pro Val Ala Ser Gly Gly Ile His Val Trp His Met
    370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
                405                 410                 415

Asn Arg Val Ala Leu Glu Ala Cys Val Gln Ala Arg Asn Glu Gly Arg
            420                 425                 430

Asp Leu Tyr Arg Glu Gly Gly Asp Ile Leu Arg Glu Ala Gly Lys Trp
        435                 440                 445

Ser Pro Glu Leu Ala Ala Ala Leu Asp Leu Trp Lys Glu Ile Lys Phe
    450                 455                 460

Glu Phe Glu Thr Met Asp Lys Leu
465                 470

<210> SEQ ID NO 39
<211> LENGTH: 1845
<212> TYPE: DNA
<213> ORGANISM: Artificial
<220> FEATURE:
<223> OTHER INFORMATION: Based on wild-type Synechococcus sp. PCC6301
      rbcLS nucleotide sequence

<400> SEQUENCE: 39
atggccaaga cgcaatctgc cgcaggctat aaggccgggg tgaaggacta caaactcacc      60
tattggaccc ccgattacac ccccaaagac actgacctgc tggcggcttt ccgcttcagc     120
cctcagccgg tgtccctgc tatcgaagct agcgcggcga tcgcggctga atcttcgacc      180
ggtacctgga ccaccgtgtg gaccgacttg ctgaccgaca tggatcggta caaaggcaag     240

```
gcctaccacg tggagccggt gcaaggcgaa gagaactcct actttgcgtt catcgcttac    300
ccgctcgacc tgtttgaaga agggtcggtc accaacatcc tgacctcgat cgtcggtaac    360
gtgtttggct tcaaagctat ccgttcgctg cgtctggaag acatccgctt ccccgtcgcc    420
ttggtcaaaa ccttccaagg tcctccccac ggtatccaag tcgagcgcga cctgctgaac    480
aagtacggcc gtccgatgct gggttgcacg atcaaaccaa aactcggtct gtcggcgaaa    540
aactacggtc gtgccgtcta cgaatgtctg cgcggcggtc tggacttcac caaagacgac    600
gaaaacatca actcgcagcc gttccaacgc tggcgcgatc gcttcctgtt tgtggctgat    660
gcaatccaca aatcgcaagc agaaaccggt gaaatcaaag tcactacct gaacgtgacc    720
gcgccgacct gcgaagaaat gatgaaacgg gctgagttcg ctaaagaact cggcatgccg    780
atcatcatgc atgacttctt gacggctggt tcaccgcca acaccaccct tggcaaaatgg    840
tgccgcgaca acggcgtcct gctgcacatc caccgtgcaa tgcacgcggt gatcgaccgt    900
cagcgtaacc acgggattca cttccgtgtc ttggccaagt gtttgcgtct gtccggtggt    960
gaccacctcc actccggcac cgtcgtcggc aaactggaag cgacaaagc ttcgaccttg   1020
ggctttgttg acttgatgcg cgaagaccac atcgaagctg accgcagccg tggggtcttc   1080
ttcacccaag attgggcgtc gatgccgggc gtgctgccgg ttgcttccgg tggtatccac   1140
gtgtggcaca tgcccgcact ggtggaaatc ttcggtgatg actccgttct ccagttcggt   1200
ggcggcacct tgggtcaccc ctggggtaat gctcctggtg caaccgcgaa ccgtgttgcc   1260
ttggaagctt gcgtccaagc tcggaacgaa ggtcgcgacc tctaccgtga aggcggcgac   1320
atccttcgtg aagctggcaa gtggtcgcct gaactggctg ctgccctcga cctctggaaa   1380
gagatcaagt cgaattcga acgatggac aagctctaag gagcctctga ctatcgctgg   1440
gggagtgagc gttgctgcgt aaagctttct ccccagcctt tcgacttaac ctttcaggat   1500
ttctgaatca tgagcatgaa aactctgccc aaagagcgtc gtttcgagac tttctcgtac   1560
ctgcctcccc tcagcgatcg ccaaatcgct gcacaaatcg agtacatgat cgagcaaggc   1620
ttccacccct tgatcgagtt caacgagcac tcgaatccgg aagagttcta ctggacgatg   1680
tggaagctcc ccctgtttga ctgcaagagc cctcagcaag tcctcgatga agtgcgtgag   1740
tgccgcagcg aatacggtga ttgctacatc cgtgtcgctg gcttcgacaa catcaagcag   1800
tgccaaaccg tgagcttcat cgttcatcgt cccggccgat actaa                   1845
```

<210> SEQ ID NO 40
<211> LENGTH: 472
<212> TYPE: PRT
<213> ORGANISM: Artificial
<220> FEATURE:
<223> OTHER INFORMATION: Based on wild-type Synechococcus sp. PCC6301
      rbcLS translated sequence

<400> SEQUENCE: 40

Met Ala Lys Thr Gln Ser Ala Ala Gly Tyr Lys Ala Gly Val Lys Asp
1               5                   10                  15

Tyr Lys Leu Thr Tyr Trp Thr Pro Asp Tyr Thr Pro Lys Asp Thr Asp
                20                  25                  30

Leu Leu Ala Ala Phe Arg Phe Ser Pro Gln Pro Gly Val Pro Ala Ile
            35                  40                  45

Glu Ala Ser Ala Ala Ile Ala Ala Glu Ser Ser Thr Gly Thr Trp Thr
        50                  55                  60

Thr Val Trp Thr Asp Leu Leu Thr Asp Met Asp Arg Tyr Lys Gly Lys

```
            65                  70                  75                  80
Ala Tyr His Val Glu Pro Val Gln Gly Glu Glu Asn Ser Tyr Phe Ala
                85                  90                  95
Phe Ile Ala Tyr Pro Leu Asp Leu Phe Glu Glu Gly Ser Val Thr Asn
               100                 105                 110
Ile Leu Thr Ser Ile Val Gly Asn Val Phe Gly Phe Lys Ala Ile Arg
               115                 120                 125
Ser Leu Arg Leu Glu Asp Ile Arg Phe Pro Val Ala Leu Val Lys Thr
130                 135                 140
Phe Gln Gly Pro Pro His Gly Ile Gln Val Glu Arg Asp Leu Leu Asn
145                 150                 155                 160
Lys Tyr Gly Arg Pro Met Leu Gly Cys Thr Ile Lys Pro Lys Leu Gly
                165                 170                 175
Leu Ser Ala Lys Asn Tyr Gly Arg Ala Val Tyr Glu Cys Leu Arg Gly
                180                 185                 190
Gly Leu Asp Phe Thr Lys Asp Asp Glu Asn Ile Asn Ser Gln Pro Phe
                195                 200                 205
Gln Arg Trp Arg Asp Arg Phe Leu Phe Val Ala Asp Ala Ile His Lys
                210                 215                 220
Ser Gln Ala Glu Thr Gly Glu Ile Lys Gly His Tyr Leu Asn Val Thr
225                 230                 235                 240
Ala Pro Thr Cys Glu Glu Met Met Lys Arg Ala Glu Phe Ala Lys Glu
                245                 250                 255
Leu Gly Met Pro Ile Ile Met His Asp Phe Leu Thr Ala Gly Phe Thr
                260                 265                 270
Ala Asn Thr Thr Leu Ala Lys Trp Cys Arg Asp Asn Gly Val Leu Leu
                275                 280                 285
His Ile His Arg Ala Met His Ala Val Ile Asp Arg Gln Arg Asn His
                290                 295                 300
Gly Ile His Phe Arg Val Leu Ala Lys Cys Leu Arg Leu Ser Gly Gly
305                 310                 315                 320
Asp His Leu His Ser Gly Thr Val Val Gly Lys Leu Glu Gly Asp Lys
                325                 330                 335
Ala Ser Thr Leu Gly Phe Val Asp Leu Met Arg Glu Asp His Ile Glu
                340                 345                 350
Ala Asp Arg Ser Arg Gly Val Phe Phe Thr Gln Asp Trp Ala Ser Met
                355                 360                 365
Pro Gly Val Leu Pro Val Ala Ser Gly Gly Ile His Val Trp His Met
370                 375                 380
Pro Ala Leu Val Glu Ile Phe Gly Asp Asp Ser Val Leu Gln Phe Gly
385                 390                 395                 400
Gly Gly Thr Leu Gly His Pro Trp Gly Asn Ala Pro Gly Ala Thr Ala
                405                 410                 415
Asn Arg Val Ala Leu Glu Ala Cys Val Gln Ala Arg Asn Glu Gly Arg
                420                 425                 430
Asp Leu Tyr Arg Glu Gly Gly Asp Ile Leu Arg Glu Ala Gly Lys Trp
                435                 440                 445
Ser Pro Glu Leu Ala Ala Ala Leu Asp Leu Trp Lys Glu Ile Lys Phe
                450                 455                 460
Glu Phe Glu Thr Met Asp Lys Leu
465                 470

<210> SEQ ID NO 41
```

<211> LENGTH: 1845
<212> TYPE: DNA
<213> ORGANISM: Artificial
<220> FEATURE:
<223> OTHER INFORMATION: Based on wild-type Synechococcus sp. PCC6301
      rbcLS nucleotide sequence

<400> SEQUENCE: 41

```
atggccaaga cgcaatctgc cgcaggctat aaggccgggg tgaaggacta caaactcacc     60
tattggaccc ccgattacac ccccaaagac actgacctgc tggcggcttt ccgcttcagc    120
cctcagccgg tgtccctgc tgtcgaagct gcggcggcga tcgcggctga atcttcgacc    180
ggtacctgga ccaccgtgtg gaccgacttg ctgaccgaca tggatcggta caaaggcaag    240
gcctaccacg tggagccggt gcaaggcgaa gagaactcct actttgcgtt catcgcttac    300
ccgctcgacc tgtttgaaga gggtcggtc accaacatcc tgacctcgat cgtcggtaac    360
gtgtttggct tcaaagctat ccgttcgctg cgtctggaag acatccgctt ccccgtcgcc    420
ttggtcaaaa ccttccaagg tcctccccac ggtatccaag tcgagcgcga cctgctgaac    480
aagtacggcc gtccgatgct gggttgcacg atcaaaccaa aactcggtct gtcggcgaaa    540
aactacggtc gtgccgtcta cgaatgtctg cgcggcggtc tggacttcac caaagacgac    600
gaaaacatca actcgcagcc gttccaacgc tggcgcgatc gcttcctgtt tgtggctgat    660
gcaatccaca atcgcaagc agaaaccggt gaaatcaaag tcactacct gaacgtgacc    720
gcgccgacct gcgaagaaat gatgaaacgg gctgagttcg ctaaagaact cggcatgccg    780
atcatcatgc atgacttctt gacggctggt ttcaccgcca acaccacctt ggcaaaatgg    840
tgccgcgaca cggcgtcct gctgcacatc caccgtgcaa tgcacgcggt gatcgaccgt    900
cagcgtaacc acgggattca cttccgtgtc ttggccaagt gtttgcgtct gtccggtggt    960
gaccacctcc actccggcac cgtcgtcggc aaactggaag cgacaaagc ttcgaccttg   1020
ggctttgttg acttgatgcg cgaagaccac atcgaagctg accgcagccg tggggtcttc   1080
ttcacccaag attgggcgtc gatgccgggc gtgctgccgg ttgcttccgg tggtatccac   1140
gtgtggcaca tgcccgcact ggtggaaatc ttcggtgatg actccgttct ccagttcggt   1200
ggcggcacct gggtcaccc ctggggtaat gctcctggtg caaccgcgaa ccgtgttgcc   1260
ttggaagctt gcgtccaagc tcggaacgaa ggtcgcgacc tctaccgtga aggcggcgac   1320
atccttcgtg aagctggcaa gtggtcgcct gaactggctg ctgccctcga cctctggaaa   1380
gagatcaagt cgaattcga acgatggac aagctctaag gagcctctga ctatcgctgg   1440
gggagtgagc gttgctgcgt aaagctttct ccccagcctt tcgacttaac ctttcaggat   1500
ttctgaatca tgagcatgaa aactctgccc aaagagcgtc gtttcgagac tttctcgtac   1560
ctgcctcccc tcagcgatcg ccaaatcgct gcacaaatcg agtacatgat cgagcaaggc   1620
ttccaccct tgatcgagtt caacgagcac tcgaatccgg aagagttcta ctggacgatg   1680
tggaagctcc ccctgtttga ctgcaagagc cctcagcaag tcctcgatga agtgcgtgag   1740
tgccgcagcg aatacggtga ttgctacatc cgtgtcgctg gcttcgacaa catcaagcag   1800
tgccaaaccg tgagcttcat cgttcatcgt cccggccgat actaa                   1845
```

<210> SEQ ID NO 42
<211> LENGTH: 472
<212> TYPE: PRT
<213> ORGANISM: Artificial
<220> FEATURE:
<223> OTHER INFORMATION: Based on wild-type Synechococcus sp. PCC6301
      rbcLS translated sequence

<400> SEQUENCE: 42

```
Met Ala Lys Thr Gln Ser Ala Ala Gly Tyr Lys Ala Gly Val Lys Asp
1               5                   10                  15

Tyr Lys Leu Thr Tyr Trp Thr Pro Asp Tyr Thr Pro Lys Asp Thr Asp
            20                  25                  30

Leu Leu Ala Ala Phe Arg Phe Ser Pro Gln Pro Gly Val Pro Ala Val
            35                  40                  45

Glu Ala Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
65                  70                  75                  80

Ala Tyr His Val Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
            260                 265                 270

Ala Asn Thr Thr Leu Ala Lys Trp Cys Arg Asp Asn Gly Val Leu Leu
        275                 280                 285

His Ile His Arg Ala Met His Ala Val Ile Asp Arg Gln Arg Asn His
290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
                325                 330                 335

Ala Ser Thr Leu Gly Phe Val Asp Leu Met Arg Glu Asp His Ile Glu
            340                 345                 350

Ala Asp Arg Ser Arg Gly Val Phe Phe Thr Gln Asp Trp Ala Ser Met
        355                 360                 365

Pro Gly Val Leu Pro Val Ala Ser Gly Gly Ile His Val Trp His Met
370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
```

Asn Arg Val Ala Leu Glu Ala Cys Val Gln Ala Arg Asn Glu Gly Arg
        420                 425                 430

Asp Leu Tyr Arg Glu Gly Gly Asp Ile Leu Arg Glu Ala Gly Lys Trp
    435                 440                 445

Ser Pro Glu Leu Ala Ala Ala Leu Asp Leu Trp Lys Glu Ile Lys Phe
450                 455                 460

Glu Phe Glu Thr Met Asp Lys Leu
465                 470

<210> SEQ ID NO 43
<211> LENGTH: 1845
<212> TYPE: DNA
<213> ORGANISM: Artificial
<220> FEATURE:
<223> OTHER INFORMATION: Based on wild-type Synechococcus sp. PCC6301
      rbcLS nucleotide sequence

<400> SEQUENCE: 43

| | | | | | |
|---|---|---|---|---|---|
| atggccaaga | cgcaatctgc | cgcaggctat | aaggccgggg | tgaaggacta | caaactcacc | 60 |
| tattcacccc | ccgattacac | ccccaaagac | actgacctgc | tggcggcttt | ccgcttcagc | 120 |
| cctcagccgg | tgtccctgc | tgacgaagct | ggtgcggcga | tcgcggctga | atcttcgacc | 180 |
| ggtacctgga | ccaccgtgtg | gaccgacttg | ctgaccgaca | tggatcggta | caaaggcaag | 240 |
| tgctaccaca | tcgagccggt | gcaaggcgaa | gagaactcct | actttgcgtt | catcgcttac | 300 |
| ccgctcgacc | tgtttgaaga | agggtcggtc | accaacatcc | tgacctcgat | catcggtaat | 360 |
| gtgtttggct | tcaaagctat | ccgttcgctg | cgtctggaag | acatccgctt | ccccgtcgcc | 420 |
| ttggtcaaaa | ccttccaagg | tcctccccac | ggtatccaag | tcgagcgcga | cctgctgaac | 480 |
| aagtacggcc | gtccgatgct | gggttgcacg | atcaaaccaa | aactcggtct | gtcggcgaaa | 540 |
| aactacggtc | gtgccgtcta | cgaatgtctg | cgcggcggtc | tggacttcac | caaagacgac | 600 |
| gaaaacatca | actcgcagcc | gttccaacgc | tggcgcgatc | gcttcctgtt | tgtggctgat | 660 |
| gcaatccaca | atcgcaagc | agaaaccggt | gaaatcaaag | tcactacct | gaacgtgacc | 720 |
| gcgccgacct | gcgaagaaat | gatgaaacgg | gctgagttcg | ctaaagaact | cggcatgccg | 780 |
| atcatcatgc | atgacttctt | gacggctggt | ttcaccgcca | acaccacctt | ggcaaaatgg | 840 |
| tgccgcgaca | acggcgtcct | gctgcacatc | caccgtgcag | ggcacgcgac | gatcgaccgt | 900 |
| cagcgtaacc | acgggattca | cttccgtgtc | ttggccaagt | gtttgcgtct | gtccggtggt | 960 |
| gaccacctcc | actccggcac | cgtcgtcggc | aaactggaag | cgacaaagc | ttcgaccttg | 1020 |
| ggctttgttg | acttgatgcg | cgaagaccac | atcgaagctg | accgcagccg | tggggtcttc | 1080 |
| ttcacccaag | attgggcgtc | gatgccgggc | gtgctgccgg | ttgcttccgg | tggtatccac | 1140 |
| gtgtggcaca | tgcccgcact | ggtggaaatc | ttccgtgatg | actccgttct | ccagttcggt | 1200 |
| ggcggcaccc | tgggtcaccc | ctgggggtaat | gctcctggtg | caaccgcgaa | ccgtgttgcc | 1260 |
| ttggaagctt | gcgtccaagc | tcggaacgaa | ggtcgcgacc | tctaccgtga | aggcggcgac | 1320 |
| atccttcgtg | aagctggcaa | gtggtcgcct | gaactggctg | ctgccctcga | cctctggaaa | 1380 |
| gagatcaagt | tcgaattcga | aacgatggac | aagctctaag | gagcctctga | ctatcgctgg | 1440 |
| gggagtgagc | gttgctgcgt | aaagctttct | ccccagcctt | tcgacttaac | ctttcaggat | 1500 |
| ttctgaatca | tgagcatgaa | aactctgccc | aaagagcgtc | gtttcgagac | tttctcgtac | 1560 |
| ctgcctcccc | tcagcgatcg | ccaaatcgct | gcacaaatcg | agtacatgat | cgagcaaggc | 1620 |

```
ttccacccct tgatcgagtt caacgagcac tcgaatccgg aagagttcta ctggacgatg      1680
tggaagctcc ccctgtttga ctgcaagagc cctcagcaag tcctcgatga agtgcgtgag      1740
tgccgcagcg aatacggtga ttgctacatc cgtgtcgctg gcttcgacaa catcaagcag      1800
tgccaaaccg tgagcttcat cgttcatcgt cccggccgat actaa                     1845
```

<210> SEQ ID NO 44
<211> LENGTH: 472
<212> TYPE: PRT
<213> ORGANISM: Artificial
<220> FEATURE:
<223> OTHER INFORMATION: Based on wild-type Synechococcus sp. PCC6301
      rbcLS translated sequence

<400> SEQUENCE: 44

```
Met Ala Lys Thr Gln Ser Ala Ala Gly Tyr Lys Ala Gly Val Lys Asp
1               5                   10                  15

Tyr Lys Leu Thr Tyr Tyr Thr Pro Asp Tyr Thr Pro Lys Asp Thr Asp
                20                  25                  30

Leu Leu Ala Ala Phe Arg Phe Ser Pro Gln Pro Gly Val Pro Ala Asp
            35                  40                  45

Glu Ala Gly Ala Ala Ile Ala Ala Glu Ser Ser Thr Gly Thr Trp Thr
        50                  55                  60

Thr Val Trp Thr Asp Leu Leu Thr Asp Met Asp Arg Tyr Lys Gly Lys
65                  70                  75                  80

Cys Tyr His Ile Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Ile Gly Asn Val Phe Gly Phe Lys Ala Ile Arg
        115                 120                 125

Ser Leu Arg Leu Glu Asp Ile Arg Phe Pro Val Ala Leu Val Lys Thr
130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
    210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
            260                 265                 270

Ala Asn Thr Thr Leu Ala Lys Trp Cys Arg Asp Asn Gly Val Leu Leu
        275                 280                 285

His Ile His Arg Ala Gly His Ala Thr Ile Asp Arg Gln Arg Asn His
    290                 295                 300

Gly Ile His Phe Arg Val Leu Ala Lys Cys Leu Arg Leu Ser Gly Gly
305                 310                 315                 320
```

```
Asp His Leu His Ser Gly Thr Val Val Gly Lys Leu Glu Gly Asp Lys
              325                 330                 335

Ala Ser Thr Leu Gly Phe Val Asp Leu Met Arg Glu Asp His Ile Glu
        340                 345                 350

Ala Asp Arg Ser Arg Gly Val Phe Phe Thr Gln Asp Trp Ala Ser Met
    355                 360                 365

Pro Gly Val Leu Pro Val Ala Ser Gly Gly Ile His Val Trp His Met
370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
                405                 410                 415

Asn Arg Val Ala Leu Glu Ala Cys Val Gln Ala Arg Asn Glu Gly Arg
            420                 425                 430

Asp Leu Tyr Arg Glu Gly Gly Asp Ile Leu Arg Glu Ala Gly Lys Trp
        435                 440                 445

Ser Pro Glu Leu Ala Ala Ala Leu Asp Leu Trp Lys Glu Ile Lys Phe
    450                 455                 460

Glu Phe Glu Thr Met Asp Lys Leu
465                 470

<210> SEQ ID NO 45
<211> LENGTH: 1845
<212> TYPE: DNA
<213> ORGANISM: Artificial
<220> FEATURE:
<223> OTHER INFORMATION: Based on wild-type Synechococcus sp. PCC6301
      rbcLS nucleotide sequence

<400> SEQUENCE: 45
atggccaaga cgcaatctgc cgcaggctat aaggccgggg tgaaggacta caaactcacc        60 tattcaccc ccgattacac ccccaaagac actgacatac tggcggcttt ccgcttcagc       120
cctcagccgg gtgtccctgc tgacgaagct ggtgcggcga tcgcggctga atcttcgacc       180
ggtacctgga ccaccgtgtg gaccgacttg ctgaccgaca tggatcggta caaaggcaag       240
tgctaccaca tcgagccggt gcaaggcgaa gagaactcct actttgcgtt catcgcttac       300
ccgctcgacc tgtttgaaga agggtcggtc accaacctcc tgacctcgat cgtcggtaac       360
gtgtttggct tcaaagctat ccgttcgctg cgtctggaag acatccgctt gcccgtcgcc       420
ttggtcaaaa ccttccaagg tcctccccac ggtatccaag tcgagcgcga cctgctgaac       480
aagtacggcc gtccgatgct gggttgcacg atcaaaccaa aactcggtct gtcggcgaaa       540
aactacggtc gtgccgtcta cgaatgtctg cgcggcggtc tggacttcac caaagacgac       600
gaaaacatca actcgcagcc gttccaacgc tggcgcgatc gcttcctgtt tgtggctgat       660
gcaatccaca atcgcaagc agaaaccggt gaaatcaaag tcactacct gaacgtgacc       720 gcgccgacct gcgaagaaat gatgaaacgg gctgagttcg ctaaagaact cggcatgccg       780
atcatcatgc atgacttctt gacggctggt ttcaccgcca acaccacctt ggcaaaatgg       840
tgccgcgaca acggcgtcct gctgcacatc caccgtgcaa tgcacgcggt gatcgaccgt       900
cagcgtaacc acgggattca cttccgtgtc ttggccaagt gtttgcgtct gtccggtggt       960
gaccacctcc actccggcac cgtcgtcggc aaactggaag cgacaaagc ttcgaccttg      1020 ggctttgttg acttgatgcg cgaagaccac atcgaagctg accgcagccg tggggtcttc      1080
ttcacccaag attgggcgtc gatgccgggc gtgctgccgg ttgcttccgg tggtatccac      1140
```

```
gtgtggcaca tgcccgcact ggtggaaatc ttcggtgatg actccgttct ccagttcggt    1200
ggcggcacct tgggtcaccc ctggggtaat gctcctggtg caaccgcgaa ccgtgttgcc    1260
ttggaagctt gcgtccaagc tcggaacgaa ggtcgcgacc tctaccgtga aggcggcgac    1320
atccttcgtg aagctggcaa gtggtcgcct gaactggctg ctgccctcga cctctggaaa    1380
gagatcaagt tcgaattcga aacgatggac aagctctaag gagcctctga ctatcgctgg    1440
gggagtgagc gttgctgcgt aaagctttct ccccagcctt tcgacttaac ctttcaggat    1500
ttctgaatca tgagcatgaa actctgcccc aaagagcgtc gtttcgagac tttctcgtac    1560
ctgcctcccc tcagcgatcg ccaaatcgct gcacaaatcg agtacatgat cgagcaaggc    1620
ttccacccct tgatcgagtt caacgagcac tcgaatccgg aagagttcta ctggacgatg    1680
tggaagctcc ccctgtttga ctgcaagagc cctcagcaag tcctcgatga agtgcgtgag    1740
tgccgcagcg aatacggtga ttgctacatc cgtgtcgctg gcttcgacaa catcaagcag    1800
tgccaaaccg tgagcttcat cgttcatcgt cccggccgat actaa                    1845
```

<210> SEQ ID NO 46
<211> LENGTH: 472
<212> TYPE: PRT
<213> ORGANISM: Artificial
<220> FEATURE:
<223> OTHER INFORMATION: Based on wild-type Synechococcus sp. PCC6301 rbcLS translated sequence

<400> SEQUENCE: 46

```
Met Ala Lys Thr Gln Ser Ala Ala Gly Tyr Lys Ala Gly Val Lys Asp
1               5                   10                  15

Tyr Lys Leu Thr Tyr Tyr Thr Pro Asp Tyr Thr Pro Lys Asp Thr Asp
                20                  25                  30

Ile Leu Ala Ala Phe Arg Phe Ser Pro Gln Pro Gly Val Pro Ala Asp
            35                  40                  45

Glu Ala Gly Ala Ala Ile Ala Ala Glu Ser Ser Thr Gly Thr Trp Thr
        50                  55                  60

Thr Val Trp Thr Asp Leu Leu Thr Asp Met Asp Arg Tyr Lys Gly Lys
65                  70                  75                  80

Cys Tyr His Ile Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Leu Leu Thr Ser Ile Val Gly Asn Val Phe Gly Phe Lys Ala Ile Arg
        115                 120                 125

Ser Leu Arg Leu Glu Asp Ile Arg Leu Pro Val Ala Leu Val Lys Thr
    130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
    210                 215                 220

Ser Gln Ala Glu Thr Gly Glu Ile Lys Gly His Tyr Leu Asn Val Thr
225                 230                 235                 240
```

```
Ala Pro Thr Cys Glu Glu Met Met Lys Arg Ala Glu Phe Ala Lys Glu
            245                 250                 255
Leu Gly Met Pro Ile Ile Met His Asp Phe Leu Thr Ala Gly Phe Thr
        260                 265                 270
Ala Asn Thr Thr Leu Ala Lys Trp Cys Arg Asp Asn Gly Val Leu Leu
            275                 280                 285
His Ile His Arg Ala Met His Ala Val Ile Asp Arg Gln Arg Asn His
        290                 295                 300
Gly Ile His Phe Arg Val Leu Ala Lys Cys Leu Arg Leu Ser Gly Gly
305                 310                 315                 320
Asp His Leu His Ser Gly Thr Val Val Gly Lys Leu Glu Gly Asp Lys
            325                 330                 335
Ala Ser Thr Leu Gly Phe Val Asp Leu Met Arg Glu Asp His Ile Glu
        340                 345                 350
Ala Asp Arg Ser Arg Gly Val Phe Phe Thr Gln Asp Trp Ala Ser Met
            355                 360                 365
Pro Gly Val Leu Pro Val Ala Ser Gly Gly Ile His Val Trp His Met
        370                 375                 380
Pro Ala Leu Val Glu Ile Phe Gly Asp Asp Ser Val Leu Gln Phe Gly
385                 390                 395                 400
Gly Gly Thr Leu Gly His Pro Trp Gly Asn Ala Pro Gly Ala Thr Ala
            405                 410                 415
Asn Arg Val Ala Leu Glu Ala Cys Val Gln Ala Arg Asn Glu Gly Arg
        420                 425                 430
Asp Leu Tyr Arg Glu Gly Gly Asp Ile Leu Arg Glu Ala Gly Lys Trp
            435                 440                 445
Ser Pro Glu Leu Ala Ala Ala Leu Asp Leu Trp Lys Glu Ile Lys Phe
        450                 455                 460
Glu Phe Glu Thr Met Asp Lys Leu
465                 470

<210> SEQ ID NO 47
<211> LENGTH: 1845
<212> TYPE: DNA
<213> ORGANISM: Artificial
<220> FEATURE:
<223> OTHER INFORMATION: Based on wild-type Synechococcus sp. PCC6301
      rbcLS nucleotide sequence

<400> SEQUENCE: 47
atggccaaga cgcaatctgc cgcaggctat aaggccgggg tgaaggacta caaactcacc      60
tattcacccc ccgattacac ccccaaagac actgacatac tggcggcttt ccgcttcagc     120
cctcagccgg tgtccctgc tgacgaagct ggtgcggcga tcgcggctga atcttcgacc     180
ggtacctgga ccaccgtgtg gaccgacttg ctgaccgaca tggatcggta caaaggcaag     240
tgctaccaca tcgagccggt gcaaggcgaa gagaactcct actttgcgtt catcgcttac     300
ccgctcgacc tgtttgaaga agggtcggtc accaacctcc tgacctcgat catcggtaac     360
gtgtttggct tcaaagctat ccgttcgctg cgtctggaag acatccgctt gcccgtcgcc     420
ttggtcaaaa ccttccaagg tcctcccac ggtatccaag tcgagcgcga cctgctgaac     480
aagtacggcc gtccgatgct gggttgcacg atcaaaccaa aactcggtct gtcggcgaaa     540
aactacggtc gtgccgtcta cgaatgtctg cgcggcggtc tggacttcac caaagacgac     600
gaaaacatca actcgcagcc gttccaacgc tggcgcgatc gcttcctgtt tgtggctgat     660
```

-continued

```
gcaatccaca aatcgcaagc agaaaccggt gaaatcaaag gtcactacct gaacgtgacc    720
gcgccgacct gcgaagaaat gatgaaacgg gctgagttcg ctaaagaact cggcatgccg    780
atcatcatgc atgacttctt gacggctggt ttcaccgcca acaccacctt ggcaaaatgg    840
tgccgcgaca acggcgtcct gctgcacatc caccgtgcag ggcacgcgac gatcgaccgt    900
cagcgtaacc acgggattca cttccgtgtc ttggccaagt gtttgcgtct gtccggtggt    960
gaccacctcc actccggcac cgtcgtcggc aaactggaag cgacaaagc ttcgaccttg   1020 ggctttgttg acttgatgcg cgaagaccac atcgaagctg accgcagccg tggggtcttc   1080
ttcacccaag attgggcgtc gatgccgggc gtgctgccgg ttgcttccgg tggtatccac   1140
gtgtggcaca tgcccgcact ggtggaaatc ttcggtgatg actccgttct ccagttcggt   1200
ggcggcacct gggtcaccc ctggggtaat gctcctggtg caaccgcgaa ccgtgttgcc   1260
ttggaagctt gcgtccaagc tcggaacgaa ggtcgcgacc tctaccgtga aggcggcgac   1320
atccttcgtg aagctggcaa gtggtcgcct gaactggctg ctgccctcga cctctggaaa   1380
gagatcaagt tcgaattcga aacgatggac aagctctaag gagcctctga ctatcgctgg   1440
gggagtgagc gttgctgcgt aaagctttct ccccagcctt tcgacttaac ctttcaggat   1500
ttctgaatca tgagcatgaa aactctgccc aaagagcgtc gtttcgagac tttctcgtac   1560
ctgcctcccc tcagcgatcg ccaaatcgct gcacaaatcg agtacatgat cgagcaaggc   1620
ttccacccct tgatcgagtt caacgagcac tcgaatccgg aagagttcta ctggacgatg   1680
tggaagctcc ccctgtttga ctgcaagagc cctcagcaag tcctcgatga agtgcgtgag   1740
tgccgcagcg aataccggtga ttgctacatc cgtgtcgctg gcttcgacaa catcaagcag   1800
tgccaaaccg tgagcttcat cgttcatcgt cccggccgat actaa                   1845
```

<210> SEQ ID NO 48
<211> LENGTH: 472
<212> TYPE: PRT
<213> ORGANISM: Artificial
<220> FEATURE:
<223> OTHER INFORMATION: Based on wild-type Synechococcus sp. PCC6301
      rbcLS translated sequence

<400> SEQUENCE: 48

```
Met Ala Lys Thr Gln Ser Ala Ala Gly Tyr Lys Ala Gly Val Lys Asp
1               5                   10                  15

Tyr Lys Leu Thr Tyr Tyr Thr Pro Asp Tyr Thr Pro Lys Asp Thr Asp
                20                  25                  30

Ile Leu Ala Ala Phe Arg Phe Ser Pro Gln Pro Gly Val Pro Ala Asp
            35                  40                  45

Glu Ala Gly Ala Ala Ile Ala Ala Glu Ser Ser Thr Gly Thr Trp Thr
        50                  55                  60

Thr Val Trp Thr Asp Leu Leu Thr Asp Met Asp Arg Tyr Lys Gly Lys
65                  70                  75                  80

Cys Tyr His Ile Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Leu Leu Thr Ser Ile Ile Gly Asn Val Phe Gly Phe Lys Ala Ile Arg
        115                 120                 125

Ser Leu Arg Leu Glu Asp Ile Arg Leu Pro Val Ala Leu Val Lys Thr
    130                 135                 140

Phe Gln Gly Pro Pro His Gly Ile Gln Val Glu Arg Asp Leu Leu Asn
```

```
145                 150                 155                 160
Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
    210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
            260                 265                 270

Ala Asn Thr Thr Leu Ala Lys Trp Cys Arg Asp Asn Gly Val Leu Leu
        275                 280                 285

His Ile His Arg Ala Gly His Ala Thr Ile Asp Arg Gln Arg Asn His
    290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
                325                 330                 335

Ala Ser Thr Leu Gly Phe Val Asp Leu Met Arg Glu Asp His Ile Glu
            340                 345                 350

Ala Asp Arg Ser Arg Gly Val Phe Phe Thr Gln Asp Trp Ala Ser Met
        355                 360                 365

Pro Gly Val Leu Pro Val Ala Ser Gly Gly Ile His Val Trp His Met
    370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
                405                 410                 415

Asn Arg Val Ala Leu Glu Ala Cys Val Gln Ala Arg Asn Glu Gly Arg
            420                 425                 430

Asp Leu Tyr Arg Glu Gly Gly Asp Ile Leu Arg Glu Ala Gly Lys Trp
        435                 440                 445

Ser Pro Glu Leu Ala Ala Ala Leu Asp Leu Trp Lys Glu Ile Lys Phe
    450                 455                 460

Glu Phe Glu Thr Met Asp Lys Leu
465                 470

<210> SEQ ID NO 49
<211> LENGTH: 1845
<212> TYPE: DNA
<213> ORGANISM: Artificial
<220> FEATURE:
<223> OTHER INFORMATION: Based on wild-type Synechococcus sp. PCC6301
      rbcLS nucleotide sequence

<400> SEQUENCE: 49
atggccaaga cgcaatctgc cgcaggctat aaggccgggg tgatagacta caaactcggc      60
tattacaccc ccgattacac ccccaaagac actgacctgc tggcggcttt ccgcttcagc     120
cctcagccgg gtgtccctgc tgacgaagct ggtgcggcga tcgcggctga atcttcgacc     180
```

```
ggtacctgga ccaccgtgtg gaccgacttg ctgaccgaca tggatcggta caaaggcaag    240
tgctaccaca tcgagccggt gcaaggcgaa gagaactcct actttgcgtt catcgcttac    300
ccgctcgacc tgtttgaaga agggtcggtc accaacatcc tgacctcgat cgtcggtaac    360
gtgtttggct tcaaagctat ccgttcgctg cgtctggaag acatccgctt ccccgtcgcc    420
ttggtcaaaa ccttccaagg tcctccccac ggtatccaag tcgagcgcga cctgctgaac    480
aagtacggcc gtccgatgct gggttgcacg atcaaaccaa aactcggtct gtcggcgaaa    540
aactacggtc gtgccgtcta cgaatgtctg cgcggcggtc tggacttcac caaagacgac    600
gaaaacatca actcgcagcc gttccaacgc tggcgcgatc gcttcctgtt tgtggctgat    660
gcaatccaca atcgcaagc agaaaccggt gaaatcaaag gtcactacct gaacgtgacc    720
gcgccgacct gcgaagaaat gatgaaacgg gctgagttcg ctaaagaact cggcatgccg    780
atcatcatgc atgacttctt gacggctggt ttcaccgcca acaccacctt ggcaaaatgg    840
tgccgcgaca acggcgtcct gctgcacatc accgtgcaa tgcacgcggt gatcgaccgt    900
cagcgtaacc acgggattca cttccgtgtc ttggccaagt gtttgcgtct gtccggtggt    960
gaccacctcc actccggcac cgtcgtcggc aaactggaag cgacaaagc ttcgaccttg   1020 ggctttgttg acttgatgcg cgaagaccac atcaagctg accgcagccg tggggtcttc   1080
ttcacccaag attgggcgtc gatgccgggc gtgctgccgg ttgcttccgg tggtatccac   1140
gtgtggcaca tgcccgcact ggtggaaatc ttcggtgatg actccgttct ccagttcggt   1200
ggcggcacct gggtcacccc ctggggtaat gctcctggtg caaccgcgaa ccgtgttgcc   1260
ttggaagctt gcgtccaagc tcggaacgaa ggtcgcgacc tctaccgtga aggcggcgac   1320
atccttcgtg aagctggcaa gtggtcgcct gaactggctg ctgccctcga cctctggaaa   1380
gagatcaagt cgaattcga acgatggac aagctctaag gagcctctga ctatcgctgg   1440
gggagtgagc gttgctgcgt aaagctttct ccccagcctt tcgacttaac ctttcaggat   1500
ttctgaatca tgagcatgaa aactctgccc aaagagcgtc gtttcgagac tttctcgtac   1560
ctgcctcccc tcagcgatcg ccaaatcgct gcacaaatcg agtacatgat cgagcaaggc   1620 ttccaccccct tgatcgagtt caacgagcac tcgaatccgg aagagttcta ctggacgatg   1680
tggaagctcc ccctgtttga ctgcaagagc cctcagcaag tcctcgatga agtgcgtgag   1740
tgccgcagcg aatacggtga ttgctacatc cgtgtcgctg gcttcgacaa catcaagcag   1800
tgccaaaccg tgagcttcat cgttcatcgt cccggccgat actaa                   1845
```

<210> SEQ ID NO 50
<211> LENGTH: 472
<212> TYPE: PRT
<213> ORGANISM: Artificial
<220> FEATURE:
<223> OTHER INFORMATION: Based on wild-type Synechococcus sp. PCC6301
      rbcLS translated sequence

<400> SEQUENCE: 50

```
Met Ala Lys Thr Gln Ser Ala Ala Gly Tyr Lys Ala Gly Val Ile Asp
1               5                   10                  15

Tyr Lys Leu Gly Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Gly Ala Ala Ile Ala Ala Glu Ser Ser Thr Gly Thr Trp Thr
    50                  55                  60
```

```
Thr Val Trp Thr Asp Leu Leu Thr Asp Met Asp Arg Tyr Lys Gly Lys
 65                  70                  75                  80

Cys Tyr His Ile Glu Pro Val Gln Gly Glu Glu Asn Ser Tyr Phe Ala
                 85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
    210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
            260                 265                 270

Ala Asn Thr Thr Leu Ala Lys Trp Cys Arg Asp Asn Gly Val Leu Leu
        275                 280                 285

His Ile His Arg Ala Met His Ala Val Ile Asp Arg Gln Arg Asn His
    290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
                325                 330                 335

Ala Ser Thr Leu Gly Phe Val Asp Leu Met Arg Glu Asp His Ile Glu
            340                 345                 350

Ala Asp Arg Ser Arg Gly Val Phe Phe Thr Gln Asp Trp Ala Ser Met
        355                 360                 365

Pro Gly Val Leu Pro Val Ala Ser Gly Gly Ile His Val Trp His Met
370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
                405                 410                 415

Asn Arg Val Ala Leu Glu Ala Cys Val Gln Ala Arg Asn Glu Gly Arg
            420                 425                 430

Asp Leu Tyr Arg Glu Gly Gly Asp Ile Leu Arg Glu Ala Gly Lys Trp
        435                 440                 445

Ser Pro Glu Leu Ala Ala Ala Leu Asp Leu Trp Lys Glu Ile Lys Phe
450                 455                 460

Glu Phe Glu Thr Met Asp Lys Leu
465                 470
```

<210> SEQ ID NO 51
<211> LENGTH: 1848
<212> TYPE: DNA
<213> ORGANISM: Artificial
<220> FEATURE:
<223> OTHER INFORMATION: Based on wild-type Synechococcus sp. PCC6301 rbcLS nucleotide sequence

<400> SEQUENCE: 51

```
atggccaaga cgcaatctgc cgcaggctat aaggccgggg tgaaggacta cgctaagatg    60
ggatactgga cccccgatta caccccaaa gacactgacc tgctggcggc tttccgcttc    120
agccctcagc cgggtgtccc tgctgacgaa gctggtgcgg cgatcgcggc tgaatcttcg    180
accggtacct ggaccaccgt gtggaccgac ttgctgaccg acatggatcg gtacaaaggc    240
aagtgctacc acatcgagcc ggtgcaaggc gaagagaact cctactttgc gttcatcgct    300
tacccgctcg acctgtttga agaagggtcg gtcaccaaca tcctgacctc gatcgtcggt    360
aacgtgtttg gcttcaaagc tatccgttcg ctgcgtctgg aagacatccg cttcccgtc    420
gccttggtca aaccttcca aggtcctccc acggtatcc agtcgagcg cgacctgctg    480
aacaagtacg gccgtccgat gctgggttgc acgatcaaac caaaactcgg tctgtcggcg    540
aaaaactacg gtcgtgccgt ctacgaatgt ctgcgcggcg gtctggactt caccaaagac    600
gacgaaaaca tcaactcgca gccgttccaa cgctggcgcg atcgcttcct gtttgtggct    660
gatgcaatcc acaaatcgca agcagaaacc ggtgaaatca aggtcactta cctgaacgtg    720
accgcgccga cctgcgaaga aatgatgaaa cgggctgagt cgctaaaga actcggcatg    780
ccgatcatca tgcatgactt cttgacggct ggtttcaccg ccaacaccac cttggcaaaa    840
tggtgccgcg acaacggcgt cctgctgcac atccaccgtg caatgcacgc ggtgatcgac    900
cgtcagcgta ccacgggat tcacttccgt gtcttggcca agtgtttgcg tctgtccggt    960
ggtgaccacc tccactccgg caccgtcgtc ggcaaactgg aaggcgacaa agcttcgacc    1020
ttgggctttg ttgacttgat gcgcgaagac cacatcgaag ctgaccgcag ccgtgggctc    1080
ttcttcaccc aagattgggc gtcgatgccg ggcgtgctgc cggttgcttc cggtggtatc    1140
cacgtgtggc acatgcccgc actggtggaa atcttcggtg atgactccgt tctccagttc    1200
ggtggcggca ccttgggtca ccctgggggt aatgctcctg gtgcaaccgc gaaccgtgtt    1260
gccttggaag cttgcgtcca agctcggaac gaaggtcgcg acctctaccg tgaaggcggc    1320
gacatccttc gtgaagctgg caagtggtcg cctgaactgg ctgctgccct cgacctctgg    1380
aaagagatca gttcgaatt cgaaacgatg acaagctct aaggagcctc tgactatcgc    1440
tggggagtg agcgttgctg cgtaaagctt tctccccagc ctttcgactt aacctttcag    1500
gatttctgaa tcatgagcat gaaaactctg cccaaagagc gtcgtttcga cttttctcg    1560
tacctgcctc ccctcagcga tcgccaaatc gctgcacaaa tcgagtacat gatcgagcaa    1620
ggcttccacc ccttgatcga gttcaacgag cactcgaatc cggaagagtt ctactggacg    1680
atgtggaagc tcccccctgtt tgactgcaag agccctcagc aagtcctcga tgaagtgcgt    1740
gagtgccgca gcgaatacgg tgattgctac atccgtgtcg ctggcttcga caacatcaag    1800
cagtgccaaa ccgtgagctt catcgttcat cgtcccggcc gatactaa                1848
```

<210> SEQ ID NO 52
<211> LENGTH: 473
<212> TYPE: PRT
<213> ORGANISM: Artificial
<220> FEATURE:
<223> OTHER INFORMATION: Based on wild-type Synechococcus sp. PCC6301 rbcLS translated sequence

<400> SEQUENCE: 52

Met Ala Lys Thr Gln Ser Ala Gly Tyr Lys Ala Gly Val Lys Asp
1               5                   10                  15

Tyr Ala Lys Met Gly Tyr Trp Thr Pro Asp Tyr Thr Pro Lys Asp Thr
            20                  25                  30

Asp Leu Leu Ala Ala Phe Arg Phe Ser Pro Gln Pro Gly Val Pro Ala
                35                  40                  45

Asp Glu Ala Gly Ala Ala Ile Ala Ala Glu Ser Ser Thr Gly Thr Trp
    50                  55                  60

Thr Thr Val Trp Thr Asp Leu Leu Thr Asp Met Asp Arg Tyr Lys Gly
65                  70                  75                  80

Lys Cys Tyr His Ile Glu Pro Val Gln Gly Glu Glu Asn Ser Tyr Phe
                85                  90                  95

Ala Phe Ile Ala Tyr Pro Leu Asp Leu Phe Glu Glu Gly Ser Val Thr
                100                 105                 110

Asn Ile Leu Thr Ser Ile Val Gly Asn Val Phe Gly Phe Lys Ala Ile
            115                 120                 125

Arg Ser Leu Arg Leu Glu Asp Ile Arg Phe Pro Val Ala Leu Val Lys
130                 135                 140

Thr Phe Gln Gly Pro Pro His Gly Ile Gln Val Glu Arg Asp Leu Leu
145                 150                 155                 160

Asn Lys Tyr Gly Arg Pro Met Leu Gly Cys Thr Ile Lys Pro Lys Leu
                165                 170                 175

Gly Leu Ser Ala Lys Asn Tyr Gly Arg Ala Val Tyr Glu Cys Leu Arg
            180                 185                 190

Gly Gly Leu Asp Phe Thr Lys Asp Asp Glu Asn Ile Asn Ser Gln Pro
        195                 200                 205

Phe Gln Arg Trp Arg Asp Arg Phe Leu Phe Val Ala Asp Ala Ile His
        210                 215                 220

Lys Ser Gln Ala Glu Thr Gly Glu Ile Lys Gly His Tyr Leu Asn Val
225                 230                 235                 240

Thr Ala Pro Thr Cys Glu Glu Met Met Lys Arg Ala Glu Phe Ala Lys
                245                 250                 255

Glu Leu Gly Met Pro Ile Ile Met His Asp Phe Leu Thr Ala Gly Phe
            260                 265                 270

Thr Ala Asn Thr Thr Leu Ala Lys Trp Cys Arg Asp Asn Gly Val Leu
        275                 280                 285

Leu His Ile His Arg Ala Met His Ala Val Ile Asp Arg Gln Arg Asn
        290                 295                 300

His Gly Ile His Phe Arg Val Leu Ala Lys Cys Leu Arg Leu Ser Gly
305                 310                 315                 320

Gly Asp His Leu His Ser Gly Thr Val Val Gly Lys Leu Glu Gly Asp
                325                 330                 335

Lys Ala Ser Thr Leu Gly Phe Val Asp Leu Met Arg Glu Asp His Ile
            340                 345                 350

Glu Ala Asp Arg Ser Arg Gly Val Phe Phe Thr Gln Asp Trp Ala Ser
        355                 360                 365

Met Pro Gly Val Leu Pro Val Ala Ser Gly Gly Ile His Val Trp His
        370                 375                 380

Met Pro Ala Leu Val Glu Ile Phe Gly Asp Asp Ser Val Leu Gln Phe
385                 390                 395                 400

Gly Gly Gly Thr Leu Gly His Pro Trp Gly Asn Ala Pro Gly Ala Thr
            405                 410                 415

Ala Asn Arg Val Ala Leu Glu Ala Cys Val Gln Ala Arg Asn Glu Gly
        420                 425                 430

Arg Asp Leu Tyr Arg Glu Gly Gly Asp Ile Leu Arg Glu Ala Gly Lys
    435                 440                 445

Trp Ser Pro Glu Leu Ala Ala Ala Leu Asp Leu Trp Lys Glu Ile Lys
450                 455                 460

Phe Glu Phe Glu Thr Met Asp Lys Leu
465                 470

<210> SEQ ID NO 53
<211> LENGTH: 1845
<212> TYPE: DNA
<213> ORGANISM: Artificial
<220> FEATURE:
<223> OTHER INFORMATION: Based on wild-type Synechococcus sp. PCC6301
      rbcLS nucleotide sequence

<400> SEQUENCE: 53

| | |
|---|---|
| atggccaaga cgcaatctgc cgcaggctat aaggccgggg tgatagacta caaactcggc | 60 |
| tattcacccc ccgattacac ccccaaagac actgacctgc tggcggcttt ccgcttcagc | 120 |
| cctcagccgg tgtccctgc tgacgaagct ggtgcggcga tcgcggctga atcttcgacc | 180 |
| ggtacctgga ccgtcgtgtg gaccgacttg ctgaccgaca tggatcggta ccgcggcaag | 240 |
| tgctaccaca tcgagccggt gcaaggcgaa gagaactcct actttgcgtt catcgcttac | 300 |
| ccgctcgacc tgtttgaaga gggtcggtc accaacatcc tgacctcgat cgtcggtaac | 360 |
| gtgtttggct tcaaagctat ccgttcgctg cgtctggaag acatccgctt ccccgtcgcc | 420 |
| ttggtcaaaa ccttccaagg tcctccccac ggtatccaag tcgagcgcga cctgctgaac | 480 |
| aagtacggcc gtccgatgct gggttgcacg atcaaaccaa aactcggtct gtcggcgaaa | 540 |
| aactacggtc gtgccgtcta cgaatgtctg cgcggcggtc tggacttcac caaagacgac | 600 |
| gaaaacatca actcgcagcc gttccaacgc tggcgcgatc gcttcctgtt tgtggctgat | 660 |
| gcaatccaca atcgcaagc agaaaccggt gaaatcaaag tcactacct gaacgtgacc | 720 |
| gcgccgacct gcgaagaaat gatgaaacgg gctgagttcg ctaaagaact cggcatgccg | 780 |
| atcatcatgc atgacttctt gacggctggt ttcaccgcca acaccacctt ggcaaaatgg | 840 |
| tgccgcgaca cggcgtcct gctgcacatc accgtgcaa tgcacgcggt gatcgaccgt | 900 |
| cagcgtaacc acgggattca cttccgtgtc ttggccaagt gtttgcgtct gtccggtggt | 960 |
| gaccacctcc actccggcac cgtcgtcggc aaactggaag cgacaaagc ttcgaccttg | 1020 |
| ggctttgttg acttgatgcg cgaagaccac atcgaagctg accgcagccg tggggtcttc | 1080 |
| ttcacccaag attgggcgtc gatgccgggc gtgctgccgg ttgcttccgg tggtatccac | 1140 |
| gtgtggcaca tgcccgcact ggtggaaatc ttcggtgatg actccgttct ccagttcggt | 1200 |
| ggcggcacct tgggtcaccc ctggggtaat gctcctggtg caaccgcgaa ccgtgttgcc | 1260 |
| ttggaagctt gcgtccaagc tcggaacgaa ggtcgcgacc tctaccgtga aggcggcgac | 1320 |
| atccttcgtg aagctggcaa gtggtcgcct gaactggctg ctgccctcga cctctggaaa | 1380 |
| gagatcaagt tcgaattcga aacgatggac aagctctaag gagcctctga ctatcgctgg | 1440 |
| gggagtgagc gttgctgcgt aaagcttttct ccccagcctt tcgacttaac ctttcaggat | 1500 |
| ttctgaatca tgagcatgaa aactctgccc aagagcgtc gtttcgagac tttctcgtac | 1560 |
| ctgcctcccc tcagcgatcg ccaaatcgct gcacaaatcg agtacatgat cgagcaaggc | 1620 |

```
ttccacccct tgatcgagtt caacgagcac tcgaatccgg aagagttcta ctggacgatg    1680
tggaagctcc ccctgtttga ctgcaagagc cctcagcaag tcctcgatga agtgcgtgag    1740
tgccgcagcg aatacggtga ttgctacatc cgtgtcgctg gcttcgacaa catcaagcag    1800
tgccaaaccg tgagcttcat cgttcatcgt cccggccgat actaa                    1845
```

<210> SEQ ID NO 54
<211> LENGTH: 472
<212> TYPE: PRT
<213> ORGANISM: Artificial
<220> FEATURE:
<223> OTHER INFORMATION: Based on wild-type Synechococcus sp. PCC6301
      rbcLS translated sequence

<400> SEQUENCE: 54

```
Met Ala Lys Thr Gln Ser Ala Ala Gly Tyr Lys Ala Gly Val Ile Asp
1               5                   10                  15

Tyr Lys Leu Gly Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Gly Ala Ala Ile Ala Ala Glu Ser Ser Thr Gly Thr Trp Thr
    50                  55                  60

Val Val Trp Thr Asp Leu Leu Thr Asp Met Asp Arg Tyr Arg Gly Lys
65                  70                  75                  80

Cys Tyr His Ile Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
    210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
            260                 265                 270

Ala Asn Thr Thr Leu Ala Lys Trp Cys Arg Asp Asn Gly Val Leu Leu
        275                 280                 285

His Ile His Arg Ala Met His Ala Val Ile Asp Arg Gln Arg Asn His
    290                 295                 300

Gly Ile His Phe Arg Val Leu Ala Lys Cys Leu Arg Leu Ser Gly Gly
305                 310                 315                 320
```

```
Asp His Leu His Ser Gly Thr Val Val Gly Lys Leu Glu Gly Asp Lys
            325                 330                 335

Ala Ser Thr Leu Gly Phe Val Asp Leu Met Arg Glu Asp His Ile Glu
            340                 345                 350

Ala Asp Arg Ser Arg Gly Val Phe Phe Thr Gln Asp Trp Ala Ser Met
            355                 360                 365

Pro Gly Val Leu Pro Val Ala Ser Gly Gly Ile His Val Trp His Met
    370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
            405                 410                 415

Asn Arg Val Ala Leu Glu Ala Cys Val Gln Ala Arg Asn Glu Gly Arg
            420                 425                 430

Asp Leu Tyr Arg Glu Gly Gly Asp Ile Leu Arg Glu Ala Gly Lys Trp
            435                 440                 445

Ser Pro Glu Leu Ala Ala Ala Leu Asp Leu Trp Lys Glu Ile Lys Phe
    450                 455                 460

Glu Phe Glu Thr Met Asp Lys Leu
465                 470
```

<210> SEQ ID NO 55
<211> LENGTH: 1845
<212> TYPE: DNA
<213> ORGANISM: Artificial
<220> FEATURE:
<223> OTHER INFORMATION: Based on wild-type Synechococcus sp. PCC6301
      rbcLS nucleotide sequence

<400> SEQUENCE: 55

| | | |
|---|---|---|
| atggccaaga cgcaatctgc cgcaggctat aaggccgggg tgaaggacta caaactcggc | 60 |
| tattcaccc ccgattacac ccccaaagac actgacctgc tggcggcttt ccgcttcagc | 120 |
| cctcagccgg tgtccctgc tgacgaagct ggtgcggcga tcgcggctga atcttcgacc | 180 |
| ggtacctgga ccaccgtgtg gaccgacttg ctgaccgaca tggatcggta ccgcggcaag | 240 |
| tgctaccaca tcgagccggt gcaaggcgaa gagaactcct actttgcgtt catcgcttac | 300 |
| gagctcgacc tgtttgaaga agggtcggtc accaacatcc tgacctcgat cgtcggtaac | 360 |
| gtgtttggct tcaaagctat ccgttcgctg cgtctggaag acatccgctt ccccgtcgcc | 420 |
| ttggtcaaaa ccttccaagg tcctccccac ggtatccaag tcgagcgcga cctgctgaac | 480 |
| aagtacggcc gtccgatgct gggttgcacg atcaaaccaa aactcggtct gtcggcgaaa | 540 |
| aactacggtc gtgccgtcta cgaatgtctg cgcggcggtc tggacttcac caaagacgac | 600 |
| gaaaacatca actcgcagcc gttccaacgc tggcgcgatc gcttcctgtt tgtggctgat | 660 |
| gcaatccaca atcgcaagc agaaaccggt gaaatcaaag tcactaccct gaacgtgacc | 720 |
| gcgccgacct gcgaagaaat gatgaaacgg gctgagttcg ctaaagaact cggcatgccg | 780 |
| atcatcatgc atgacttctt gacggctggt ttcaccgcca acaccacctt ggcaaaatgg | 840 |
| tgccgcgaca acgcgtcct gctgcacatc accgtgcaa tgcacgcggt gatcgaccgt | 900 |
| cagcgtaacc acgggattca cttccgtgtc ttggccaagt gtttgcgtct gtccggtggt | 960 |
| gaccacctcc actccggcac cgtcgtcggc aaactggaag cgacaaagc ttcgaccttg | 1020 |
| ggctttgttg acttgatgcg cgaagaccac atcgaagctg accgcagccg tggggtcttc | 1080 |
| ttcacccaag attgggcgtc gatgccgggc gtgctgccgg ttgcttccgg tggtatccac | 1140 |

```
gtgtggcaca tgcccgcact ggtggaaatc ttcggtgatg actccgttct ccagttcggt    1200
ggcggcacct tgggtcaccc ctggggtaat gctcctggtg caaccgcgaa ccgtgttgcc    1260
ttggaagctt gcgtccaagc tcggaacgaa ggtcgcgacc tctaccgtga aggcggcgac    1320
atccttcgtg aagctggcaa gtggtcgcct gaactggctg ctgccctcga cctctggaaa    1380
gagatcaagt tcgaattcga acgatggac aagctctaag gagcctctga ctatcgctgg    1440
gggagtgagc gttgctgcgt aaagctttct ccccagcctt tcgacttaac ctttcaggat    1500
ttctgaatca tgagcatgaa aactctgccc aaagagcgtc gtttcgagac tttctcgtac    1560
ctgcctcccc tcagcgatcg ccaaatcgct gcacaaatcg agtacatgat cgagcaaggc    1620
ttccacccct tgatcgagtt caacgagcac tcgaatccgg aagagttcta ctggacgatg    1680
tggaagctcc ccctgtttga ctgcaagagc cctcagcaag tcctcgatga agtgcgtgag    1740
tgccgcagcg aatacggtga ttgctacatc cgtgtcgctg gcttcgacaa catcaagcag    1800
tgccaaaccg tgagcttcat cgttcatcgt cccggccgat actaa                   1845
```

<210> SEQ ID NO 56
<211> LENGTH: 472
<212> TYPE: PRT
<213> ORGANISM: Artificial
<220> FEATURE:
<223> OTHER INFORMATION: Based on wild-type Synechococcus sp. PCC6301
      rbcLS translated sequence

<400> SEQUENCE: 56

```
Met Ala Lys Thr Gln Ser Ala Ala Gly Tyr Lys Ala Gly Val Lys Asp
1               5                   10                  15

Tyr Lys Leu Gly Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Gly Ala Ala Ile Ala Ala Glu Ser Ser Thr Gly Thr Trp Thr
    50                  55                  60

Thr Val Trp Thr Asp Leu Leu Thr Asp Met Asp Arg Tyr Arg Gly Lys
65                  70                  75                  80

Cys Tyr His Ile Glu Pro Val Gln Gly Glu Glu Asn Ser Tyr Phe Ala
                85                  90                  95

Phe Ile Ala Tyr Glu Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
    210                 215                 220

Ser Gln Ala Glu Thr Gly Glu Ile Lys Gly His Tyr Leu Asn Val Thr
```

```
              225                 230                 235                 240
Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
                260                 265                 270

Ala Asn Thr Thr Leu Ala Lys Trp Cys Arg Asp Asn Gly Val Leu Leu
                275                 280                 285

His Ile His Arg Ala Met His Ala Val Ile Asp Arg Gln Arg Asn His
            290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
                325                 330                 335

Ala Ser Thr Leu Gly Phe Val Asp Leu Met Arg Glu Asp His Ile Glu
                340                 345                 350

Ala Asp Arg Ser Arg Gly Val Phe Phe Thr Gln Asp Trp Ala Ser Met
                355                 360                 365

Pro Gly Val Leu Pro Val Ala Ser Gly Gly Ile His Val Trp His Met
370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
                405                 410                 415

Asn Arg Val Ala Leu Glu Ala Cys Val Gln Ala Arg Asn Glu Gly Arg
                420                 425                 430

Asp Leu Tyr Arg Glu Gly Gly Asp Ile Leu Arg Glu Ala Gly Lys Trp
                435                 440                 445

Ser Pro Glu Leu Ala Ala Ala Leu Asp Leu Trp Lys Glu Ile Lys Phe
            450                 455                 460

Glu Phe Glu Thr Met Asp Lys Leu
465                 470

<210> SEQ ID NO 57
<211> LENGTH: 1845
<212> TYPE: DNA
<213> ORGANISM: Artificial
<220> FEATURE:
<223> OTHER INFORMATION: Based on wild-type Synechococcus sp. PCC6301
      rbcLS nucleotide sequence

<400> SEQUENCE: 57
atggccaaga cgcaatctgc cgcaggctat aaggccgggg tgaagcccta caaactcggc        60 tattcaccc cgattacac ccccaaagac actgacctgc tggcggcttt ccgcttcagc        120
cctcagccgg tgtccctgc tgacgaagct ggtgcggcga tcgcggctga atcttcgacc        180
ggtacctgga ccaccgtgtg gaccgacttg ctgaccgaca tggatcggta ccgcggcaag        240
tgctaccaca tcgagccggt gcaaggcgaa gagaactcct actttgcgtt catcgcttac        300
ccgctcgacc tgtttgaaga agggtcggtc accaacatcc tgacctcgat cgtcggtaac        360
gtgtttggct tcaaagctat ccgttcgctg cgtctggaag acatccgctt ccccgtcgcc        420
ttggtcaaaa ccttccaagg tcctccccac ggtatccaag tcgagcgcga cctgctgaac        480
aagtacggcc gtccgatgct gggttgcacg atcaaaccaa aactcggtct gtcggcgaaa        540
aactacggtc gtgccgtcta cgaatgtctg cgcggcggtc tggacttcac caaagacgac        600
gaaaacatca actcgcagcc gttccaacgc tggcgcgatc gcttcctgtt tgtggctgat        660
```

-continued

```
gcaatccaca aatcgcaagc agaaaccggt gaaatcaaag gtcactacct gaacgtgacc    720
gcgccgacct gcgaagaaat gatgaaacgg gctgagttcg ctaaagaact cggcatgccg    780
atcatcatgc atgacttctt gacggctggt ttcaccgcca acaccacctt ggcaaaatgg    840
tgccgcgaca acgcgtcct gctgcacatc caccgtgcaa tgcacgcggt gatcgaccgt     900
cagcgtaacc acgggattca cttccgtgtc ttggccaagt gtttgcgtct gtccggtggt    960
gaccacctcc actccggcac cgtcgtcggc aaactggaag cgacaaagc ttcgaccttg    1020 ggctttgttg acttgatgcg cgaagaccac atcgaagctg accgcagccg tggggtcttc   1080
ttcacccaag attgggcgtc gatgccggc gtgctgccgg ttgcttccgg tggtatccac   1140
gtgtggcaca tgcccgcact ggtggaaatc ttcggtgatg actccgttct ccagttcggt   1200
ggcggcacct gggtcaccc ctggggtaat gctcctggtg caaccgcgaa ccgtgttgcc   1260
ttggaagctt gcgtccaagc tcggaacgaa ggtcgcgacc tctaccgtga aggcggcgac   1320
atccttcgtg aagctggcaa gtggtcgcct gaactggctg ctgccctcga cctctggaaa   1380
gagatcaagt tcgaattcga aacgatggac aagctctaag gagcctctga ctatcgctgg   1440
gggagtgagc gttgctgcgt aaagctttct ccccagcctt tcgacttaac ctttcaggat   1500
ttctgaatca tgagcatgaa aactctgccc aaagagcgtc gtttcgagac tttctcgtac   1560
ctgcctcccc tcagcgatcg ccaaatcgct gcacaaatcg agtacatgat cgagcaaggc   1620
ttccacccct tgatcgagtt caacgagcac tcgaatccgg aagagttcta ctggacgatg   1680
tggaagctcc ccctgtttga ctgcaagagc cctcagcaag tcctcgatga agtgcgtgag   1740
tgccgcagcg aatacggtga ttgctacatc cgtgtcgctg gcttcgacaa catcaagcag   1800
tgccaaaccg tgagcttcat cgttcatcgt cccggccgat actaa                   1845
```

```
<210> SEQ ID NO 58
<211> LENGTH: 472
<212> TYPE: PRT
<213> ORGANISM: Artificial
<220> FEATURE:
<223> OTHER INFORMATION: Based on wild-type Synechococcus sp. PCC6301
      rbcLS translated sequence

<400> SEQUENCE: 58
```

```
Met Ala Lys Thr Gln Ser Ala Ala Gly Tyr Lys Ala Gly Val Lys Pro
1               5                   10                  15

Tyr Lys Leu Gly Tyr Tyr Thr Pro Asp Tyr Thr Pro Lys Asp Thr Asp
                20                  25                  30

Leu Leu Ala Ala Phe Arg Phe Ser Pro Gln Pro Gly Val Pro Ala Asp
            35                  40                  45

Glu Ala Gly Ala Ala Ile Ala Ala Glu Ser Ser Thr Gly Thr Trp Thr
        50                  55                  60

Thr Val Trp Thr Asp Leu Leu Thr Asp Met Asp Arg Tyr Arg Gly Lys
65                  70                  75                  80

Cys Tyr His Ile Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
                100                 105                 110

Ile Leu Thr Ser Ile Val Gly Asn Val Phe Gly Phe Lys Ala Ile Arg
            115                 120                 125

Ser Leu Arg Leu Glu Asp Ile Arg Phe Pro Val Ala Leu Val Lys Thr
        130                 135                 140
```

-continued

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
            165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
            195                 200                 205

Gln Arg Trp Arg Asp Arg Phe Leu Phe Val Ala Asp Ala Ile His Lys
        210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
            260                 265                 270

Ala Asn Thr Thr Leu Ala Lys Trp Cys Arg Asp Asn Gly Val Leu Leu
        275                 280                 285

His Ile His Arg Ala Met His Ala Val Ile Asp Arg Gln Arg Asn His
290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
                325                 330                 335

Ala Ser Thr Leu Gly Phe Val Asp Leu Met Arg Glu Asp His Ile Glu
            340                 345                 350

Ala Asp Arg Ser Arg Gly Val Phe Phe Thr Gln Asp Trp Ala Ser Met
        355                 360                 365

Pro Gly Val Leu Pro Val Ala Ser Gly Gly Ile His Val Trp His Met
370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
                405                 410                 415

Asn Arg Val Ala Leu Glu Ala Cys Val Gln Ala Arg Asn Glu Gly Arg
            420                 425                 430

Asp Leu Tyr Arg Glu Gly Gly Asp Ile Leu Arg Glu Ala Gly Lys Trp
        435                 440                 445

Ser Pro Glu Leu Ala Ala Ala Leu Asp Leu Trp Lys Glu Ile Lys Phe
450                 455                 460

Glu Phe Glu Thr Met Asp Lys Leu
465                 470

<210> SEQ ID NO 59
<211> LENGTH: 1845
<212> TYPE: DNA
<213> ORGANISM: Artificial
<220> FEATURE:
<223> OTHER INFORMATION: Based on wild-type Synechococcus sp. PCC6301
      rbcLS nucleotide sequence

<400> SEQUENCE: 59
atggccaaga cgcaatctgc cgcaggctat aaggccgggg tgaaggacta caaactcggc      60
tattacaccc ccgattacac ccccaaagac actgacctgc tggcggcttt ccgcttcagc     120
cctcagccgg gtgtccctgc tgacgaagct ggtgcggcga tcgcggctga atcttcgacc    180

```
ggtacctgga ccaccgtgtg gaccgacttg ctgaccgaca tggatcggta ccgcggcaag      240
tgctaccaca tcgagccggt gcaaggcgaa gagaactcct actttgcgtt catcgcttac      300
ccgctcgacc tgtttgaaga agggtcggtc accaacatcc tgacctcgat catcggtaac      360
gtgtttggct tcaaagctat ccgttcgctg cgtctggaag acatccgctt ccccgtcgcc      420
ttggtcaaaa ccttccaagg tcctccccac ggtatccaag tcgagcgcga cctgctgaac      480
aagtacggcc gtccgatgct gggttgcacg atcaaaccaa aactcggtct gtcggcgaaa      540
aactacggtc gtgccgtcta cgaatgtctg cgcggcggtc tggacttcac caaagacgac      600
gaaaacatca actcgcagcc gttccaacgc tggcgcgatc gcttcctgtt tgtggctgat      660
gcaatccaca atcgcaagc agaaaccggt gaaatcaaag gtcactacct gaacgtgacc      720
gcgccgacct gcgaagaaat gatgaaacgg gctgagttcg ctaaagaact cggcatgccg      780
atcatcatgc atgacttctt gacggctggt ttcaccgcca acaccacctt ggcaaaatgg      840
tgccgcgaca acgcgtcct gctgcacatc accgtgcag gcacgcgac gatcgaccgt      900 cagcgtaacc acgggattca cttccgtgtc ttggccaagt gtttgcgtct gtccggtggt      960
gaccacctcc actccggcac cgtcgtcggc aaactggaag cgacaaagc ttcgaccttg     1020 ggctttgttg acttgatgcg cgaagaccac atcgaagctg accgcagccg tggggtcttc     1080
ttcacccaag attgggcgtc gatgccgggc gtgctgccgg ttgcttccgg tggtatccac     1140
gtgtggcaca tgcccgcact ggtggaaatc ttcggtgatg actccgttct ccagttcggt     1200
ggcggcacct gggtcaccc ctggggtaat gctcctggtg caaccgcgaa ccgtgttgcc     1260
ttggaagctt gcgtccaagc tcggaacgaa ggtcgcgacc tctaccgtga aggcggcgac     1320
atccttcgtg aagctggcaa gtggtcgcct gaactggctg ctgccctcga cctctggaaa     1380
gagatcaagt tcgaattcga aacgatggac aagctctaag gagcctctga ctatcgctgg     1440
gggagtgagc gttgctgcgt aaagctttct ccccagcctt tcgacttaac cttcaggat     1500 ttctgaatca tgagcatgaa aactctgccc aaagagcgtc gtttcgagac tttctcgtac     1560
ctgcctcccc tcagcgatcg ccaaatcgct gcacaaatcg agtacatgat cgagcaaggc     1620
ttccacccct tgatcgagtt caacgagcac tcgaatccgg aagagttcta ctggacgatg     1680
tggaagctcc ccctgtttga ctgcaagagc cctcagcaag tcctcgatga agtgcgtgag     1740
tgccgcagcg aatacggtga ttgctacatc cgtgtcgctg gcttcgacaa catcaagcag     1800
tgccaaaccg tgagcttcat cgttcatcgt cccggccgat actaa              1845
```

<210> SEQ ID NO 60
<211> LENGTH: 472
<212> TYPE: PRT
<213> ORGANISM: Artificial
<220> FEATURE:
<223> OTHER INFORMATION: Based on wild-type Synechococcus sp. PCC6301 rbcLS translated sequence

<400> SEQUENCE: 60

```
Met Ala Lys Thr Gln Ser Ala Ala Gly Tyr Lys Ala Gly Val Lys Asp
1               5                   10                  15

Tyr Lys Leu Gly Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Gly Ala Ala Ile Ala Ala Glu Ser Ser Thr Gly Thr Trp Thr
    50                  55                  60
```

```
Thr Val Trp Thr Asp Leu Leu Thr Asp Met Asp Arg Tyr Arg Gly Lys
 65                  70                  75                  80

Cys Tyr His Ile Glu Pro Val Gln Gly Glu Asn Ser Tyr Phe Ala
                 85                  90                  95

Phe Ile Ala Tyr Pro Leu Asp Leu Phe Glu Glu Gly Ser Val Thr Asn
            100                 105                 110

Ile Leu Thr Ser Ile Ile Gly Asn Val Phe Gly Phe Lys Ala Ile Arg
            115                 120                 125

Ser Leu Arg Leu Glu Asp Ile Arg Phe Pro Val Ala Leu Val Lys Thr
            130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
            195                 200                 205

Gln Arg Trp Arg Asp Arg Phe Leu Phe Val Ala Asp Ala Ile His Lys
            210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
                260                 265                 270

Ala Asn Thr Thr Leu Ala Lys Trp Cys Arg Asp Asn Gly Val Leu Leu
            275                 280                 285

His Ile His Arg Ala Gly His Ala Thr Ile Asp Arg Gln Arg Asn His
            290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
                325                 330                 335

Ala Ser Thr Leu Gly Phe Val Asp Leu Met Arg Glu Asp His Ile Glu
            340                 345                 350

Ala Asp Arg Ser Arg Gly Val Phe Phe Thr Gln Asp Trp Ala Ser Met
            355                 360                 365

Pro Gly Val Leu Pro Val Ala Ser Gly Gly Ile His Val Trp His Met
            370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
                405                 410                 415

Asn Arg Val Ala Leu Glu Ala Cys Val Gln Ala Arg Asn Glu Gly Arg
            420                 425                 430

Asp Leu Tyr Arg Glu Gly Gly Asp Ile Leu Arg Glu Ala Gly Lys Trp
            435                 440                 445

Ser Pro Glu Leu Ala Ala Ala Leu Asp Leu Trp Lys Glu Ile Lys Phe
            450                 455                 460

Glu Phe Glu Thr Met Asp Lys Leu
465                 470
```

<210> SEQ ID NO 61
<211> LENGTH: 1845
<212> TYPE: DNA
<213> ORGANISM: Artificial
<220> FEATURE:
<223> OTHER INFORMATION: Based on wild-type Synechococcus sp. PCC6301 rbcLS nucleotide sequence

<400> SEQUENCE: 61

```
atggccaaga cgcaatctgc cgcaggctat aaggccgggg tgaaggacta caaactcggc      60
tattacaccc ccgattacac ccccaaagac actgacctgc tggcggcttt ccgcttcagc     120
cctcagccgg tgtccctgc tgacgaagct ggtgcggcga tcgcggctga atcttcgacc      180
ggtacctgga ccaccgtgtg gaccgacttg ctgaccgaca tggatcggta caaaggcaag     240
tgctaccaca tcgagccggt gcaaggcgaa gagaactcct actttgcgtt catcgcttac     300
ccgctcgacc tgtttgaaga agggtcggtc accaacatcc tgacctcgat cgtcggtaac     360
gtgtttggct tcaaagctat ccgttcgctg cgtctggaag acatccgctt ccccgtcgcc     420
ttggtcaaaa ccttccaagg tcctccccac ggtatccaag tcgagcgcga cctgctgaac     480
aagtacggcc gtccgatgct gggttgcacg atcaaaccaa aactcggtct gtcggcgaaa     540
aactacggtc gtgccgtcta cgaatgtctg cgcggcggtc tggacttcac caaagacgac     600
gaaaacatca actcgcagcc gttccaacgc tggcgcgatc gcttcctgtt tgtggctgat     660
gcaatccaca atcgcaagc agaaaccggt gaaatcaaag gtcactacct gaacgtgacc     720
gcgccgacct gcgaagaaat gatgaaacgg gctgagttcg ctaaagaact cggcatgccg     780
atcatcatgc atgacttctt gacggctggt ttcaccgcca acaccacctt ggcaaaatgg     840
tgccgcgaca acgcgtcct gctgcacatc accgtgcaa tgcacgcggt gatcgaccgt      900
cagcgtaacc acgggattca cttccgtgtc ttggccaagt gtttgcgtct gtccggtggt     960
gaccacctcc actccggcac cgtcgtcggc aaactggaag gcgacaaagc ttcgaccttg    1020
ggctttgttg acttgatgcg cgaagaccac atcgaagctg accgcagccg tggggtcttc    1080
ttcacccaag attgggcgtc gatgccgggc gtgctgccgg ttgcttccgg tggtatccac    1140
gtgtggcaca tgcccgcact ggtggaaatc ttcggtgatg actccgttct ccagttcggt    1200
ggcggcacct tgggtcaccc ctggggtaat gctcctggtg caaccgcgaa ccgtgttgcc    1260
ttggaagctt gcgtccaagc tcggaacgaa ggtcgcgacc tctaccgtga aggcggcgac    1320
atccttcgtg aagctggcaa gtggtcgcct gaactggctg ctgccctcga cctctggaaa    1380
gagatcaagt tcgaattcga aacgatggac aagctctaag gagcctctga ctatcgctgg    1440
gggagtgagc gttgctgcgt aaagctttct ccccagcctt tcgacttaac ctttcaggat    1500
ttctgaatca tgagcatgaa aactctgccc aaagagcgtc gtttcgagac tttctcgtac    1560
ctgcctcccc tcagcgatcg ccaaatcgct gcacaaatcg agtacatgat cgagcaaggc    1620
ttccacccct tgatcgagtt caacgagcac tcgaatccgg aagagttcta ctggacgatg    1680
tggaagctcc ccctgtttga ctgcaagagc cctcagcaag tcctcgatga agtgcgtgag    1740
tgccgcagcg aatacggtga ttgctacatc cgtgtcgctg gcttcgacaa catcaagcag    1800
tgccaaaccg tgagcttcat cgttcatcgt cccggccgat actaa                    1845
```

<210> SEQ ID NO 62
<211> LENGTH: 472
<212> TYPE: PRT
<213> ORGANISM: Artificial
<220> FEATURE:

<223> OTHER INFORMATION: Based on wild-type Synechococcus sp. PCC6301 rbcLS translated sequence

<400> SEQUENCE: 62

```
Met Ala Lys Thr Gln Ser Ala Ala Gly Tyr Lys Ala Gly Val Lys Asp
 1               5                  10                  15

Tyr Lys Leu Gly Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Gly Ala Ala Ile Ala Ala Glu Ser Ser Thr Gly Thr Trp Thr
50                  55                  60

Thr Val Trp Thr Asp Leu Leu Thr Asp Met Asp Arg Tyr Lys Gly Lys
65                  70                  75                  80

Cys Tyr His Ile Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
            260                 265                 270

Ala Asn Thr Thr Leu Ala Lys Trp Cys Arg Asp Asn Gly Val Leu Leu
        275                 280                 285

His Ile His Arg Ala Met His Ala Val Ile Asp Arg Gln Arg Asn His
290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
                325                 330                 335

Ala Ser Thr Leu Gly Phe Val Asp Leu Met Arg Glu Asp His Ile Glu
            340                 345                 350

Ala Asp Arg Ser Arg Gly Val Phe Phe Thr Gln Asp Trp Ala Ser Met
        355                 360                 365

Pro Gly Val Leu Pro Val Ala Ser Gly Gly Ile His Val Trp His Met
370                 375                 380

Pro Ala Leu Val Glu Ile Phe Gly Asp Asp Ser Val Leu Gln Phe Gly
385                 390                 395                 400
```

```
Gly Gly Thr Leu Gly His Pro Trp Gly Asn Ala Pro Gly Ala Thr Ala
                405                 410                 415

Asn Arg Val Ala Leu Glu Ala Cys Val Gln Ala Arg Asn Glu Gly Arg
            420                 425                 430

Asp Leu Tyr Arg Glu Gly Gly Asp Ile Leu Arg Glu Ala Gly Lys Trp
        435                 440                 445

Ser Pro Glu Leu Ala Ala Ala Leu Asp Leu Trp Lys Glu Ile Lys Phe
    450                 455                 460

Glu Phe Glu Thr Met Asp Lys Leu
465                 470

<210> SEQ ID NO 63
<211> LENGTH: 1845
<212> TYPE: DNA
<213> ORGANISM: Artificial
<220> FEATURE:
<223> OTHER INFORMATION: Based on wild-type Synechococcus sp. PCC6301
      rbcLS nucleotide sequence

<400> SEQUENCE: 63
```

| | | | | |
|---|---|---|---|---|
| atggccaaga | cgcaatctgc | cgcaggctat | aaggccgggg | tgaaggacta caaactcacc | 60 |
| tattcaccc | ccgattacac | ccccaaagac | actgacctgc | tggcggcttt ccgcttcagc | 120 |
| cctcagccgg | tgtccctgc | tgacgaagct | ggtgcggcga | tcgcggctga atcttcgacc | 180 |
| ggtacctgga | ccaccgtgtg | gaccgacttg | ctgaccgaca | tggatcggta ccgcggcaag | 240 |
| tgctaccaca | tcgagccggt | gcaaggcgaa | gagaactcct | actttgcgtt catcgcttac | 300 |
| ccgctcgacc | tgtttgaaga | agggtcggtc | accaacatcc | tgacctcgat cgtcggtaac | 360 |
| gtgtttggct | tcaaagctat | ccgttcgctg | cgtctggaag | acatccgctt ccccgtcgcc | 420 |
| ttggtcaaaa | ccttccaagg | tcctccccac | ggtatccaag | tcgagcgcga cctgctgaac | 480 |
| aagtacggcc | gtccgatgct | gggttgcacg | atcaaaccaa | aactcggtct gtcggcgaaa | 540 |
| aactacggtc | gtgccgtcta | cgaatgtctg | cgcggcggtc | tggacttcac caaagacgac | 600 |
| gaaaacatca | actcgcagcc | gttccaacgc | tggcgcgatc | gcttcctgtt tgtggctgat | 660 |
| gcaatccaca | aatcgcaagc | agaaaccggt | gaaatcaaag | tcactaccct gaacgtgacc | 720 |
| gcgccgacct | gcgaagaaat | gatgaaacgg | gctgagttcg | ctaaagaact cggcatgccg | 780 |
| atcatcatgc | atgacttctt | gacggctggt | ttcaccgcca | acaccacctt ggcaaaatgg | 840 |
| tgccgcgaca | acggcgtcct | gctgcacatc | caccgtgcaa | tgcacgcggt gatcgaccgt | 900 |
| cagcgtaacc | acgggattca | cttccgtgtc | ttggccaagt | gtttgcgtct gtccggtggt | 960 |
| gaccacctcc | actccggcac | cgtcgtcggc | aaactggaag | cgacaaagc ttcgaccttg | 1020 |
| ggctttgttg | acttgatgcg | cgaagaccac | atcgaagctg | accgcagccg tggggtcttc | 1080 |
| ttcacccaag | attgggcgtc | gatgccgggc | gtgctgccgg | ttgcttccgg tggtatccac | 1140 |
| gtgtggcaca | tgcccgcact | ggtggaaatc | ttcggtgatg | actccgttct ccagttcggt | 1200 |
| ggcggcacct | ggggtcaccc | ctggggtaat | gctcctggtg | caaccgcgaa ccgtgttgcc | 1260 |
| ttggaagctt | gcgtccaagc | tcggaacgaa | ggtcgcgacc | tctaccgtga aggcggcgac | 1320 |
| atccttcgtg | aagctggcaa | gtggtcgcct | gaactggctg | ctgccctcga cctctggaaa | 1380 |
| gagatcaagt | tcgaattcga | aacgatggac | aagctctaag | agcctctga ctatcgctgg | 1440 |
| gggagtgagc | gttgctgcgt | aaagcttttct | ccccagcctt | tcgacttaac ctttcaggat | 1500 |
| ttctgaatca | tgagcatgaa | aactctgccc | aaagagcgtc | gtttcgagac tttctcgtac | 1560 |

-continued

```
ctgcctcccc tcagcgatcg ccaaatcgct gcacaaatcg agtacatgat cgagcaaggc    1620
ttccacccct tgatcgagtt caacgagcac tcgaatccgg aagagttcta ctggacgatg    1680
tggaagctcc ccctgtttga ctgcaagagc cctcagcaag tcctcgatga agtgcgtgag    1740
tgccgcagcg aatacggtga ttgctacatc cgtgtcgctg gcttcgacaa catcaagcag    1800
tgccaaaccg tgagcttcat cgttcatcgt cccggccgat actaa                    1845
```

<210> SEQ ID NO 64
<211> LENGTH: 472
<212> TYPE: PRT
<213> ORGANISM: Artificial
<220> FEATURE:
<223> OTHER INFORMATION: Based on wild-type Synechococcus sp. PCC6301
      rbcLS translated sequence

<400> SEQUENCE: 64

```
Met Ala Lys Thr Gln Ser Ala Gly Tyr Lys Ala Gly Val Lys Asp
1               5                   10                  15

Tyr Lys Leu Thr Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Gly Ala Ala Ile Ala Ala Glu Ser Ser Thr Gly Thr Trp Thr
    50                  55                  60

Thr Val Trp Thr Asp Leu Leu Thr Asp Met Asp Arg Tyr Arg Gly Lys
65                  70                  75                  80

Cys Tyr His Ile Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
    210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
            260                 265                 270

Ala Asn Thr Thr Leu Ala Lys Trp Cys Arg Asp Asn Gly Val Leu Leu
        275                 280                 285

His Ile His Arg Ala Met His Ala Val Ile Asp Arg Gln Arg Asn His
    290                 295                 300

Gly Ile His Phe Arg Val Leu Ala Lys Cys Leu Arg Leu Ser Gly Gly
```

```
                305                 310                 315                 320
Asp His Leu His Ser Gly Thr Val Val Gly Lys Leu Glu Gly Asp Lys
                    325                 330                 335
Ala Ser Thr Leu Gly Phe Val Asp Leu Met Arg Glu Asp His Ile Glu
                340                 345                 350
Ala Asp Arg Ser Arg Gly Val Phe Phe Thr Gln Asp Trp Ala Ser Met
            355                 360                 365
Pro Gly Val Leu Pro Val Ala Ser Gly Gly Ile His Val Trp His Met
    370                 375                 380
Pro Ala Leu Val Glu Ile Phe Gly Asp Asp Ser Val Leu Gln Phe Gly
385                 390                 395                 400
Gly Gly Thr Leu Gly His Pro Trp Gly Asn Ala Pro Gly Ala Thr Ala
                405                 410                 415
Asn Arg Val Ala Leu Glu Ala Cys Val Gln Ala Arg Asn Glu Gly Arg
            420                 425                 430
Asp Leu Tyr Arg Glu Gly Gly Asp Ile Leu Arg Glu Ala Gly Lys Trp
        435                 440                 445
Ser Pro Glu Leu Ala Ala Ala Leu Asp Leu Trp Lys Glu Ile Lys Phe
    450                 455                 460
Glu Phe Glu Thr Met Asp Lys Leu
465                 470
```

<210> SEQ ID NO 65
<211> LENGTH: 1845
<212> TYPE: DNA
<213> ORGANISM: Artificial
<220> FEATURE:
<223> OTHER INFORMATION: Based on wild-type Synechococcus sp. PCC6301 rbcLS nucleotide sequence

<400> SEQUENCE: 65

```
atggccaaga cgcaatctgc cgcaggctat aaggccgggg tgaaggacta caaactcacc    60
tattcaccc ccgattacac ccccaaagac actgacctgc tggcggcttt ccgcttcagc    120
cctcagccgg tgtccctgc tgacgaagct ggtgcggcga tcgcggctga atcttcgacc    180
ggtacctgga ccaccgtgtg gaccgacttg ctgaccgaca tggatcggta caaaggcaag    240
tgctaccaca tcgagccggt gcaaggcgaa gagaactcct actttgcgtt catcgcttac    300
ccgctcgacc tgtttgaaga agggtcggtc accaacatcc tgacctcgat catcggtaac    360
gtgtttggct tcaaagctat ccgttcgctg cgtctggaag acatccgctt ccccgtcgcc    420
ttggtcaaaa ccttccaagg tcctccccac ggtatccaag tcgagcgcga cctgctgaac    480
aagtacggcc gtccgatgct gggttgcacg atcaaaccaa aactcggtct gtcggcgaaa    540
aactacggtc gtgccgtcta cgaatgtctg cgcggcggtc tggacttcac caaagacgac    600
gaaaacatca actcgcagcc gttccaacgc tggcgcgatc gcttcctgtt tgtggctgat    660
gcaatccaca atcgcaagc agaaaccggt gaaatcaaag tcactacct gaacgtgacc    720
gcgccgacct gcgaagaaat gatgaaacgg gctgagttcg ctaaagaact cggcatgccg    780
atcatcatgc atgacttctt gacggctggt ttcaccgcca acaccacctt ggcaaaatgg    840
tgccgcgaca acgcgtcct gctgcacatc accgtgcag gcacgcggt gatcgaccgt    900
cagcgtaacc acgggattca cttccgtgtc ttggccaagt gtttgcgtct gtccggtggt    960
gaccacctcc actccggcac cgtcgtcggc aaactggaag cgacaaagc ttcgaccttg    1020
ggctttgttg acttgatgcg cgaagaccac atcgaagctg accgcagccg tgggggtcttc    1080
```

```
ttcacccaag attgggcgtc gatgccgggc gtgctgccgg ttgcttccgg tggtatccac   1140
gtgtggcaca tgcccgcact ggtggaaatc ttcggtgatg actccgttct ccagttcggt   1200
ggcggcacct tgggtcaccc ctggggtaat gctcctggtg caaccgcgaa ccgtgttgcc   1260
ttggaagctt gcgtccaagc tcggaacgaa ggtcgcgacc tctaccgtga aggcggcgac   1320
atccttcgtg aagctggcaa gtggtcgcct gaactggctg ctgccctcga cctctggaaa   1380
gagatcaagt tcgaattcga acgatggaca agctctaag gagcctctga ctatcgctgg   1440
gggagtgagc gttgctgcgt aaagctttct ccccagcctt tcgacttaac cttcaggat    1500 ttctgaatca tgagcatgaa aactctgccc aaagagcgtc gtttcgagac tttctcgtac   1560
ctgcctcccc tcagcgatcg ccaaatcgct gcacaaatcg agtacatgat cgagcaaggc   1620
ttccacccct tgatcgagtt caacgagcac tcgaatccgg aagagttcta ctggacgatg   1680
tggaagctcc ccctgtttga ctgcaagagc cctcagcaag tcctcgatga agtgcgtgag   1740
tgccgcagcg aatacggtga ttgctacatc cgtgtcgctg gcttcgacaa catcaagcag   1800
tgccaaaccg tgagcttcat cgttcatcgt cccggccgat actaa                  1845
```

<210> SEQ ID NO 66
<211> LENGTH: 472
<212> TYPE: PRT
<213> ORGANISM: Artificial
<220> FEATURE:
<223> OTHER INFORMATION: Based on wild-type Synechococcus sp. PCC6301
      rbcLS translated sequence

<400> SEQUENCE: 66

```
Met Ala Lys Thr Gln Ser Ala Ala Gly Tyr Lys Ala Gly Val Lys Asp
1               5                   10                  15

Tyr Lys Leu Thr Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Gly Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
65                  70                  75                  80

Cys Tyr His Ile Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Ile Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
    210                 215                 220
```

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
            245                 250                 255

Leu Gly Met Pro Ile Ile Met His Asp Phe Leu Thr Ala Gly Phe Thr
        260                 265                 270

Ala Asn Thr Thr Leu Ala Lys Trp Cys Arg Asp Asn Gly Val Leu Leu
    275                 280                 285

His Ile His Arg Ala Gly His Ala Val Ile Asp Arg Gln Arg Asn His
290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
                325                 330                 335

Ala Ser Thr Leu Gly Phe Val Asp Leu Met Arg Glu Asp His Ile Glu
            340                 345                 350

Ala Asp Arg Ser Arg Gly Val Phe Phe Thr Gln Asp Trp Ala Ser Met
        355                 360                 365

Pro Gly Val Leu Pro Val Ala Ser Gly Gly Ile His Val Trp His Met
370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
                405                 410                 415

Asn Arg Val Ala Leu Glu Ala Cys Val Gln Ala Arg Asn Glu Gly Arg
            420                 425                 430

Asp Leu Tyr Arg Glu Gly Gly Asp Ile Leu Arg Glu Ala Gly Lys Trp
        435                 440                 445

Ser Pro Glu Leu Ala Ala Ala Leu Asp Leu Trp Lys Glu Ile Lys Phe
    450                 455                 460

Glu Phe Glu Thr Met Asp Lys Leu
465                 470

<210> SEQ ID NO 67
<211> LENGTH: 1845
<212> TYPE: DNA
<213> ORGANISM: Artificial
<220> FEATURE:
<223> OTHER INFORMATION: Based on wild-type Synechococcus sp. PCC6301
      rbcLS nucleotide sequence

<400> SEQUENCE: 67
atggccaaga cgcaatctgc cgcaggctat aaggccgggg tgaaggacta caaactcacc      60 tattcaccc ccgattacac ccccaaagac actgacctgc tggcggcttt ccgcttcagc      120
cctcagccgg tgtccctgc tgacgaagct ggtgcggcga tcgcggctga atcttcgacc      180
ggtacctgga ccaccgtgtg gaccgacttg ctgaccgaca tggatcggta caaaggcaag      240
tgctaccaca tcgagccggt gcaaggcgaa gagaactcct actttgcgtt catcgcttac      300
ccgctcgacc tgtttgaaga agggtcggtc accaacatcc tgacctcgat cgtcggtaac      360
gtgtttggct tcaaagctat ccgttcgctg cgtctggaag acatccgctt ccccgtcgcc      420
ttggtcaaaa ccttccaagg tcctccccac ggtatccaag tcgagcgcga cctgctgaac      480
aagtacggcc gtccgatgct gggttgcacg atcaaaccaa aactcggtct gtcggcgaaa      540
aactacggtc gtgccgtcta cgaatgtctg cgcggcggtc tggacttcac caaagacgac      600

```
gaaaacatca actcgcagcc gttccaacgc tggcgcgatc gcttcctgtt tgtggctgat      660
gcaatccaca aatcgcaagc agaaaccggt gaaatcaaag gtcactacct gaacgtgacc      720
gcgccgacct gcgaagaaat gatgaaacgg gctgagttcg ctaaagaact cggcatgccg      780
atcatcatgc atgacttctt gacggctggt ttcaccgcca acaccacctt ggcaaaatgg      840
tgccgcgaca acggcgtcct gctgcacatc caccgtgcag ggcacgcggt gatcgaccgt      900
cagcgtaacc acgggattca cttccgtgtc ttggccaagt gtttgcgtct gtccggtggt      960
gaccacctcc actccggcac cgtcgtcggc aaactggaag gcgacaaagc ttcgaccttg     1020
ggctttgttg acttgatgcg cgaagaccac atcgaagctg accgcagccg tggggtcttc     1080
ttcacccaag attgggcgtc gatgccgggc gtgctgccgg ttgcttccgg tggtatccac     1140
gtgtggcaca tgcccgcact ggtggaaatc ttcggtgatg actccgttct ccagttcggt     1200
ggcggcacct tgggtcaccc ctggggtaat gctcctggtg caaccgcgaa ccgtgttgcc     1260
ttggaagctt gcgtccaagc tcggaacgaa ggtcgcgacc tctaccgtga aggcggcgac     1320
atccttcgtg aagctggcaa gtggtcgcct gaactggctg ctgccctcga cctctggaaa     1380
gagatcaagt tcgaattcga aacgatggac aagctctaag gagcctctga ctatcgctgg     1440
gggagtgagc gttgctgcgt aaagctttct ccccagcctt tcgacttaac ctttcaggat     1500
ttctgaatca tgagcatgaa aactctgccc aaagagcgtc gtttcgagac tttctcgtac     1560
ctgcctcccc tcagcgatcg ccaaatcgct gcacaaatcg agtacatgat cgagcaaggc     1620
ttccacccct tgatcgagtt caacgagcac tcgaatccgg aagagttcta ctggacgatg     1680
tggaagctcc ccctgtttga ctgcaagagc cctcagcaag tcctcgatga agtgcgtgag     1740
tgccgcagcg aatacggtga ttgctacatc cgtgtcgctg gcttcgacaa catcaagcag     1800
tgccaaaccg tgagcttcat cgttcatcgt cccggccgat actaa                     1845
```

<210> SEQ ID NO 68
<211> LENGTH: 472
<212> TYPE: PRT
<213> ORGANISM: Artificial
<220> FEATURE:
<223> OTHER INFORMATION: Based on wild-type Synechococcus sp. PCC6301
      rbcLS translated sequence

<400> SEQUENCE: 68

```
Met Ala Lys Thr Gln Ser Ala Ala Gly Tyr Lys Ala Gly Val Lys Asp
1               5                   10                  15

Tyr Lys Leu Thr Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Gly Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
65                  70                  75                  80

Cys Tyr His Ile Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140
```

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
            165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
            195                 200                 205

Gln Arg Trp Arg Asp Arg Phe Leu Phe Val Ala Asp Ala Ile His Lys
            210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
            245                 250                 255

Leu Gly Met Pro Ile Ile Met His Asp Phe Leu Thr Ala Gly Phe Thr
            260                 265                 270

Ala Asn Thr Thr Leu Ala Lys Trp Cys Arg Asp Asn Gly Val Leu Leu
            275                 280                 285

His Ile His Arg Ala Gly His Ala Val Ile Asp Arg Gln Arg Asn His
            290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
            325                 330                 335

Ala Ser Thr Leu Gly Phe Val Asp Leu Met Arg Glu Asp His Ile Glu
            340                 345                 350

Ala Asp Arg Ser Arg Gly Val Phe Phe Thr Gln Asp Trp Ala Ser Met
            355                 360                 365

Pro Gly Val Leu Pro Val Ala Ser Gly Gly Ile His Val Trp His Met
370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
            405                 410                 415

Asn Arg Val Ala Leu Glu Ala Cys Val Gln Ala Arg Asn Glu Gly Arg
            420                 425                 430

Asp Leu Tyr Arg Glu Gly Gly Asp Ile Leu Arg Glu Ala Gly Lys Trp
            435                 440                 445

Ser Pro Glu Leu Ala Ala Ala Leu Asp Leu Trp Lys Glu Ile Lys Phe
            450                 455                 460

Glu Phe Glu Thr Met Asp Lys Leu
465                 470

<210> SEQ ID NO 69
<211> LENGTH: 1845
<212> TYPE: DNA
<213> ORGANISM: Artificial
<220> FEATURE:
<223> OTHER INFORMATION: Based on wild-type Synechococcus sp. PCC6301
      rbcLS nucleotide sequence

<400> SEQUENCE: 69
atggccaaga cgcaatctgc cgcaggctat aaggccgggg tgaaggacta caaactcacc      60
tattacaccc ccgattacac ccccaaagac actgacctgc tggcggcttt ccgcttcagc     120

```
cctcagccgg gtgtccctgc tgacgaagct ggtgcggcga tcgcggctga atcttcgacc    180
ggtacctgga ccaccgtgtg gaccgacttg ctgaccgaca tggatcggta caaaggcaag    240
tgctaccaca tcgagccggt gcaaggcgaa gagaactcct actttgcgtt catcgcttac    300
ccgctcgacc tgtttgaaga agggtcggtc accaacatcc tgacctcgat catcggtaac    360
gtgtttggct tcaaagctat ccgttcgctg cgtctggaag acatccgctt cccgtcgcc     420
ttggtcaaaa ccttccaagg tcctccccac ggtatccaag tcgagcgcga cctgctgaac    480
aagtacggcc gtccgatgct gggttgcacg atcaaaccaa aactcggtct gtcggcgaaa    540
aactacggtc gtgccgtcta cgaatgtctg cgcggcggtc tggacttcac caaagacgac    600
gaaaacatca actcgcagcc gttccaacgc tggcgcgatc gcttcctgtt gtgtggctgat   660
gcaatccaca aatcgcaagc agaaaccggt gaaatcaaag tcactacctg aacgtgacc    720
gcgccgacct gcgaagaaat gatgaaacgg gctgagttcg ctaaagaact cggcatgccg    780
atcatcatgc atgacttctt gacggctggt ttcaccgcca acaccacctt ggcaaaatgg    840
tgccgcgaca acggcgtcct gctgcacatc accgtgcaa tgcacgcggt gatcgaccgt     900
cagcgtaacc acgggattca cttccgtgtc ttggccaagt gtttgcgtct gtccggtggt    960
gaccacctcc actccggcac cgtcgtcggc aaactggaag cgacaaaagc ttcgaccttg   1020
ggctttgttg acttgatgcg cgaagaccac atcgaagctg accgcagccg tggggtcttc   1080
ttcacccaag attgggcgtc gatgccgggc gtgctgccgg ttgcttccgg tggtatccac   1140
gtgtggcaca tgcccgcact ggtggaaatc ttcggtgatg actccgttct ccagttcggt   1200
ggcggcacct gggtcaccc ctggggtaat gctcctggtg caaccgcgaa ccgtgttgcc   1260
ttggaagctt gcgtccaagc tcggaacgaa ggtcgcgacc tctaccgtga aggcggcgac   1320
atccttcgtg aagctggcaa gtggtcgcct gaactggctg ctgccctcga cctctggaaa   1380
gagatcaagt tcgaattcga acgatggac aagctctaag gagcctctga ctatcgctgg   1440
gggagtgagc gttgctgcgt aaagctttct ccccagcctt cgacttaac ctttcaggat   1500
ttctgaatca tgagcatgaa aactctgccc aaagagcgtc gtttcgagac tttctcgtac   1560
ctgcctcccc tcagcgatcg ccaaatcgct gcacaaatcg agtacatgat cgagcaaggc   1620
ttccacccct tgatcgagtt caacgagcac tcgaatccgg aagagttcta ctggacgatg   1680
tggaagctcc ccctgtttga ctgcaagagc cctcagcaag tcctcgatga agtgcgtgag   1740
tgccgcagcg aatacggtga ttgctacatc cgtgtcgctg gcttcgacaa catcaagcag   1800
tgccaaaccg tgagcttcat cgttcatcgt cccggccgat actaa                   1845
```

<210> SEQ ID NO 70
<211> LENGTH: 472
<212> TYPE: PRT
<213> ORGANISM: Artificial
<220> FEATURE:
<223> OTHER INFORMATION: Based on wild-type Synechococcus sp. PCC6301
      rbcLS translated sequence

<400> SEQUENCE: 70

Met Ala Lys Thr Gln Ser Ala Ala Gly Tyr Lys Ala Gly Val Lys Asp
1               5                   10                  15

Tyr Lys Leu Thr Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Gly Ala Ala Ile Ala Ala Glu Ser Ser Thr Gly Thr Trp Thr

```
                50                  55                  60
Thr Val Trp Thr Asp Leu Leu Thr Asp Met Asp Arg Tyr Lys Gly Lys
 65                  70                  75                  80

Cys Tyr His Ile Glu Pro Val Gln Gly Glu Asn Ser Tyr Phe Ala
                 85                  90                  95

Phe Ile Ala Tyr Pro Leu Asp Leu Phe Glu Glu Gly Ser Val Thr Asn
                100                 105                 110

Ile Leu Thr Ser Ile Ile Gly Asn Val Phe Gly Phe Lys Ala Ile Arg
                115                 120                 125

Ser Leu Arg Leu Glu Asp Ile Arg Phe Pro Val Ala Leu Val Lys Thr
130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
                180                 185                 190

Gly Leu Asp Phe Thr Lys Asp Asp Glu Asn Ile Asn Ser Gln Pro Phe
                195                 200                 205

Gln Arg Trp Arg Asp Arg Phe Leu Phe Val Ala Asp Ala Ile His Lys
210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
                260                 265                 270

Ala Asn Thr Thr Leu Ala Lys Trp Cys Arg Asp Asn Gly Val Leu Leu
                275                 280                 285

His Ile His Arg Ala Met His Ala Val Ile Asp Arg Gln Arg Asn His
                290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
                325                 330                 335

Ala Ser Thr Leu Gly Phe Val Asp Leu Met Arg Glu Asp His Ile Glu
                340                 345                 350

Ala Asp Arg Ser Arg Gly Val Phe Phe Thr Gln Asp Trp Ala Ser Met
                355                 360                 365

Pro Gly Val Leu Pro Val Ala Ser Gly Gly Ile His Val Trp His Met
370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
                405                 410                 415

Asn Arg Val Ala Leu Glu Ala Cys Val Gln Ala Arg Asn Glu Gly Arg
                420                 425                 430

Asp Leu Tyr Arg Glu Gly Gly Asp Ile Leu Arg Glu Ala Gly Lys Trp
                435                 440                 445

Ser Pro Glu Leu Ala Ala Ala Leu Asp Leu Trp Lys Glu Ile Lys Phe
450                 455                 460

Glu Phe Glu Thr Met Asp Lys Leu
465                 470
```

<210> SEQ ID NO 71
<211> LENGTH: 1434
<212> TYPE: DNA
<213> ORGANISM: Nicotiana tabacum

<400> SEQUENCE: 71

```
atgtcaccac aaacagagac taaagcaagt gttggattca aagctggtgt taaagagtac      60
aaattgactt attatactcc tgagtaccaa accaaggata ctgatatatt ggcagcattc     120
cgagtaactc ctcaacctgg agttccacct gaagaagcag gggccgcggt agctgccgaa     180
tcttctactg gtacatggac aactgtatgg accgatggac ttaccagcct tgatcgttac     240
aaagggcgat gctaccgcat cgagcgtgtt gttggagaaa agatcaata tattgcttat      300
gtagcttacc ctttagacct ttttgaagaa ggttctgtta ccaacatgtt tacttccatt     360
gtaggtaacg tatttgggtt caaagccctg cgcgctctac gtctggaaga tctgcgaatc     420
cctcctgctt atgttaaaac tttccaaggt ccgcctcatg ggatccaagt tgaaagagat     480
aaattgaaca gtatggtcg tcccctgttg ggatgtacta ttaaacctaa attggggtta      540
tctgctaaaa actacggtag agccgtttat gaatgtcttc gcggtggact tgattttact     600
aaagatgatg agaacgtgaa ctcacaacca tttatgcgtt ggagagatcg tttcttattt     660
tgtgccgaag cactttataa agcacaggct gaaacaggtg aaatcaaagg cattacttg      720
aatgctactg caggtacatg cgaagaaatg atcaaaagag ctgtatttgc tagagaattg     780
ggcgttccga tcgtaatgca tgactactta acgggggat tcaccgcaaa tactagcttg      840
gctcattatt gccgagataa tggtctactt cttcacatcc accgtgcaat gcatgcggtt     900
attgatagac agaagaatca tggtatccac ttccgggtat tagcaaaagc gttacgtatg     960
tctggtggag atcatattca ctctggtacc gtagtaggta aacttgaagg tgaaagagac    1020
ataactttgg gctttgttga tttactgcgt gatgattttg ttgaacaaga tcgaagtcgc    1080
ggtatttatt tcactcaaga ttgggtctct ttaccaggtg ttctacccgt ggcttcagga    1140
ggtattcacg tttggcatat gcctgctctg accgagatct tgggggatga ttccgtacta    1200
cagttcggtg gaggaacttt aggacatcct tggggtaatg cgccaggtgc cgtagctaat    1260
cgagtagctc tagaagcatg tgtaaaagct cgtaatgaag acgtgatct tgctcaggaa     1320
ggtaatgaaa ttattcgcga ggcttgcaaa tggagcccgg aactagctgc tgcttgtgaa    1380
gtatggaaag agatcgtatt taattttgca gcagtggacg ttttggataa gtaa          1434
```

<210> SEQ ID NO 72
<211> LENGTH: 477
<212> TYPE: PRT
<213> ORGANISM: Nicotiana tabacum

<400> SEQUENCE: 72

```
Met Ser Pro Gln Thr Glu Thr Lys Ala Ser Val Gly Phe Lys Ala Gly
1               5                   10                  15

Val Lys Glu Tyr Lys Leu Thr Tyr Tyr Thr Pro Glu Tyr Gln Thr Lys
            20                  25                  30

Asp Thr Asp Ile Leu Ala Ala Phe Arg Val Thr Pro Gln Pro Gly Val
        35                  40                  45

Pro Pro Glu Glu Ala Gly Ala Ala Val Ala Ala Glu Ser Ser Thr Gly
    50                  55                  60

Thr Trp Thr Thr Val Trp Thr Asp Gly Leu Thr Ser Leu Asp Arg Tyr
65                  70                  75                  80
```

Lys Gly Arg Cys Tyr Arg Ile Glu Arg Val Gly Glu Lys Asp Gln
            85                  90                  95

Tyr Ile Ala Tyr Val Ala Tyr Pro Leu Asp Leu Phe Glu Glu Gly Ser
            100                 105                 110

Val Thr Asn Met Phe Thr Ser Ile Val Gly Asn Val Phe Gly Phe Lys
            115                 120                 125

Ala Leu Arg Ala Leu Arg Leu Glu Asp Leu Arg Ile Pro Pro Ala Tyr
            130                 135                 140

Val Lys Thr Phe Gln Gly Pro Pro His Gly Ile Gln Val Glu Arg Asp
145                 150                 155                 160

Lys Leu Asn Lys Tyr Gly Arg Pro Leu Leu Gly Cys Thr Ile Lys Pro
            165                 170                 175

Lys Leu Gly Leu Ser Ala Lys Asn Tyr Gly Arg Ala Val Tyr Glu Cys
            180                 185                 190

Leu Arg Gly Gly Leu Asp Phe Thr Lys Asp Asp Glu Asn Val Asn Ser
            195                 200                 205

Gln Pro Phe Met Arg Trp Arg Asp Arg Phe Leu Phe Cys Ala Glu Ala
            210                 215                 220

Leu Tyr Lys Ala Gln Ala Glu Thr Gly Glu Ile Lys Gly His Tyr Leu
225                 230                 235                 240

Asn Ala Thr Ala Gly Thr Cys Glu Glu Met Ile Lys Arg Ala Val Phe
            245                 250                 255

Ala Arg Glu Leu Gly Val Pro Ile Val Met His Asp Tyr Leu Thr Gly
            260                 265                 270

Gly Phe Thr Ala Asn Thr Ser Leu Ala His Tyr Cys Arg Asp Asn Gly
            275                 280                 285

Leu Leu Leu His Ile His Arg Ala Met His Ala Val Ile Asp Arg Gln
            290                 295                 300

Lys Asn His Gly Ile His Phe Arg Val Leu Ala Lys Ala Leu Arg Met
305                 310                 315                 320

Ser Gly Gly Asp His Ile His Ser Gly Thr Val Val Gly Lys Leu Glu
            325                 330                 335

Gly Glu Arg Asp Ile Thr Leu Gly Phe Val Asp Leu Leu Arg Asp Asp
            340                 345                 350

Phe Val Glu Gln Asp Arg Ser Arg Gly Ile Tyr Phe Thr Gln Asp Trp
            355                 360                 365

Val Ser Leu Pro Gly Val Leu Pro Val Ala Ser Gly Gly Ile His Val
            370                 375                 380

Trp His Met Pro Ala Leu Thr Glu Ile Phe Gly Asp Asp Ser Val Leu
385                 390                 395                 400

Gln Phe Gly Gly Gly Thr Leu Gly His Pro Trp Gly Asn Ala Pro Gly
            405                 410                 415

Ala Val Ala Asn Arg Val Ala Leu Glu Ala Cys Val Lys Ala Arg Asn
            420                 425                 430

Glu Gly Arg Asp Leu Ala Gln Glu Gly Asn Glu Ile Ile Arg Glu Ala
            435                 440                 445

Cys Lys Trp Ser Pro Glu Leu Ala Ala Ala Cys Glu Val Trp Lys Glu
            450                 455                 460

Ile Val Phe Asn Phe Ala Ala Val Asp Val Leu Asp Lys
465                 470                 475

<210> SEQ ID NO 73
<211> LENGTH: 1434

<212> TYPE: DNA
<213> ORGANISM: Artificial
<220> FEATURE:
<223> OTHER INFORMATION: Based on Nicotiana tabacum wt (wild-type) rbcL
      coding sequence

<400> SEQUENCE: 73

```
atgtcaccac aaacagagac taaagcaagt gttggattca aagctggtgt taaagagtac      60
aaattgactt attatactcc tgagtaccaa accaaggata ctgatatatt ggcagcattc     120
cgagtaactc ctcaacctgg agttccacct gaagaagcag gggccgcggt agctgccgaa     180
tcttctactg gtacatggac aactgtatgg accgatggac ttaccagcct tgatcgttac     240
agagggcgat gctaccgcat cgagcgtgtt gttggagaaa aagatcaata tattgcttat     300
gtagcttacc ctttagacct ttttgaagaa ggttctgtta ccaacatgtt tacttccatt     360
gtaggtaacg tatttgggtt caaagccctg cgcgctctac gtctggaaga tctgcgaatc     420
cctcctgctt atgttaaaac tttccaaggt ccgcctcatg ggatccaagt tgaaagagat     480
aaattgaaca gtatggtcg tcccctgttg ggatgtacta ttaaacctaa attggggtta     540
tctgctaaaa actacggtag agccgtttat gaatgtcttc gcggtggact tgattttact     600
aaagatgatg agaacgtgaa ctcacaacca tttatgcgtt ggagagatcg tttcttattt     660
tgtgccgaag cactttataa agcacaggct gaaacaggtg aaatcaaagg cattacttg     720
aatgctactg caggtacatg cgaagaaatg atcaaaagag ctgtatttgc tagagaattg     780
ggcgttccga tcgtaatgca tgactactta cgggggat tcaccgcaaa tactagcttg     840
gctcattatt gccgagataa tggtctactt cttcacatcc accgtgcaat gcatgcggtt     900
attgatagac agaagaatca tggtatccac ttccgggtat tagcaaaagc gttacgtatg     960
tctggtggaa atcatattca ctctggtacc gtagtaggta aacttgaagg tgaaagagac    1020
ataactttgg gctttgttga tttactgcgt gatgattttg ttgaacaaga tcgaagtcgc    1080
ggtatttatt tcactcaaga ttgggtctct ttaccaggtg ttctacccgt ggcttcagga    1140
ggtattcacg tttggcatat gcctgctctg accgagatct tggggatga ttccgtacta    1200
cagttcggtg gaggaactt aggacatcct tggggtaatg cgccaggtgc cgtagctaat    1260
cgagtagctc tagaagcatg tgtaaaagct cgtaatgaag acgtgatct tgctcaggaa    1320
ggtaatgaaa ttattcgcga ggcttgcaaa tggagcccgg aactagctgc tgcttgtgaa    1380
gtatggaaag agatcgtatt taattttgca gcagtggacg ttttggataa gtaa          1434
```

<210> SEQ ID NO 74
<211> LENGTH: 477
<212> TYPE: PRT
<213> ORGANISM: Artificial
<220> FEATURE:
<223> OTHER INFORMATION: Based on Nicotiana tabacum wt (wild-type)
      translated wild type L-subunit sequence

<400> SEQUENCE: 74

```
Met Ser Pro Gln Thr Glu Thr Lys Ala Ser Val Gly Phe Lys Ala Gly
1               5                   10                  15

Val Lys Glu Tyr Lys Leu Gly Tyr Tyr Thr Pro Glu Tyr Gln Thr Lys
            20                  25                  30

Asp Thr Asp Ile Leu Ala Ala Phe Arg Val Thr Pro Gln Pro Gly Val
        35                  40                  45

Pro Pro Glu Glu Ala Gly Ala Ala Val Ala Ala Glu Ser Ser Thr Gly
    50                  55                  60
```

```
Thr Trp Thr Thr Val Trp Thr Asp Gly Leu Thr Ser Leu Asp Arg Tyr
 65              70                  75                  80

Arg Gly Arg Cys Tyr Arg Ile Glu Arg Val Val Gly Glu Lys Asp Gln
                 85                  90                  95

Tyr Ile Ala Tyr Val Ala Tyr Pro Leu Asp Leu Phe Glu Glu Gly Ser
                100                 105                 110

Val Thr Asn Met Phe Thr Ser Ile Val Gly Asn Val Phe Gly Phe Lys
                115                 120                 125

Ala Leu Arg Ala Leu Arg Leu Glu Asp Leu Arg Ile Pro Pro Ala Tyr
            130                 135                 140

Val Lys Thr Phe Gln Gly Pro Pro His Gly Ile Gln Val Glu Arg Asp
145                 150                 155                 160

Lys Leu Asn Lys Tyr Gly Arg Pro Leu Leu Gly Cys Thr Ile Lys Pro
                165                 170                 175

Lys Leu Gly Leu Ser Ala Lys Asn Tyr Gly Arg Ala Val Tyr Glu Cys
                180                 185                 190

Leu Arg Gly Gly Leu Asp Phe Thr Lys Asp Asp Glu Asn Val Asn Ser
            195                 200                 205

Gln Pro Phe Met Arg Trp Arg Asp Arg Phe Leu Phe Cys Ala Glu Ala
    210                 215                 220

Leu Tyr Lys Ala Gln Ala Glu Thr Gly Glu Ile Lys Gly His Tyr Leu
225                 230                 235                 240

Asn Ala Thr Ala Gly Thr Cys Glu Glu Met Ile Lys Arg Ala Val Phe
                245                 250                 255

Ala Arg Glu Leu Gly Val Pro Ile Val Met His Asp Tyr Leu Thr Gly
            260                 265                 270

Gly Phe Thr Ala Asn Thr Ser Leu Ala His Tyr Cys Arg Asp Asn Gly
        275                 280                 285

Leu Leu Leu His Ile His Arg Ala Met His Ala Val Ile Asp Arg Gln
            290                 295                 300

Lys Asn His Gly Ile His Phe Arg Val Leu Ala Lys Ala Leu Arg Met
305                 310                 315                 320

Ser Gly Gly Asp His Ile His Ser Gly Thr Val Val Gly Lys Leu Glu
                325                 330                 335

Gly Glu Arg Asp Ile Thr Leu Gly Phe Val Asp Leu Leu Arg Asp Asp
            340                 345                 350

Phe Val Glu Gln Asp Arg Ser Arg Gly Ile Tyr Phe Thr Gln Asp Trp
        355                 360                 365

Val Ser Leu Pro Gly Val Leu Pro Val Ala Ser Gly Gly Ile His Val
    370                 375                 380

Trp His Met Pro Ala Leu Thr Glu Ile Phe Gly Asp Asp Ser Val Leu
385                 390                 395                 400

Gln Phe Gly Gly Gly Thr Leu Gly His Pro Trp Gly Asn Ala Pro Gly
                405                 410                 415

Ala Val Ala Asn Arg Val Ala Leu Glu Ala Cys Val Lys Ala Arg Asn
                420                 425                 430

Glu Gly Arg Asp Leu Ala Gln Glu Gly Asn Glu Ile Ile Arg Glu Ala
            435                 440                 445

Cys Lys Trp Ser Pro Glu Leu Ala Ala Ala Cys Glu Val Trp Lys Glu
            450                 455                 460

Ile Val Phe Asn Phe Ala Ala Val Asp Val Leu Asp Lys
465                 470                 475
```

-continued

<210> SEQ ID NO 75
<211> LENGTH: 1434
<212> TYPE: DNA
<213> ORGANISM: Artificial
<220> FEATURE:
<223> OTHER INFORMATION: Based on Nicotiana tabacum wt (wild-type) rbcL
      coding sequence

<400> SEQUENCE: 75

```
atgtcaccac aaacagagac taaagcaagt gttggattca agctggtgt taaagagtac      60
aaattgactt attatactcc tgagtaccaa accaaggata ctgatatatt ggcagcattc     120
cgagtaactc ctcaacctgg agttccacct gaagaagcag gggccgcggt agctgccgaa     180
tcttctactg gtacatggac aactgtatgg accgatggac ttaccagcct tgatcgttac     240
agagggcgat gctaccgcat cgagcgtgtt gttggagaaa aagatcaata tattgcttat     300
gtagcttacc ctttagacct ttttgaagaa ggttctgtta ccaacatgtt tacttccatt     360
gtaggtaacg tatttgggtt caaagccctg cgcgctctac gtctggaaga tctgcgaatc     420
cctcctgctt atgttaaaac tttccaaggt ccgcctcatg gatccaagt tgaaagagat     480
aaattgaaca gtatggtcg tcccctgttg ggatgtacta ttaaacctaa attggggtta     540
tctgctaaaa actacggtag agccgtttat gaatgtcttc gcggtggact tgattttact     600
aaagatgatg agaacgtgaa ctcacaacca tttatgcgtt ggagagatcg tttcttattt     660
tgtgccgaag cactttataa agcacaggct gaaacaggtg aaatcaaagg cattacttg     720
aatgctactg caggtacatg cgaagaaatg atcaaaagag ctgtatttgc tagagaattg     780
ggcgttccga tcgtaatgca tgactactta acgggggat tcaccgcaaa tactagcttg     840
gctcattatt gccgagataa tggtctactt cttcacatcc accgtgcaat gcatgcggtt     900
attgatagac agaagaatca tggtatccac ttccgggtat tagcaaaagc gttacgtatg     960
tctggtggag atcatattca ctctggtacc gtagtaggta aacttgaagg tgaaagagac    1020
ataactttgg gctttgttga tttactgcgt gatgattttg ttgaacaaga tcgaagtcgc    1080
ggtatttatt tcactcaaga ttgggtctct ttaccaggtg ttctacccgt ggcttcagga    1140
ggtattcacg tttggcatat gcctgctctg accgagatct tggggatga ttccgtacta    1200
cagttcggtg gaggaacttt aggacatcct tggggtaatg cgccaggtgc cgtagctaat    1260
cgagtagctc tagaagcatg tgtaaaagct cgtaatgaag acgtgatct tgctcaggaa    1320
ggtaatgaaa ttattcgcga ggcttgcaaa tggagcccgg aactagctgc tgcttgtgaa    1380
gtatggaaag agatcgtatt taattttgca gcagtggacg ttttggataa gtaa         1434
```

<210> SEQ ID NO 76
<211> LENGTH: 477
<212> TYPE: PRT
<213> ORGANISM: Artificial
<220> FEATURE:
<223> OTHER INFORMATION: Based on Nicotiana tabacum wild type translated
      L-subunit

<400> SEQUENCE: 76

```
Met Ser Pro Gln Thr Glu Thr Lys Ala Ser Val Gly Phe Lys Ala Gly
1               5                   10                  15

Val Lys Glu Tyr Lys Leu Thr Tyr Tyr Thr Pro Glu Tyr Gln Thr Lys
            20                  25                  30

Asp Thr Asp Ile Leu Ala Ala Phe Arg Val Thr Pro Gln Pro Gly Val
        35                  40                  45

Pro Pro Glu Glu Ala Gly Ala Ala Val Ala Ala Glu Ser Ser Thr Gly
```

```
            50                  55                  60
Thr Trp Thr Thr Val Trp Thr Asp Gly Leu Thr Ser Leu Asp Arg Tyr
 65                  70                  75                  80

Arg Gly Arg Cys Tyr Arg Ile Glu Arg Val Val Gly Glu Lys Asp Gln
                 85                  90                  95

Tyr Ile Ala Tyr Val Ala Tyr Pro Leu Asp Leu Phe Glu Glu Gly Ser
            100                 105                 110

Val Thr Asn Met Phe Thr Ser Ile Val Gly Asn Val Phe Gly Phe Lys
            115                 120                 125

Ala Leu Arg Ala Leu Arg Leu Glu Asp Leu Arg Ile Pro Pro Ala Tyr
        130                 135                 140

Val Lys Thr Phe Gln Gly Pro Pro His Gly Ile Gln Val Glu Arg Asp
145                 150                 155                 160

Lys Leu Asn Lys Tyr Gly Arg Pro Leu Leu Gly Cys Thr Ile Lys Pro
                165                 170                 175

Lys Leu Gly Leu Ser Ala Lys Asn Tyr Gly Arg Ala Val Tyr Glu Cys
            180                 185                 190

Leu Arg Gly Gly Leu Asp Phe Thr Lys Asp Asp Glu Asn Val Asn Ser
        195                 200                 205

Gln Pro Phe Met Arg Trp Arg Asp Arg Phe Leu Phe Cys Ala Glu Ala
210                 215                 220

Leu Tyr Lys Ala Gln Ala Glu Thr Gly Glu Ile Lys Gly His Tyr Leu
225                 230                 235                 240

Asn Ala Thr Ala Gly Thr Cys Glu Glu Met Ile Lys Arg Ala Val Phe
                245                 250                 255

Ala Arg Glu Leu Gly Val Pro Ile Val Met His Asp Tyr Leu Thr Gly
            260                 265                 270

Gly Phe Thr Ala Asn Thr Ser Leu Ala His Tyr Cys Arg Asp Asn Gly
        275                 280                 285

Leu Leu Leu His Ile His Arg Ala Met His Ala Val Ile Asp Arg Gln
290                 295                 300

Lys Asn His Gly Ile His Phe Arg Val Leu Ala Lys Ala Leu Arg Met
305                 310                 315                 320

Ser Gly Gly Asp His Ile His Ser Gly Thr Val Val Gly Lys Leu Glu
                325                 330                 335

Gly Glu Arg Asp Ile Thr Leu Gly Phe Val Asp Leu Leu Arg Asp Asp
            340                 345                 350

Phe Val Glu Gln Asp Arg Ser Arg Gly Ile Tyr Phe Thr Gln Asp Trp
        355                 360                 365

Val Ser Leu Pro Gly Val Leu Pro Val Ala Ser Gly Gly Ile His Val
370                 375                 380

Trp His Met Pro Ala Leu Thr Glu Ile Phe Gly Asp Asp Ser Val Leu
385                 390                 395                 400

Gln Phe Gly Gly Gly Thr Leu Gly His Pro Trp Gly Asn Ala Pro Gly
                405                 410                 415

Ala Val Ala Asn Arg Val Ala Leu Glu Ala Cys Val Lys Ala Arg Asn
            420                 425                 430

Glu Gly Arg Asp Leu Ala Gln Glu Gly Asn Glu Ile Ile Arg Glu Ala
        435                 440                 445

Cys Lys Trp Ser Pro Glu Leu Ala Ala Ala Cys Glu Val Trp Lys Glu
450                 455                 460

Ile Val Phe Asn Phe Ala Ala Val Asp Val Leu Asp Lys
465                 470                 475
```

<210> SEQ ID NO 77
<211> LENGTH: 1434
<212> TYPE: DNA
<213> ORGANISM: Artificial
<220> FEATURE:
<223> OTHER INFORMATION: Based on Nicotiana tabacum wt (wild-type) rbcL
      coding sequence

<400> SEQUENCE: 77

| | | |
|---|---|---|
| atgtcaccac aaacagagac taaagcaagt gttggattca aagctggtgt taaagagtac | 60 |
| aaattgggtt attatactcc tgagtaccaa accaaggata ctgatatatt ggcagcattc | 120 |
| cgagtaactc ctcaacctgg agttccacct gaagaagcag gggccgcggt agctgccgaa | 180 |
| tcttctactg gtacatggac aactgtatgg accgatggac ttaccagcct tgatcgttac | 240 |
| aaagggcgat gctaccgcat cgagcgtgtt gttggagaaa aagatcaata tattgcttat | 300 |
| gtagcttacc ctttagacct ttttgaagaa ggttctgtta ccaacatgtt tacttccatt | 360 |
| gtaggtaacg tatttggggtt caaagccctg cgcgctctac gtctggaaga tctgcgaatc | 420 |
| cctcctgctt atgttaaaac tttccaaggt ccgcctcatg gatccaagt tgaaagagat | 480 |
| aaattgaaca agtatggtcg tccccctgttg ggatgtacta ttaaacctaa attggggtta | 540 |
| tctgctaaaa actacggtag agccgtttat gaatgtcttc gcggtggact tgattttact | 600 |
| aaagatgatg agaacgtgaa ctcacaacca tttatgcgtt ggagagatcg tttcttattt | 660 |
| tgtgccgaag cactttataa agcacaggct gaaacaggtg aaatcaaagg cattacttg | 720 |
| aatgctactg caggtacatg cgaagaaatg atcaaaagag ctgtatttgc tagagaattg | 780 |
| ggcgttccga tcgtaatgca tgactactta acgggggggat tcaccgcaaa tactagcttg | 840 |
| gctcattatt gccgagataa tggtctactt cttcacatcc accgtgcaat gcatgcggtt | 900 |
| attgatagac agaagaatca tggtatccac ttccgggtat tagcaaaagc gttacgtatg | 960 |
| tctggtggag atcatattca ctctggtacc gtagtaggta aacttgaagg tgaaagagac | 1020 |
| ataactttgg gctttgttga tttactgcgt gatgattttg ttgaacaaga tcgaagtcgc | 1080 |
| ggtatttatt tcactcaaga ttgggtctct ttaccaggtg ttctacccgt ggcttcagga | 1140 |
| ggtattcacg tttggcatat gcctgctctg accgagatct tggggatga ttccgtacta | 1200 |
| cagttcggtg gaggaacttt aggacatcct tggggtaatg cgccaggtgc cgtagctaat | 1260 |
| cgagtagctc tagaagcatg tgtaaaagct cgtaatgaag gacgtgatct tgctcaggaa | 1320 |
| ggtaatgaaa ttattcgcga ggcttgcaaa tggagcccgg aactagctgc tgcttgtgaa | 1380 |
| gtatggaaag agatcgtatt taattttgca gcagtggacg ttttggataa gtaa | 1434 |

<210> SEQ ID NO 78
<211> LENGTH: 477
<212> TYPE: PRT
<213> ORGANISM: Artificial
<220> FEATURE:
<223> OTHER INFORMATION: Based on Nicotiana tabacum wild type translated
      L-subunit

<400> SEQUENCE: 78

Met Ser Pro Gln Thr Glu Thr Lys Ala Ser Val Gly Phe Lys Ala Gly
1               5                   10                  15

Val Lys Glu Tyr Lys Leu Gly Tyr Tyr Thr Pro Glu Tyr Gln Thr Lys
            20                  25                  30

Asp Thr Asp Ile Leu Ala Ala Phe Arg Val Thr Pro Gln Pro Gly Val
        35                  40                  45

```
Pro Pro Glu Glu Ala Gly Ala Ala Val Ala Ala Glu Ser Ser Thr Gly
 50                  55                  60
Thr Trp Thr Thr Val Trp Thr Asp Gly Leu Thr Ser Leu Asp Arg Tyr
 65                  70                  75                  80
Lys Gly Arg Cys Tyr Arg Ile Glu Arg Val Val Gly Glu Lys Asp Gln
                 85                  90                  95
Tyr Ile Ala Tyr Val Ala Tyr Pro Leu Asp Leu Phe Glu Glu Gly Ser
             100                 105                 110
Val Thr Asn Met Phe Thr Ser Ile Val Gly Asn Val Phe Gly Phe Lys
         115                 120                 125
Ala Leu Arg Ala Leu Arg Leu Glu Asp Leu Arg Ile Pro Pro Ala Tyr
     130                 135                 140
Val Lys Thr Phe Gln Gly Pro Pro His Gly Ile Gln Val Glu Arg Asp
145                 150                 155                 160
Lys Leu Asn Lys Tyr Gly Arg Pro Leu Leu Gly Cys Thr Ile Lys Pro
                165                 170                 175
Lys Leu Gly Leu Ser Ala Lys Asn Tyr Gly Arg Ala Val Tyr Glu Cys
            180                 185                 190
Leu Arg Gly Gly Leu Asp Phe Thr Lys Asp Asp Glu Asn Val Asn Ser
        195                 200                 205
Gln Pro Phe Met Arg Trp Arg Asp Arg Phe Leu Phe Cys Ala Glu Ala
    210                 215                 220
Leu Tyr Lys Ala Gln Ala Glu Thr Gly Glu Ile Lys Gly His Tyr Leu
225                 230                 235                 240
Asn Ala Thr Ala Gly Thr Cys Glu Glu Met Ile Lys Arg Ala Val Phe
                245                 250                 255
Ala Arg Glu Leu Gly Val Pro Ile Val Met His Asp Tyr Leu Thr Gly
            260                 265                 270
Gly Phe Thr Ala Asn Thr Ser Leu Ala His Tyr Cys Arg Asp Asn Gly
        275                 280                 285
Leu Leu Leu His Ile His Arg Ala Met His Ala Val Ile Asp Arg Gln
    290                 295                 300
Lys Asn His Gly Ile His Phe Arg Val Leu Ala Lys Ala Leu Arg Met
305                 310                 315                 320
Ser Gly Gly Asp His Ile His Ser Gly Thr Val Val Gly Lys Leu Glu
                325                 330                 335
Gly Glu Arg Asp Ile Thr Leu Gly Phe Val Asp Leu Leu Arg Asp Asp
            340                 345                 350
Phe Val Glu Gln Asp Arg Ser Arg Gly Ile Tyr Phe Thr Gln Asp Trp
        355                 360                 365
Val Ser Leu Pro Gly Val Leu Pro Val Ala Ser Gly Gly Ile His Val
    370                 375                 380
Trp His Met Pro Ala Leu Thr Glu Ile Phe Gly Asp Asp Ser Val Leu
385                 390                 395                 400
Gln Phe Gly Gly Gly Thr Leu Gly His Pro Trp Gly Asn Ala Pro Gly
                405                 410                 415
Ala Val Ala Asn Arg Val Ala Leu Glu Ala Cys Val Lys Ala Arg Asn
            420                 425                 430
Glu Gly Arg Asp Leu Ala Gln Glu Gly Asn Glu Ile Ile Arg Glu Ala
        435                 440                 445
Cys Lys Trp Ser Pro Glu Leu Ala Ala Ala Cys Glu Val Trp Lys Glu
    450                 455                 460
```

Ile Val Phe Asn Phe Ala Ala Val Asp Val Leu Asp Lys
465             470             475

<210> SEQ ID NO 79
<211> LENGTH: 1434
<212> TYPE: DNA
<213> ORGANISM: Artificial
<220> FEATURE:
<223> OTHER INFORMATION: Based on Nicotiana tabacum wt (wild type) rbcL
      coding sequence

<400> SEQUENCE: 79

```
atgtcaccac aaacagagac taaagcaagt gttggattca agctggtgt taaagagtac         60 aaattgggtt attggactcc tgagtaccaa accaaggata ctgatatatt ggcagcattc        120
cgagtaactc ctcaacctgg agttccacct atagaagcag gggccgcggt agctgccgaa        180
tcttctactg gtacatggac aactgtatgg accgatggac ttaccagcct tgatcgttac        240
agagggcgat gctaccgcat cgagcgtgtt gttggagaaa aagatcaata tattgcttat        300
gtagcttacc ctttagacct ttttgaagaa ggttctgtta ccaacatgtt tacttccatt        360
gtaggtaacg tatttgggtt caaagccctg cgcgctctac gtctggaaga tctgcgaatc        420
cctcctgctt atgttaaaac tttccaaggt ccgcctcatg gatccaagt tgaaagagat         480 aaattgaaca gtatggtcg tcccctgttg ggatgtacta ttaaacctaa attggggtta         540
tctgctaaaa actacggtag agctgtttat gaatgtcttc gcggtggact tgattttacc        600
aaagatgatg agaacgtgaa ctcacaacca tttatgcgtt ggagagatcg tttcttattt        660
tgtgccgaag cactttataa agcacaggct gaaacaggtg aaatcaaagg cattacttg         720 aatgctactg caggtacatg cgaagaaatg atcaaaagag ctgtatttgc tagagaattg        780
ggcgttccga tcgtaatgca tgactactta acgggggat tcaccgcaaa tactagcttg         840
gctcattatt gccgagataa tggtctactt cttcacatcc accgtgcaat gcatgcggtt        900
attgatagac agaagaatca tggtatccac ttccgggtat tagcaaaagc gttacgtatg        960
tctggtggag atcatattca ctctggtacc gtagtaggta aacttgaagg tgaaagagac       1020
ataactttgg gctttgttga tttactgcgt gatgattttg ttgaacaaga tcgaagtcgc       1080
ggtatttatt tcactcaaga ttgggtctct ttaccaggtg ttctacccgt ggcttcagga       1140
ggtattcacg tttggcatat gcctgctctg accgagatct tggggatga ttccgtacta       1200 cagttcggtg gaggaacttt aggacatcct tggggtaatg cgccaggtgc cgtagctaat       1260
cgagtagctc tagaagcatg tgtaaaagct cgtaatgaag acgtgatct tgctcaggaa       1320 ggtaatgaaa ttattcgcga ggcttgcaaa tggagcccgg aactagctgc tgcttgtgaa       1380
gtatggaaag agatcgtatt taattttgca gcagtggacg ttttggataa gtaa            1434
```

<210> SEQ ID NO 80
<211> LENGTH: 477
<212> TYPE: PRT
<213> ORGANISM: Artificial
<220> FEATURE:
<223> OTHER INFORMATION: Based on Nicotiana tabacum wild type translated
      L-subunit

<400> SEQUENCE: 80

Met Ser Pro Gln Thr Glu Thr Lys Ala Ser Val Gly Phe Lys Ala Gly
1               5                   10                  15

Val Lys Glu Tyr Lys Leu Gly Tyr Trp Thr Pro Glu Tyr Gln Thr Lys
            20                  25                  30

```
Asp Thr Asp Ile Leu Ala Ala Phe Arg Val Thr Pro Gln Pro Gly Val
         35                  40                  45

Pro Pro Ile Glu Ala Gly Ala Val Ala Ala Glu Ser Ser Thr Gly
 50                  55                  60

Thr Trp Thr Thr Val Trp Thr Asp Gly Leu Thr Ser Leu Asp Arg Tyr
 65                  70                  75                  80

Arg Gly Arg Cys Tyr Arg Ile Glu Arg Val Val Gly Glu Lys Asp Gln
             85                  90                  95

Tyr Ile Ala Tyr Val Ala Tyr Pro Leu Asp Leu Phe Glu Glu Gly Ser
                100                 105                 110

Val Thr Asn Met Phe Thr Ser Ile Val Gly Asn Val Phe Gly Phe Lys
            115                 120                 125

Ala Leu Arg Ala Leu Arg Leu Glu Asp Leu Arg Ile Pro Pro Ala Tyr
        130                 135                 140

Val Lys Thr Phe Gln Gly Pro Pro His Gly Ile Gln Val Glu Arg Asp
145                 150                 155                 160

Lys Leu Asn Lys Tyr Gly Arg Pro Leu Leu Gly Cys Thr Ile Lys Pro
                165                 170                 175

Lys Leu Gly Leu Ser Ala Lys Asn Tyr Gly Arg Ala Val Tyr Glu Cys
            180                 185                 190

Leu Arg Gly Gly Leu Asp Phe Thr Lys Asp Asp Glu Asn Val Asn Ser
        195                 200                 205

Gln Pro Phe Met Arg Trp Arg Asp Arg Phe Leu Phe Cys Ala Glu Ala
    210                 215                 220

Leu Tyr Lys Ala Gln Ala Glu Thr Gly Glu Ile Lys Gly His Tyr Leu
225                 230                 235                 240

Asn Ala Thr Ala Gly Thr Cys Glu Glu Met Ile Lys Arg Ala Val Phe
                245                 250                 255

Ala Arg Glu Leu Gly Val Pro Ile Val Met His Asp Tyr Leu Thr Gly
            260                 265                 270

Gly Phe Thr Ala Asn Thr Ser Leu Ala His Tyr Cys Arg Asp Asn Gly
        275                 280                 285

Leu Leu Leu His Ile His Arg Ala Met His Ala Val Ile Asp Arg Gln
    290                 295                 300

Lys Asn His Gly Ile His Phe Arg Val Leu Ala Lys Ala Leu Arg Met
305                 310                 315                 320

Ser Gly Gly Asp His Ile His Ser Gly Thr Val Val Gly Lys Leu Glu
                325                 330                 335

Gly Glu Arg Asp Ile Thr Leu Gly Phe Val Asp Leu Leu Arg Asp Asp
            340                 345                 350

Phe Val Glu Gln Asp Arg Ser Arg Gly Ile Tyr Phe Thr Gln Asp Trp
        355                 360                 365

Val Ser Leu Pro Gly Val Leu Pro Val Ala Ser Gly Gly Ile His Val
    370                 375                 380

Trp His Met Pro Ala Leu Thr Glu Ile Phe Gly Asp Asp Ser Val Leu
385                 390                 395                 400

Gln Phe Gly Gly Gly Thr Leu Gly His Pro Trp Gly Asn Ala Pro Gly
                405                 410                 415

Ala Val Ala Asn Arg Val Ala Leu Glu Ala Cys Val Lys Ala Arg Asn
            420                 425                 430

Glu Gly Arg Asp Leu Ala Gln Glu Gly Asn Glu Ile Ile Arg Glu Ala
        435                 440                 445

Cys Lys Trp Ser Pro Glu Leu Ala Ala Ala Cys Glu Val Trp Lys Glu
```

```
                450               455               460
Ile Val Phe Asn Phe Ala Ala Val Asp Val Leu Asp Lys
465                 470               475
```

PROCESS FOR GENERATION OF PROTEIN AND USES THEREOF

CROSS-REFERENCE TO RELATED APPLICATIONS

This application is a divisional of U.S. patent application Ser. No. 12/422,190, filed on Apr. 10, 2009, which is a continuation-in-part of International Application PCT/AU2007/001542, with an international filing date of Oct. 10, 2007, which claims the benefit of Australian Provisional Patent Application No. 2006905622, filed Oct. 10, 2006. U.S. patent application Ser. No. 12/422,190 also claims the benefit of U.S. Provisional Application No. 61/045,552, filed Apr. 16, 2008. Each of the foregoing is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 284502002010SeqList.txt, date recorded: Feb. 2, 2017, size: 271 KB).

FIELD OF THE INVENTION

The present invention relates to a process for the generation of proteins with improved properties, in particular Rubisco proteins, and uses thereof.

BACKGROUND OF THE INVENTION

Ribulose-1,5-bisphosphate (RuBP) carboxylase/oxygenase is more commonly known by the abbreviation Rubisco. Rubisco is an enzyme participating in carbon fixation in the Calvin Cycle whereby atmospheric carbon dioxide is fixed and made available to biological systems in the form of energy-rich molecules.

In plants, algae, cyanobacteria and phototropic and chemoautotrophic proteobacteria, Rubisco comprises large subunit (LSU) chains and small subunit (SSU) chains. The substrate binding sites are located in the large chains. The large chains form dimers in which amino acids from each large chain contribute to the binding sites. A total of four large chain dimers and eight small chains assemble into a larger complex of about 540,000 Da.

Rubisco catalyzes the first step in photosynthetic $CO_2$ assimilation (carbon reduction), as well as the competitive fixation of $O_2$ which produces the waste product that is recycled in photorespiratory carbon oxidation. The importance of Rubisco is underlined by the fact that it is the major catalyst in the key chemical reaction by which inorganic carbon enters biological systems. Furthermore, Rubisco is a very abundant protein. Parry et al. (2003) suggest that Rubisco accounts for 30-50% of total soluble protein in chloroplasts.

However, the relative abundance of Rubisco may be attributable to the fact that it is a very slow acting enzyme, which only fixes a few $CO_2$ molecules per second, in contrast to the thousands of chemical reactions per second characterizing many enzymes. The enzyme is inefficient as a catalyst for the carboxylation of RuBP and is subject to competitive inhibition by $O_2$, to inactivation by loss of carbamylation, and to dead-end inhibition by RuBP binding prior to activation of the enzyme by carbamylation by $CO_2$.

This nonoptimal behavior makes Rubisco rate limiting for photosynthesis. Consequently, under most conditions and when light is not otherwise limiting photosynthesis, Rubisco is the primary rate-limiting enzyme of the Calvin Cycle.

As Rubisco is often rate limiting for photosynthesis in plants, improved forms of Rubisco would have considerable impact on increasing agricultural productivity. Several attempts have been made to increase the efficiency of Rubisco-mediated reactions. Previous approaches include introducing constructs which express Rubisco from one organism into another organism, increasing the level of expression of Rubisco subunits, expressing Rubisco small subunits from the chloroplast DNA, and altering Rubisco genes by mutagenesis so as to try to increase specificity for carbon dioxide (over oxygen) or otherwise increase the rate of carbon fixation.

Attempts have been made to introduce foreign Rubiscos, for example that from red algae such as *Galdieria partita* having a high $CO_2/O_2$ specificity, into flowering green plants. This would have been expected to improve the photosynthetic efficiency of crop plants, but these attempts failed due to problems with production, assembly and regulation of the foreign Rubisco in the host plant (Spreitzer and Salvucci, 2002; Parry et al., 2003). On the other hand, the large subunit of tobacco Rubisco has been successfully replaced with the homologous large subunit of the simpler purple photosynthetic bacterium *Rhodospirillum rubrum* which does not require a small subunit to fold and assemble into an active enzyme (Andrews and Whitney, 2003). While demonstrating that Rubisco replacement was achievable, the transgenic plant exhibited the very inferior specificity and catalytic properties of *R. rubrum* Rubisco.

Numerous attempts to define the roles of the active-site residues in specific steps of the reaction or to modify and improve the catalytic properties of Rubisco have been made using site-directed mutagenesis coupled with insights from X-ray crystallographic structures of Rubisco complexes from several species. However, these studies have failed to provide a detailed and self-consistent definition of the various roles of the residues of the active site over the complete reaction time course. These techniques have been uniformly unsuccessful in engineering a "better" Rubisco. While one mechanism by which Rubisco operates may be deduced by these studies, it may not be unique due to different possible interpretations of the incomplete experimental data, and, thus, it may not be the mechanism which exists in reality. For example, the mechanisms proposed in the Cleland consensus mechanism for Rubisco assume that a water molecule was displaced from the magnesium at the active site before formation of the reactive complex for carboxylation, and that consequently all subsequent steps in the reaction also proceed on the assumption that this displacement takes place. However, there is no experimental evidence that water is in fact displaced.

This contrasts with re-engineering programs for many other enzymes where single mutations, or in some cases multiple mutations, which were deduced straightforwardly from structural and mechanistic data obtained experimentally have proven successful in modifying substrate specificity or catalytic efficiency in predictable desired directions.

A major difficulty in implementing a rational re-engineering approach for Rubisco is that none of the reported experimental studies has provided direct evidence of the structure for all the intermediates involved, nor the precise roles of all the participating active-site residues, due to the aforementioned incompleteness of experimental data.

Experimental approaches are inherently unable to define precise roles for protons and water molecules involved in catalytic processes, as they are "invisible" to experimental probes. This difficulty is compounded by the complexity both of the Rubisco active site and by the fact that a sequence of reactions is involved. There is proposed to be a number of active-site "elements" comprising different combinations of active-site residues which take part in the different reactions steps, with the residue groups often being "reused".

It appears that current Rubiscos represent only "partial evolutionary solutions" to optimizing the enzymic efficiency, i.e. that evolutionary processes have been unable to sample effectively the LSU sequence space, and that these current solutions represent far-from-optimum solutions. Thus, there is an opportunity to create more optimum solutions by a different route, or combination of routes, than biological evolution has been able to provide so far.

The creation or identification and introduction of more efficient forms of Rubiscos into photosynthetic organisms by transformation, selective breeding or other manipulations may allow more efficient growth of these organisms, including green plants and in particular flowering plants, as they would make more efficient use of water and nitrogen, and may grow more efficiently at higher temperatures. This in turn offers prospects for better yielding crops, the revegetation of degraded or drought-prone land, improved options for carbon sequestration and improvements in the production of biofuel or biomass energy and so on.

In summary, there is a need for generating proteins, such as a Rubisco, having improved functional properties wherein, for example, such proteins have improved efficiency and are adapted specifically for particular environmental conditions.

SUMMARY OF THE INVENTION

The present inventors have hypothesised that extant Rubiscos have sampled only a fraction of the theoretically available mutational space to improve their efficiency and that different spaces may have been sampled by different groups of Rubiscos. Hence, they propose the coupling of these partial evolutionary "solutions" by grafting features from more than one phylogenetic group, or from more than one environmentally adapted species, onto a host Rubisco in order to gain the benefits of wider evolutionary mutational sampling than has been possible naturally. They propose that this process will identify Rubiscos with improved efficiency or other functional properties.

According to a first aspect of the invention, there is provided a method of generating a protein with an improved functional property, the method comprising:

(a) identifying at least one Target amino acid Residue in a first protein, wherein said Target amino acid Residue is associated with said functional property;

(b) comparing at least one homologous second protein from the same or a different phylogenetic branch as the first protein with the first protein and identifying at least one Variant amino acid Residue between the first protein and the second protein;

(c) selecting at least one Candidate amino acid Residue from the Variant amino acid Residue identified in (b) on the basis of said Candidate amino acid Residue affecting said Target amino acid Residue with respect to said functional property;

(d) forming at least one Candidate Mutant protein in silico or producing at least one Candidate Mutant protein in vitro in which said at least one Candidate amino acid Residue from the second protein substitutes a corresponding residue in the first protein; and (e) screening said at least one Candidate Mutant protein produced in (d) to identify a protein having said improved functional property.

In one embodiment, step (a) and step (b) may be performed simultaneously.

In another embodiment, step (b) may be performed before step (a).

In one embodiment, the identification of at least one Target amino acid Residue in a first protein of step (a) may reduce the amount of sequence space to be examined for the identification of Candidate amino acid Residues from the Variant amino acid Residues identified in step (b).

In one embodiment, step (d) comprises forming or producing at least one Candidate Mutant protein by using the at least one Candidate amino acid Residue from the second protein to substitute a corresponding residue in a homologous protein and/or in homologous proteins other than or in addition to the first protein.

In another embodiment, step (d) comprises forming or producing at least one Candidate Mutant protein in which at least two Candidate amino acid Residues from the second protein substitute corresponding residues in the first protein and/or in a homologous protein other than the first protein.

In one embodiment, the at least one Target amino acid Residue is contained in a first protein or in a set of proteins containing the first protein.

In certain embodiments, the at least one Target amino acid Residue is at least 2, at least 3, at least 4, at least 5, at least 10, at least 12, at least 15, at least 20, at least 30, or at least 50 Target amino acid Residues.

In one embodiment, the protein is an enzyme and the improved functional property is selected from any one or more of improved kinetic efficiency of the enzyme, an altered specificity of the enzyme for one or more substrates, an altered specificity for one or more products of the enzyme and an altered effective temperature range for enzyme catalysis. Where the protein is Rubisco, the improved functional property may be any one or more of improved carboxylation efficiency, improved $k^c_{cat}$, improved $K_c$, improved specificity ($S_{c/o}$), or improved temperature dependence. In particular embodiments the improved functional property is a combination of any two or more of improved carboxylation efficiency, improved $k^c_{cat}$, improved $K_c$, improved specificity ($S_{c/o}$), or improved temperature dependence.

In one embodiment, the Target amino acid Residues are selected from those residues directly interacting with a substrate or a reaction intermediate, which include for example in Rubisco those residues directly coordinating to the reaction centre ("first shell" residues), or directly coordinating with one or more of the aforesaid residues, (i.e. "second shell" residues). Where the protein is Rubisco, the first-shell residues of Rubisco may be selected from any one or more of Glu60, Asn123, Lys175, LYS177, KCX201, Asp203, Glu204, His294 and Lys334.

In one embodiment, the Target amino acid Residues of the Rubisco protein are in the N-terminal domain of the Rubisco Large subunit. The N-terminal domain Target amino acid Residues may be involved in the gas-addition step of carboxylase catalysis mediated by a Rubisco enzyme. In a particular embodiment, the N-terminal domain Target amino acid Residues involved in the gas-addition step are selected from the group consisting of ASN123, GLU60 and Tyr20.

In one embodiment the protein is an enzyme, and the second protein is selected on the basis of kinetic and functional features adapted for particular growth environments, such as hot- or cold-adaptation, or drought resistance. These features may be identified, for example, from environmental diversity data for the second protein.

In yet another embodiment, the at least one Candidate amino acid Residue is identified as a residue being capable of affecting said at least one Target amino acid Residue identified in (a) and the at least one Candidate amino Residue modulates the functional property of the formed protein. The Candidate amino acid Residue may affect the at least one Target amino acid Residue with respect to the functional property due to proximity of the Candidate amino acid Residue to the at least one Target amino acid Residue. For example, the effect may be due to steric, electrostatic or hydrophobic effects.

In certain alternative embodiments, step (c) comprises selecting at least one Divergent Candidate amino acid Residue, instead of at least one Candidate amino acid Residue, from the Variant amino acid Residues identified in (b). In particular embodiments, step (c) comprises selecting at least 2 Divergent Candidate amino acid Residues.

In certain alternative embodiments, step (c) comprises selecting at least one Alternative Candidate amino acid Residue, instead of at least one Candidate amino acid Residue, from the Variant amino acid Residues identified in (b). In particular embodiments, step (c) comprises selecting at least 2 Alternative Candidate amino acid Residues.

In other particular embodiments, step (c) comprises selecting at least one Alternative Candidate amino acid Residue and at least one Divergent Candidate amino acid Residue instead of at least two Candidate amino acid Residues, from the Variant amino acid Residues identified in (b).

In one embodiment, step (a) of identifying at least one Target amino acid Residue comprises the step of active-site fragment QM calculations and/or hybrid QM/QM and/or QM/MM calculations based on empirical data of the structure of the protein. In one embodiment, the empirical data is X-ray crystal structure or solution NMR structure. In one embodiment, the empirical data may further comprise any one or more of mutational data, kinetic data, isotope discrimination, calorimetric, and spectroscopic data (Fersht, 1998; Frey and Hegeman, 2007). In one embodiment, the QM/MM calculations are complemented by molecular dynamics (MD) simulations with a QM/MM potential (Gready et al., 2006).

In one embodiment, the step of selecting at least one Candidate amino acid Residue from the at least one Variant amino acid Residue comprises assessing the proximity of the at least one Target amino acid Residue identified in (a) to Variant amino acid Residues identified in (b) and/or relative position to secondary structural units.

The step (c) of selecting at least one Candidate amino acid Residue may comprise identifying changes between said first protein and said second protein with respect to electrostatic and/or hydrophobic interactions of the one or more Variant amino acid Residue identified in (b) with the at least one Target amino acid Residue identified in (a) and/or a secondary structural unit which contains the at least one Target Residue identified in step (a). Said selection procedure also comprises identification of compensatory mutations necessary to remove steric hindrance effects created by introducing a Candidate amino acid Residue into the first protein.

In yet another embodiment, the step of screening the at least one Candidate Mutant protein comprises any one or more of in silico analysis, biochemical assessment and physiological assessment. The biochemical assessment may include assessment of correct folding and/or assembly of the protein, assessment of the structure of the protein, assessment of the catalytic activity and/or other binding function of the protein or assessment of the stability of the protein in vitro. The physiological assessment may include assessment of correct expression, correct folding and/or assembly of the protein, assessment of the structure of the protein, assessment of the catalytic activity of the protein or assessment of the stability of the protein in vivo.

In yet another embodiment of the first aspect, the method also includes the further step performed after step (c) and prior to step (d) of grouping Candidate amino acid Residues predicted as having a cumulative effect on said at least one Target amino acid Residue. For example said cumulative effect may be effected via one or more of electrostatic and/or hydrophobic and/or steric effects, for example by coordinated or compensating effects on positioning of secondary structural units and loops, which modify such effects.

In yet another embodiment, the method also includes the further step performed immediately after step (d) of ranking said Candidate Mutant proteins having said improved functional property. The process of ranking said Candidate Mutant proteins may comprise assessing their likelihood of having said improved functional property. This procedure comprises assessing the relative potential contributions of Candidate amino acid Residues and/or Alternative Candidate amino acid Residues and/or Divergent Candidate amino acid Residues in said Candidate Mutant proteins to said improved functional property.

In one embodiment, the first aspect comprises the additional step of using information derived from at least one round of screening Candidate Mutant proteins in step (e) for the identification of Sub-regions within the protein structure that preferentially influence the properties of Target amino acid Residues linked to said Region.

In another embodiment, the Sub-regions may provide a basis for identifying additional Candidate Residues, Alternative Candidate Residues, Co-variant residues and/or Divergent Candidate Residues predicted to interact with Candidate Residues, Alternative Candidate Residues and/or Divergent Candidate Residues identified by steps (a) to (e). The rounds of screening may be used to generate a set of preferred mutational sites, and a preferred set of combinations thereof.

In yet another embodiment of the first aspect, the method comprises the further step of performing directed evolution on said protein having said improved functional property and screening products thereof.

According a second aspect of the invention, there is provided a method of generating a Rubisco protein with an improved functional property, the method comprising:

(a) identifying at least one Target amino acid Residue in a first Rubisco protein, wherein said Target amino acid Residue is associated with said functional property;

(b) comparing at least one second Rubisco protein from the same or a different phylogenetic branch as the first Rubisco protein with the first Rubisco protein and identifying at least one Variant amino acid Residue between the first Rubisco protein and the second Rubisco protein;

(c) selecting at least one Candidate amino acid Residue from the Variant amino acid Residues identified in (b) on the basis of said Candidate amino acid Residue affecting said Target amino acid Residue with respect to said functional property;

(d) forming at least one Mutant Rubisco protein in silico or producing at least one Mutant Rubisco protein in vitro in which said at least one Candidate amino acid Residue from the second Rubisco protein substitutes a corresponding residue in the first Rubisco protein; and (e) screening said at least one Candidate Mutant Rubisco protein produced in (d) to identify a Rubisco protein having said improved functional property.

In one embodiment, step (a) and step (b) may be performed simultaneously.

In another embodiment, step (b) may be performed before step (a).

In another embodiment, the identification of at least one Target amino acid Residue in a first protein of step (a) reduces the amount of sequence space to be examined for the identification of Candidate amino acid Residues from the Variant amino acid Residues identified in step (b).

In another embodiment of the second aspect, the residues of the second Rubisco protein used for comparison with the first Rubisco protein comprise all residues directly coordinated to the active site of a Rubisco protein, all residues interacting with the reactive centre of the substrate or intermediate reaction species of a Rubisco protein, and other residues within a proximate distance from the active site of a Rubisco protein or a subset of such residues. For example the proximate distance may be between 3 and 28 Å from any atom of substrate or intermediate reaction species. Typically the proximate distance is between 6 and 20 Å from any atom of substrate or intermediate reaction species. More typically, the proximate distance is between 9 and 15 Å from any atom of substrate or intermediate reaction species.

In one embodiment of the second aspect, the first Rubisco protein is taken from species of green plants and cyanobacteria and the second Rubisco protein is taken from species of red algae. In a particular embodiment the first Rubisco protein is taken from species of flowering plants and cyanobacteria and the second Rubisco protein is taken from species of red algae.

In one embodiment of the second aspect, step (c) comprises selecting at least one Divergent Candidate amino acid Residue, instead of at least one Candidate amino acid Residue, from the Variant amino acid Residues identified in (b). In particular embodiments, step (c) comprises selecting at least 2 Divergent Candidate amino acid Residues.

In certain alternative embodiments of the second aspect, step (c) comprises selecting at least one Alternative Candidate amino acid Residue, instead of at least one Candidate amino acid Residue, from the Variant amino acid Residues identified in (b). In particular embodiments, step (c) comprises selecting at least 2 Alternative Candidate amino acid Residues.

In other particular embodiments, step (c) comprises selecting at least one Alternative Candidate amino acid Residue and at least one Divergent Candidate amino acid Residue instead of at least two Candidate amino acid Residues, from the Variant amino acid Residues identified in (b).

In one embodiment of the second aspect, there is provided a method of purifying the Rubisco protein, the method comprising the steps of:

(a) fusing into a first vector the coding sequence for a $H_6$ tagged ubiquitin (Ub) sequence ($H_6$Ub) to the 5' end of an rbcS gene;

(b) co-transforming the first vector with a second vector coding for the large subunit and small subunit of the Rubisco protein into a host;

(c) inducing expression of said Rubisco protein and vectors;

(d) purifying the Rubisco protein based on the expression of the ubiquitin tag fused to the Rubisco small subunit;

(e) removing Ub fragments from the Rubisco.

In one embodiment, step (d) of purifying said protein is performed using chromatography such as metal affinity chromatography.

In one embodiment, the first and/or second vector is a plasmid.

In one embodiment, the host is *E. coli*.

In one embodiment, the large subunit comprises one or more mutations.

In one embodiment, the Ub fragments are removed using a Ub-specific protease.

According to a third aspect of the invention, there is provided a protein produced by the method of the first or second aspects of the invention.

According to a fourth aspect of the invention, there is provided a Rubisco protein produced by the method of the first or second aspects of the invention.

According to a fifth aspect of the invention, there is provided a Rubisco protein which comprises the sequence as set forth in any one of SEQ ID NOS: 26, 28, 30, 32, 34, 36, 38, 40, 42, 44, 46, 48, 50, 52, 54, 56, 58, 60, 62, 64, 66, 68, 70, 74, 76, 78, 80 or a functional equivalent thereof.

According to a sixth aspect of the invention, there is provided a Rubisco protein encoded by a polynucleotide comprising the sequence set forth in any one of SEQ ID NOS: 25, 27, 29, 31, 33, 35, 37, 39, 41, 43, 45, 47, 49, 51, 53, 55, 57, 59, 61, 63, 65, 67, 69, 73, 75, 77, 79 or a functional equivalent thereof.

According to a seventh aspect of the invention, there is provided a Rubisco large subunit polypeptide comprising one amino acid residue substitution or a combination of amino acid residue substitutions selected from the group consisting of (Y25W, D51I), (Y25W, D51V), (T23G, K81R), (G54A, C84A, I87V), (G54S, C84A, I87V), (T23G, Y25W, D51I, K81R), (T23G, Y25W, E51I, K81R), (Y25W, D51I, G54A, C84A, I87V), (Y25W, D51I, G54S, C84A, I87V), (Y25W, D51V, G54A, C84A, I87V), (V121I, M297G, V300T), (L36I, I116L, F140L), (L36I, I116L, V121I, F140L, M297G, V300T), (K18I, T23G), (K21A, L22K, (gap)M, T23G, Y25W), (T23G, K18I, T68V, K81R), (T23G, K81R, P104E), (T23G, D19P, K81R), (T23G, K81R, V121I, M297G, V300T), (T23G), (K81R), (V121I, M297G), (M297G), (V121I).

In one embodiment, the Rubisco large subunit is present in a Rubisco protein. In one embodiment, the Rubisco is provided in the form of a fusion protein or a fragment which retains the biological activity of the Rubisco.

Also provided is a polynucleotide which encodes a Rubisco LSU polypeptide according to the seventh aspect.

Also provided is a vector which comprises the polynucleotide sequence of the fifth aspect or the polynucleotide sequence defined in sixth aspect.

In one embodiment the vector comprises a constitutive or selectable expression promoter. In one embodiment, the vector comprises a selectable marker.

According to a eighth aspect of the invention, there is provided a host cell transformed with a nucleic acid sequence or the vector according to the above aspects.

In one embodiment, the host cell is a prokaryotic cell or a eukaryotic cell. In certain embodiments, the prokaryotic host cell is a bacterial cell such as *E. coli*.

According to a ninth aspect of the invention, there is provided a photosynthetic organism transformed with a nucleic acid sequence or a vector of one of the above aspects. In one embodiment, the photosynthetic organism is a cyanobacterium.

In another embodiment, the photosynthetic organism is a *Synechococcus*, such as *Synechococcus* sp. PCC7942 or *Synechococcus* sp. PCC6301.

In one embodiment the photosynthetic organism is a flowering plant. The flowering plant may be a wild type or transgenic tobacco (*Nicotiana tabacum*). The transgenic tobacco may be a tobacco in which native tobacco rbcL has been replaced by rbcM from *Rhodospirillum rubrum*.

In one embodiment, the protein is expressed in photosynthetic organelles.

In yet another embodiment, the organelle is a plastid.

In yet another embodiment, the organelle may be chosen from the group of plastids of photosynthetic eukaryotes comprising chloroplast (chlorophyll-containing plastid), etioplast (chloroplast not exposed to light), chromoplast (non-chlorophyll-containing plastid), or leucoplast (non-pigmented plastids for storing starch (amyloplast), lipid (elaioplast) or protein (proteinoplast)).

According to a tenth aspect of the invention, there is provided a method of increasing photosynthetic efficiency of an organism, the method comprising introducing a nucleic acid sequence which encodes a Rubisco protein according any one of the above aspects into said organism and expressing the Rubisco protein.

According to a eleventh aspect of the invention, there is provided a method of increasing crop yield, the method comprising introducing a nucleic acid sequence encoding a Rubisco protein of one of the above aspects into said crop plant.

According to a twelfth aspect of the invention, there is provided a method of increasing drought resistance in a plant wherein said method comprises introducing a nucleic acid sequence encoding a Rubisco protein according to one of the above aspects into said plant.

According to a thirteenth aspect of the invention, there is provided a method of increasing biomass in one or more plants or other photosynthetic organism(s), wherein said method comprises introducing a nucleic acid sequence encoding a Rubisco protein according to one of the above aspects into said plant(s) or organism(s).

According to a fourteenth aspect of the invention, there is provided a method of producing a biofuel comprising material from a plant or plants or other photosynthetic organism(s), wherein said method comprises introducing a nucleic acid sequence encoding a Rubisco protein according to one of the above aspects into said plant(s) or organism(s).

In one embodiment of the tenth to fourteenth aspects, the introduction of proteins may comprise the step of transformation, sexual reproduction, or a combination thereof.

ABBREVIATIONS aadA plasmid gene conferring resistance to streptomycin and spectinomycin
ACR Alternative Candidate Residue
2CABP 2-carboxyarabinitol 1,5-bisphosphate
2C3KABP 2-carboxy-3-ketoarabinitol 1,5-bisphosphate
3-PGA 3-phospho-D-glycerate
CM Candidate Mutant
CPK model Corey-Pauling-Koltun space-filling molecular representation of spherical atoms with radii proportional to the atom's van der Waals radius
CR Candidate Residue
CvR Co-variant Residue
DCR Divergent Candidate Residue
DFT density functional theory
ESP electrostatic potential
FM fragment model
$H_6$ 6× histidine affinity tag
$K_c^{0\%}$ Rubisco Michaelis constant ($K_m$) for $CO_2$ at 0% oxygen
$K_c^{air}$ Rubisco Michaelis constant ($K_m$) for $CO_2$ at 21% (ambient) oxygen
$k_{cat}^c$ Rubisco carboxylation turnover rate
$k_{cat}^c/K_c^{air}$ Rubisco carboxylation efficiency
$k_{cat}$ turnover rate of an enzyme
$K_m$ Michaelis constant of an enzyme
$k_{cat}/K_m$ catalytic efficiency of an enzyme
$K_o$ or $K_{io}$ Rubisco Michaelis constant ($K_m$) for $O_2$
LSU Large subunit
MD molecular dynamics
PDB code Protein Data Bank identity number
ONIOM Our owN n-layered Integrated molecular Orbital+ molecular mechanics Method
QM quantum mechanical
QM/MM hybrid quantum mechanical/molecular mechanical
QM/QM hybrid quantum mechanical/quantum mechanical
rbcL polynucleotide encoding a Rubisco large subunit
rbcLS polynucleotide encoding a Rubisco large subunit of *Synechococcus* sp.
rbcLS-rbcSS (or rbcL-S) polynucleotide encoding a Rubisco large subunit and Rubisco small subunit of *Synechococcus* sp.
rbcM polynucleotide encoding the Form II Rubisco from *Rhodospirillum rubrum*
rbcS polynucleotide encoding a Rubisco small subunit
rbcSS polynucleotide encoding a Rubisco small subunit of *Synechococcus* sp.
RuBP Ribulose-1,5-bisphosphate
Rubisco Ribulose-1,5-bisphosphate carboxylase/oxygenase
$S_{C/O}$ Rubisco specificity for $CO_2$ compared with $O_2$ defined as $(k_{cat}^c/K_c^{0\%})/(k_{cat}^o/K_o)$
SSU Small subunit
SsVR Species-specific Variant Residue
TIM barrel a protein domain structure first defined in triosephosphate isomerase
TR Target Residue
TS transition state
Ub ubiquitin
$V_c^{max}$ extrapolated maximal Rubisco carboxylase activity
VR Variant Residue Definitions As used in this application, the singular form "a", "an" and "the" include plural references unless the context clearly dictates otherwise. For example, the term "a plant cell" also includes a plurality of plant cells.

As used herein, the term "comprising" means "including." Variations of the word "comprising", such as "comprise" and "comprises," have correspondingly varied meanings. Thus, for example, a polynucleotide "comprising" a sequence encoding a protein may consist exclusively of that sequence or may include one or more additional sequences.

By "host cell" is meant a cell which contains an introduced nucleic acid construct and supports the replication and/or expression of the construct. Host cells may be prokaryotic cells such as *E. coli*, or eukaryotic cells such as algae, fungi, yeast, insect, amphibian, nematode, plant or mammalian cells. The host cells may be plant cells, such as monocotyledonous plant cells or dicotyledonous plant cells. An example of a host cell is an *E. coli* host cell.

The term "green plant" as used herein is intended to encompass organisms including, but not necessarily limited to, unicellular or multicellular organisms from the Divisions Pteridophyta (ferns), Bryophyta (mosses), Charophyta and Chlorophyta (aquatic green algae), Magnoliophyta (flowering plants or angiosperms), and Pinophyta (conifers).

As used herein, "homologous" proteins are proteins which share an evolutionary origin. Homologous proteins may share the same essential function (orthologous proteins) or may exhibit significantly different, evolutionarily diverged, functions (paralogous proteins).

As used herein, "nucleic acid" means a polynucleotide and includes single or double-stranded polymer of deoxyribonucleotide or ribonucleotide bases. Nucleic acids may also include fragments and modified nucleotides.

As used herein "operably linked" includes reference to a functional linkage of at least two sequences. Operably linked includes linkage between a promoter and a second sequence, wherein the promoter sequence initiates and mediates transcription of the DNA sequence corresponding to the second sequence. The rbcL-S is an example of an operably linked sequence.

As used herein, "photosynthesis" refers to the process in green plants and certain other organisms by which carbohydrates are synthesized from carbon dioxide and water using light as an energy source. Most forms of photosynthesis release oxygen as a byproduct.

As used herein, "phylogenetic branch" refers to a group of lineage-connected organisms. In the context of the present invention, phylogenetics constitutes a means of classifying groups of organisms according to degree of evolutionary relatedness. A phylogenetic branch may contain organisms of different taxonomic divisions, class, order, family, genus or species.

"Phylogenetic grafting" refers to the process of introducing at least one amino acid residue of a donor protein from an organism of one phylogenetic branch into a recipient protein from an organism of a different phylogenetic branch for the purpose of improving the functional properties of the recipient protein. Phylogenetic grafting may be carried out by substituting at least one amino acid residue into a given position in the sequence of a recipient protein, the at least one amino acid residue being at the same position in the second donor protein selected on the basis of the phylogenetic analysis.

As used herein, "plant" includes plants and plant parts including but not limited to plant cells, plant tissue such as leaves, stems, roots, flowers, and seeds.

As used herein, "promoter" includes reference to a region of DNA that is involved in recognition and binding of an RNA polymerase and other proteins to initiate transcription.

As used herein, "protein" refers to any polymer of amino acids linked through peptide bonds or modified peptide bonds, whether produced naturally or synthetically. The protein of the invention may comprise non-peptidic components, such as carbohydrate groups. Carbohydrates and other non-peptidic substituents may be added to a protein by the cell in which the protein is produced, and vary with the type of cell. Proteins are defined herein, in terms of their amino acid backbone structures; substituents such as carbohydrate groups are generally not specified, but may be present nonetheless.

As defined herein, the "function" of a protein refers to the normal role for the protein in the cell, or a role for which a protein may be engineered to carry out. In one embodiment the protein is an enzyme. Where the protein is an enzyme, the function may be the catalysis of at least one chemical reaction. In other embodiments the function may be structural (e.g. serving as a cytoskeletal protein). The function may involve the active or passive transport of a substance within the cell or between the cell interior and exterior, or between different compartments within the cell, or between different regions of the organism, for example where the protein is involved in a channel or a membrane pore, or the protein is involved in trafficking of materials to specific cellular compartments or the protein acts as a chaperone or a transporter. The function may be involved with ligand/receptor interactions, for example where the protein is a growth factor, a cytokine, a neurotransmitter or an intracellular or extracellular ligand, or the protein is a receptor for the growth factor, cytokine, neurotransmitter or the intracellular or extracellular ligand.

Where the protein is an enzyme, the enzyme may be involved in catabolism or metabolism. The enzyme may be involved in the synthesis of at least one product. The enzyme may be involved in the breakdown of at least one substrate. The enzyme may be involved in the chemical modification of at least one substrate, for example the addition or deletion of one or more phosphate groups from a molecule. The enzymes may be involved in degradation of at least one substrate.

Thus, a "functional property" of a protein is a property which contributes to the function of the protein. For example where a protein is an enzyme, the functional property may be the specificity of the enzyme for a particular substrate, the kinetic efficiency of the enzyme, its effective temperature range for catalysis, or its specificity for catalysing its normal reaction and minimizing side-reactions to unwanted and/or potentially toxic byproducts.

The term "residue" in the context of a polypeptide refers to an amino-acid unit in the linear polypeptide chain. It is what remains of each amino acid, i.e —NH—CHR—C—, after water is removed in the formation of the polypeptide from α-amino-acids, i.e. $NH_2$—CHR—COOH.

The terms "Target amino acid Residue" or "Target Residue" (TR) refer to an amino acid residue which is identified and/or predicted to contribute directly to the function of the protein. Where the protein is an enzyme, the contribution of a Target Residue to the functional property may be a direct influence of the Target Residue on the catalytic reaction(s) carried out by the enzyme at one or more of the enzyme's active site(s), via direct interaction or involvement in the active site. A Target Residue will not be distant from an enzyme active site. Where the protein is a receptor, the Target Residue will be directly involved in the receptor site. In the methods described herein, a Target Residue may be identified by computational and/or molecular simulation methods, as these methods are able to consider positions of water molecules, protons, ionisation states and hydrogen bonds associated with the Target Residues in the enzyme active site, or receptor site, which are not unambiguously definable by experiment. In the methods of the present invention, it is anticipated that the mutation of the Target Residues would in general lead to a disruption or reduction of function. Accordingly in the methods of the present invention, the Target Residues are not directly altered by substitution with another amino acid, but rather the properties of the Target Residues such as their position and charge are "tuned" by the manipulation of one or more residues which interact with the Target Residues.

The terms "Variant amino acid Residue" or "Variant Residue" (VR) refer to a specific amino acid residue of a second protein or a specific amino acid residue identified in a consensus sequence of a plurality of second proteins which is identified as being different from the corresponding amino acid residue found in a first protein which is homologous to the second protein. Variant Residues may be identified, for example, using an alignment of the amino acid sequences of the first and second proteins. The sequences of the first and/or second proteins may be consensus sequences. The sequences may be derived from organisms of the same or of a different phylogenetic branch. For the Rubisco large subunit, it is rare for there to be sequence additions or deletions between the sequences of different organisms, apart from in the N- or C-terminal regions which are not important for the catalytic function of Rubisco. Nevertheless, for the purposes of the present invention, in one embodiment a Variant amino acid Residue may be a residue which is present in a first protein but absent in a second protein, or which is absent in a first protein but present in a second protein.

The terms "Candidate amino acid Residue" or "Candidate Residue" (CR) refer to an amino acid residue from a second protein which is selected from amongst a plurality of Variant Residues and which is suspected of being able to influence one or more Target Residues sterically and/or electrostatically, and thereby influence the function of the protein mediated by the one or more Target Residues. A Candidate Residue is a residue which may be selectively transplanted into a first protein of a host in order to attempt to modulate the functional activity of the first protein towards the desired functional activity of the second protein.

In some embodiments, the Candidate Residue may be selected on the basis of commonality and/or difference of amino acid residues between two or more phylogenetic branches. In the context of selecting Candidate Residues for Rubisco, a Candidate Residue is one which is suspected of being able to influence one or more Rubisco Target Residues sterically and/or electrostatically, for example by modifying the charge distribution over the Target Residue and/or by modifying the spatial position of the Target Residue and/or by modifying the ability of the Target Residue to move.

Where the protein is Rubisco, the Candidate Residue may be present in the consensus sequence from red algae but different in the corresponding residue position in the consensus sequences from flowering plants and cyanobacteria, and at a position where the amino acid is the same in flowering plants and cyanobacteria. In particular embodiments, the Candidate amino acid Residue may be chosen from the residue present in red algae.

Where the protein is Rubisco, identification of a Candidate Residue as one suspected of affecting the gas-addition step allows it to be differentiated from other Variant Residues showing non-conserved changes between branches or sub-branches, which may represent neutral phylogenetic drift, or which may have a branch-specific physiological role, such as in folding, assembly, including interactions with the small subunit, or stability.

The terms "Divergent Candidate amino acid Residue" or "Divergent Candidate Residue" (DCR) refer to an amino acid residue which is selected from amongst a plurality of Variant Residues and which is suspected of being able to influence one or more Target Residues sterically and/or electrostatically, and thereby influence the function of the protein mediated by the one or more Target Residues. The Divergent Candidate Residue is selected on the basis of difference of amino acid residues at a given position in the consensus sequence of the protein among at least three phylogenetic branches. For example, in the context of selecting Divergent Candidate Residues for Rubisco, a Divergent Candidate Residue is one which is suspected of being able to influence one or more Rubisco Target amino acid Residues sterically and/or electrostatically, and which may be present in the consensus sequence from red algae but different in the corresponding residue from the consensus sequence of flowering plants and the consensus sequence of cyanobacteria, and also different at the corresponding residue from the consensus sequence of flowering plants and the consensus sequence of cyanobacteria. The Divergent Candidate Residue may be selected from the sequence or consensus sequence from the protein of any one of the phylogenetic branches which were compared.

The terms "Alternative Candidate amino acid Residue" or "Alternative Candidate residue" (ACR) refer to an alternative amino acid at the position of a Candidate Residue which is expressed in a second protein, but which is not the amino acid which is expressed in the consensus sequence of the second protein. Thus an Alternative Candidate Residue provides a residue which is expressed at the given position in at least one species of the second protein but which is not expressed in the majority of sequences from the same phylogenetic branch. Where the protein is Rubisco, an ACR may be selected, for example, from the sequence of *Griffithsia monolis* Rubisco which exhibits a significantly higher catalytic rate than a Rubisco from a typical red algal species.

The terms "Co-Variant amino acid Residue" or "Co-Variant Residue" (CvR) refer to a residue which is identified in the sequence of a second protein from a particular species, as being in the vicinity of an Alternative Candidate Residue and showing complementary variation to the Alternative Candidate Residue. This variation of the Co-Variant Residue, which is not present in the consensus sequence for the second protein, may be suspected to reflect complementary changes in the structural and/or electrostatic properties of the Alternative Candidate Residue and Co-Variant Residue. Identification of Co-Variant Residues provides a means to identify auxiliary residue positions which may be mutated in the first protein to better accommodate changes made from transferring Alternative Candidate Residues.

The terms "Species-specific Variant amino acid Residue" or "Species-specific Variant Residue" (SsVR) refer to residues which vary among closely related species of a protein. In conjunction with associated functional data for each variant protein, SsVRs may be used to map sequence-structure-function relationships. These correlations may be used to predict which variable residues might be contributing most to the improvement in the desired property for the protein. This SsVR information may be used in conjunction with the general method to identify CRs. Predictions of a Candidate Mutant protein containing groups of residues may include SsVRs in addition to the CRs, ACRs, DCRs or CvRs which more directly affect Target Residues.

The terms "Candidate Mutant protein" or "Candidate Mutant" (CM) refers to a mutant protein in which at least one or groups of two or more CRs and/or ACRs and/or DCRs, with optional additional CvRs or SsVRs, are combined into a single protein.

The term "Region" refers to a division of the protein structure surrounding the Target Residues which may be made on the basis of proximity of a particular Target Residue or Target Residues to particular parts of the reactive centre or binding site. A Region comprises a spatially contiguous volume of protein structure containing subsets of CRs, DCRs, ACRs, CvRs and SsVRs which may preferentially influence the interactions of a particular Target Residue or Target Residues with particular parts of the reactive centre or binding site. The boundaries of Regions are not precisely defined. Regions may have overlapping segments of protein structure. The purpose of defining Regions is to facilitate the application of the phylogenetic grafting method by loosely identifying the subsets of CRs, DCRs, ACRs, CvRs and SsVRs which may be grouped to form Candidate Mutants. For example, where the protein is Rubisco, a region labelled Region 1, which comprises most of the large subunit N-terminal domain and several small segments of structure from the C-terminal domain of the adjacent large subunit, may be identified as being able to influence the Target Residues Asn123, Glu60 and Tyr20, which specifically interact, directly or indirectly, with the nascent carboxylate group of the reactive species during the gas-addition step.

The term "Sub-region" refers to a division of a Region which may be made on the basis of proximity of a particular Target Residue or Target Residues to a component part of the Region. A Sub-region comprises a spatially contiguous volume of protein structure containing a subset of the Region's CRs, DCRs, ACRs, CvRs and SsVRs which are predicted to preferentially influence the properties of the particular Target Residue or Target Residues linked to the Region. The boundaries of Sub-regions are not precisely defined. Sub-regions may have overlapping segments of protein structure. Defining Sub-regions may facilitate the application of the phylogenetic grafting method by loosely identifying the subsets of the Region's CRs, DCRs, ACRs, CvRs and SsVRs which may be preferentially grouped to form Candidate Mutants. For example, where the protein is Rubisco, component regions of Region 1, labelled 1A, 1B and 1C, may be identified, which are predicted to preferentially influence the properties of Target Residues Tyr20, Asn123 and Glu60, respectively.

The term "sequence space" broadly refers to the set of all possible sequences of residues for a polymer of specific length. For example, the complete sequence space for a protein or polypeptide of 100 amino acid residues in length is the set of all sequences consisting of all possible variations of the 100 amino acids. If single mutations are considered only, then the sequence space for a protein or polypeptide of 100 amino acid residues in length is 100 times 19 (for the 20 amino acid residue set). A reduction in the sequence space of a protein or polypeptide of given length will, therefore, reduce the number of possible sequences of amino acid residues in a set of protein or polypeptide mutants. In the context of the present invention, the independent identification of Target amino acid Residues and Variant amino acid Residues produces two different reduced sets of sequence space to be examined. The subsequent intersection of these sets effected when the Target amino acid Residues are used to identify Candidate amino acid Residues from Variant Residues further reduces the sequence space for consideration. Accordingly, the number of residues of the protein and their combinations which need to be considered for mutation are thereby greatly reduced.

A kinetic parameter is associated with a value. Jointly the kinetic parameter and its value define the magnitude of a functional property. In the case of Rubisco, a kinetic parameter may be but need not be limited to, for example, carboxylation efficiency, or a value for $k^c_{cat}$, or a value for $K_c$, or a value for specificity ($S_{c/o}$), or a value for temperature dependence.

The term "kinetic profile" refers to a set of kinetic parameters and their associated values for an enzyme. For example a kinetic profile for a Rubisco may refer to a set of parameters with values for a single Rubisco mutant which show changes in the values of certain kinetic parameters over the wild type Rubisco.

The term "Rubisco phenotype" refers to a particular combination of key kinetic parameters (such as specificity, carboxylation efficiency, and temperature dependence) and their associated values.

As used herein, the term "directed evolution" refers to methods aimed at modifying the function and/or structure of target protein/s. In general, directed evolution is a process by which proteins are "adapted" to act in different or existing natural or artificial chemical or biological environments and/or to elicit new functions and/or increase or decrease a given activity, and/or to modulate a given feature.

BRIEF DESCRIPTION OF THE FIGURES

The present invention will now be described by way of example with reference to the accompanying figures.

FIG. 1 provides a flowchart of the Rubisco re-engineering strategy, highlighting the roles of computational chemistry and bioinformatics in providing the mechanistic, sequence, structural and phylogenetic information which is integrated by the phylogenetic grafting procedure to produce the in silico predictions of Candidate Mutant proteins. This integration provides a means by which the Target Residues may be used to select out Candidate Residues from Variant Residues, thereby greatly reducing the number of residues of the protein, and their combinations, which need to be considered for mutation towards improvement of the functional property. Candidate Residues, as shown in the middle column, may optionally comprise ACRs and/or DCRs. These procedures are shown in more detail in FIG. 2. The prediction steps are followed by experimental screening and assessment of improvement of the functional property. The results may be fed back into the prediction procedure to refine the predictions of Candidate Mutant proteins, followed by further cycles of computational and experimental screening and assessment of improvement of the functional property, to optimize the protein's activity. The dotted-line boxes represent optional extensions to the core phylogenetic grafting procedure which are shown in an expanded form in FIG. 3.

FIG. 2 provides a flowchart detailing the prediction strategy for the phylogenetic grafting method, showing the integration of the computational chemistry with the bioinformatics analysis to produce the ranked list of Candidate Mutant proteins. This procedure involves steps of selecting Variant Residues against Target Residues to produce Candidate Residues (which optionally may comprise ACRs and/or DCRs), grouping and combining groups of Candidate Residues (and/or Divergent Candidate Residues or Alternative Candidate Residues), and ranking the groups and combined groups to produce a ranked list of Candidate Mutant proteins for optional computational pre-screening and experimental screening.

FIG. 3 provides a flowchart which details an optional extension of the method for phylogenetic grafting, in which a list of Candidate Residues is assessed and assembled into Candidate Mutants, and then further Candidate Residues, Alternative Candidate Residues, Divergent Candidate Residues, Co-variant Residues and Species-specific Variant Residues may be recruited and grouped, based on their influence on Target Residues, and formed into new refined Candidate Mutants.

FIG. 4 provides a summary of a strategy for reduction of the sequence space of the Rubisco LSU which may be considered for predicting Candidate Mutants. Step 1 represents the starting point of 475 residues (open squares) in the LSU. In step 2, the five Target Residues (filled squares) that are most involved in the gas-addition reactions are identified by computational chemistry. In step 3, the approximately 130 Variant Residues (filled circles) that may encode superior functional properties of Rubisco are identified by bioinformatic analysis. In step 4, the 26 Candidate Residues (shown by *) are selected from the Variant Residues based on their potential to influence the Target Residues. The candidate sites for mutation are shown specifically numbered in 5. In step 6, the Candidate Residues are grouped using bioinformatic analysis to form Candidate Mutants; some of those in Table 3 are shown.

Figure 5:
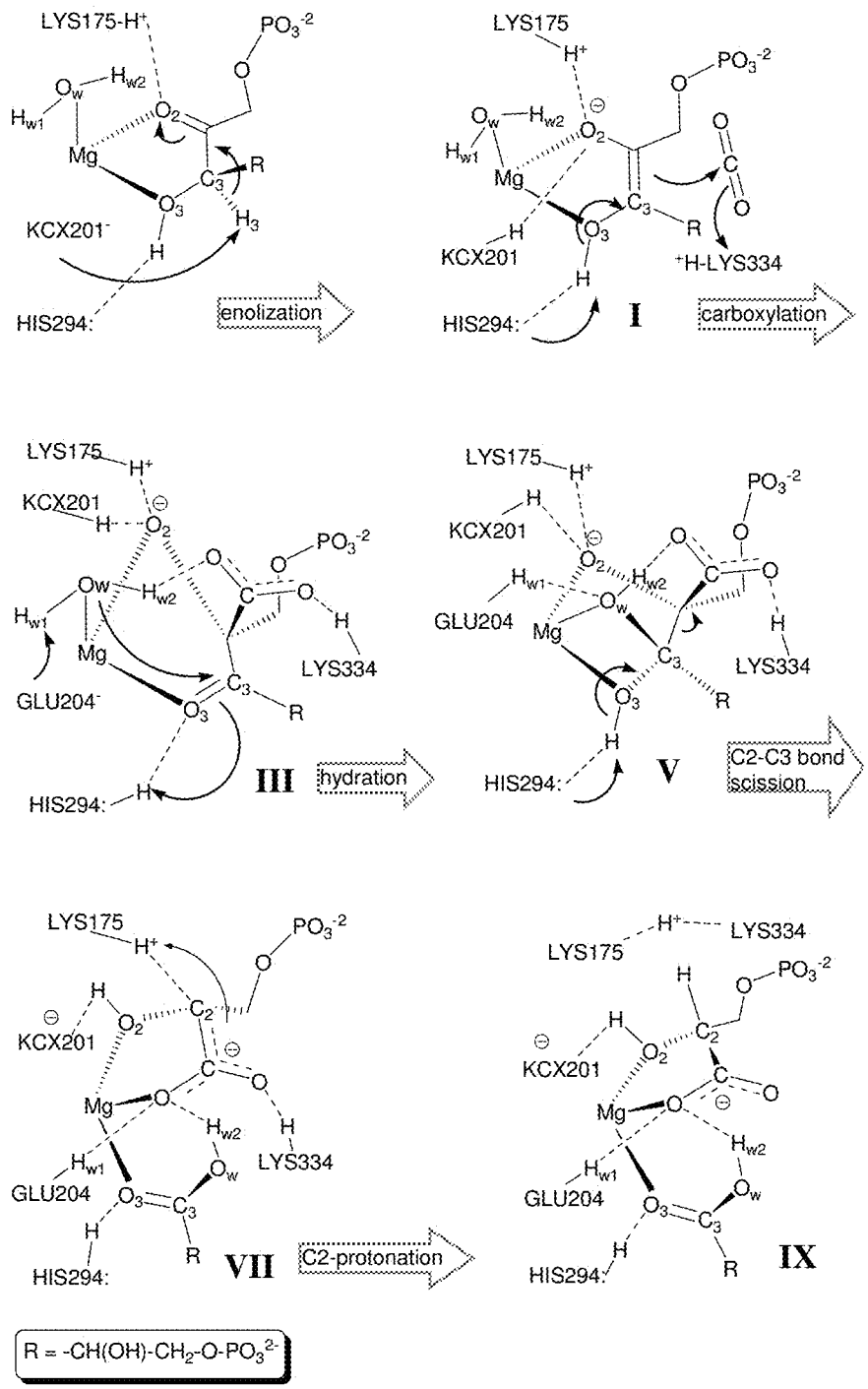

FIG. 5 provides an illustration of the molecular structures involved in the proposed reaction mechanism for the conversion of RuBP to two molecules of 3-PGA at the Rubisco active site. The five steps of enolization, carboxylation, hydration, C2-C3 bond scission and C2 protonation are shown. The Roman numerals correspond to the intermediate and product species shown in FIGS. 7 and 8. Group $R=-CH(OH)-CH_2-O-PO_3^{2-}$.

Figure 6:
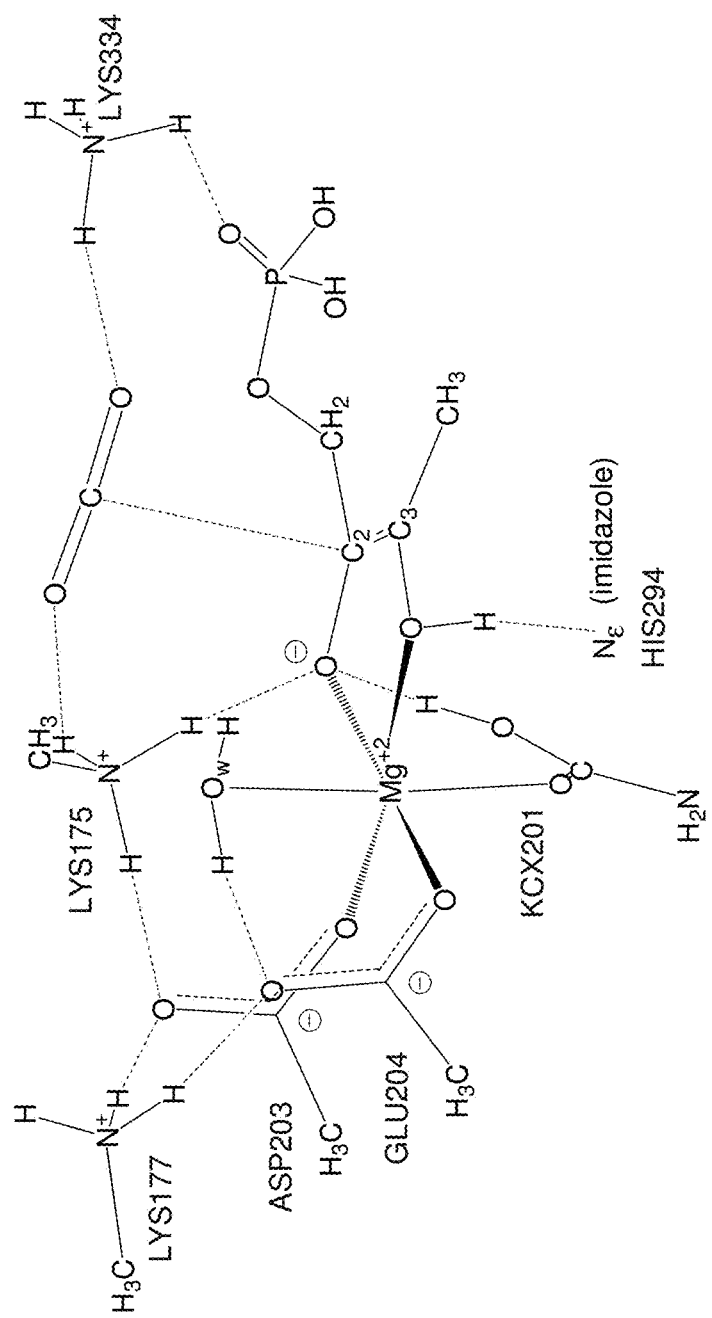

FIG. 6 illustrates the molecular structure for the 77-atom fragment model of the Rubisco active site designated FM20 which was used for ab initio QM computational chemistry studies of the reaction pathway. It shows the molecular-fragment species which were used to represent the LYS175, LYS177, ASP203, GLU204, KCX201 (carbamylated LYS201), HIS294, and LYS334 amino acid residues, the water molecule, the carbon dioxide molecule, and the 4-carbon fragment of the enediolate form of the substrate RuBP. In addition, it shows the charge states of the component species, and their interactions, namely the six atoms co-ordinated to the Mg atom, hydrogen bonds and the van der Waals interaction between $CO_2$ and C2.

FIGS. 7A to 7E provides a series of molecular structures calculated using ab initio QM methods for the FM20 fragment model shown in FIG. 6. These show geometries of local minima along the reaction pathway from enediolate to the end products in the Rubisco carboxylase reaction. Hydrogen atoms of the Mg-coordinated water molecule are highlighted by black circles. Relevant distances for each structure which demonstrate changing interactions between component species as the reaction proceeds are shown through labels. Labels on some structures may be obscured. Label "d" refers to $R_{KCX201-H...O2}$, "i" refers to $R_{Ow...G3}$, "j" refers to $R_{H2O[Mg]-Hw1...O-GLU204}$ and "k" refers to $R_{H2O[Mg]...Hw1}$. The Roman numerals correspond to the intermediate, transition-state and product species shown in FIG. 8.

Figure 8:
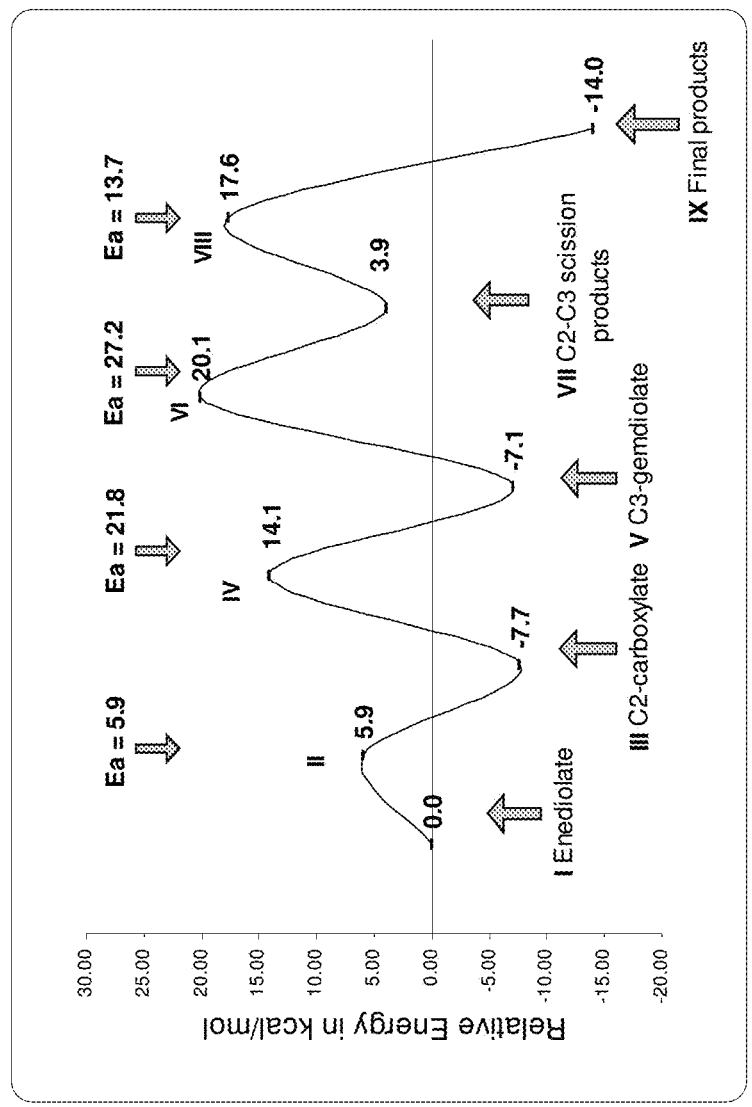

FIG. 8 provides a graph illustrating the potential energy surface for the carboxylation and subsequent reactions in the carboxylase pathway computed using ab initio QM computational chemistry calculations on the fragment model with 77 atoms (FM20). Different stages of the progress of the carboxylase reaction are distributed along the X-axis. The Roman numerals along the reaction pathway designate the starting (I) intermediate (III, V, VII) and product states (IX) of the carboxylase reaction shown in FIG. 5, and their connecting transition states (II, IV, VI, VIII). The structures of all these states are shown in FIG. 7. Energies (in kcal/mol) of all states are shown relative to that of the starting enedioloate state I, and transition state energies relative to the starting or relevant intermediate state are shown by Ea and an arrow.

Figure 9A:
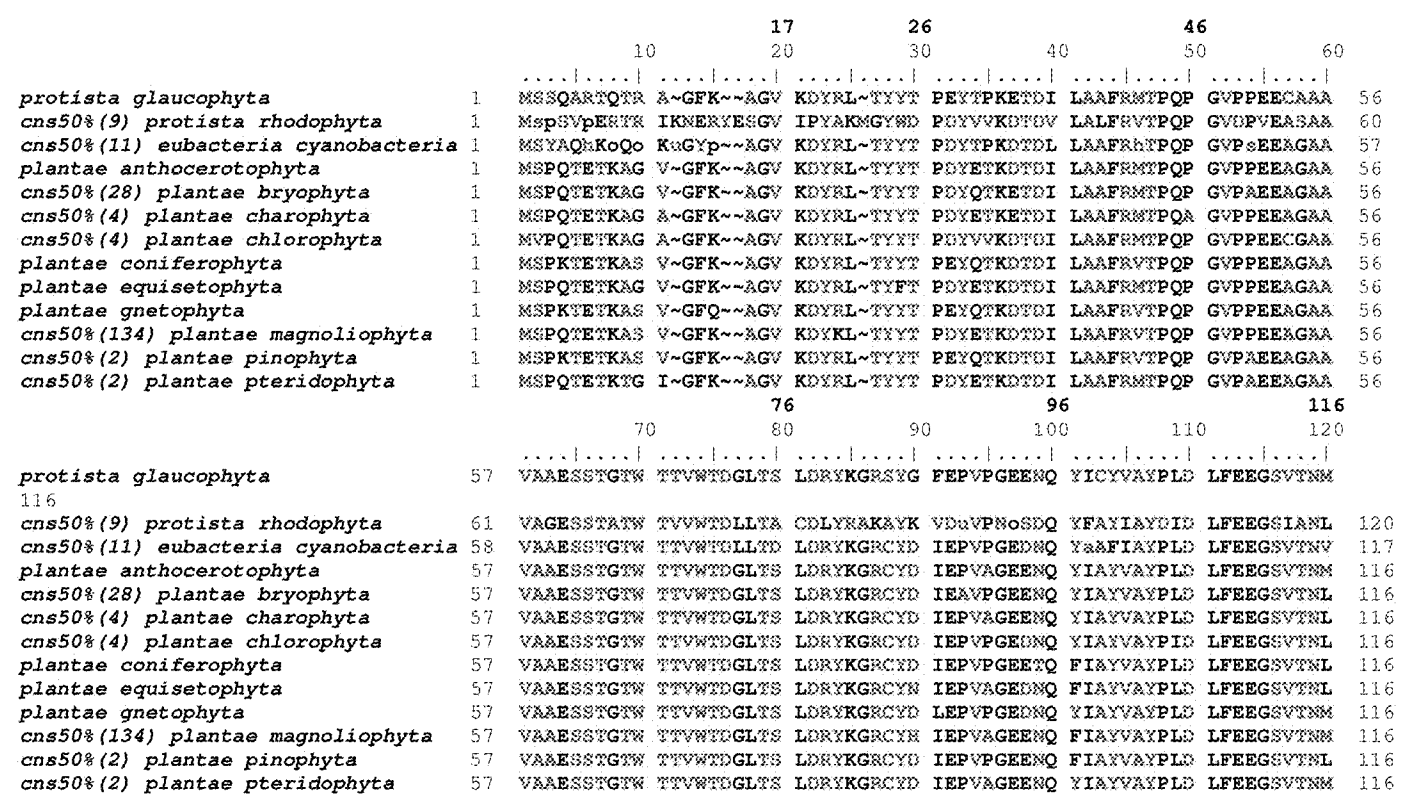
Figure 9C:
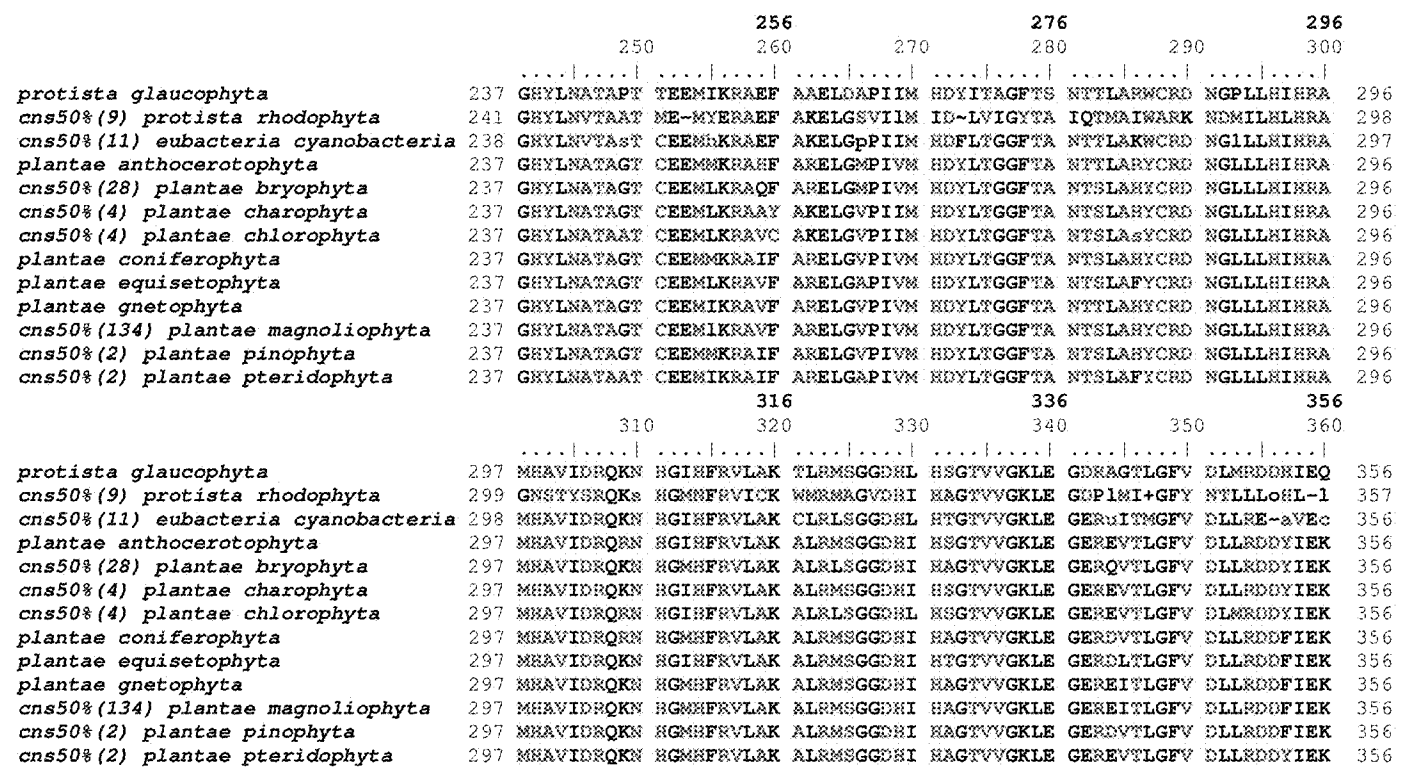
Figure 9D:
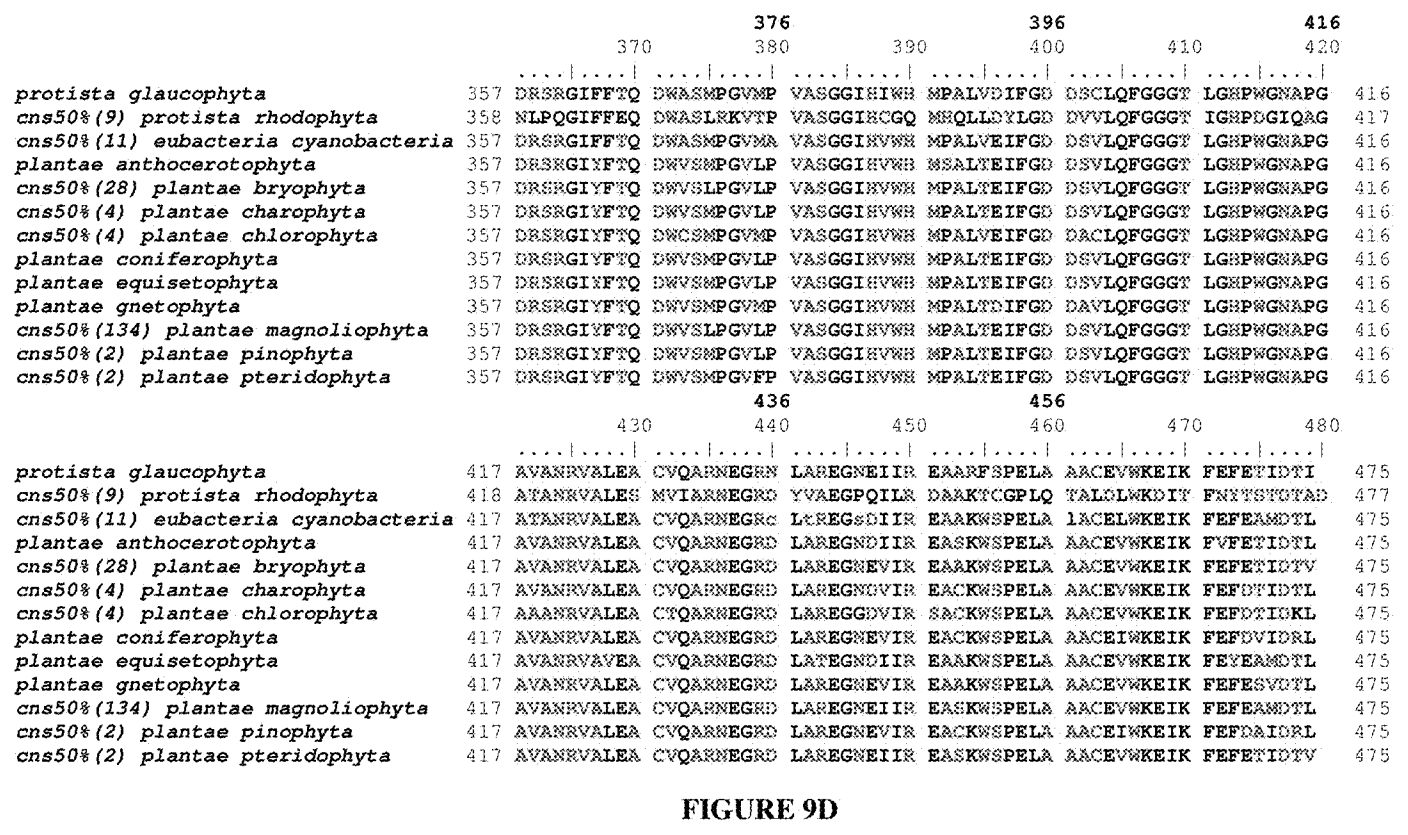

FIGS. 9A to 9D provides a sequence alignment of the Rubisco LSU amino acid sequences from photosynthetic organisms belonging to thirteen different phyla covering red algae, cyanobacteria, glaucophyta and plants (10 phyla), using single letter amino acid symbology. These sequences are also provided as SEQ ID NOS: 1-13. Where more than one Rubisco sequence was available in a phylum, a 50% consensus sequence was used to represent that phylum. For the consensus sequences, the numeral in brackets represents the number of genera whose sequences were used to generate the consensus sequence. The database accession numbers for all sequences used in the alignment are given in Table 1. The figure shows that the Rubisco LSU sequence is highly conserved, including the almost complete absence of gaps except for minor differences at the N- and C-termini, and codes for a long polypeptide chain of 475 residues (plants and cyanobacteria). The symbol "~" denotes sequence gaps. The single-letter uppercase letters denote the amino acid residue alphabet, while lowercase letters and other symbols are shown in positions in consensus sequences where only the type of residue is conserved: "h", hydrophobic (A, C, F, G, H, I, K, L, M, R, T, V, W, Y); "s", small (A, C, D, G, N, P, S, T, V); "u", tiny (A, G, S); "a", aromatic (F, H, W, Y); "c", charged (D, E, H, K, R); "l", aliphatic (I, L, V); "p", polar (C, D, E, H, K, N, Q, R, S, T); "o", alcohol (S, T); "t", turnlike (A, C, D, E, G, H, K, N, Q, R, S, T); "−", negatively charged (D, E); and "+" positively charged (H, K, R). The consensus sequences were obtained using the server at http://coot.embl.de/Alignment//consensus.html. The alignment was corrected around the gap position near CR T271 (alignment position 273) based on structural comparisons between the x-ray structures for spinach (pdb 8ruc), *Synechococcus* (pdb 1rbl) and *Galdieri partita* (pdb 1bwv) complexes with $Mg^{2+}$ and 2CABP. The SEQ ID NOS for the structures are 17, 16 and 14, respectively, as shown in Table 1. The numbers at the ends of the lines denote the sequence number. The evenly spaced numbers at the top are alignment markers, while the numbers in bold denote the sequence number for spinach.

Figure 10B:
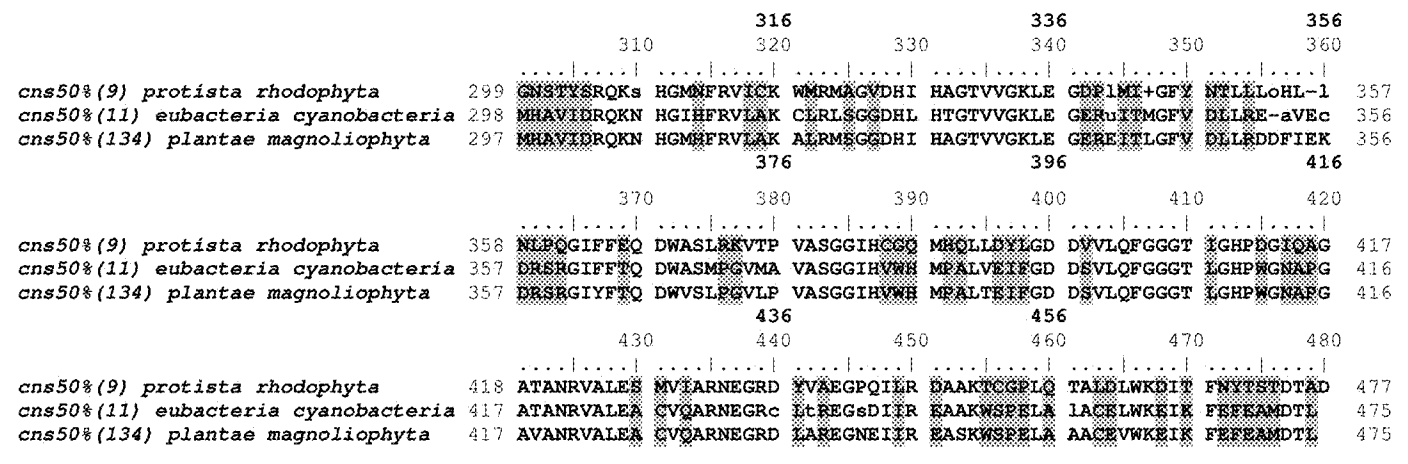

FIGS. 10A and 10B provides 50% consensus sequences of Rubisco LSUs from red algae (rhodophyta; 9 species), cyanobacteria (11 species) and flowering plants (magnoliophyta; 134 species). These sequences are presented in the sequence listing as SEQ ID NOS: 2, 3 and 11, respectively, as shown in Table 1. Light grey shading indicates the 134 residues that are the same in flowering plants and cyanobacteria but different in red algae, i.e. the Variant Residues. Gaps in the sequence are shown by "~". The definitions of uppercase and lowercase letters and "−" and "+" symbols are the same as in FIG. 9. The numbers at the ends of the lines denote the sequence number. The evenly spaced numbers at the top are alignment markers, while the numbers in bold denote the sequence number for spinach.

FIGS. 11A and 11B provide 50% consensus sequences of Rubisco LSUs from red algae (rhodophyta; 9 species), cyanobacteria (11 species) and flowering plants (magnoliophyta; 134 species), the same sequences shown in FIG. 10. Positions where the amino acid residues are conserved among all three consensus sequences are shown by the single-letter symbol for red algae (top line) and dots in lines for cyanobacteria and plants. Positions where the amino acid residue is the same for either cyanobacteria and plants as for red algae, are shown by the single-letter symbol for red algae (top line) and dots in lines for either cyanobacteria or plants. Positions where the amino acid residue is the same in cyanobacteria and plants but different in red algae, i.e. the 134 Variant Residues shown in FIG. 10, are shown by the single-letter symbol for red algae (top line) and the single-letter symbol for cyanobacteria (second line), while the residue position has a blank space for plants (third line). Reverse shading highlights those VR positions which were selected as Candidate Residues for Region 1, as shown in Table 2, and which were grouped into predicted Candidate Mutants, as shown in Tables 3 and 4. Positions where the amino acid residues are different in all three consensus sequences are shown by the single-letter symbols in all three lines, with grey shading highlighting those positions selected as Divergent Candidate Residues for Region 1, as shown in Table 2, and which were grouped into predicted Candidate Mutants, as shown in Tables 3 and 4. The symbol "~" denotes sequence gaps. Definitions of uppercase and lowercase letters and "−" and "+" symbols are the same as in FIG. 9. The numbers at the ends of the lines denote the sequence number. The evenly spaced numbers at the top are alignment markers, while the numbers in bold denote the sequence number for spinach.

Figure 12:
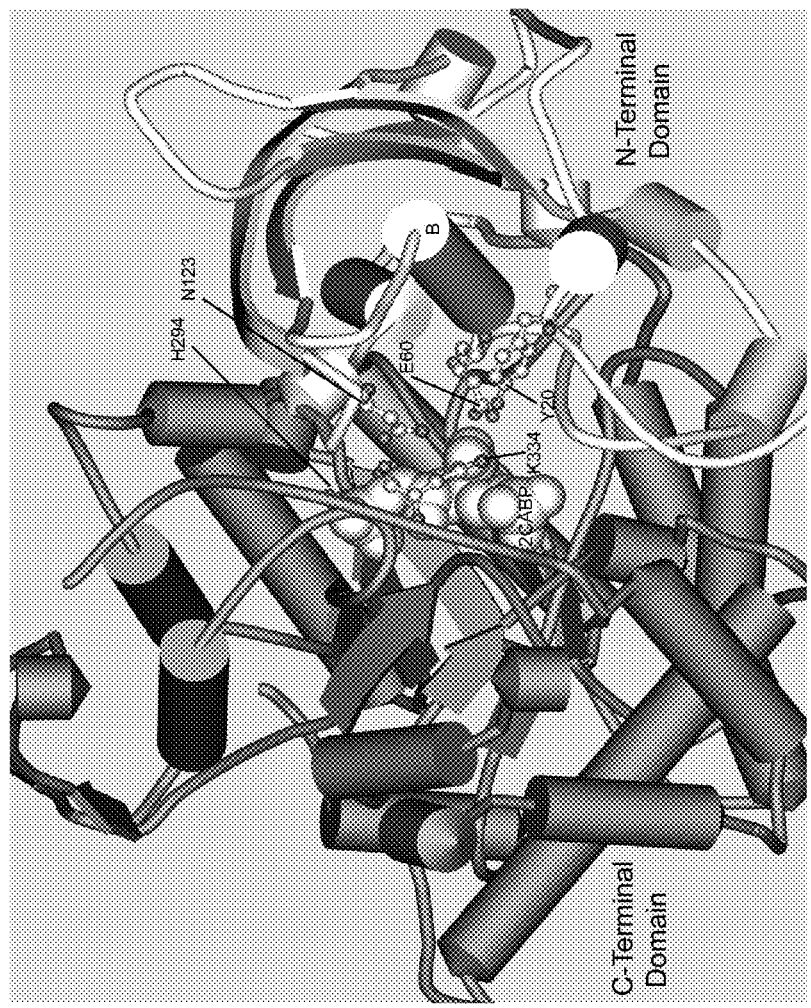

FIG. 12 provides a lateral view of the structure of the C-terminal TIM barrel (residues 151-475) of one LSU polypeptide and the N-terminal domain (residues 1-150) of an adjacent LSU which comprise the unit harbouring one active site of Rubisco. It shows the positions of the Target Residues, E60, N123 and Y20 for Region 1, H294 for Region 2 and K334 for Region 3. This structure was drawn using atom co-ordinates from the complete $L_8S_8$ hexadecameric x-ray structure of wild-type spinach Rubisco in the complex with $Mg^{2+}$ and 2CABP (pdb 8ruc). 2CABP is shown as a CPK model. Residues E60 and N123 are located in helix αB and near the C-terminal end of helix αC, respectively, of the N-terminal domain. The side chains of these two residues are located on either side of the carboxylate group of 2CABP. Helices αB and αC have hydrophobic interactions with the β-strands of the N-terminal domain. Y20 is located on single-coil structure near the N-terminal end of βA. Both K334 and H294 are located in the C-terminal domain which contains most of the first-shell residues of the active site. K334 is in loop 6, whereas H294 is in β5.

Figure 13:
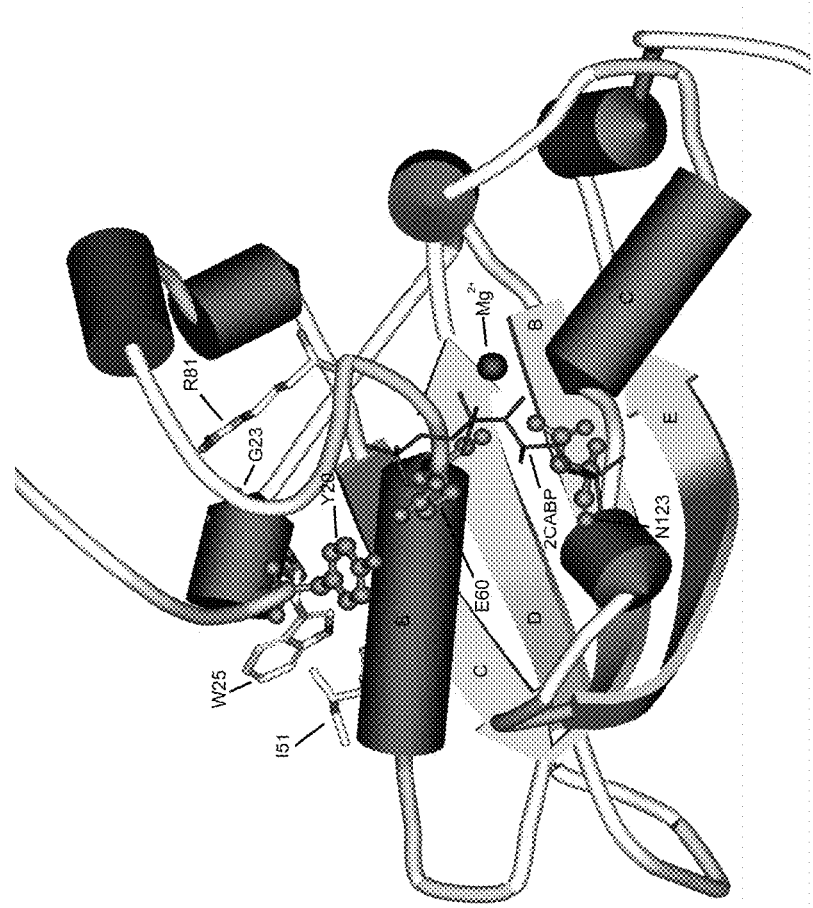

FIG. 13 provides a view of the structure of the N-terminal domain of the Rubisco LSU polypeptide (using co-ordinates from the spinach x-ray structure 8ruc) with the sidechains of the mutated residues (G23, R81, W25 and I51) for Mutant #6 (T23G, Y25W, D51I$^{Gp}$, K81R), and the component Mutants #4 (T23G, K81R) and #1a (Y25W, D51I$^{Gp}$), modelled in as stick models. See Table 3 for Mutant definitions. It shows the relative positions of these residues in the structure, and the interactions between residues 25 (W25) and 51 (I51), and between residues 23 (G23) and 81 (R81). The mutations add a hydrophobic interaction between residues W25 and I51, compared with the wildtype Y25 and D51, and remove a hydrogen-bonding interaction between residues 23 and 81 (wildtype T23, K81 to mutant G23, R81). Severally or in combination, these two double mutations are predicted to alter the orientation of residue Y20. The positions of the Target Residues Y20, E60 and N123 are shown for reference as ball-and-stick models, while the reaction intermediate mimic 2CABP is shown in wire-model form.

Figure 14:
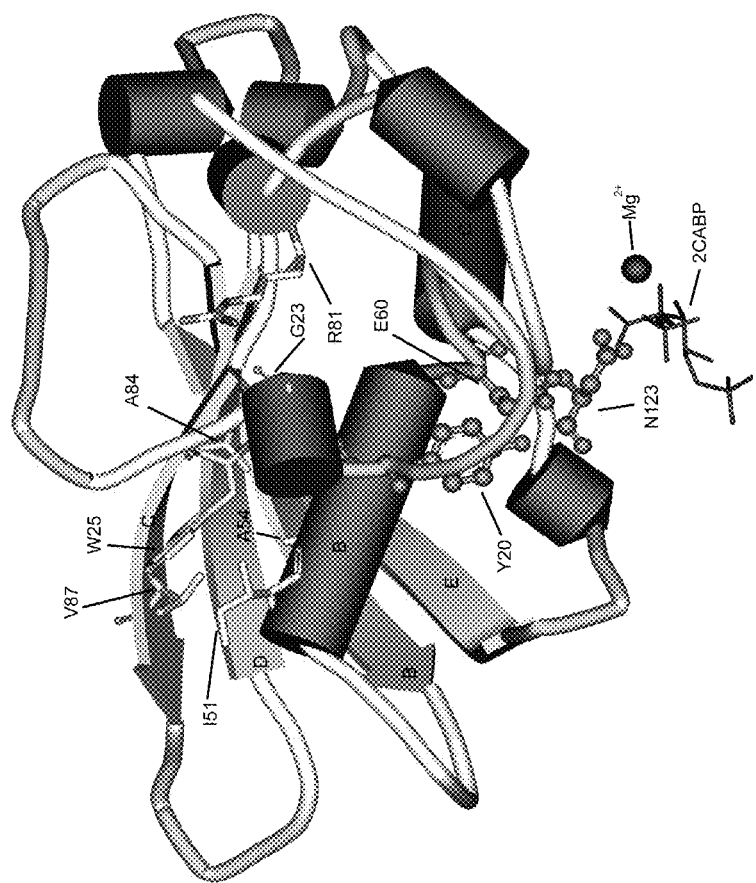

FIG. 14 provides a view of the structure of the N-terminal domain of the Rubisco LSU polypeptide (using co-ordinates from the spinach x-ray structure 8ruc) with the sidechains of the mutated residues (W25, I51, A54, A84, V87) for Mutant #7a (Y25W, D51I$^{Gp}$, G54A$^{Gp}$, C84A, I87V), and the component Mutants #1a (Y25W, D51I$^{Gp}$) and #5a (G54A$^{Gp}$, C84A, I87V), modelled in as stick models. The figure illustrates the formation of a hydrophobic region by mutations at sites 54 (G→A), 84 (C→A) and 87 (I→V). Additionally, if wildtype G54 was mutated to S54$^{Gm}$ instead of A54$^{Gp}$ (Mutant #7b, #5b), then an extra hydrogen bond with the backbone of residue 51 is predicted to be introduced. In turn, I51 has a hydrophobic interaction with residue W25. All these changes are predicted to affect the positioning of Target Residue Y20, shown in ball-and-stick form. The positions of the other Region 1 Target Residues E60 and N123 are shown for reference as ball-and-stick models, while the reaction intermediate mimic 2CABP is shown in wire-model form. For reference, the positions of the mutations for Mutant #4 (G23, R81) are also shown.

Figure 15:
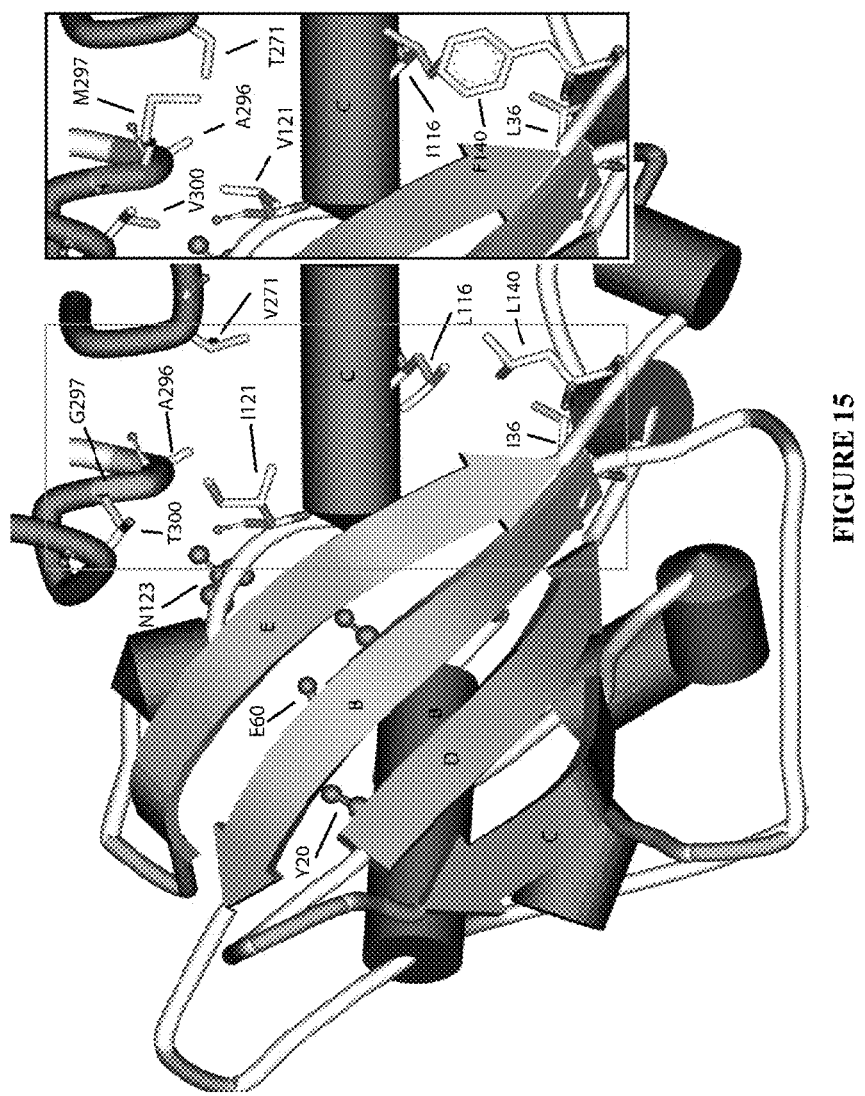

FIG. 15 provides a view of the N-terminal domain of the Rubisco LSU polypeptide (using co-ordinates from the spinach x-ray structure 8ruc) with the sidechains of the mutated residues (V$^{Gp}$ or I$^{Gm}$36, L116, I121, L$^{Gp}$ or I$^{Gm}$140, G297, T300) for Mutant #10a (L36V, I116L, V121I, F140L, M297G, V300T) and other Mutant #10 Gp/Gm variants (#10b,c,d), and the component Mutants #8 (V121I, M297G, V300T) and #9a (L36V, I116L, F140L) and other Mutant #9 Gp/Gm variants (#9b,c,d), modelled in as stick models. Residues A296 and V271 which are not mutated are also shown as stick models. To facilitate understanding of the changes in interactions predicted to result from the mutations, the RHS boxed inset shows the corresponding residues in wild type Synechococcus as stick model. The figure illustrates the predicted disruption of a hydrophobic interaction between residues V300, M297 and V121 in wild type to form a new hydrophobic interaction between A296, V271 and I121 in the Mutant (#8 or #10a). The prediction is based on structural comparisons between the x-ray structures for spinach (pdb 8ruc), Synechococcus (pdb 1rb1) and Galdieri partita (pdb 1bwv) complexes with $Mg^{2+}$ and 2CABP. A new hydrophobic interaction between residues 36, 140 and 116 is also predicted by the mutations L→V, F→L and I→L. Severally or in combination, these new hydrophobic interactions mediated by these groups of mutations are predicted to affect the position and orientation of Target Residue N123, which is shown in ball-and-stick model. The positions of the other Region 1 Target Residues E60 and Y20 are shown for reference as ball-and-stick models.

Figure 16:
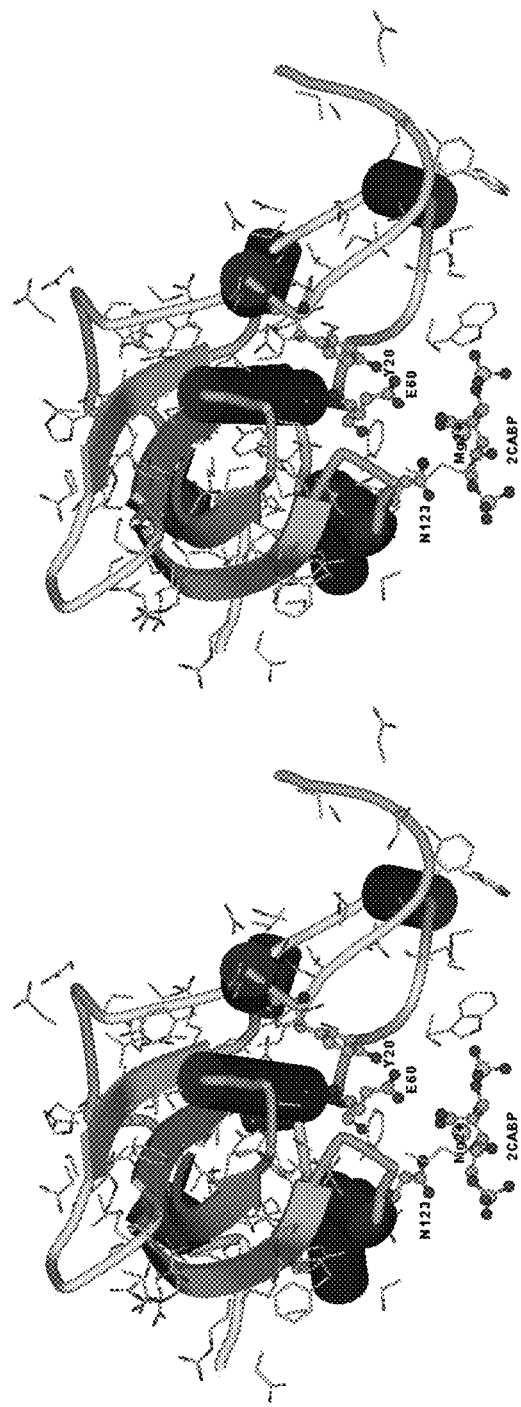

FIG. 16 provides a stereo view of the N-terminal domain of the spinach Rubisco LSU (using co-ordinates from the spinach x-ray structure 8ruc). The side chains of all the N-terminal residues are shown in wire-frame model. Target Residues (Y20, E60 and N123) are shown in stick model. The carboxylated-intermediate analogue 2CABP and $Mg^{2+}$ are shown as ball-and-stick models. The figure shows a complete 3-D representation of all the residue sidechains of the N-terminal domain from which are selected CRs which are predicted to influence the TRs Y20, E60 and N123, as shown in FIG. 17. For reference, the orientation of the structure is the same as in FIG. 19.

FIG. 17 provides a stereo view of the N-terminal domain of spinach Rubisco LSU (using co-ordinates from the spinach x-ray structure 8ruc), with the 20 Candidate Residues and 6 Divergent Candidate Residues listed in Table 2 shown as stick models and the Target Residues labelled N123, E60 and Y20. The figure shows a complete 3-D representation of the CR and DCR sidechains in the N-terminal domain which are predicted to influence the TRs Y20, E60 and N123, as well as a small segment from the C-terminal domain of the partner LSU showing CRs M297 and V300 which are also predicted to influence these TRs. Residues labelled T23 and K81 are those which are mutated in Mutant #4 (T23G, K81R), while the residues labelled Y25 and E51 are additionally mutated in Mutant #6 (T23G, Y25W, D51I$^G$), K81R).

Figure 18A:
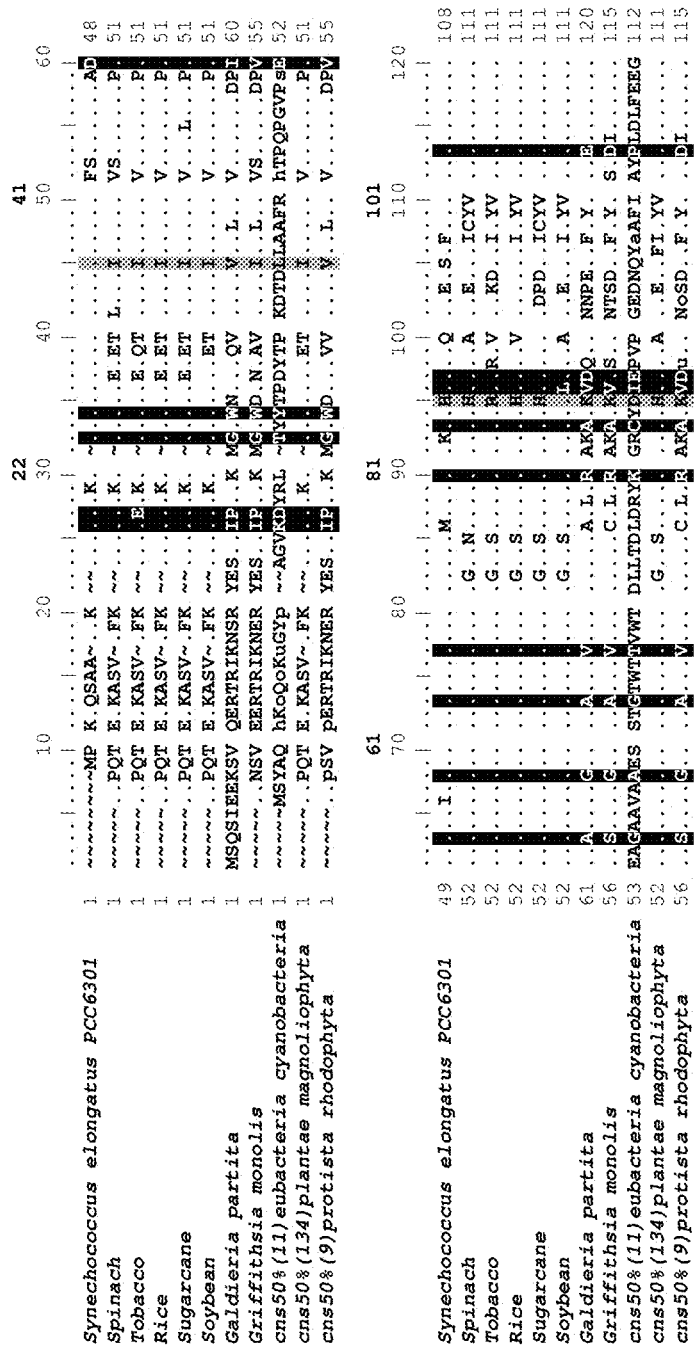

FIGS. 18A and 18B provide an amino acid sequence alignment of 50% consensus sequences of the N-terminal domain of Rubisco LSUs from flowering plants (magnoliophyta; 134 species), cyanobacteria (11 species), and red algae (rhodophyta; 9 species), as well as sequences of several plants (spinach, tobacco, rice, soybean and sugarcane), *Synechococcus* sp. PCC6301 and red algae (*Galdieri partita* and *Griffithsia monolis*) species of special interest. The sequences presented in this figure are also set out in SEQ ID NOS 2, 3 and 11, used previously in FIGS. 9-11 and 18-25. These are listed with database accession numbers in Table 1. The full sequence is shown in single-letter and symbol form for the cyanobacteria consensus (see FIG. 9 for an explanation of the symbols), with amino acid residues in other sequences shown by dots if conserved or by the single-letter/symbol format if not conserved. The numbers at the ends of the lines denote the sequence number. The evenly spaced numbers at the top are alignment markers, while the numbers in bold denote the sequence number for spinach. Black reverse shaded vertical strips highlight the 17 current Candidate Residues (i.e. those residues common between 50% consensus sequences from flowering plants and cyanobacteria but different in red algae) in the N-terminal domain—residues 18, 19, 23, 25, 51, 54, 59, 64, 68, 81, 84, 87, 88, 104, 114, 118, 121. Grey shaded vertical strips highlight the 6 current Divergent Candidate residues (i.e. those residues which differ in green plants, cyanobacteria and red algae): residues 36, 86, 116, 117, 138, 140.

Figure 19:
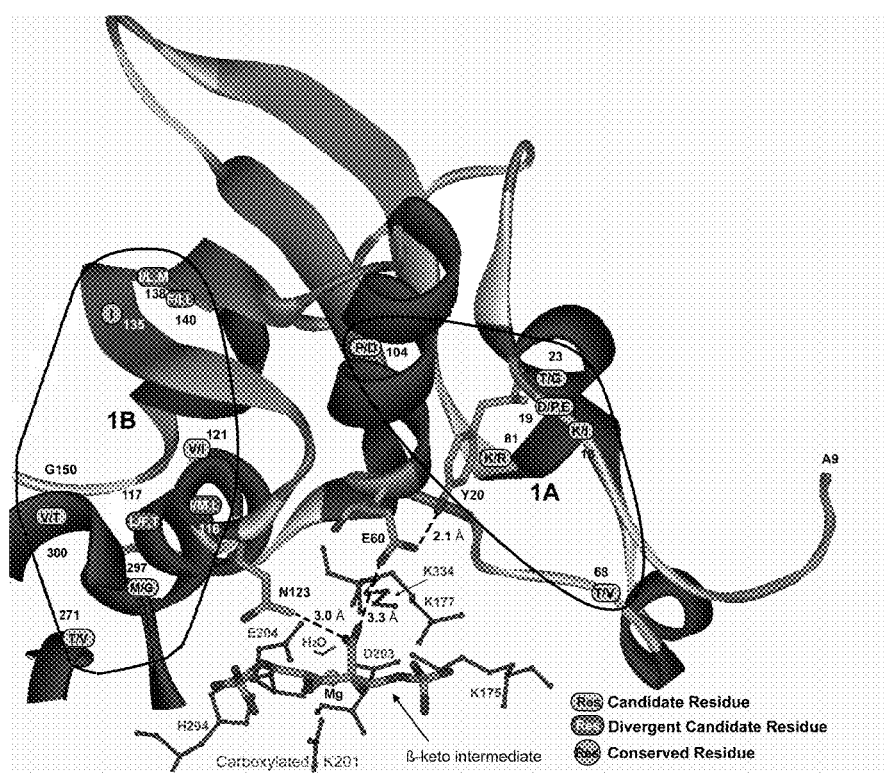

FIG. 19 provides a view of the N-terminal domain and segments of the C-terminal domain of the adjacent subunit of spinach Rubisco LSU (using co-ordinates from the spinach x-ray structure 8ruc). At the bottom the β-keto reaction intermediate (2-carboxy-3-ketoarabinitol 1,5-bisphosphate (2C3KABP); III; see FIG. 5), $Mg^{2+}$ and other residues from the C-terminal domain of the partner LSU co-ordinated in the first-shell of the active site (see FIG. 6) and their disposition to the Target Residues Y20, E60 and N123. Y20, E60, N123 and the β-keto reaction intermediate are shown as thick-stick models, while the active-site residues are shown in thin-stick model. The figure shows Sub-region 1A in the N-terminal domain and Sub-region 1B in the N-terminal domain and segments of the C-terminal domain of the adjacent subunit. Sub-region 1A includes the positions of CR 18 and new CRs 19, 68 and 104 which are expected to improve Mutant #4 (T23G/K81R) if mutated in combinations (#17-1A (#4+K18I/T68V), #18-1A (#4+P104E(D)), #19 (#4+D19P)) and further combinations thereof. Subregion 1B includes positions in the new Candidate Mutant #20-1B (V116L/L117T/V121I/I138M/F140L) containing DCRs 116, 117, 138 and 140, CR 121, and totally conserved residue 135.

Figure 20A:
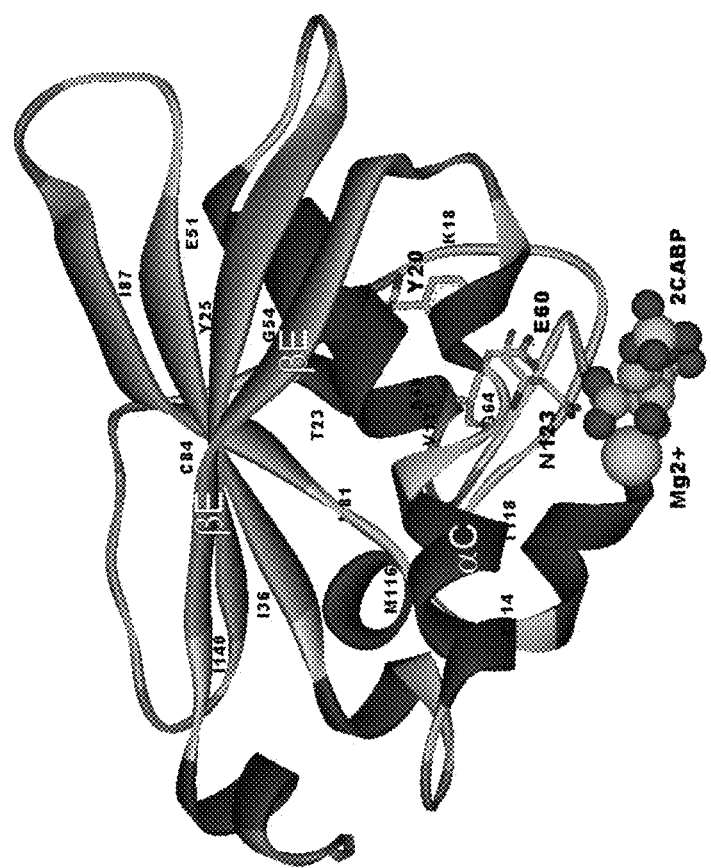
Figure 20B:
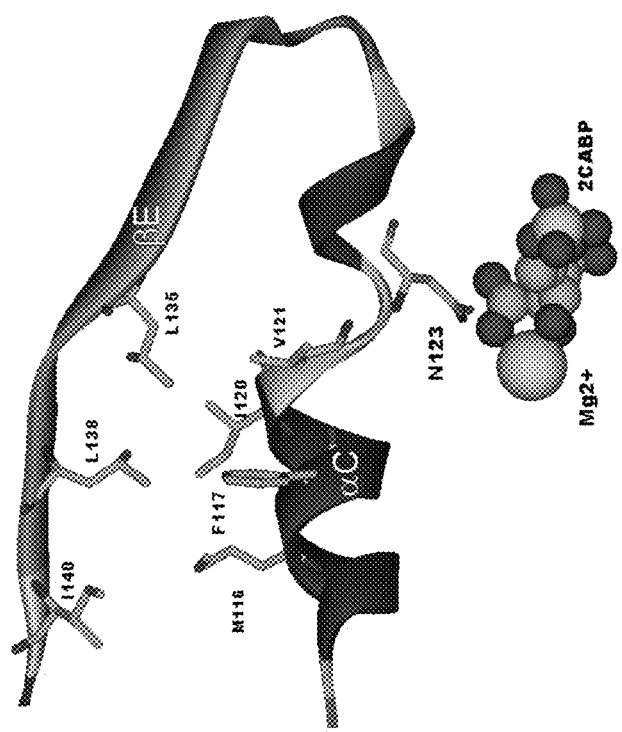

FIGS. 20A and 20B provide a graphic with an expanded view of interactions in Candidate Mutant #20-1B (V116L/L117T/V121I/I138M/F140L) in Sub-region 1B. Panel A shows for reference the complete N-terminal domain, positions of TRs N123, E60 and Y20 and the active-site centre (2CABP, $Mg^{2+}$), and helix C and strand E. Panel B shows how the component residues 116, 117, 120, 121 and 135, 138 and 140 located on helix C and strand E interact, and how changes to these interactions are predicted to influence the nearby TR N123; another view is in FIG. 21. 2CABP and $Mg^{2+}$ are shown in CPK model. N123, E60 and Y20 are shown in thick-stick model.

Figure 21:
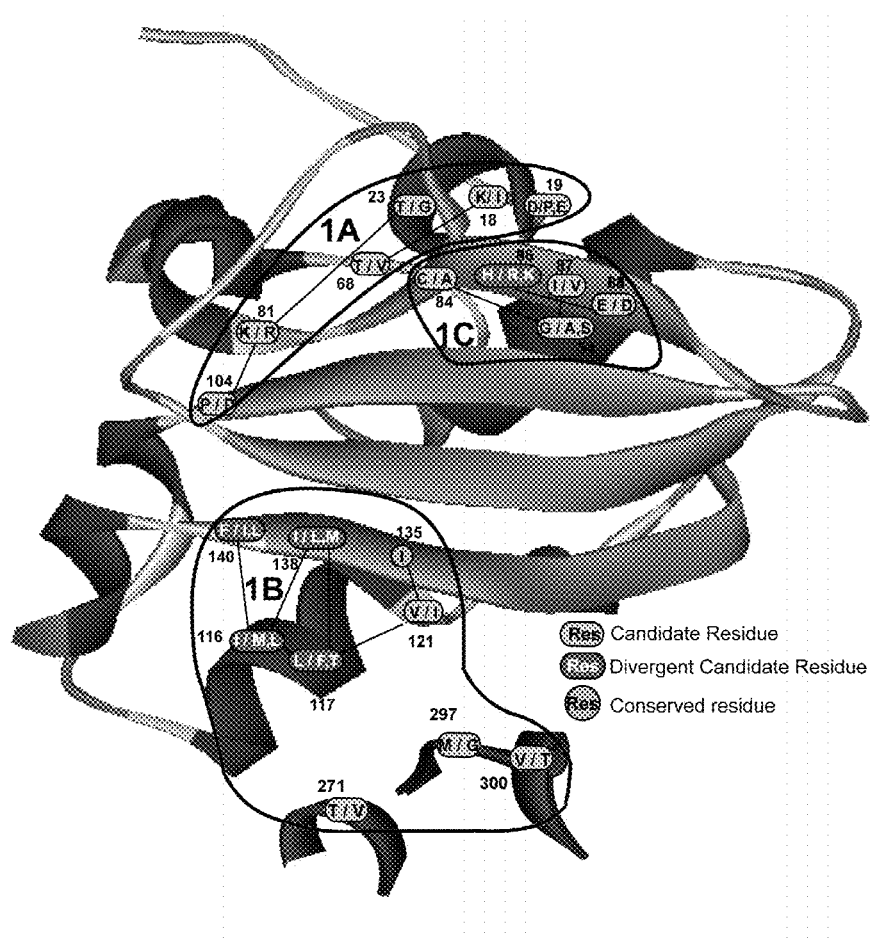

FIG. 21 provides a graphic of the N-terminal domain of the Rubisco LSU and segments of the C-terminal domain of the adjacent subunit as a ribbon model showing the relative positions of all the three Subregions, 1A, 1B and 1C, and some of the CRs and DCRs in these Subregions. Some of the key predicted interactions used in designing Region 1 Candidate Mutants are shown by lines connecting CRs and DCRs.

Figure 22:
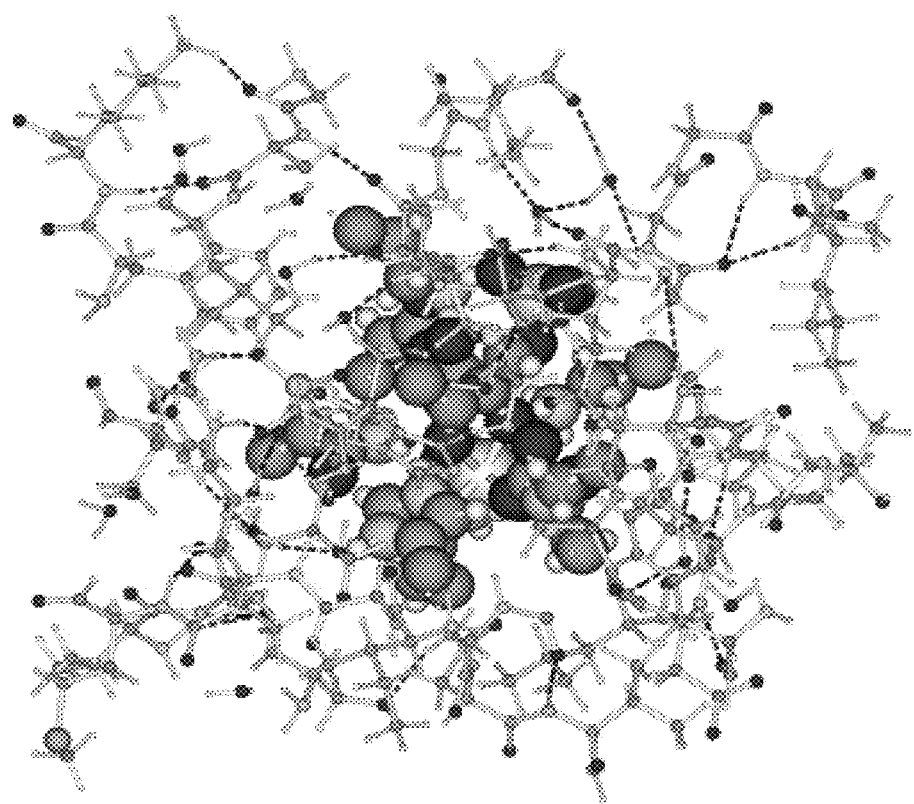

FIG. 22 provides a structural model used in ONIOM QM/QM calculations undertaken with DFT as the high layer and semiempirical QM (PM3)) as the low layer. The DFT layer (shown as large ball and stick model) comprises 93 atoms including fragments of all residues in the first coordination shell of the active site and substrate: the magnesium atom ($Mg^{2+}$), enediolate of RuBP, GLU60, ASN123, LYS175, LYS177, carbamylated LYS201, ASP203, GLU204, HIS294, LYS334. This core layer is surrounded by a further 711 atoms in the PM3 (semi-empirical QM) layer, which comprises amino acid residues up to ~12 Å from $Mg^{2\pm}$. The starting co-ordinates were taken from the X-ray structure of the spinach Rubisco-2CABP complex (pdb 8ruc). The size of the entire system is 804 atoms.

Figure 23:
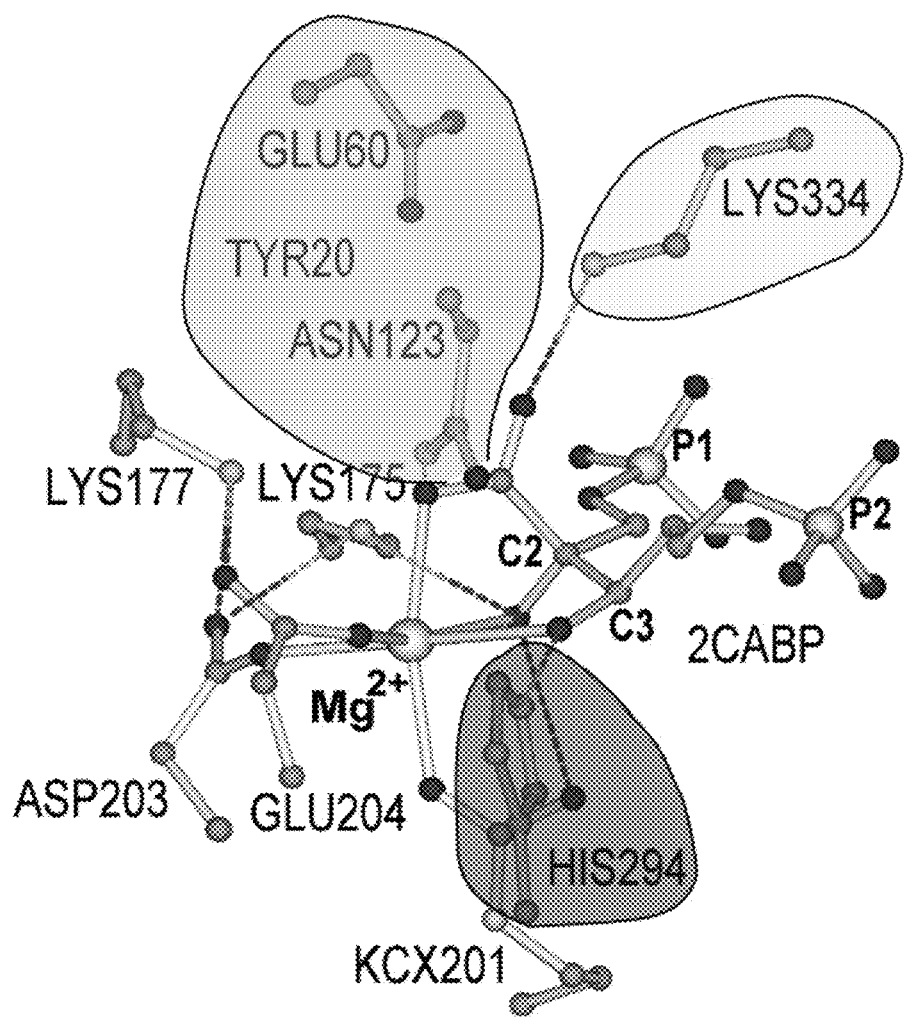

FIG. 23 provides a graphic showing the core structure of the Rubisco active site and the division of the structure surrounding the Target Residues into three spatially contiguous Regions. Region 1 comprises amino acid residues that can influence the TRs GLU60, ASN123 and TYR20 and comprises the N-terminal domain and small segments of the C-terminal domain of the adjacent subunit. Regions 2 and 3 are in the C-terminal domain and comprise amino acid residues that can influence the TRs HIS294 and LYS334, respectively.

Figure 24:
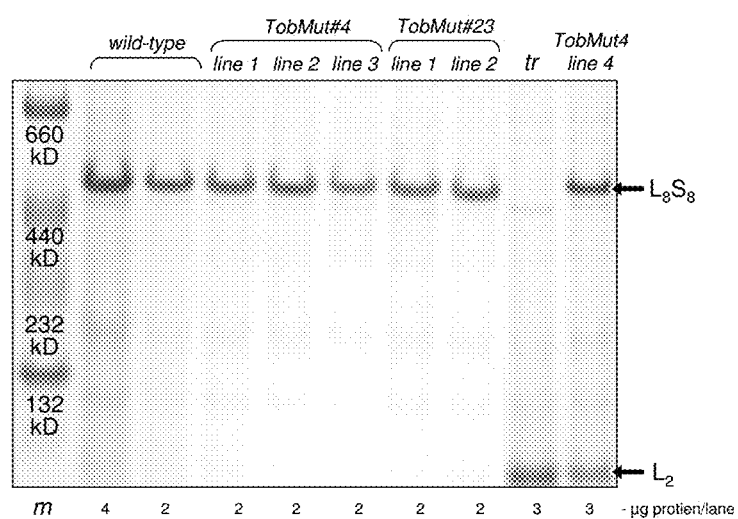

FIG. 24 provides a gel showing the separation of *R. rubrum* $L_2$ Rubisco and tobacco $L_8S_8$ Rubisco by non-denaturing polyacrylamide electrophoresis. Soluble leaf protein from wild-type tobacco, tobacco Mutant #4 and tobacco Mutant #23-1B lines used for the kinetics measurements was separated by non-denaturing polyacrylamide electrophoresis and visualised by Coomassie staining. The $L_2$ Rubisco that is present in the ΔaadA tobacco-*rubrum* line (tr) and in the heteroplasmic tobacco Mutant #4 transformant line #4 (i.e. it produces both $L_2$ and mutated $L_8S_8$ Rubiscos) is not present in the other tobacco Mutant lines or wild-type tobacco transformant Marker proteins with sizes are indicated (m). The amount of soluble leaf protein loaded per lane is shown.

Figure 25:
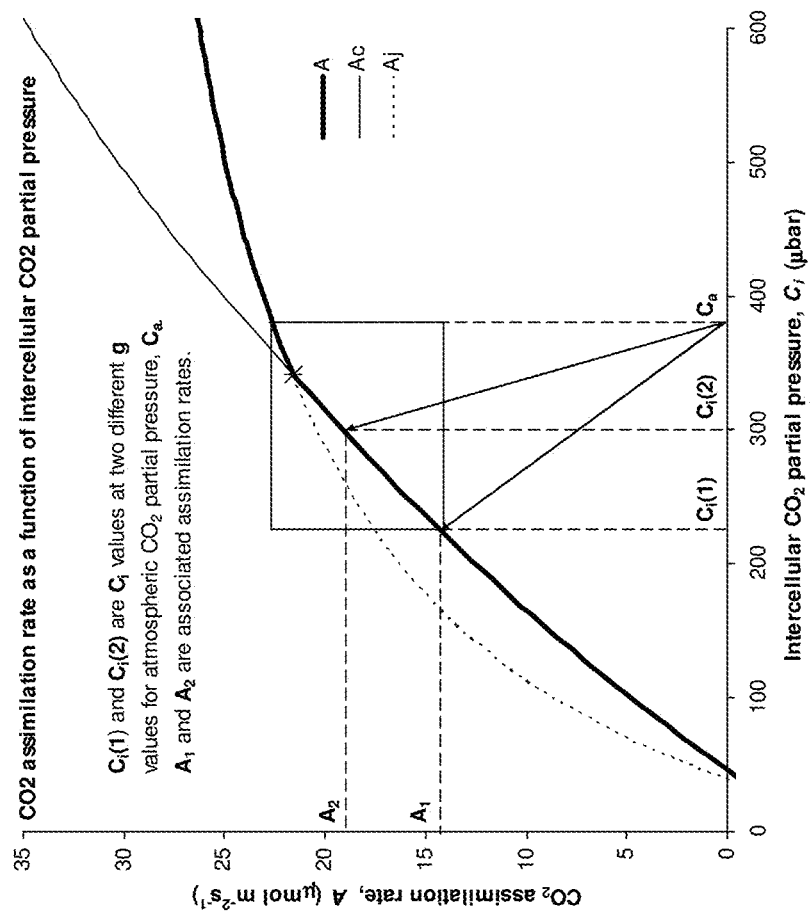
Figure 26:
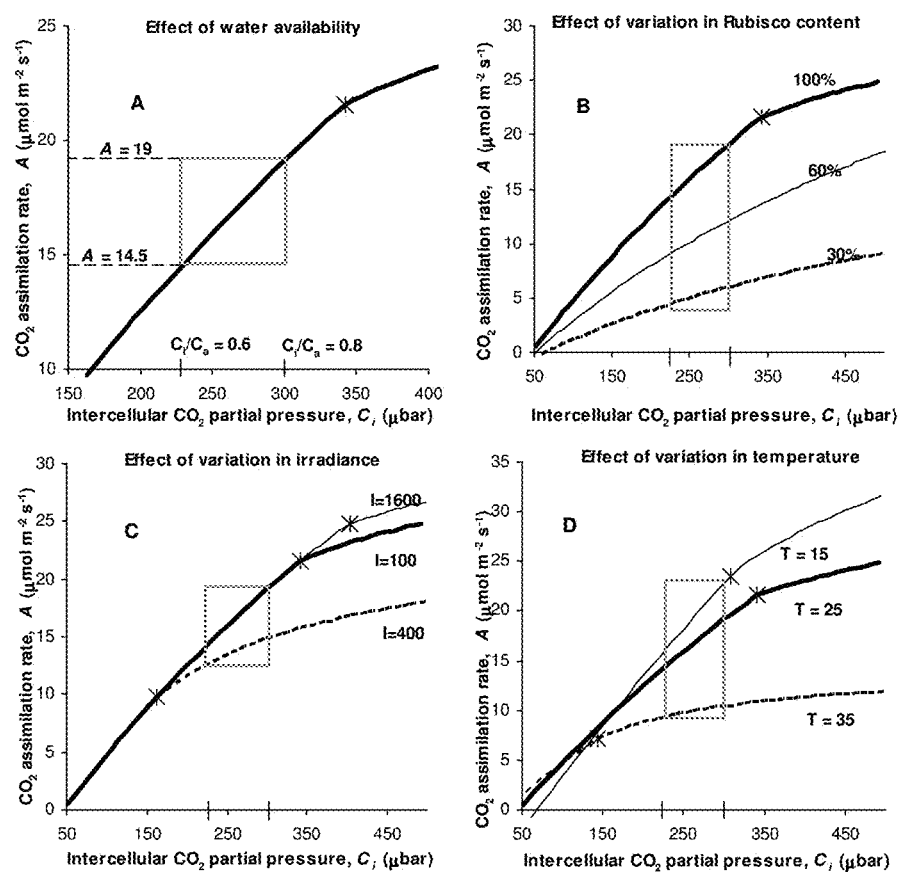
Figure 27:
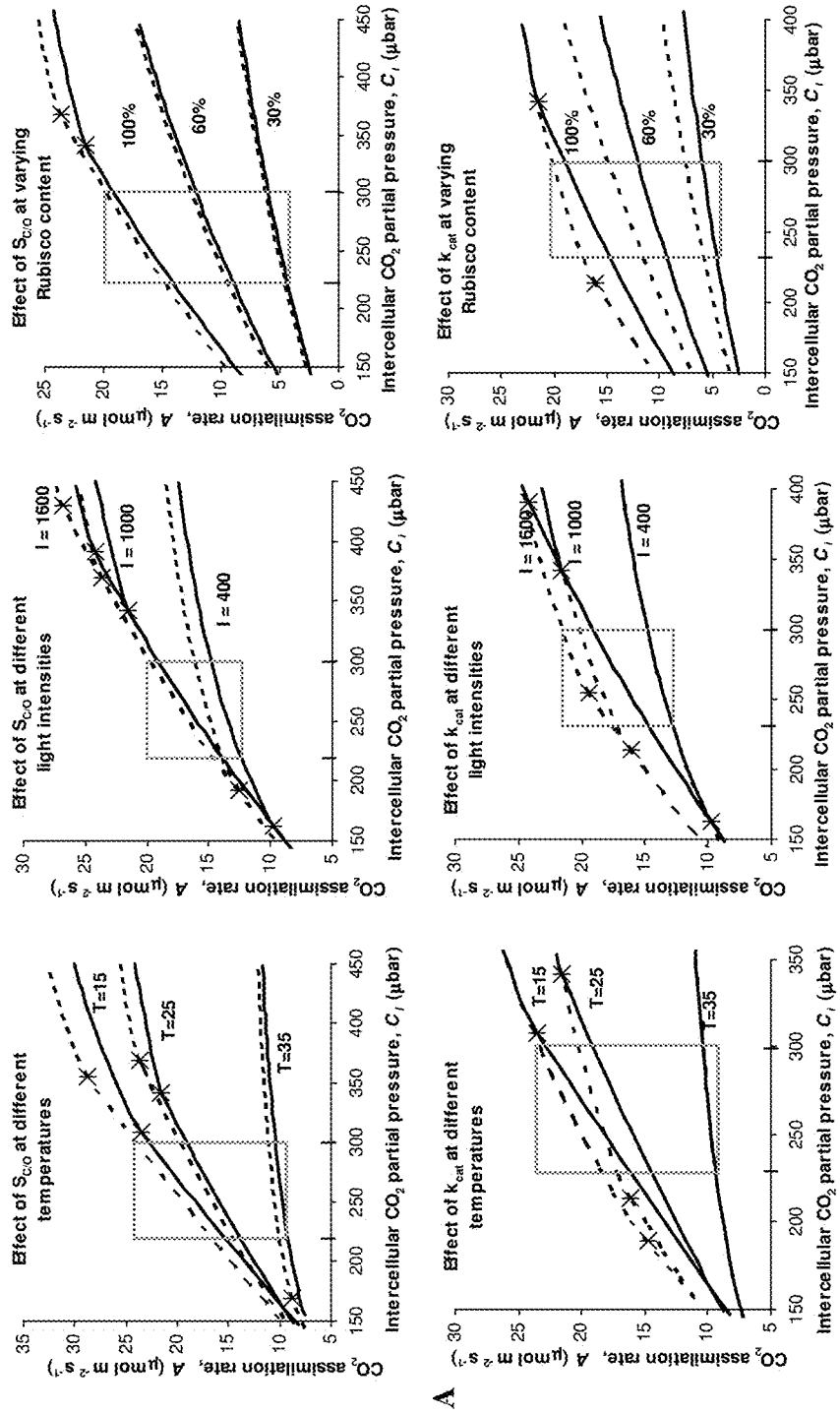
Figure 27:
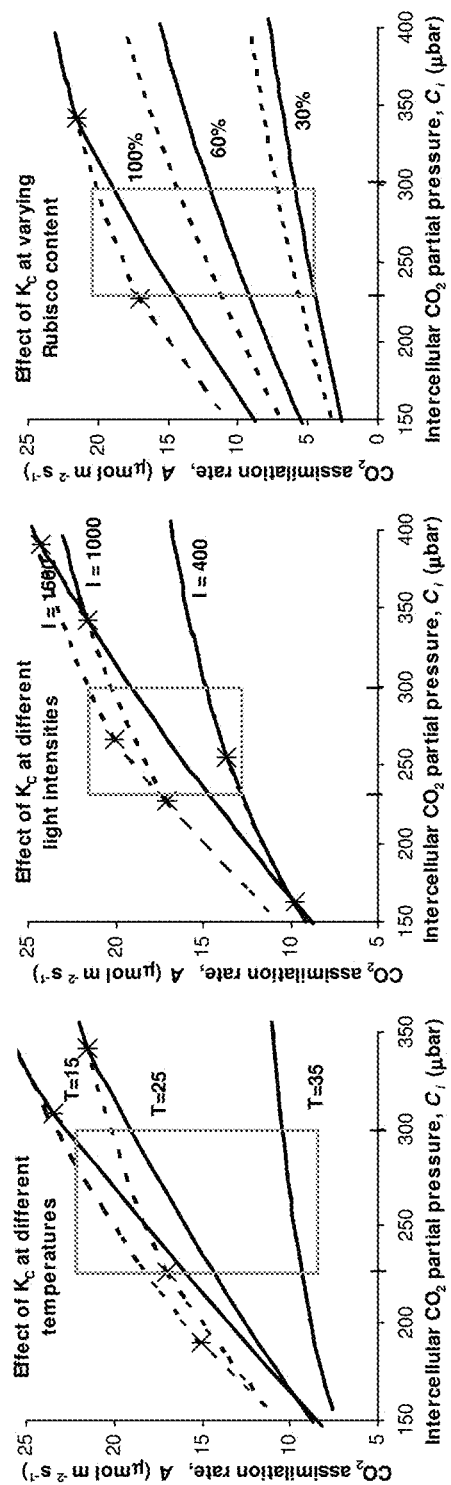
Figure 28:
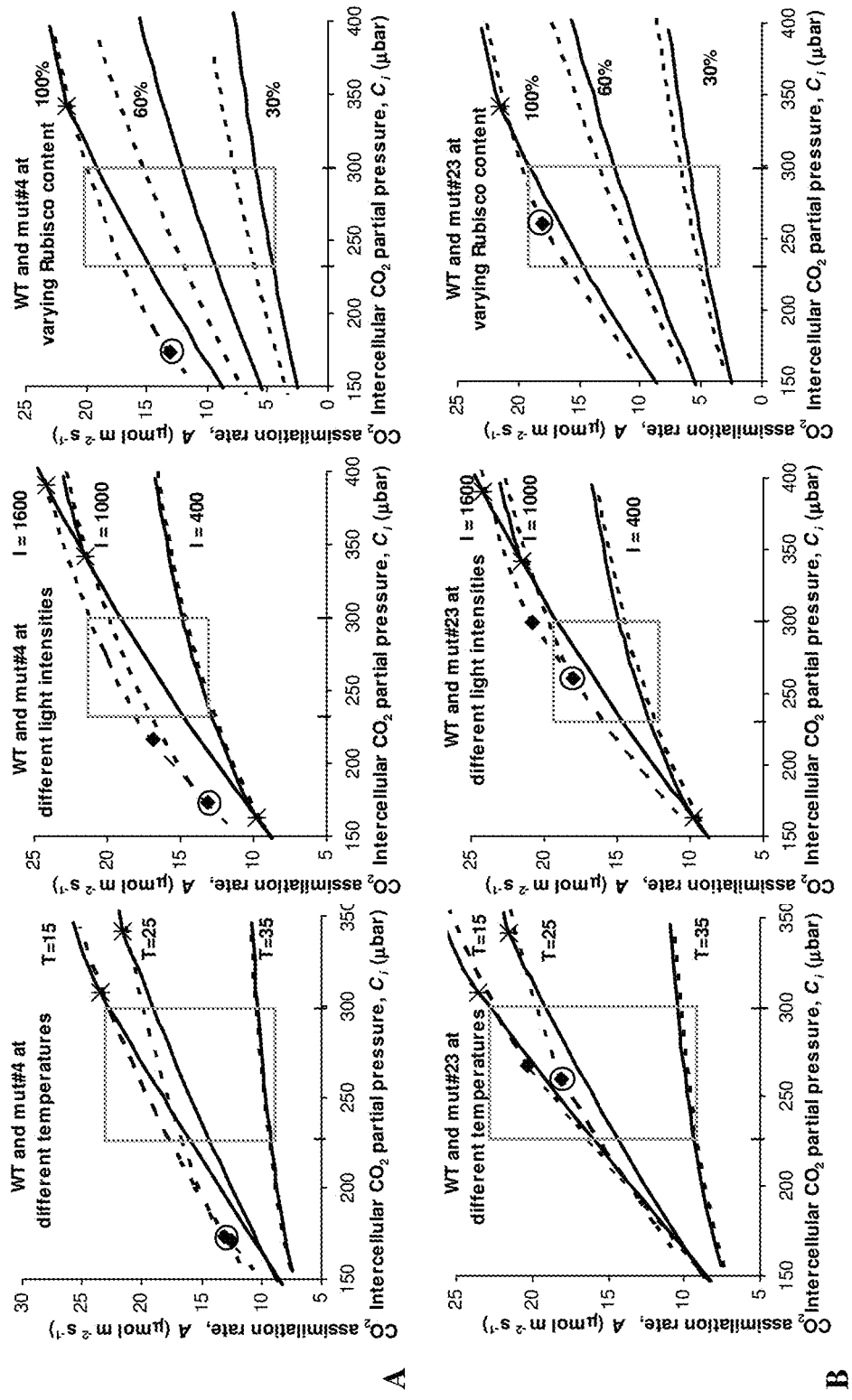
Figure 28:
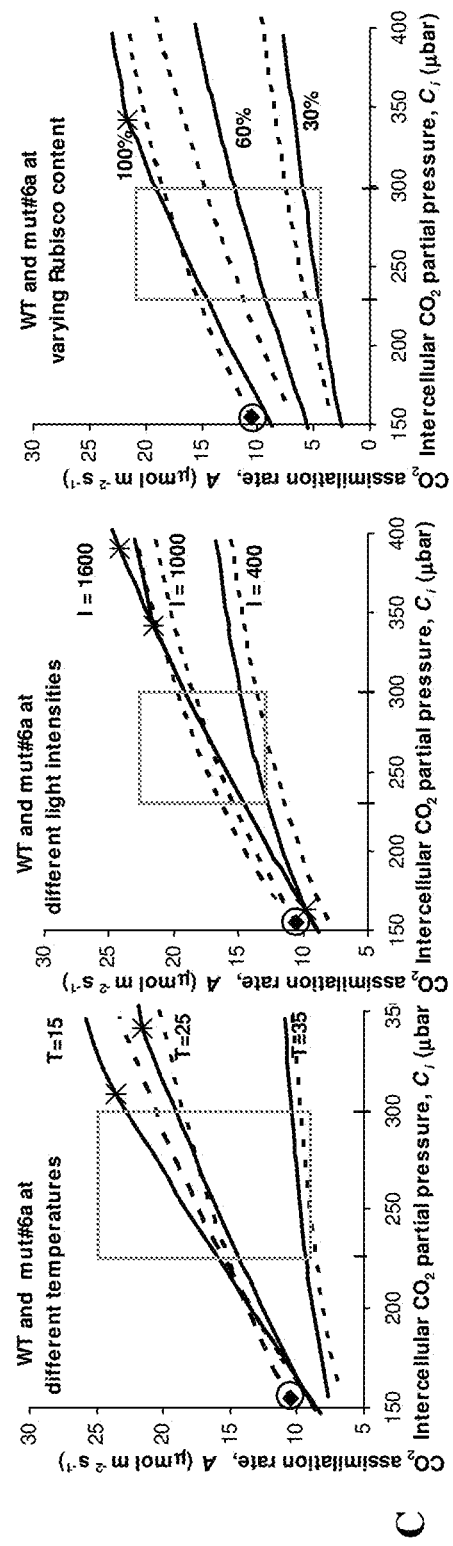

FIG. 25 provides a plot demonstrating the dependence of the rate of $CO_2$ assimilation by plant leaves on the kinetic properties of wildtype tobacco Rubisco. The two lines show the rate under Rubisco limited (solid line) or electron-transport limited (dotted line) conditions, given by equations for $A_c$ and $A_j$, respectively, with the observed rate shown by the thick solid line. In the equations for $A_c$ and $A_j$, C is the chloroplast $CO_2$ partial pressure in μbar, Γ• is the $CO_2$ compensation point (38.6 μbar), $V_{cmax}$ is the substrate saturated rate of carboxylation (80 mmol $m^{-2}$ $s^{-1}$), $K_c^{0\%}$ is the Michaelis constant for $CO_2$ at 0% $O_2$ (260 μbar), O is the $O_2$ partial pressure (200 mbar), $K_o$ is the Michaelis constant for $O_2$ (179 mbar), $R_d$ is the day (non-photorespiratory) respiration (1 μmol $m^{-2}$ $s^{-1}$), and J is the rate of electron transport (variable in units of μmol $m^{-2}$ $s^{-1}$). The temperature and irradiance values used in the model are 25° C. and 1000 μmol quanta $m^{-2}$ $s^{-1}$, respectively. The plot shows that the rate is Rubisco-limited and electron-transport limited at lower and higher $CO_2$ concentrations, respectively. The boxed region shows that most relevant to the $CO_2$ concentrations likely to be experienced in the leaf intercellular space. The position of the intersection of the lines for $A_c$ and $A_j$, shown by *, with respect to the boxed region indicates which limiting conditions will be relevant over the accessible range of $CO_2$ concentrations. As shown in FIGS. 26-28, this position varies with growth conditions and Rubisco phenotype. The arrowed lines show the dependence of the actual intercellular $CO_2$ concentration, $C_i$, with atmospheric $CO_2$ concentration, $C_a$, on stomatal conductance (given by the equation $-g=A/(C_a-C_i)$), which reflects the extent of opening of the leaf stomates to allow $CO_2$ to enter (and water to escape). Increased stomatal closure leading to lower C, values is shown by arrowed lines of decreasing slope. At leaf internal $CO_2$ concentrations of $C_i(1)$ and $C_i(2)$ at values of ~230 and 300 μbar, which correspond to stomatal conductances representing drought and average water-use conditions, respectively, the carbon assimilation rates are $A_1$ and $A_2$. The method and parameter values are based on von Caemmerer (2000).

FIG. 26 provides plots demonstrating the predicted dependence of the rate of $CO_2$ assimilation by plant leaves on different limiting growth conditions, using the kinetic properties of wildtype tobacco Rubisco shown in FIG. 25. The position of the intersection of the lines for $A_c$ and $A_j$ is shown by *. Panel A: limiting water; values of ~230 and 300 μbar correspond to stomatal conductances representing drought ($C_i/C_a=0.6$) and average water-use ($C_i/C_a=0.8$) conditions, respectively (von Caemmerer, 2000). Panel B; limiting nitrogen; modelled by varying Rubisco content (100%, 60%, 30%). Panel C; limiting light; modelled by varying irradiance 1 (1000, 1600 and 400 μmol quanta $m^{-2}$ $s^{-1}$) Panel D; increasing temperature (25, 35 and 15° C.). Kinetic parameters at different temperatures were obtained using equation 2.32 from von Caemmerer (2000).

FIG. 27 provides plots comparing the predicted rate of $CO_2$ assimilation by plant leaves for examples of mutant tobacco Rubisco phenotypes showing hypothetical improvements for an increase of 25% in one of the key kinetic parameters ($S_{c/o}$, $k^c_{cat}$, $K_c$) with that for wildtype tobacco Rubisco. Plots are shown for variable temperature, light and Rubisco content (N content), as for FIG. 26, with water availability shown by the boxed regions. Full and dotted lines are for wildtype and mutant, respectively. In cases where no dotted line is visible the wildtype and mutants lines overlay. The position of the intersection of the lines for $A_c$ and $A_j$ is shown by *. The boxed region of each plot is that most relevant to the $CO_2$ concentrations likely to be experienced in the leaf intercellular space. Panel A: effect of 25% improvement in specificity $S_{c/o}$; Panel B: effect of 25% improvement in $k^c_{cat}$; Panel C: effect of 25% improvement in $K_c$.

FIG. 28 provides plots comparing the predicted rate of $CO_2$ assimilation by plant leaves for three different Rubisco phenotypes modelled from kinetic data given in Tables 6 and 7. Plots are shown for variable temperature, light and Rubisco content (N content), as for FIG. 26, with water availability shown by the boxed regions. Full and dotted lines are for wildtype and mutant, respectively. In cases where no dotted line is visible the wildtype and mutants lines overlay. The position of the intersection of the lines for $A_c$ and $A_j$ is shown by * for wildtype and ◆ for mutant, with points for the latter being circled for normal growth conditions. The boxed region of each plot is that most relevant to the $CO_2$ concentrations likely to be experienced in the leaf intercellular space. Panel A: predictions for tobacco mutant #4 with kinetic profile {$S_{c/o}=-4\%$; $k^c_{cat}=+13\%$; $K_c=+10\%$; $K_o=+87\%$}. Panel B: predictions for tobacco mutant #23-1A with kinetic profile of {$S_{c/o}=-6\%$; $k^c_{cat}=+9\%$; $K_c=+30\%$; $K_o=+92\%$}. Panel C: predictions for tobacco mutant #6a with kinetic profile of {$S_{c/o}=-18\%$; $k^c_{cat}=+9\%$, $K_c=+5\%$; $K_o=+89\%$}.

DETAILED DESCRIPTION OF THE INVENTION

The present invention provides a method of generating a protein with an improved functional property. The invention comprises a procedure to narrow the sequence space for conventional mutational test by defining mutants with one or, preferably, multiple mutations using mechanistic (computational) and bioinformatic and database (phylogenetic-specific/environment-specific sequence changes, kinetic data, 3-D structure and modelling) information, in the first instance. A summary of how the problem of reduction of sequence space may be solved by certain embodiments of the invention is illustrated for Rubisco in FIG. 4. The procedure seeks to maximize the use of all available information, particularly partial evolutionary adaptations encoded in Rubisco sequences, so that the protein improvement process for the required functional property starts at a functional level closer to the required level of functional efficiency.

A first step of the method comprises the process of identifying Target amino acid Residues in a first protein. As described in more detail below, the process of identifying Target amino acid Residues may comprise active-site fragment QM calculations (step (i) using, for example, DFT methods), and hybrid QM/QM or QM/MM calculations (step (ii) using, for example, ONIOM methods), in conjunction with use of empirical data (for example, kinetic data and X-ray crystal structures). Molecular dynamics (MD) simulations (step (iii)), and calculations using combinations of QM, QM/QM or QM/MM, and MD methods (steps (iv) and (v)) may be used, respectively, for evaluating the stability of the predicted Candidate Mutant proteins, or for more detailed understanding of the roles of the Target Residues in the enzymic reaction. These Target amino acid Residues will usually be cornerstone residues for the proper functioning of the protein with respect to the functional property under investigation. It is a preferred feature of the invention that the improved functional property is achieved by modifying the chemical properties of these residues (by mutation of other residues) in order to improve, for example, their kinetic activity.

Convention for Numbering of Rubisco Amino Acid Residues

Throughout this specification, when identifying a residue of a Rubisco LSU by number, the residue numbering was based on the numbering of the residue from the amino acid sequence of spinach Rubisco LSU (SEQ ID NO: 17). This numbering convention was used for all residues identified in computational chemistry, in protein structures and in mutations. This does not create ambiguity as these numbers can be mapped to sequence numbers on alignments and from structural comparisons, and accordingly a given spinach residue number can be mapped with total confidence to a structurally equivalent cyanobacterial or red algal residue number.

Sequence Listings

Table 1 provides a summary of the naturally occurring and 50% consensus Rubisco amino acid sequences discussed herein and which are provided in the computer-readable sequence listing, with the SEQ ID NOS as shown in the "SEQ ID" column. Where multiple sequences were used to produce a 50% consensus sequence, the total number of sequences involved in the consensus sequence creation is listed in brackets in the "Description" column. The database accession numbers provide unique identifiers for each of the sequences which were used, including those sequences which were considered in the creation of consensus sequences. The numbers of the figures in which the sequences are used in alignments is also given in the "Figure Nos" column

TABLE 1

Database accession numbers for Rubisco LSU Sequences used in FIGS. 9, 10, 11 and 18. The Sequence ID numbers correspond to those in the computer-readable sequence listing.

| SEQ ID NO: | Description | FIG. Nos | Database accession number(s) | | | |
|---|---|---|---|---|---|---|
| 1 | Protista glaucophyta | 9 | P24312 | | | |
| 2 | Protista rhodophyta (9) | 9, 10, 11,18 | BAA75676 ABU53651 BAE78409 | AAB17222 BAE78417 | BAA75796 CAB58236 | AAR13681 AAD04746 |
| 3 | Eubacteria cyanobacteria (11) | 9, 10, 11, 18 | P00879 5199140 4296100 | 400856410 P27568 403238160 | 4797620 403124030 P00880 | 402041420 Q8DIS5 |
| 4 | Plantae anthocerotophyta | 9 | Q31795 | | | |
| 5 | Plantae bryophyta (28) | 9 | Q95G53 Q76GQ0 Q76HL3 Q94N80 Q8HW62 Q5TM99 Q5TM97 | Q76GQ2 Q50L57 Q5TM93 Q5TMA1 Q8SN97 Q5TMA5 Q9GGM2 | Q5TM96 Q5TMB1 Q9BB41 Q9TM58 Q95G62 Q9GIF5 Q5TM95 | Q75W61 Q75W60 Q95G63 Q75VP7 Q9TM63 Q5TMA3 NP_904194 |
| 6 | Plantae charophyta (4) | 9 | Q8SN66 | P48716 | Q32RY7 | Q32RQ1 |
| 7 | Plantae chlorophyta (4) | 9 | NP_958405 | BAE48225 | AAD00447 | BAC06367 |
| 8 | Plantae coniferophyta | 9 | P41621 | | | |
| 9 | Plantae equisetophyta | 9 | P48702 | | | |
| 10 | Plantae gnetophyta | 9 | Q9THI3 | | | |
| 11 | Plantae magnoliophyta (134) | 9, 10, 11, 18 | Q3T5C7 Q31857 Q3V6M3 Q5I221 Q6R615 P48690 Q9XQE3 Q5EKL6 CAA57001 Q9XQB9 Q9XQE7 Q3L237 Q33449 Q9BBC7 Q9GGC1 Q95F23 Q32488 Q75VD6 Q9GHT6 Q42916 Q32685 Q9GHS0 Q37257 Q95A48 Q9XK53 Q5MB28 O98612 Q8WIA8 Q8WIC4 Q9GHN0 Q8WIC3 Q8WKR2 P28459 Q75VD7 | Q5EKM0 Q9MRW9 Q31670 Q06022 Q3T5C1 Q75VD8 Q9XPK2 O63123 Q42674 Q6R613 Q5EKM4 Q5EKM2 Q9ZT30 P19161 Q42828 Q3T5G1 Q5EKL5 Q9BBU1 Q8WIB0 O98611 NP_054507 Q68RZ8 Q36849 Q32916 Q9XQA7 Q5EKL2 Q8WKT8 Q95F20 P48715 Q3T5E2 Q9XPK3 AAP92166 Q95F10 NP_054944 | Q95EI0 Q3V6P6 O63085 Q37167 P48688 Q42664 Q8WJD8 Q8SLM3 P92255 Q32072 Q8WLJ3 P92287 Q32188 P48703 Q4VWN7 Q95BC5 AAK72524 Q32518 Q32622 Q5EKL8 Q5C9P7 Q3T5F6 Q95F15 P04717 Q32820 Q8M962 Q6R614 AAX44985 ABB90049 Q33064 Q6R617 Q6USP5 P92364 | Q06021 Q9GDM8 Q3T5G3 AAF78948 Q06023 Q7YKF9 P48693 Q7YKF8 O98530 Q3T575 Q95F13 Q37319 Q9SB16 CAB08877 Q5XLF7 Q95F12 Q01873 Q95EH6 Q9MVF1 Q3T5E7 BAA00147 Q7YL87 Q95F24 Q8WGU4 Q8ME88 Q75VD3 Q9MTS7 O62943 Q9XQ93 Q37281 Q8LUX7 Q3T5E4 CAA60294 |
| 12 | Plantae pinophyta (2) | 9 | P26961 | P26962 | | |
| 13 | Plantae pteridophyta (2) | 9 | Q85WR7 | Q33015 | | |
| 14 | Galdieria partita | 18 | BAA75796 | | | |
| 15 | Griffithsia monlis | 18 | ABU53651 | | | |
| 16 | Synechococcus elongatus PCC6301 | 18 | P00880 | | | |
| 17 | Spinach (Spinacia oleracea) | 18 | NP_054944 | | | |
| 18 | Tobacco (Nicotiana tabacum) | 18 | NP_054507 | | | |
| 19 | Rice (Oriza sativa) | 18 | BAA00147 | | | |
| 20 | Soybean (Glycine max) | 18 | YP_538747 | | | |

TABLE 1-continued

Database accession numbers for Rubisco LSU Sequences used in FIGS. 9, 10, 11 and 18. The Sequence ID numbers correspond to those in the computer-readable sequence listing.

| SEQ ID NO: | Description | FIG. Nos | Database accession number(s) |
|---|---|---|---|
| 21 | Sugarcane (Saccharum officinarum) | 18 | BAD27301 |

Identification of Target Residues—Computational Mechanism

Steps (i) and (ii) hereafter relating to the identification of Target amino acid Residues were performed using the GAUSSIAN program package, for ab initio QM and ONIOM calculations (Frisch et al., 2004), but there are several other proprietary or free-to-use programs available which might be used alternatively. Step (iii) uses the generally available AMBER program (Case et al., 2006) to perform protein MD simulations; this capability is also available in many other programs. Steps (iv) and (v) employ published theory, protocols and programs for enzyme mechanism simulations (Gready et al., 2006); the core semi-empirical QM/MM MD simulation methods (Cummins and Gready, 1997, 1998, 1999, 2003, 2005; Cummins et al., 2007) are implemented in the program MOPS (Cummins, 1996).

(i) Active-Site Fragment-Complex QM Calculations

The following description relates to calculations in respect of the Rubsico LSU, in which active-site residues are totally conserved between species. These calculations use a high level ab initio QM method (B3LYP/6-31G(d,p)) to define the energetics and structures of the reaction species (substrate, transition-state (TS), intermediate, and product complexes) in the multi-step Rubisco reaction mechanism, as shown in FIG. 5. Computations were performed for the reaction steps starting from the gas-addition reaction, using the Gaussian 03 suite of programs (Frisch et al., 2004) and with starting co-ordinates taken from the X-ray structure of the spinach Rubisco-2CABP complex (pdb 8ruc). The active-site fragment model, FM20 as shown in FIG. 6, was large enough to contain all the residues and water molecules immediately interacting with the reaction centre and the co-ordinated Mg atom in the active site, and to allow definition of their roles in the different reaction steps, including the key gas ($CO_2$ or $O_2$) addition steps. The structures of the reaction species and the reaction energy pathway for the carboxylation and subsequent reaction steps are shown in FIGS. 7 and 8, respectively.

(ii) ONIOM Hybrid QM/QM and QM/MM Calculations:

These calculations define the perturbations to the energetics and structures of the reaction-pathway species, and mainly focused on the gas-addition step from the next nearest neighbours and beyond of the active-site residues. This was done using methods which use a high, but computationally expensive, ab initio QM model for the system core (i.e. as in (i)) and a less expensive QM (semi-empirical QM) or MM model for an extended region.

The calculations (QM/QM and QM/MM) were performed at several stages using the ONIOM module in GAUSSIAN 03. The ONIOM QM/QM calculations used a model of a high-level ab initio QM core layer of 93 atoms. For study of the starting point at the gas-addition step, the QM core layer comprises the magnesium atom ($Mg^{2+}$), enediolate of RuBP (to compute the structure and energies of subsequent reaction species the corresponding RuBP-derived chemical species were used), GLU60, ASN123, LYS175, LYS177, carbamylated LYS201, ASP203, GLU204, HIS294 and LYS334. The core layer is surrounded by a further 711 atoms in the outer layer computed at the PM3 (semi-empirical QM) level, which comprises amino acid residues up to ~12 Å from the magnesium atom. The starting co-ordinates were taken from the X-ray structure of the spinach Rubisco-2CABP complex (pdb 8ruc). This model is illustrated in FIG. 22. The role of these calculations is to compare the effects of grafted residues in the vicinity of the active site with those of the wild type on the energetics and structures of the reaction-pathway species, mainly focussed on the gas-addition step. These calculations allowed the structures and energies of the 93-atom active-site fragments of the reaction species, analogous to those for the QM FM20 model shown in FIGS. 7 and 8, to be re-optimized in the environment of surrounding enzyme residues (the 711-atom outer layer), and, thus, allowed perturbations to the energy profile of the reaction due to grafted residues to be estimated. These calculations may thus provide valuable insights on perturbations to the basic mechanism of, in this case, wild-type spinach Rubisco to be determined, and, in particular, the details of the structure of bound $CO_2$ and the nascent carboxylate group in the gas-addition step. By these means, the magnitude and direction of electrostatic perturbations of the interactions of Target Residues with reaction species due to grafted residues in Candidate Mutants, can be calculated. This information may be used to pre-screen Candidate Mutants for experimental test and/or used in interpretation of experimental test results, as shown in FIG. 1, left hand column.

(iii) Molecular Dynamics (MD) Simulations of Protein Complexes

These simulations assessed whether the protein structure of grafted Rubisco Candidate Mutants could accommodate the changed residues, i.e. whether the mutant protein structure was conformationally stable or whether it tended to unravel. MD simulations are particularly useful for multiply-grafted mutants, and provide a global stability screening test to complement the electronic tests on the chemical mechanism from (ii).

These calculations were performed with the AMBER8 or AMBER9 program package (Case et al., 2006), but other protein MD simulation packages (e.g. GROMACS) could be used to obtain similar results.

(iv) Multiple ONIOM Hybrid QM/QM or QM/MM Calculations of Different Sampled Conformational States of Complexes In this method a series of calculations is undertaken using coordinates for protein complexes (e.g. for different reaction steps) taken from snapshots of trajectories of QM/MM MD simulations, as described by Gready et al. (2006). These calculations allowed a more detailed examination of features of the catalytic pathway, namely the effects of protein conformational flexibility on the enzyme-complex geometries and the activation and reaction energies.

(v) Generation of the Full Reaction Free Energy Surfaces for the Gas-Addition Reactions A complete statistical ensemble (conformational average) of enzyme states over the complete course of a reaction step may be generated from semi-empirical QM/MM MD simulations for a grid of points defined by the reaction coordinates (a free energy hypersurface). A more accurate free-energy surface may then generated at ab initio QM level by ONIOM QM/MM calculations using multiple configurations, for example up to 120, sampled from the points on the semi-empirical QM/MM reaction hypersurface (Gready et al., 2006; Cummins et al., 2007). These enzymic free energy surfaces provide reaction and activation free energies that may be compared directly with experimental data, such as experimentally measured kinetic constants, and also may be used to calculate differences in the reaction and activation free energies between wild type and mutants.

(vi) Definition of Reaction Mechanism and Target Residues

Based on the results of these computations, the inventors were able to deduce a mechanism for the entire sequence of reactions in the carboxylase catalysis, and to define precise roles for the active-site residues, singly and in concert (Kannappan and Gready, 2008). From the QM fragment calculations, a pair of key amino acid residues were identified, one acting as a base and the other acting as an acid, for each reaction step. In particular, the pair HIS294 and LYS334 were identified for the gas-addition step.

For the Rubisco carboxylase reaction, the starting point is the Rubisco complex with the enediolate form of RuBP bound to the active site and the $CO_2$ molecule held at a van der Waals interaction distance to the C2 carbon of the enediolate. This state is represented as I in FIGS. 5, 7 and 8. The reaction proceeds through a transition state characterized by the formation of a partial covalent bond between the carbon atom of $CO_2$ and the C2 carbon of the enediolate, accompanied by partial double bonds between the C2 and C3 carbon atoms and between the C3 and O3 atoms of the enediolate. This state is represented as II in FIGS. 7 and 8. The reaction step ends with the complete formation of a covalent bond between the gas molecule and the C2 carbon of the β-keto intermediate (2C3KABP). This state is represented as III in FIGS. 5, 7 and 8.

In the gas-addition step, HIS294 acts as a base to remove a proton completely from the O3 atom; this transfers a partial negative charge to the C2 carbon and enables it to form a covalent bond with the carbon atom of $CO_2$, and also transfers the negative charge to the nascent carboxylate group. LYS334, which is positively charged, helps in stabilizing this negative charge developing on the nascent carboxylate group. These features can be seen in the detailed structures for I-III in FIG. 7. Hence, the basicity of HIS294 and the acidity (charge) of LYS334 are crucial to the gas-addition step.

Modifying the properties of these two residues, for example, by sterically altering the orientation/distance of their interactions with the enediolate substrate or β-keto intermediate or electronically altering the charge on the atoms interacting with the enediolate substrate or β-keto intermediate may affect the energetics of the gas-addition step. HIS294 and LYS334 are, thus, identified as "Target Residues", broadly defined to be residues predicted to have a significant effect on the reaction mechanism and energetics. HIS294 and LYS334 are in the C-terminal domain, are spatially separated, and affect different parts of the enediolate substrate or β-keto intermediate. Hence, the amino acids which may affect their properties have been classified into different regions; Region 2 for His294 and Region 3 for Lys334, as shown in FIG. 23.

Although residue ASN123 was not included in the FM20 active-site fragment model for the QM calculations, examination of crystal structures and the preliminary QM/QM calculations suggested that it also is involved in stabilizing the charge on the nascent carboxylate group added at C2. Furthermore, examination of crystal structures showed residues E60 and Y20 are positioned to directly alter the charge on LYS334 (i.e. the charge/orientation of LYS334 can be altered by manipulating E60 and Y20), and the C2-carboxylate group of the intermediate, 2C3KABP. Thus, E60, Y20 and N123 were also identified as Target Residues. These three residues are in the N-terminal domain of the LSU and, thus, amino acids which may affect their properties were classified as belonging to a different region (Region 1) from those of HIS294 and LYS334 (FIG. 23). These three residues are strictly conserved in all catalytically active Rubisco LSUs and predicted to act in a concerted manner in the gas-addition step. This may be gauged by inspection of FIGS. 12, 13, 14, 16 and 19, which provide different views of the relative disposition of ASN123, GLU60 and Tyr20 with respect to the carboxylate group of the β-keto intermediate analogue (2C3KABP). These figures show that ASN123, GLU60 and Tyr20 are attached to three separate secondary structure regions of the N-terminal domain and that their sidechains extend into the active site in a tripartite constellation.

In summary, the above method comprises a full suite of computational methods for investigating mechanistic, energetic and stability issues at global or more detailed levels for the carboxylation and oxygenation steps for wild type and any predicted Candidate Mutant of Rubisco. In this manner, it was possible to identify one or more Target Residues to act as the focus for the phylogenetic grafting.

Protein Comparisons—Phylogenetic Grafting

In its broadest form, the method described herein also comprises the comparison of at least one second protein with at least the first protein. The second protein may originate from the same or a different phylogenetic branch as the first protein. The process of comparison entails the identification of at least one Variant amino acid Residue between the first protein and the second protein. A plurality of Variant Residues of the second protein act as a pool of different specific amino acid residue identities which may be "grafted" onto the first protein in an attempt to improve the functional property of the first protein mediated by the Target Residues.

Taking Rubisco as an example, phylogenetic branch-specific changes in the Rubisco amino acid sequence, such as changes in Rubiscos from phylogenetic groups of different evolutionary lineages or in Rubiscos which express environment-specific changes, represent possible partial optimizations of the Rubiscos' catalytic efficiency. A strategy, termed "phylogenetic grafting", was developed to identify the key residues which represent these partial evolutionary solutions and to selectively "transplant" these residues into a host Rubisco, such as a Rubisco from *Synechococcus* sp., by changing the specific host residues to those of the donor Rubisco or donor group of Rubiscos with one or more improved (or preferred) kinetic features, with a view to producing a host Rubisco with these improved kinetic features.

Partial evolutionary solutions described above were identified by a procedure of combining the results of the computational studies (the Target Residues), as shown in FIG. 1, left hand column, with those of the phylogenetic analysis (the Variant Residues), as shown in FIG. 1, right hand column, to select the Candidate Residues, as shown in FIG. 1, middle column. These solutions are distributed amongst the Candidate Residues in characteristic (consensus) conserved sequence changes of the LSU among different phylogenetic branches of Rubiscos, or in changes among Rubiscos from the same branch which are better adapted to specific environments, e.g. dry/wet or hot/cold.

The integration of the results of the computational studies with those of the phylogenetic analysis to identify a specific subset of Variant Residues (i.e. the Candidate Residues) allows differentiation between residues which may affect a functional property, for example, the efficiency of the gas-addition step, from other characteristic (consensus) conserved sequence changes between phylogenetic branches, which may represent, for example, neutral phylogenetic drift or a branch-specific physiological role. Taking the example of a Rubisco enzyme, a branch-specific physiological role may include folding and assembly of the protein, including interactions with the small subunit, or protein stability.

(i) Identification of Variant Residues by Phylogenetic Analyses

The combined use of the computationally-deduced mechanisms to identify Target Residues with sequence conservation and phylogenetic information in order to identify the Variant Residues is illustrated by the following discussion of specificity factors of Rubisco. The very high specificity factors of red-algal Rubiscos may be attributed to residues which are in common between cyanobacterial and flowering plant Rubiscos, but differ in red-algal Rubiscos. Such residues are defined herein as "Variant Residues". If single Variant Residues or a plurality of Variant Residues which act as specificity-determining factors in red-algal Rubiscos are identified and selectively incorporated into flowering plant/cyanobacterial Rubiscos, then a Rubisco which is physiologically active in the host organism may be produced which has higher specificity for $CO_2$ than the native enzyme.

First-shell residues, i.e. those residues directly coordinating to the reaction centre (Glu60, Asn123, Lys175, LYS177, KCX201, Asp203, Glu204, His294 and Lys334) are totally conserved among Rubiscos. This conservation is illustrated in FIG. 9, which shows an alignment of Rubisco LSU sequences from photosynthetic organisms belonging to thirteen different phyla covering red algae, cyanobacteria, glaucophyta and plants (10 phyla). Where more than one Rubisco sequence was available in a phylum, a 50% consensus sequence was used to represent that phylum. The consensus sequences were obtained using the server at http://coot.embl.de/Alignment//consensus.html. FIG. 9 also shows that the Rubisco LSU sequence of 475 residues (plants and cyanobacteria) is in general highly conserved, including the almost complete absence of gaps except for minor differences at the N- and C-termini However, residues in the second and subsequent shells surrounding the reaction centre show variation among the main Rubisco branches of flowering plants, red algae and cyanobacteria. Red algae show the greatest specificity for $CO_2$, as identified by the $CO_2/O_2$ ratio of ~160 compared with ~80 for green plants and ~40 for cyanobacteria. The sequence variation among flowering plants, red algae and cyanobacteria is more clearly illustrated in the alignment in FIG. 10 which comprises only the 50% consensus sequences of Rubisco LSUs from red algae (rhodophyta; 9 species), cyanobacteria (11 species) and flowering plants (magnoliophyta; 134 species), already shown in FIG. 9. FIG. 10 shows that there are 134 residues that are the same in flowering plants and cyanobacteria but different in red algae, i.e. the Variant Residues. The database accession numbers for each of the sequences used in the alignments in FIGS. 9 and 10 are given in Table 1, together with the SEQ ID NOS for the computer-readable sequence listings.

In this example, 134 Variant Residues were identified from the Rubisco LSU, amongst which are distributed the residues which are responsible for the partial evolutionary solution for increased specificity which is exhibited by red algal Rubiscos. These are shown as grey-shaded residues in the alignment in FIG. 10. As the specificity-determining factors may be encoded by combinations of several Variant Residues, many thousands of such combinations are possible. Hence, in order to be of any practical use, the subset which comprises the specificity determinants needs to be selected from the list of Variant Residues.

(ii)(a) Identification of Candidate Residues

Using methods described below, specific Variant Residues were identified which have the potential to affect the gas-addition step of the reaction catalysed by Rubisco, and these were termed "Candidate Residues". This allowed conserved changes between phylogenetic branches or sub-branches/sub-species, which may represent neutral phylogenetic drift or which may have a branch-specific physiological role, such as in the stability, folding or assembly of the Rubsico LSU, to be disregarded.

Many of the Variant Residues may not contribute to the improved property of the Rubisco and consequently may not be part of the evolutionary solution for, in this example, increased $CO_2$ specificity, but rather are silent mutations or mutations relevant to other enzyme properties, such as the folding and assembly of the protein, or its stability, in the cell. In order to identify the Variant Residues most likely to be part of the evolutionary solution for the improved property, in this example increased $CO_2$ specificity, the mechanistic insights obtained from the QM calculations were employed to select Candidate Residues from the plurality of Variant Residues. This procedure was based on the hypothesis that Variant Residues which can influence the functionality of the Target Residues identified by the computational chemistry step as involved in the gas-addition step in Rubisco, form a part of the evolutionary solution. This was the primary criterion used to select from the Variant Residues to obtain a subset of residues here called "Candidate Residues".

In general, the selection process was based on assessing the spatial proximity of the Variant Residues to the Target Residues and estimating and ranking their ability to influence the electrostatics and orientation of the Target Residues. Selection may utilise visual screening of crystallographic structures using a molecular modelling and visualization program package such as Accelrys Discovery Studio v2.0 (Accelrys Software Inc., San Diego, Calif., 2007), although other similar modelling packages could be used. Standard chemical concepts for intermolecular interactions, such as charge-charge electrostatic pairing, typical van der Waals and hydrogen-bonding distances, and space-filling models for amino acid sidechains may be used in an initial scan of residues for selection. The procedure may also be systematized, for example, by mapping all the atom-to-atom electrostatic and hydrophobic interactions of each of the Variant Residues with all other amino acid residues that are within 3-5 Å in distance and excluding those interactions which are equivalent in the sequences of the first and second protein.

Examples of such equivalent interactions include backbone-backbone interactions which are generally, but not always, unaltered by mutation. Interactions were also considered equivalent, for example, if a hydrophobic interaction in the sequence of one protein involved an α or β aliphatic carbon of the side chain of a Variant Residue with an atom of a non-Variant Residue, and in the sequence of the second protein the amino acid Variant Residue, while different from that in the sequence of the other protein, also had an α or β aliphatic carbon in the side chain interacting with the same non-Variant Residue as in the first protein sequence.

Interactions of methyl groups in the amino acid side chains, such as those in valine, leucine and isoleucine were considered equivalent if only the particular methyl group was involved in the interaction with a non-Variant Residue. Hydrogen bonds formed by the carboxylate groups of aspartate and glutamate residues were also considered equivalent if the corresponding hydrogen-bonding distances were similar.

After screening the Variant Residues for differences in interaction patterns between the sequences of the first and second protein, only those Variant Residues which had the potential to affect an identified Target Residue through changed interaction patterns were retained. The potential of a Variant Residue to affect a Target Residue was recognized by the interaction of a Variant Residue with the Target Residue or with amino acid residues adjacent to Target Residues or with amino acid residues in the secondary structural unit harbouring the Target Residue. Even Variant Residues that are parts of loops, turns or unstructured strands, but which are connected to the secondary structural units harbouring the Target Residue, have the potential to alter the orientation of a Target Residue by assisting in repositioning of the secondary structural units through changed interactions. The selected Variant Residues, which had one or more variant interactions and the potential to influence Target Residues constituted the set of "Candidate Residues". The 20 Candidate Residues identified as able to influence the Target Residues in Region 1, i.e. ASN123, Glu60 and TYR20, are identified by reverse shading in the alignment in FIG. 11, and are shown graphically in FIG. 17. They are also listed in Table 2.

(ii)(b) Identification of Alternative Candidate Residues and Divergent Candidate Residues (ACRs and DVRs)

The above-described scheme for the selection of a Candidate Residue relies on a selection criterion that the Candidate Residue is present in a consensus sequence of a second protein exhibiting an improved or desirable property, while being different from the corresponding residue in a plurality of consensus sequences of first proteins not exhibiting the improved or desirable property, and where the consensus sequences of the first proteins share the same residue. Thus, using the example of $CO_2$ specificity in Rubisco, the Candidate Residue will be a residue which is present in the red algae consensus sequence, and which is different from the residue common to both the consensus sequences of flowering plants and cyanobacteria.

Other partial evolutionary solutions may also be expressed in residues found in the pool of Variant Residues. These have been termed Alternative Candidate Residues and Divergent Candidate Residues. These partial solutions found in nature may be used to extend the process of selecting Candidate Mutants, to produce an expanded pool of alternative or supplementary residues with which to influence Target Residues.

For example, where the selected residue of the second protein is not the majority residue found in the consensus sequence of the second protein but instead is found at lower frequency in a plurality of the second proteins, while still different from the residues present in a plurality of consensus sequences of first proteins, and where the consensus sequences of the first proteins share the same residue, the residue is termed an Alternative Candidate Residue (ACR). The ACR represents an alternative to the consensus residue at a Candidate Residue position. As for a Candidate Residue, an ACR must still satisfy the selection criteria related to influencing a relevant Target Residue. A purpose for introducing ACRs may be to provide residues for grafting which are suspected to be associated with a greater improvement of the desirable property than the majority residue of the consensus sequence of the second protein.

Thus, using the example of $CO_2$ specificity in Rubisco, the Alternative Candidate Residue will be a residue which is expressed by at least one of the red algae which contribute to the red algae consensus sequence but which is not the majority residue which is contained in the consensus sequence, and which is different to the residue common to both the consensus sequences of green plants and cyanobacteria The red algal species *Griffithsia monolis* has a higher catalytic rate compared with other red algal species while maintaining the high specificity typical of red algae (Whitney et al., 2001), and hence the *Griffithsia monolis* sequence may be used as a source of ACRs. The variation of the Rubisco N-terminal domain sequence between *G. monolis* and that of the red algae consensus sequence and a typical (reference) red algal species, *Galdieri partita*, is illustrated in FIG. 18. This shows ACRs at residues 36, 51, 54, 88 and 104. Note that residue 36 is also a DCR.

A Co-variant Residue (CvR) may be identified in the sequence of a second protein from a particular species, as being in the vicinity of an Alternative Candidate Residue (ACR) and showing complementary variation to the ACR. This variation at the position of the CvR, which is not present in the consensus sequence for the second protein, may be suspected to reflect complementary changes in the structural and/or electrostatic properties of the ACR and CvR. These complementary changes may constitute a partial evolutionary solution. Identification of CvRs provides a means to identify auxiliary residue positions which may be mutated in the first protein to better accommodate changes made from transplanting ACRs.

Yet another partial evolutionary solution may also be expressed in residues found in the pool of Variant Residues where residues from at least three phylogenetic branches are examined and the selected residue is predicted to influence at least one Target Residue and is found in the consensus sequence of the second protein from one branch while being different from the residues present in the consensus sequences of at least two other branches, and where the consensus sequences of the first proteins are also different at the same position. Such a residue is termed a Divergent Candidate Residue (DCR). As for a Candidate Residue, a DCR must still satisfy the selection criteria related to influencing a relevant Target Residue. A purpose for introducing a DCR may be to provide residues for grafting which are suspected of being associated with the improved or desirable property, but which may also be expected to produce a greater variation of the expressed properties when substituted into different first (host) proteins from the at least two phylogenetic branches than would be expected if the substitution was with a Candidate Residue.

Thus, using the example of $CO_2$ specificity in Rubisco, the Divergent Candidate Residue may be a residue which is expressed in the red algae consensus sequence, but which is different from the residue expressed in the consensus sequences of flowering plants and in the consensus sequence of cyanobacteria, while at the same time residues of the flowering plant and cyanobacteria consensus sequences also differ at this position. Six Divergent Candidate Residues identified as able to influence the Target Residues in Region 1 (ASN123, Glu60 and TYR20) are identified by grey shading in the alignment in FIG. 11, and are shown graphically in FIG. 17. Table 2 shows the variation in residue between flowering plants and cyanobacteria at these six positions.

TABLE 2

Residue composition table (in percentage) for cyanobacteria, flowering plants and red algae at current 20 Candidate Residues (including three from the C-terminal domain of partner LSU) and 6 Divergent Candidate Residue sites. Number of sequences used is shown in brackets. The DCRs are at the bottom of the table (36, 86, 116, 117, 138, 140).

| Res | Cyano-bacteria (11) | | Flowering plants (134) | | Red algae (9) | | Substitution in *Synechococcus* PCC6301 by residue in | | | Sub- |
|---|---|---|---|---|---|---|---|---|---|---|
| No | Res | % | Res | % | Res | % | red algae | flowering plants | cyano-bacteria | region |
| 18 | K | 73 | K | 100 | I | 67 | K18I | | K18Q | 1A |
| | Q | 27 | | | — | 33 | | | | |
| 19 | D | 81 | D | 92 | P | 67 | D19P | D19E | D19E | 1A |
| | E | 18 | E | 8 | — | 33 | | | | |
| 23 | T | 100 | T | 99 | G | 100 | 123G | 123N | | 1A |
| | | | N | 1 | | | | | | |
| 25 | Y | 82 | Y | 98 | W | 100 | Y25W | Y25H | | |
| | W | 18 | H | 2 | | | | | | |
| 51 | E | 91 | E | 100 | V | 56 | D51V | | D51E | |
| | D | 9 | | | I | 44 | D51I | | | |
| 54 | G | 55 | G | 99 | S | 78 | G54A | G54R | | 1C |
| | A | 45 | R | 1 | A | 22 | G54S | | | |
| 59 | A | 100 | A | 100 | G | 100 | A59G | | | |
| 64 | G | 100 | G | 100 | A | 100 | G64A | | | |
| 68 | T | 100 | T | 99 | V | 100 | 168V | | | 1A |
| | | | A | 1 | | | | | | |
| 81 | K | 100 | K | 100 | R | 100 | K81R | | | 1A |
| 84 | C | 100 | C | 100 | A | 89 | C84A | | | 1C |
| | | | | | C | 11 | | | | |
| 87 | I | 82 | I | 98 | V | 100 | I87V | I87L | | 1C |
| | L | 9 | L | 2 | | | | | | |
| | V | 9 | | | | | | | | |
| 88 | E | 100 | E | 100 | D | 78 | E88D | | | 1C |
| | | | | | E | 22 | | | | |
| 104 | P | 100 | P | 100 | D | 89 | P104D | | | 1A |
| | | | | | E | 11 | P104E | | | |
| 114 | T | 100 | T | 100 | A | 100 | T114A | | | |
| 118 | T | 100 | T | 100 | A | 100 | T118A | | | |
| 121 | V | 100 | V | 100 | I | 100 | V121I | | | 1B |
| 271 | T | 100 | T | 100 | V | 100 | T271V | | | |
| 297 | M | 100 | M | 100 | G | 100 | M297G | | | |
| 300 | V | 100 | V | 100 | T | 100 | V300T | | | |
| 36 | L | 73 | I | 100 | V | 89 | L36V | | | |
| | I | 18 | | | I | 11 | L36I | | | |
| | V | 9 | | | | | | | | |
| 86† | D | 63 | H | 57 | K | 89 | H86K | H86G | H86D | 1C |
| | R | 18 | G | 20 | R | 11 | H86R | H86D | H86R | |
| | | | D | 16 | | | | | | |
| 116 | V | 64 | M | 99 | L | 100 | I116L | I116M | I116V | 1B |
| | M | 18 | L | 1 | | | | | | |
| | I | 18 | | | | | | | | |
| 117 | L | 100 | F | 99 | T | 100 | L117T | L117F | | 1B |
| | | | L | 1 | | | | | | |
| 138 | I | 82 | L | 100 | M | 100 | I138M | I138L | I138L | 1B |
| | L | 18 | | | | | | | | |
| 140 | F | 82 | I | 97 | L | 56 | F140L | F140V | | 1B |
| | I | 18 | V | 2 | I | 44 | F140I | F140S | | |
| | | | S | 1 | | | | | | |

†For residue 86, only those alternate residues with more than 5% occurrence are displayed for cyanobacteria and flowering plants.

As shown in Table 2, most CRs have an alternative residue in one or more of the 3 groups (cyanobacteria, flowering plants, red algae) although in most cases the consensus residue occurs with >70% frequency. Exceptions are 59, 64, 81, 114, 118 and 121, and all three CRs (271, 297 and 300) in the C-terminal domain segments of the adjacent LSU (Sub-region 1B). However, the magnitude of this variation is of little significance as the sequence sets for each group are not phylogenetically balanced. Rather this variation should only be taken as a approximate indication of degree of conformity with the CR definition. The strongest Mutant #4 (T23G/K81R) (see Examples 7 and 11) showed almost no variation. Similarly the strongest mutant of subregion 1B, Mutant #8 (V121I/M297G/V300T) (see Example 7), also showed no variation of the 3CRs.

(iii) Grouping Candidate Residues, Alternative Candidate Residues and Divergent Candidate Residues into Candidate Mutants More than one Candidate Residue (CR), Alternative Candidate Residue (ACR) or Divergent Candidate Residue (DCR), or combinations thereof, may contribute to changes in a single contiguous interaction region between the sequences of the first and second protein. For example, a single non-Variant amino acid Residue may interact with two CRs, two ACRs, two DCRs, or a combination of two residues derived from two of these groups, such that both of the changed interactions may affect the same Target Residue. The two CRs, two ACRs, two DCRs, or combination may then be grouped into a single Candidate Mutant. Similarly, a given CR, ACR or DCR may contribute to changes in more than one contiguous interaction region affecting a Target Residue. Thus, there may be other CRs and/or ACRs and/or DCRs with which a given CR, ACR or DCR may be grouped to form other Candidate Mutants. These grouped CRs, ACRs, DCRs or combinations thereof may contribute to a proposed Candidate Mutant enzyme where each grouped CRs, ACRs, DCRs or combination thereof is "grafted" onto the host, replacing the corresponding residues in the sequence of the first (host) protein.

(iv) Combining Candidate Mutants to Produce a Cumulative Effect

If the residue mutations from two or more Candidate Mutants (groups of one or more CRs and/or ACRs and/or DCRs) affect the same secondary structural unit harbouring a Target Residue and mutations of each of these Candidate Mutants is expected to act in a coordinated fashion in changing the interaction, then the Candidate Mutants can be further combined to form a single combined Candidate Mutant. For example, if a Target Residue is part of a helix with one Candidate Mutant interacting with the N-terminal end of the helix and another Candidate Mutant interacting with the C-terminal end of the helix, with both interactions involving addition of a strong hydrophobic interaction in going from the sequence of the first protein to the sequence of the second protein, then a combined Candidate Mutant with both the Candidate Mutants grafted into the sequence of the first protein would be predicted to show concerted effects in repositioning the helix.

(v) Ranking Mutants

Despite the large reduction in the number of residues for consideration for mutation that may be effected by the initial selection of the Variant Residues against Target Residues to produce the list of Candidate Residues (CRs), and, optionally, Alternative Candidate Residues (ACRs) and Divergent Candidate Residues (DCRs), the number of predicted Candidate Mutants that could result from grouping the CRs, ACRs and DCRs could still be large. Consequently, it is useful to rank the Candidate Mutants based on their predicted potential to show enhancement of the desired functional property. The higher ranked Candidate Mutants may then be the first choice for further computational and experimental assessments, thus minimizing effort and cost. As illustrated in FIG. 2, several principles may be considered in the ranking;

(a) The Target Residue(s) affected by the Candidate Mutant. Different Target Residues may have different levels of participation in the reaction step, and, hence, relative importance. For example, one Target Residue may be directly involved in a proton transfer, while another may just be a passive hydrogen-bond donor/acceptor. For a Target Residue with greater participation in the reaction step, the effect of mutation of a related Candidate Mutant is predicted to be greater, and, hence, the corresponding Candidate Mutant is ranked higher.

(b) Level of interaction of the CRs and/or ACRs and/or DCRs in the Candidate Mutant. If the predicted change in interactions associated with mutations for a Candidate Mutant involves formation, or elimination, of a strong electrostatic or hydrophobic interaction, then the ranking will be higher.

(c) Number of interaction changes accompanying mutations for a Candidate Mutant. Even if the mutations involve addition, or removal, of only weak interactions, the total changes may involve many such interactions within the Target-Residue protein environment, leading to a large net cumulative effect on the structure and electrostatics, and, hence, produce a pronounced effect on the functional property. Hence, such mutations may be ranked highly.

(vi) Extended Phylogenetic Grafting Predictions

Extended phylogenetic grafting predictions may be used to exploit the capacity of the phylogenetic grafting procedure to "learn from experience" through interpretation of the results (successes and failures) from cycles of application of the core method of prediction and testing of Candidate Mutants for proteins of interest described above. While the core method described above focusses on recognizing Candidate Residues, Alternative Candidate Residues and Divergent Candidate Residues and grouping them into Candidate Mutants based on networks of interactions of these residues, the initial results for Rubisco detailed in Example 3 showed that a proportion of these Candidate Mutants were ineffective or even slightly deleterious to the Rubisco function, although not greatly. The extended phylogenetic grafting strategy allowed this accumulated knowledge, both successes and failures, to be re-interpreted and built into a method further customized for the particular protein application, and that may continue to be refined as additional results are obtained. The interaction between the extended phylogenetic grafting technology and the core method described above is shown in FIGS. 1 to 3.

The extended phylogenetic grafting strategy has three main components. Firstly, refinement of the concept of interacting networks of Candidate Residues, and/or Alternative Candidate Residues and/or Divergent Candidate Residues as the basis of the core method for grouping into Candidate Mutants. Examination of the initial successes and failures of Region 1 mutants of Rubisco, and in particular comparing *Synechococcus* Mutant #6a and its component Mutants #4 and #1a (discussed further in Examples 3 and 4), suggested that an improved framework for prediction would involve recognising that there are "hotspots" for evolutionary adaptation which contain the partial evolutionary solutions to improved Rubisco, and that identification of these "mutatable subregions" provides a better, or supplementary, basis for identifying Candidate Residues, Alternative Candidate Residues and Divergent Candidate Residues which should be preferentially grouped to form Candidate Mutants in order to manipulate Rubisco's functional properties, rather than using solely the interaction networks within the Regions, as in the core method. Thus, in the extended method, the focus of investigation was more on identifying spatial regions than on identifying interacting networks of residues.

Secondly, re-interpretation of the initial results for Region 1 mutants of Rubisco within this framework allowed identification of spatially contiguous volumes of protein structure, called Sub-regions, containing a subset of the Region's CRs (including initially identified ACRs and DCRs), and, which could be predicted to preferentially influence the properties of a particular Target Residue or Target Residues linked to the Region. Identification of these subsets of the Region's CRs, ACRs and DCRs provides a means by which they may be preferentially grouped to form Candidate Mutants.

Thirdly, identification of Sub-regions with imprecise and overlapping boundaries provides a basis for identifying additional CRs, ACRs, CvRs and DCRs which are predicted to interact with the core subsets of CRs, ACRs and DCRs and which may be recruited to the core subsets to provide additional residues for grouping into Candidate Mutants.

Furthermore, identification of Sub-regions as hotspots of natural sequence variation provides the means to identify and exploit other types of sequence diversity data, such as Species-specific Variant Residues (SsVRs) which vary among closely related species, and which may represent partial evolutionary solutions, such as for adaptation to particular environments such as hot/dry or cold/wet. Using Rubisco as an example, FIG. 18 illustrates the natural sequence variation among two red algal species and five flowering plant species.

For example, three Sub-regions of Region 1 of the Rubisco LSU were identified as mutatable hotspots, and labelled regions 1A, 1B and 1C, as shown in FIGS. 19 and 21. As detailed in Example 4, the inventors have used the extended method to recruit additional residues to Region 1's set of preferred residues for mutation and to form additional Candidate Mutants predicted to be improvements of the best "lead" mutants produced from application of the core method, detailed in Example 3.

In summary, the development of the extended phylogenetic grafting method provides a means to improve the functional properties of "lead" mutants. The development of the concept of Sub-regions as evolutionary hotspots and as a framework for building a database of protein sequence mapped to experimental data from test of predictions, also positions the phylogenetic grafting technology to better exploit sequence-diversity data. For example, the aforementioned database may be interrogated against sequence-diversity data to identify residues which may be recruited as species-specific variant residues (SsVRs) for possible inclusion in Candidate Mutants. For example for Rubisco, sequence data and, in some cases, kinetic data are available for photosynthetic organisms growing under varied or atypical environments, including for related C3 plant species such as those found in the Balearic Islands with different tolerances to drought and temperature (Galmés et al., 2005), the drought-adapted southern African Marama bean (Parry et al., 2007), and extremophilic Cyanidiales red algae (Ciniglia et al., 2004). Alternatively for Rubisco, in cases where such sequence diversity and other functional data are available for crop plants such as wheat (Evans and Austin, 1986), the aforementioned database may be used to identify natural species with improved functional properties that may be used as germplasm in selective breeding.

Producing Proteins

Proteins with at least one Candidate Residue and/or Alternative Residue and/or Divergent Candidate Residue, and optionally including other substitutions of CvRs and/or SsVRs, from the second protein may be modelled in silico, or may be engineered in vitro and/or in vivo, for example by site directed mutagenesis of a polynucleotide encoding the protein and then expressed in an expression system.

Screening Mutant Proteins

Candidate Mutant proteins comprising the combination of Target Residues with one or more Candidate Residues and/or Alternative Candidate Residues and/or Divergent Candidate Residues, and optionally including other substitutions of Co-variant Residues (CvRs) and/or Species-specific Variant Residues (SsVRs) are thereafter screened to identify those Candidate Mutant proteins having said improved functional property. The process of screening the Candidate Mutant proteins may use any one or more of several techniques and may comprise catalytic assessment, biochemical assessment, and physiological assessment.

Directed Evolution

The proteins of the invention may be modified by directed evolution. Accordingly, the function of a protein produced by the methods of the invention may be improved or otherwise modified. In general, directed evolution may involve mutagenizing one or more parental molecular templates and identifying any desirable molecules among the progeny molecules. Progeny molecules may then be screened for the desired property, by assessing, for example, the activity of the molecule, the stability of the molecule, and/or frequency of mutation in the molecule. Progeny molecules with desirable properties may then be selected and further rounds of mutagenesis and screening performed. Methods by which directed evolution may be performed are well known in the art. Exemplary methods include, among others, rational directed evolution methods described in U.S. application Ser. No. 10/022,249; and U.S. Published Application No. US-2004-0132977-A1. For a general description of experimental methodology and techniques involved in directed evolution, reference may be made to Sambrook et al., Molecular Cloning, A Laboratory Manual $2^{nd}$ ed., Cold Spring Harbor Laboratory Press, 1989.

In one embodiment of the invention, mutant proteins produced by the methods of the invention may be used as a "starting point" for directed evolution. Taking the example of a Rubisco protein, Candidate Mutant proteins found to have improved enzymatic activity may be selected and further optimised by directed evolution. This optimisation may facilitate, for example, the relief of steric conflicts by recruitment of SvRs and other naturally occurring variant residues which may be identified as complementary to mutations in the Candidate Mutant proteins. Candidate Mutant proteins with improved enzymatic activity may thus serve as a novel starting point for directed evolution as they have different potential for exploring sequence space compared with wild type Rubisco protein. Systems suitable for directed evolution of Rubisco include, but are not limited to those which employ *E. coli* strain MMI as recently been reported (Mueller-Cajar et al., 2007).

Rubisco Proteins

The proteins generated in accordance with the invention include functional equivalents, variants, active fragments and fusion proteins. For the avoidance of doubt, the following are included within the scope of the invention: functional equivalents of the active fragments and fusion proteins; active fragments of the functional equivalents and fusion proteins; and fusion proteins comprising a functional equivalent or active fragment.

The term "fragment" refers to a nucleic acid or polypeptide sequence that encodes a constituent or is a constituent of full-length protein. In terms of the polypeptide, the fragment possesses qualitative biological activity in common with the full-length protein. A biologically active fragment of use in accordance with the present invention may typically possess at least about 50% of the activity of the corresponding full-length protein, more typically at least about 60% of such activity, more typically at least about 70% of such activity, more typically at least about 80% of such activity, more typically at least about 90% of such activity, and more typically at least about 95% of such activity.

Methods of measuring protein sequence identity are well known in the art and it will be understood by those of skill in the art that in the present context, sequence identity is calculated on the basis of amino acid identity (sometimes referred to as "hard homology"). Sequence identity is calculated after aligning the sequences. The inventors have used the ClustalW (Thompson et al., 1994) program provided within the BioEdit Sequence Alignment Editor (Hall, 1999) to align the sequences. There are several free-to-use and proprietary software packages available that perform sequence alignments and yield effectively the same results. The identification of Variant Residues may also be performed by collecting Rubisco sequences, using, for example, BLAST searches from one or more phylogenetic groups that differ in the kinetic property selected for improvement, and aligning them against said first sequence, using, for example, CLUSTALW.

The functional equivalents, active fragments and fusion proteins of the invention retain the ability of the protein (SEQ ID NO: 23 for $Synechococcus$ sp. PCC7942 and SEQ ID NO: 72 for tobacco) to act as a Rubisco enzyme with improved efficiency. Persons skilled the art will, however, be able to devise assays or means for assessing enzymatic activity.

Functionally-equivalent proteins according to the invention are, therefore, intended to include mutants (such as mutants containing amino acid substitutions, insertions or deletions). Such mutants may include proteins in which one or more of the amino acid residues are substituted with a conservative or non-conservative amino acid residue and such substituted amino acid residue(s) may or may not be one encoded by the genetic code.

Particularly preferred are proteins in which several, i.e. 30 and 50, between 20 and 30, between 15 and 20, between 10 and 15, between 5 and 10, 1 and 5, 1 and 3, 1 and 2 or just 1 amino acids are substituted, deleted or added in any combination. "Mutant" proteins also include proteins in which one or more of the amino acid residues include a substituent group.

Such fragments may be "free-standing", i.e. not part of or fused to other amino acids or proteins, or they may be comprised within a larger protein of which they form a part or region. When comprised within a larger protein, the fragment of the invention in one embodiment forms a single continuous region. Additionally, several fragments may be comprised within a single larger protein.

In one embodiment of the invention there is provided a fusion protein comprising a protein of the invention fused to a peptide or other protein, such as a label, which may be, for instance, bioactive, radioactive, enzymatic or fluorescent, or an antibody.

For example, it is often advantageous to include one or more additional amino acid sequences which may contain secretory or leader sequences, pro-sequences, sequences which aid in purification, or sequences that confer higher protein stability, for example during recombinant production. Alternatively or additionally, the mature protein may be fused with another compound, such as a compound to increase the half-life of the protein (for example, polyethylene glycol).

Enzyme Functions

In another embodiment the protein generated in accordance with the invention is an enzyme. Where the protein is an enzyme, the function may be the catalysis of at least one chemical reaction. In other embodiments the function may be structural (e.g. serving as a cytoskeletal protein). The function may involve the active or passive transport of a substance within the cell or between the cell interior and exterior, or between different compartments within the cell, or between different regions of the organism, for example where the protein is involved in a channel or a membrane pore, or the protein is involved in trafficking of materials to specific cellular compartments or the protein acts as a chaperone or a transporter. The function may be involved with ligand/receptor interactions, for example where the protein is a growth factor, a cytokine, a neurotransmitter or an intracellular or extracellular ligand, or the protein is a receptor for the growth factor, cytokine, neurotransmitter or the intracellular or extracellular ligand.

Where the protein is an enzyme, the enzyme may be involved in catabolism or metabolism. The enzyme may be involved in the synthesis of at least one product. The enzyme may be involved in the breakdown of at least one substrate. The enzyme may be involved in the chemical modification of at least one substrate, for example the addition or deletion of one or more phosphate groups from a molecule.

The enzymes may suitable for use in, for example, degradation of pesticides, and detergent residues, for mineral extraction, or for "bulk" or fine chemical processes, such as amylases. The enzymes may also be suitable for use in medical applications, and in particular may be used for minimizing changes to biological and physicochemical stability.

The enzymes may have specifically engineered properties, for example, the ability to perform optimally in a desired temperature range, a narrower, wider or altered substrate specificity, or the ability to prevent the production and/or release of toxic or potentially toxic byproducts. The enzyme may be re-designed such that it is an efficient catalyst for a minor reaction of the wildtype enzyme using either its natural substrate or an alternative substrate to produce a different product.

In the context of Rubisco, an improved functional property of Rubisco may comprise any one or more of improved specificity for $CO_2$ over $O_2$ ($S_{c/o}$), improved carboxylation efficiency $k^c_{cat}/K_c^{air}$ or improvements in one or both of its component parameters $k^c_{cat}$, the carboxylation rate, or $K_c$, the affinity for substrate ($CO_2$), or improvements in these functional properties over a range of temperatures, especially at higher temperature. At higher temperature wildtype Rubisco efficiency is limited by decreased specificity due mostly to a relative increase in the efficiency of the oxygenation reaction compared with that of the carboxylation reaction. Improved $S_{c/o}$ over a range of temperatures may be exhibited by a Rubisco if the efficiency of the oxygenation reaction does not increase with increasing temperature to the extent exhibited by a wildtype Rubisco, i.e. there is a decreased rate of increase or no increase in the efficiency of the oxygenation reaction catalyzed by the Rubisco with elevated temperatures, for example as measured between 25° C. and 35° C., when compared with a wild-type Rubisco.

The improved functional property of a Rubisco may be any two of improved specificity for $CO_2$ over $O_2$ ($S_{c/o}$), improved carboxylation efficiency $K^c_{cat}/K_c^{air}$ or improvements in one or both of its component parameters $k^c_{cat}$, the carboxylation rate, or $K_c$, the affinity for substrate ($CO_2$), or improvements in these functional properties over a range of temperatures, especially at higher temperature. The improved functional property may be any three of improved specificity for $CO_2$ over $O_2$ ($S_{c/o}$), improved carboxylation efficiency $K^c_{cat}/K_c^{air}$ or improvements in one or both of its component parameters $k_c^{cat}$, the carboxylation rate, or $K_c$, the affinity for substrate ($CO_2$), or improvements in these functional properties over a range of temperatures, especially at higher temperature.

The improved functional property of Rubisco, when functionally incorporated into a plant may result in the generation of a plant with improvements in any one or more of growth rate, biomass production, leaf index area, Rubisco content (Rubisco mRNA and protein content), carbon to nitrogen ratios of plant leaves, starch content, and photosynthetic performance. The improvements may be exhibited under optimal growth conditions for the plant. The improvements may be exhibited under sub-optimal growth conditions for the plant, for example but not limited to under elevated temperatures for growth, or where water, nitrogen or illumination is limiting plant growth, or a combination of any two or more of the above.

Purification of Rubisco Proteins

The invention provides a method of purifying a Rubisco protein produced according to the methods of the invention. The holoenzyme of the functional form of Rubisco from eukaryotic organisms (form I Rubisco) is a hexadecamer made of 8 large subunits (LSUs) and 8 small subunits (SSUs), and requires appropriate chaperones to correctly fold and assemble the enzyme correctly. *E. coli* is the most widely used microbial host for expressing recombinant DNA and proteins. When the operon coding for the Rubisco genes (rbcLS and rbcSS) from *Synechococcus* sp. PCC7942 is expressed in *E. coli* both subunits are abundantly synthesized, however only about 1 to 5% of the expressed LSUs are correctly folded and assembled into functional form with the amount of functional Rubisco accumulating to ~1 to 3% (wt/wt) of the *E. coli* soluble protein.

In order to overcome these difficulties, a recently adapted system (Baker et al., 2005, the entire contents of which are incorporated herein by reference) may be used to purify native or mutant Rubisco proteins. In this case, the aforementioned system was used for the purification of *Synechococcus* sp. PCC7942 Rubisco expressed in *E. coli*. The first step of the purification method involves fusing into a first vector the coding sequence for a $H_6$ tagged ubiquitin (Ub) sequence ($H_6$Ub) to the 5' end of an rbcSS gene. A host is then co-transformed with the first vector and second vector coding for the the native (or mutated) large subunit and small subunit of the Rubisco protein, and expression of the Rubisco protein and vectors is then induced, producing all three Rubisco subunit peptides (i.e. LSU, SSU and $H_6$UbSSU). Some are assembled into functional Rubisco hexadecamers made up of 8×LSU octameric cores and different ratios of SSU (at most 8) and $H_6$UbSSU. The Rubisco protein is purified based on the expression of the $H_6$ tag fused to the Rubisco small subunit. This purification may be performed, for example, using chromatography techniques such as metal affinity chromatography. The Ub fragments may then removed from the Rubisco using, for example, a Ub-specific protease.

The present invention will now be described with reference to specific examples, which should not be construed as in any way limiting the scope of the invention.

EXAMPLES

Example 1

Identification of Target Residues—Computational Chemistry

A computational study of the complete Rubisco carboxylation mechanism (Kannappan and Gready, 2008) and complementary oxygenation mechanism using ab initio QM calculations on an extended active-site fragment complex provides the basis for the strategy.

This fragment complex model comprises fragments of most of the active-site amino acid residues that have either been established or mooted to have a key role in the series of reactions that are catalyzed at the Rubisco active site. It contains all residues directly co-ordinated to $Mg^{2+}$ or interacting with the reactive centre of the substrate. This fragment complex model was built from the coordinates of the crystal structure with PDB code 8ruc (crystal structure of the complex of activated Rubisco with $Mg^{2+}$ and 2-carboxyarabinitol 1, 5-bisphosphate (2CABP)). Initially, the fragment complex model of Rubisco with 2-carboxy-3-ketorarabinitol 1,5-bisphosphate (2C3KABP), a structural analogue of 2CABP and the actual reaction intermediate produced during the Rubisco carboxylase activity, was built from the crystallographic coordinates. As shown in FIG. 6, the 77-atom fragment model, named FM20, comprises molecular-fragment species to represent the LYS175, LYS177, ASP203, GLU204, KCX201 (carbamylated LYS201), HIS294, and LYS334 amino acid residues and the 4-carbon fragment of the enediolate form of the substrate RuBP, plus the water and carbon dioxide molecules. This structure was optimized using the quantum chemistry package Gaussian 03 (Frisch et al., 2004). Guess geometries for all the other reaction species on the carboxylase reaction pathway (shown in FIGS. 5 and 7) were generated by modifying this optimized geometry, and their optimum energy structures were then obtained, also using the Gaussian 03 package. In general, several possible structures for each species differing, for example, by H-bonding pattern or orientation of atoms, were considered. Consequently the roles of these groups in the gas-addition and subsequent steps of the carboxylase and oxygenase reactions were examined leading to more confident predictions, in particular, for definition of the groups involved directly in the gas-addition ($CO_2$ or $O_2$) steps and the relative energetics of the two steps.

The analysis is focused entirely on the large subunit (LSU). Although most Rubiscos, including green plants, algae and cyanobacteria, are complex multimeric (hexadecameric) proteins consisting of 8 large subunits (LSU; ~475 residues) and 8 small subunits (SSU; ~140 residues), the active-site chemistry is conducted by a protein region consisting of a dimer of LSUs only, with 8 such dimer active sites in the hexadecameric protein. A moiety of the C-terminal (TIM-barrel) domain of one LSU contains most of the active-site residues while a smaller region of the N-terminal domain of the adjacent LSU completes the active site. However, predictions arising more generally from bioinformatics studies suggest other regions may be involved in modulating the chemistry, e.g., intersubunit contacts (LSU-LSU or LSU-SSU).

FIG. 5 shows a schematic of the proposed carboxylase reaction mechanism based on the QM calculations. The curved arrows indicate the flow of electrons, signifying the bond-formation and bond-breaking events, which lead to the successive reaction species. The schematic defines the participation of amino acid residues in each reaction step, and the gas-addition step (carboxylation), in particular. The residues predicted to have a role in the gas-addition step comprise the set of Target Residues defined previously. FIGS. 7 and 8 provide geometries and relative energies, respectively, of the carboxylase reaction species.

The most significant features of the proposed reaction mechanism are discussed hereafter.

Firstly the inventors have made the surprising discovery that $H_2O[Mg]$ is not displaced from Mg-coordination by $CO_2$ during carboxylation. The water molecule in fact assists in binding $CO_2$ to the active site and contributes to the stability of the carboxylated product and the corresponding TS. The same water molecule acts as the water of hydration in the later step. Previously this role of hydration had been assigned to a water molecule found in the vicinity of the coordination sphere.

The inventors have made the further surprising discovery that the O2 atom remains unprotonated in the enediolate intermediate, despite expectations from general chemical principles that it would need to be deprotonated in order to direct carboxylation exclusively to C2, rather than to C3. ESP-derived atomic charges also show that O3 is more negative than O2. However, this unexpected result is explained by the observation of strong hydrogen bonds between LYS175 and protonated KCX201 with O2, which effectively prevent O2 from directing carboxylation to C3. Additionally, as LYS334 is H-bonded to the P1-phosphate group in the enzyme, its interaction with the substrate $CO_2$ would be disrupted if C3 carboxylation were to take place, leaving no scope for stabilization of the corresponding TS and intermediate.

Further features of the reaction mechanism elucidated by the inventors are as follows. KCX201 has a direct role only in the initial enolization reaction and it remains in a protonated state after enolization. KCX201 and LYS175 have a role in hindering C3-carboxylation by partially neutralizing the negative charge on O2. HIS294 has a significant role in the multi-step catalysis of Rubisco. It shuttles the proton between $N_E$ and O3, modulating the C3-O3 bond length appropriately. GLU204 activates the Mg-coordinated water molecule for hydration by abstracting its proton. Thus, both carboxylation and hydration take place on the same face of the enediolate intermediate. The H3 proton is eventually transferred to O2 only after the formation of the aci-acid intermediate (VII). The charge on the aci-acid intermediate is stabilized by LYS175 and LYS334. LYS175 ensures stereospecific protonation of the C2-carbon to yield the final products. LYS334 shares its proton with LYS175.

On the basis of the above findings, the inventors have identified two amino acid residues, one acting as a base the other as an acid, for each reaction step. For the gas-addition step, HIS294 acts as a base by abstracting the proton from O3, while LYS334 is the acid donating a proton to stabilize the carboxylate group formed by addition of $CO_2$. Alteration in the steric or electronic environment of these two key residues, or any other residues that are structurally or chemically (through electrostatic interactions) linked to them, would impact the specificity of the enzyme and likely also affect $k_{cat}$.

Residues TYR20 GLU60, ASN123 were also identified as being crucial for appropriate orientation of gas molecules relative to the substrate prior to addition, and for the stability of the gas-adduct and the corresponding transition state structures. These five residues comprise an initial group of Target Residues for further examination.

Figure 4:
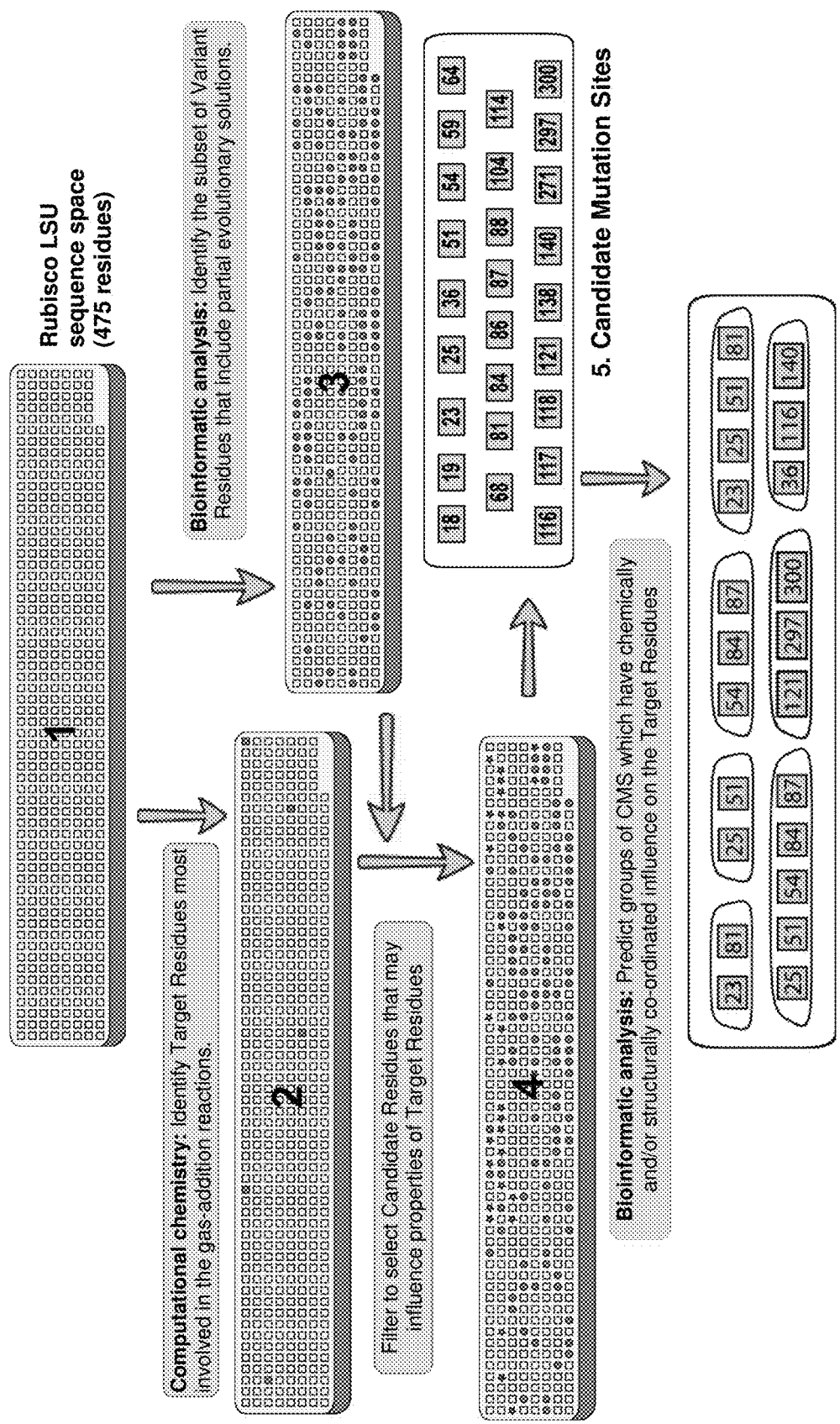

At this stage in the summary of the solution of the problem of reduction of sequence space for Rubisco illustrated in FIG. 4, step 2 is achieved.

Example 2

Phylogenetic Analysis to Identify Variant Residues Containing Specificity-Determining Residues Rubisco LSU sequences from available phyla of photosynthetic organisms were collected for phylogenetic analysis from publicly available databases at NCBI (www.ncbi.nlm.nih.gov/) and JGI (http://img.jgi.doe.gov/cgi-bin/pub/main.cgi) by performing protein BLAST searches (Altschul et al., 1997) using the spinach Rubisco LSU sequence as the query sequence. As the LSU sequences are so distinctive, and the conservation relatively high compared with most protein-homologue classes over such wide evolutionary distances, they are easy to identify and other free-to-use or proprietary search software would work equally well.

Alignment of the extracted Rubisco LSU sequences from photosynthetic organisms belonging to thirteen different phyla covering red algae, cyanobacteria, glaucophyta and plants (10 phyla) was carried out using ClustalW software (Thompson et al., 1994) within the BioEdit Sequence Alignment Editor (Hall, 1999) to assess their diversity. An alignment is shown in FIG. 9; in cases where there is more than one sequence from a single phylum, a 50% consensus sequence has been used for efficiency. The consensus sequences were obtained using the server at http://coot.embl.de/Alignment//consensus.html. Any other proprietary or free-to-use alignment tool could be used for the same purpose due to the fact that the overall conservation of these Rubiscos is so high that effectively the same alignment results would be obtained.

FIG. 9 shows how diverse the Rubisco LSU sequences from distant phylogenies can be. Thus, although information on partial evolutionary solutions for adaptation of Rubiscos to specific environments is embedded in this diversity, it is impossible to analyze this information directly to identify residues responsible for specific adaptations, such as increased specificity.

To solve this problem, the inventors have developed the hypothesis-based phylogenetic grafting method and applied it to identification of Rubisco residues which already represent natural partial evolutionary solutions for enhanced specificity ($S_{C/O}$). It is well known that diverse photosynthetic organisms exhibit characteristically different values for $S_{C/O}$. The majority of land plants possess a typical $S_{C/O}$ value of 80, while red algae are known to have the highest specificity factor (~160). The specificity factor for cyanobacteria has a modest value of about 40.

As cyanobacteria are a common ancestor to both land plants and red algae, and as land plants diverged from cyanobacteria earlier in evolution compared with red algae (http://www.geocities.com/we_evolve/Plants/chloroplast.html) the partial evolutionary solution for enhanced specificity embedded in amino acid residue changes in red algae can be partially revealed by comparison of Rubisco LSU sequences from these three groups. FIG. 10 shows the alignment of 50% consensus sequences of Rubisco LSUs from red algae, cyanobacteria and flowering (green) plants previously shown in FIG. 9, but now shown with grey shading to highlight the 134 residues in red algae which differ from those in common in cyanobacteria and flowering plants, i.e. the Variant Residues. As there is a general agreement that single-residue changes will not result in substantial improvement in Rubisco specificity (otherwise evolution would have been able to explore sequence space reasonably easily to optimize specificity in given organisms), the number of multiple mutations, for example of 2-10 residues, which would need to be tested to explore even the reduced sequence space of these 134 residues to identify the specificity-determining residues is impossibly large. In making use of this list of Variant Residues, variations that are not relevant to the enzyme property of interest are filtered (i.e. specificity). The problem of sequenced space to be solved is illustrated in FIG. 4.

At this stage in the summary of the solution of the problem of reduction of sequence space for Rubisco illustrated in FIG. 4, step 3 is achieved.

Example 3

Identification, Grouping and Ranking of Candidate Residues, and Prediction of Candidate Mutants Using Core Phylogenetic Grafting Method In order to identify the specificity-determining residues that account for the increased specificity of red algal Rubiscos, the inventors used the enzyme-mechanistic insights from the QM calculations described in Example 1 to develop a procedure for selecting a subset of the 134 Variant Residues identified in Example 2. The Variant Residues, identified in Example 2, were selected against the Target Residues, identified in Example 1 to have a functional role in the gas-addition step, in order to identify Candidate Residues. Several of the selected Candidate Residues were also Alternative Candidate Residues. In addition, several Divergent Candidate Residues were also selected. This used a procedure based on the general principle that evolutionary changes of residues which modified the properties of these Target Residues would alter their specificity and kinetic efficiency. Thus, any Variant Residue that has the potential to affect the Target Residues electronically or structurally, and, hence, cause a change in the functional property of the enzyme, in this case specificity and kinetic efficiency, is deemed to be part of the partial evolutionary solution to optimisation of the property.

The selection procedure was applied to identify such Candidate Residues, Alternative Candidate Residues and Divergent Candidate Residues. Selection was carried out by visual analysis and comparison of differences in inter-residue interactions with Accelrys Discovery Studio v1.5.1 (Accelrys Software Inc., San Diego, Calif., 2005), using the crystal structures of Rubiscos from spinach (PDB code: 8ruc) and *Galdieria partita* (PDB code: 1BWV). The crystal structure of spinach Rubisco was used instead of Rubisco from *Synechococcus* sp. PCC6301 (PDB code: 1RB1) because the resolution of the available structures is superior for the spinach Rubisco structure. However, the inventors accounted for residue changes between LSUs of spinach and *Synechococcus* sp. PCC6301 Rubiscos when analyzing the inter-residue interactions, and used the *Synechococcus* structure also for reference.

Three of the five Target Residues, TYR20, GLU60 and ASN123 are in the N-terminal domain of the Rubisco LSU, while HIS294 and LYS334 are in the C-terminal domain that forms the TIM-barrel structure (FIG. 12). For the purpose of classifying groups of CRs, ACRs and DCRs that can form subsets of residues of the partial evolutionary solutions, the Target Residues were classified as belonging to three different Regions. Residues TYR20, GLU60 and ASN123 collectively interact with the carboxylate group of the intermediate formed after $CO_2$ addition (FIGS. 12, 13 and 19). The secondary structural units containing these three residues also intertwine with other helices and sheets of the N-terminal domain (FIGS. 12, 13 and 19). As evident in FIG. 19, ASN123, GLU60 and TYR20 are attached to three separate secondary structure regions of the N-terminal domain and their sidechains extend into the active site in a tripartite constellation. Hence, these three Target Residues are classified as Region 1 residues. HIS294 is in strand β4, which is a part of the TIM barrel; the region surrounding HIS294 is defined as Region 2. Although LYS334 is in the vicinity of HIS294 and Region 1 residues, it is in 'loop 6' of the LSU (FIG. 12) and in the open form of the LSU it is separated from the other Target Residues; hence, the region containing LYS334 is classified as Region 3.

At this stage in the summary of the solution of the problem of reduction of sequence space for Rubisco illustrated in FIG. 4, steps 4 and 5 are achieved.

The initial analysis and Candidate Mutant design is illustrated by consideration of the Variant Residues in Region 1. As the N-terminal domain of the LSU of Rubisco is a compact domain (FIGS. 13 and 19), protein-structural considerations suggest that amino acid residue variations in most of the domain can influence the Target Residues TYR20, GLU60 and ASN123. The selection procedure was started by mapping all the electrostatic and hydrophobic interactions between each of the Variant Residues and all other residues in the LSU in both the crystal structures. Variant Residues that have equivalent interactions in both the crystal structures were ignored. The equivalent interactions mainly comprise interactions involving a backbone atom of a Variant Residue, and such interactions occur largely within a helix or between two β-strands. The interactions were also considered equivalent if Variant Residues in spinach (or *Synechococcus* sp. PCC6301) and *Galdieria partita* differ only in the length of the sidechain and the interacting atoms are of the same chemical type and within approximately the same distance in both the crystal structures. Similarly, interactions involving valine, leucine and isoleucine were considered equivalent if only one methyl group of the sidechain is involved in the interaction and the interaction distance does not differ significantly between the two crystal structures. This process removed some of the Variant Residues from further consideration as potential Candidate Residues (or Divergent Candidate Residues). The remainder of the interactions involving Variant Residues were then analysed for their potential to affect Target Residues.

A Variant Residue whose sidechain interacts with the backbone or sidechains of Target Residues or with residues that are part of the secondary structural units harbouring the Target Residues was considered a Candidate Residue (or Divergent Candidate Residue). As an example, Target Residue GLU60 is at the C-terminal end of helix αB and the Variant Residue ILE51, at the N-terminal end of this helix, interacts with another Variant Residue TRP25 in the *Galdieria partita* LSU (see FIG. 18 and Table 2), but this interaction is absent in the spinach and *Synechococcus* sp. PCC6301 LSUs. "Grafting" these Variant Residues from *Galdieria partita* into *Synechococcus* sp. PCC6301 is predicted to have an effect on the orientation of helix αB and, hence, on GLU60. Both these Variant Residues 51 and 25 were, thus, considered as Candidate Residues. The positions of these residues in the LSU structure are shown in FIG. 13. In this case, it is useful to group these two Candidate Residues that share a contiguous interaction region into a single mutation, as it is likely they form a co-ordinated part of the partial evolutionary solution. This simplest grouping is numbered Candidate Mutant #1a in Table 3. Such grouped Candidate Residues represent mutations for replacement of residues (grafting) from the sequence of *Galdieria partita* onto the *Synechococcus* sp. PCC6301 sequence, with the view to transferring features of higher specificity into *Synechococcus* sp. PCC6301 Rubisco.

Before grafting, the groups of Candidate Residues can be further combined into groups that can act further in coordinating and amplifying the perturbative effect on a given Target Residue or Target Residues. Such extended grouping is useful if two different groups of Candidate Residues affect the same secondary structural unit. For example, both of the Candidate-Residue groups {25, 51} and {54, 84, 87} affect helix αB, which harbours GLU60, through two different interactions. Hence, one of the predicted mutants comprised these combined groups (Shown as Mutant #7a in Table 3).

The potential grafted Candidate Mutants were further assessed to check for new unfavourable steric interactions introduced by grafting residues from *Galdieria partita* into *Synechococcus* sp. PCC6301. Such undesirable steric interactions may be rectified by adding spatially complementing mutations to the Candidate Mutant, or could be investigated by MD simulations to assess whether structural relaxation to relieve such bad contacts is energetically accessible.

The final step in the Candidate-Mutant prediction procedure is to rank the potential grafted mutants to develop a ranked list for use in prioritising experimental testing or detailed computational in silico pre-screening. The ranking reflects the expected degree to which the combined mutations in the individual Candidate Mutants is expected to change the functional property, in this example in the direction towards improvement of specificity by influencing the chemistry, and relative chemistry, of the gas-addition steps for $CO_2$ and $O_2$. Ranking depends on a number of parameters such as the Target Residue affected by the Candidate-Residue group, the strength of the changed interactions of the Candidate-Residue group within the Target-Residue Region, and the number of such interactions for each Candidate-Residue group.

In addition to the Rubisco sequence from *Galdieria partita*, the sequence of another red-algal species *Griffithsia monolis*, which is known to have a better $k^c_{cat}$ than *Galdieria partita*, was considered in the analysis. For the initial set of Candidate Residues selected, two residues (51 and 54) show differences between *G. partita* and *G. monolis*, i.e. they are Alternative Candidate Residues. Candidate Mutants with both residue variants in positions 51 and 54 were formed, as shown in Table 3 for CM's #1, #5, #6, #7 and #13.

As an example, the set of sixteen Candidate-Residue groups shown in Table 3 was predicted from initial analysis of Region 1 Target Residues, forming 21 potential Candidate Mutants (with *G. partita* and *G. monolis* variants). For each Candidate Mutant, the last column in Table 3 details the predicted structural change associated with the mutations. For some Candidate Mutants, these changes are explained graphically in a figure; the second column of the table gives the figure number for these CMs. Table 3 also shows the rankings of priorities for experimental test.

Table 3 shows that two Divergent Candidate Residues (36, 116 and 140; see Table 2) were selected in this initial analysis for the reasons summarized for the relevant Candidate Mutants (#9 and #10). Two of these DCRs (36 and 140) also show differences between *G. partita* and *G. monolis* (see Table 2); for Candidate Mutants #9 and #10, the Gm variant of 36 and the Gp variant of 140 were judged to be the most promising for transplant into *Synechococcus*.

At this stage in the summary of the solution of the problem of reduction of sequence space for Rubisco illustrated in FIG. 4, step 6 is achieved.

TABLE 3

Predicted and Ranked Candidate Mutants from Analysis of Region 1 in the N-terminal Domain of the Rubisco LSU surrounding Target Residues TYR20, GLU60 and ASN123. Superscript Gp and Gm denote the residue from *Galdieria partita* and *Griffithsia monolis*, respectively.

| No # | FIG.[a] | Mutant | Rank | Region Affected |
|---|---|---|---|---|
| 1a | 13, 14 | Y25W/D51I$^{Gp}$ | 3 | Adds a new hydrophobic interaction between the C-terminal end of αB and βA. βA is close to Y20 in sequence. |
| 1b | 13, 14 | Y25W/D51V$^{Gm}$ | 3 | Adds a new hydrophobic interaction between the C-terminal end of αB and βA. βA is close to Y20 in sequence. |
| 2 | — | A59G/G64A | 6 | Swapping mutation. Interaction between αB and the long chain that connects αB to βC. The swapped methyl group is spatially close to Y20 and adjacent to E60. |
| 3 | — | P49D/D51I | 10 | Alters the interaction in the short loop connecting αB and βB. |
| 4 | 13, 14 | T23G/K81R | 4 | Interaction between βA and βC is broken. Affects the positioning of Y20. |
| 5a | 14 | G54A$^{Gp}$/C84A/I87V | 5 | Introduces a strong hydrophobic interaction between αB and βC. |
| 5b | 14 | G54S$^{Gm}$/C84A/I87V | 5 | Introduces a strong hydrophobic interaction between αB and βC. |
| 6a | 13 | T23G/Y25W/D51I$^{Gp}$/K81R | 1 | Mutant #1a adds a hydrophobic interaction between βA and αB, while Mutant #4 breaks the interaction of βA with βC. These two sets of mutations together may have a large effect on Y20. |
| 6b | 13 | T23G/Y25W/D51V$^{Gm}$/K81R | 1 | Mutant #1b adds a hydrophobic interaction between βA and αB, while Mutant #4 breaks the interaction of βA with βC. These two sets of mutations together may have a large effect on Y20. |
| 7a | 14 | Y25W/D51I$^{Gp}$/G54A$^{Gp}$/C84A/I87V | 2 | Cumulative effect of Mutants #1a and #5a on E60. |

TABLE 3-continued

Predicted and Ranked Candidate Mutants from Analysis of Region 1 in
the N-terminal Domain of the Rubisco LSU surrounding Target Residues
TYR20, GLU60 and ASN123. Superscript Gp and Gm denote the residue
from *Galdieria partita* and *Griffithsia monolis*, respectively.

| No # | FIG.[a] | Mutant | Rank | Region Affected |
|---|---|---|---|---|
| 7b | 14 | Y25W/D51I$^{Gp}$/G54S$^{Gm}$/C84A/I87V | 2 | Cumulative effect of Mutants #1a and #5b on E60. |
| 7c | 14 | Y25W/D51V$^{Gm}$/G54A$^{Gp}$/C84A/I87V | 2 | Cumulative effect of Mutants #1b and #5a on E60. |
| 7d | 14 | Y25W/D51V$^{Gm}$/G54S$^{Gm}$/C84A/I87V | 2 | Cumulative effect of Mutants #1b and #5b on E60. |
| 8 | 15 | V121I/M297G/V300T | 7 | Hydrophobic interaction between the two LSUs are broken (residues 297 and 300 are from the neighbouring LSU that contains the Mg-complex of the active site being considered). Affects N123. |
| 9 | 15 | L36I$^{Gm}$/I116L/F140L$^{Gp}$ | 8 | Forms a large hydrophobic region involving the ends of two adjacent β-strands (βB and βE) and αC. Could alter the orientation/positioning of N123. |
| 10 | 15 | L36I$^{Gm}$/I116L/V121I/F140L$^{Gp}$/M297G/V300T | 3 | Could together act on α-C and have a cumulative effect on N123. |
| 11 | | T114A/T118A/T271V/V121I | 2 | Polar interaction of 114 and 118 with 271 in the partner LSU is broken. 271 forms a new hydrophobic interaction with 121. Impacts N123 |
| 12 | 21 | K18I/T23G | 5 | Polar interaction between side-chains of T23 and K18 is broken. Impacts Y20. |
| 13a | 13, 14 | Y25W/D51I$^{Gp}$/insert A21 | 6 | (1a + A21) Insertion of A21 moves K21 away from residue 51 and forms a new hydrophobic interaction with I51. |
| 14 | 21 | KLTYY-(21-25)-AKMGYW | 4 | Shape of a coil adjacent to Y20 is altered, affects orientation of Y20. Involves an insertion (M); see FIG. 10. |
| 15 | 21 | K18I/KLTYY-(21-25)-AKMGYW/K81R | 1 | The change of shape of coil next to Y20 is associated with changes to its interaction with 18 (loss of polar interaction) and 81 (change in length) and may have a coordinated effect on Y20. |
| 16 | — | A15S/K18I/T68V/L407I | 9 | Possible interaction between residues 18 and 68 which could bind N-terminal tail to rest of domain,; conserved residue 69 interacts with 407 of partner LSU,; S15 can form strong H-bonds with backbone carbonyl groups of 408 and 409 of partner LSU in red algae. Targets Y20. |

[a]FIGS. 13-15 and 21 show the predicted mutation sites.

Example 4

Figure 3:
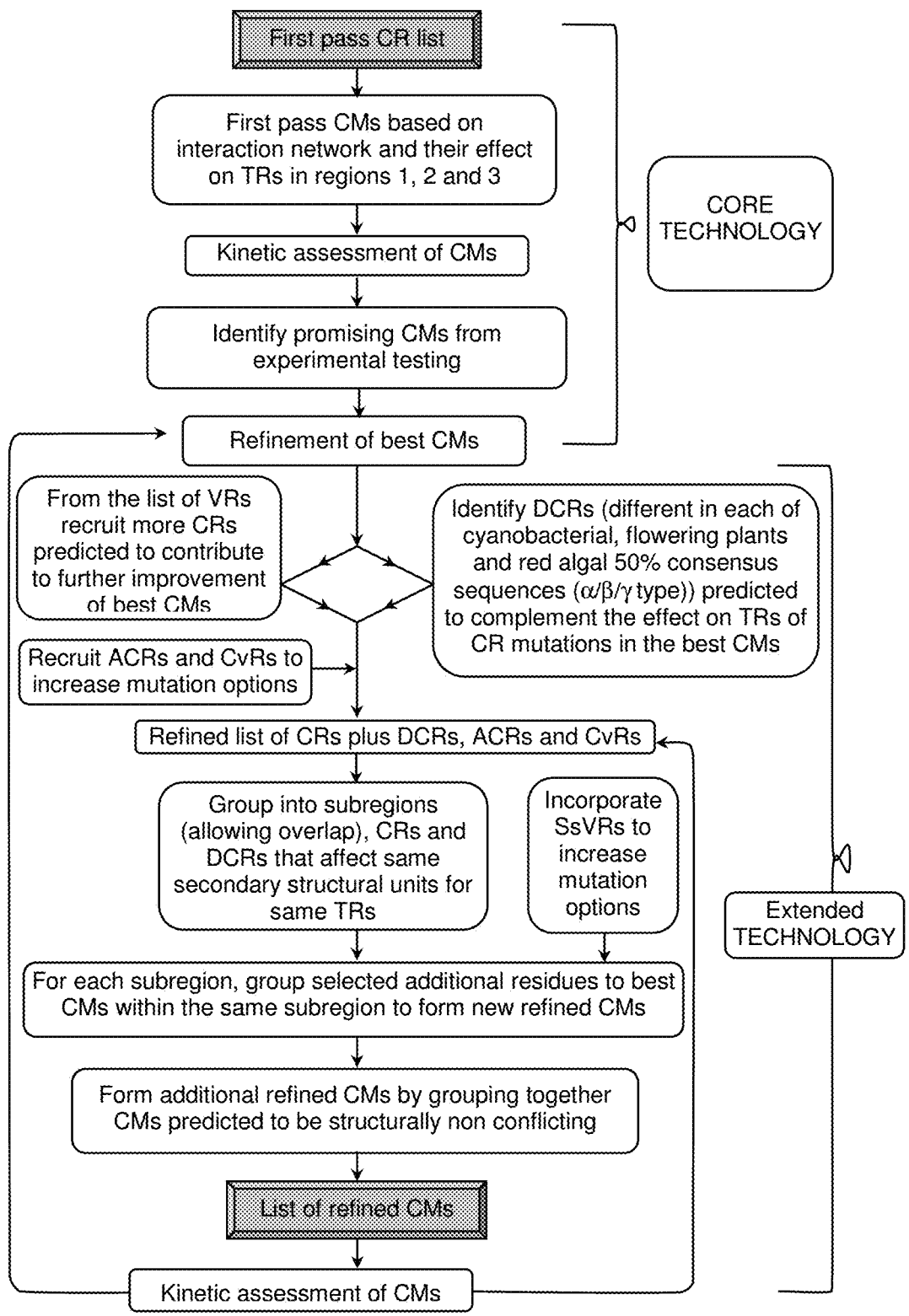

Identification, Grouping and Ranking of Candidate Residues, and Prediction of Candidate Mutants Using Extended Phylogenetic Grafting Method As aforementioned and as shown in FIGS. 1 and 3, the extended phylogenetic grafting method provides a means to utilise effectively knowledge of the "map" of function to mutations, developed from experience gained from cycles of application of the core method of prediction and testing of Candidate Mutants. Use of the extended method is illustrated in this example with reference to the initial results for predicted Region 1 Candidate Mutants (Example 3) given in Table 5 and discussed in more detail in Example 7.

The extended method was first used to interpret the core-method results. This resulted in identification of a new model for grouping of already identified CRs, ACRs and DCRs (see CMs in Table 3), which was based on Sub-regions as mutatable hotspots rather than focussed on networks of interactions as in the core method. The three Sub-regions (1A, 1B and 1C) exhibited the property of being predicted to preferentially influence the properties of one of the three Target Residues linked to Region 1: Sub-region 1A to TYR20, 1B to ASN123 and 1C to GLU60. This "anchoring" of the three TRs to the Sub-regions of Region 1 is shown graphically in FIG. 19. The Sub-regions are shown graphically in an alternative orientation in FIG. 21. The Sub-regions are confined entirely to the N-terminal domain, except for fragments of the C-terminal domain of the adjacent LSU which form part of Sub-region 1B.

Identification of the Sub-regions provided the basis for identification of additional CRs and DCRs, using visual inspection and other analyses described previously for identifying CRs and DCRs using the core method, which may be preferentially grouped with CRs and DCRs already identified by the core method to form new Candidate Mutants (see Table 4). Additional CRs and DCRs so identified were positions 19, 68, 88 and 104, and 86, 117 and 138, respectively. Alternatively, the identification of the Sub-regions provides a new basis for preferential regrouping the CRs and DCRs already identified by the core method to form new Candidate Mutants.

The use of the extended method, and the basis for recruiting particular additional CRs and DCRs, is illustrated below with reference to examples for refinement of activity of mutants predicted by the core method and initially tested (Table 5). The new predicted CMs are shown in Table 4.

TABLE 4

Candidate Mutants predicted using the extended phylogenetic grafting method to refine the most promising initially predicted Candidate Mutants (Table 3). Also listed are additional single and double-residue component mutations of these most promising initially predicted Candidate Mutants.

| No. | FIG. | Mutation | Rank | Comments |
|---|---|---|---|---|
| 17-1A | 21 | T23G/K18I/T68V/K81R | 2 | Prediction based on refined |
| 18a-1A | 21 | T23G/K81R/P104E$^{Gp}$ | 5 | phylogenetic grafting on subregion |
| 18b-1A | 21 | T23G/K81R/P104D$^{Gm}$ | 5 | 1A. |
| 19-1A | 21 | T23G/D19P/K81R | 4 | |
| 20-1B | 20, 21 | I116L/L117T/V121I/ I138M/F140L | 3 | Prediction based on refined phylogenetic grafting on subregion 1B. Targets residue N123. |
| 21-1A, B | 21 | T23G/K81R/V121I/ M297G/V300T | 1 | Combination of two predicted CMs that showed maximum overall improvement in the enzyme efficiency in kinetic assessment study. |
| 22-1A | 13, 14 | T23G | | Single-residue components of |
| 23-1A | 13, 14 | K81R | | Mutant #4. |
| 24 | 15 | V121I/M297G | | Double-residue component of Mutant #8. |
| 25 | 15 | M297G | | Single-residue components of |
| 26-1B | 15 | V121I | | Mutant #8. |

The first example below focuses on the refinement of the best mutant, Mutant #4 (T23G/K81R), from first-round testing, and on subregion 1A. As shown in Table 3, Mutant #4 is a component with Mutant #1a (Y25W/D51I$^{Gp}$) of Mutant #6a (T23G/Y25W/D51I$^{Gp}$/K81R). However, although Mutant #6a showed increased specificity (8.5%, see Table 5), it showed no efficiency improvement, and overall is inferior to Mutant #4, which showed both increased specificity (10%) and efficiency (8%). Reference to the results for Mutant #1a indicated it is a relatively poor mutant with increased specificity of only 3.4% and no change in efficiency. Thus, it was concluded that grouping of the Mutant #4 mutations with those of Mutant #1a was ineffective, as the net effect was not a cumulative improvement but rather the two groups of mutations apparently interfered disadvantageously. As Sub-region 1A contains the residue positions of the mutations in Mutant #4, it was deduced that coupling of the Mutant #4 mutations with mutations of other CRs and/or DCRs in subregion 1A, may provide a better strategy for further improving on the properties of this “lead” mutant.

Examination of the sequence and structural data by visual and other analysis procedures already described, especially an analysis of species-specific covariation data for already identified CRs and DCRs in Sub-region 1A, identified three additional CRs, 19, 68 and 104, which may influence TR TYR20 or residue 81 (component of #Mutant #4). Hence, the following new CMs, showing the indicated changes in interactions, were predicted as potential improvements on Mutant #4.

In relation to Mutant #17-1A (#4+K18I/T68V), the mutations of K18I and T68V are predicted to result in an altered interaction between the N-terminal tail and the region between βB and helix B. In combination with the mutations in Mutant #4 (T23G and K81R) this is expected to have an increased impact on TR TYR20.

In relation to Mutant #18a(b)-1A (#4+P104E$^{Gp}$)(D$^{Gm}$)), the mutation of CR 104 (which is also an ACR), i.e. P104E$^{Gp}$) or P104D$^{Gm}$, is expected to result in a new interaction with the backbone N of residue 81. It is expected that the three mutations in the combined CM #18-1A would have an increased impact on TR TYR20.

In relation to Mutant #19-1A (#4+D19P), residue 19 forms a salt bridge with residue 21 (K or R) in cyanobacteria and plants, which is absent in red algae where residue 19 is P. It is expected that the mutation D19P will influence the reach of TR TYR20 into the active site, and that in combination with the Mutant #4 mutations, this would produce an increased impact on TR TYR20.

These predictions are shown graphically in FIGS. 19 and 21.

The second example below relates to the identification of a major new mutational area (subregion 1B) which in turn led to the initial prediction of Mutant #20-1B (V116L/L117T/V121I/I138M/F140L). This mutant has Mutant #8 (V121I/M297G/V300T), identified by the core method (Table 3), as a component. As shown in Table 5, initial testing of Mutant #8 showed improvement in specificity (5.6%) which providing a basis for further characterisation. Following identification of Sub-region 1B, as described, examination of residue variations near residue 121 (CR adjacent to TR N123; see FIG. 20A) led to the discovery of a network of interactions between helix C and β-sheet E. This network may be seen more clearly in FIG. 20B. Changes in this interaction network can affect the orientation of TR N123. The interactions involve residues 116, 117, 120, 121, 124, 133, 135, 138 and 140. Of these, residue 121 is a CR and residues 120, 124, 133 and 135 are conserved in all major groups of organisms (see FIG. 9). Residues 116, 117, 138 and 140 are DCRs, i.e. differ among the three major organism groups, red algae, cyanobacteria and flowering plants (Table 2). It was observed that changes in the CR and DCRs interacting in this spatial region (i.e. 21, and 116, 117, 138 and 140) appear to be compensating in the major organism groups. Thus, as an initial test of the effect of such changes on the orientation of N123, Mutant #20-1B (V116L/L117T/V121I/I138M/F140L) was predicted (Table 4).

Example 5

Generation of Mutant Rubiscos and Screening Thereof

Based on the ranked predicted Candidate Mutants in Tables 3 and 4, proof-of-principle studies were conducted by mutating the red-algal specific residues into Region 1 of Synechococcus sp. PCC7942, in groups of multiple mutations. Initially fourteen of the predicted LSU mutants detailed in Example 3 and listed in Table 3 (Mutants #1a, #1b, #4, #5a, #5b, #6a, #7a, #7b, #7d, #8, #9, #10, #12 and #14, where "a" and "b" refer to variants where the CR for G. partita or the ACR for G. monolis, respectively, were ai transplanted) were engineered by mutating the Synechococcus sp. PCC7942 rbcLS gene with the QuickChange multi-mutagenesis kit (Stratagene) using appropriate primers. In addition, several mutants with single (#22-1A, #23-1A, #25, #26-1B) or double (#24) mutations, which are components of predicted mutants (#4, #8, #21-1A,B), were engineered as controls.

The genomic sequence for the rbcL-rbcS sequence (operon) of 'wildtype' Synechococcus sp. PCC7942 is shown in SEQ ID No. 22. This sequence is the same as for Synechococcus sp. PCC6301. In the native genome sequence, the rbcLS coding sequence reads ATG CCC (coding Met then Pro) but in all the cloned rbcLS sequences it is ATG GCC (coding Met then Ala). This nucleotide substitution was introduced to code for a unique restriction site (NcoI) used for cloning of the gene. A silent mutation in the second last codon (Arg) in the rbcSS sequence (CGA to CGC) was also introduced for cloning purposes. The translated sequence for the wildtype large subunit is shown in SEQ ID No. 24 and the translated sequence for the wildtype small subunit is shown in SEQ ID No. 23. The nucleotide and protein sequences for mutants are shown by SEQ ID NOS in Table 5, for example SEQ ID NOS: 25 and 26, respectively, for Mutant #1a.

After consideration of these initial results and development of the extended phylogenetic grafting method, a further four of the predicted LSU mutants detailed in Example 4 and listed in Table 4 (Mutant #17-1A, #18-1A, #19-1A, #21-1A,B) were engineered by the same method. All of the control mutants (#22-1A, #23-1A, #24, #25, #26-1B) mentioned above are components of these four mutants and are relevant, in particular, to Mutants #4 and #21-1A,B. The nucleotide and protein sequences for these mutants are shown by SEQ ID NOS in Table 5, for example SEQ ID NOS: 53 and 54, respectively, for Mutant #17-1A.

The mutated rbcLS genes were sequenced before cloning back into the second expression plasmid which coded for the mutated LSU and the native SSU. The mutant Rubiscos were expressed and purified using a procedure described in Example 6. These initial experiments on the eighteen Synechococcus sp. PCC7942 mutants and five control mutants showed good expression in E. coli of active (i.e. properly folded and assembled hexadecameric) mutant Rubiscos, with specificity and kinetic constants comparable with, or better than, wild type, as described in Example 7. The way in which experimental test and optimisation procedures, detailed in Examples 6-11 are integrated with the prediction and in silico screening steps is shown in FIG. 1. FIG. 1 also shows how experimental results may be fed back into the prediction procedure to refine the predictions of mutant proteins, followed by further cycles of in silico screening and experimental screening and assessment of the improvement in the functional property, in order to optimize it.

Example 6

Expression and Purification of Mutant Rubiscos

Although E. coli is the most widely used microbial host for expressing recombinant DNA and proteins, obtaining the functional form of Rubisco from eukaryotic organisms (defined herein as "form I" protein) is more complex. As the holoenzyme of form I Rubisco is a hexadecamer made of 8 large subunits (LSUs) and 8 small subunits (SSUs), it requires appropriate chaperones to correctly fold and assemble the enzyme correctly. Conveniently, however, when the operon coding for the Rubisco genes (rbcLS and rbcSS) from Synechococcus sp. PCC7942 is expressed in E. coli both LSU and SSU subunits are abundantly synthesized. Hence, Synechococcus sp. PCC7942 was used here as the model $L_8S_8$ enzyme for initial testing of the Rubisco predictions, and E. coli was used as the natural choice of expression host for producing the mutant Rubiscos.

However, only about 1 to 5% of the expressed LSUs are correctly folded and assembled into functional form with the amount of functional Rubisco accumulating to ~1 to 3% (wt/wt) of the E. coli soluble protein. Purification of the functional Rubisco by traditional methods is a laborious and protracted process that may take up to 3 days.

The use of 6×Histidine ($H_6$) affinity tags is an attractive alternative that could save substantial effort and time toward enzyme purification. But experiments have shown that fusion of $H_6$ tags to either termini of the LSU or SSU of form I Rubisco can compromise the catalytic activity. To overcome these difficulties, a recently adapted system (Baker et al., 2005, the entire contents of which are incorporated herein by reference) was used to simplify and speed up the purification of Synechococcus sp. PCC7942 Rubisco expressed in E. coli. This system involved the construction of a unique (pACYC-based) plasmid vector that incorporates fusing in frame the coding sequence for a $H_6$-tagged ubiquitin (Ub) sequence ($H_6$Ub) to the 5' end of rbcSS. The wild-type rbcLS in plasmid pTrcSynLS (that contains the PCC7942 rbcL-rbcS operon; Emlyn-Jones et al., 2006) was replaced with the mutated rbcLS (rbcLS*) and then co-transformed into E. coli with the pACYC-based plasmid that codes for $H_6$Ub-tagged wild-type SSU ($H_6$Ub-SSU). When Rubisco subunit expression was induced with IPTG, all three Rubisco subunit peptides were produced (i.e. LSU, SSU and $H_6$UbSSU). Some were assembled into functional Rubisco hexadecamers made up of 8×LSU octameric cores and different ratios of SSU (at most 8) and $H_6$UbSSU. Rubiscos with one or more $H_6$ tags were easily purified from other E. coli proteins using immobilized metal affinity chromatography (IMAC) and the $H_6$Ub sequence then cleaved with a $H_6$Ub-specific protease which, along with unassembled $H_6$Ub peptides, may be removed by IMAC. Using this method, purified Rubiscos were isolated from the E. coli in approximately 1 hour.

Eighteen of the mutant Rubiscos and five control mutants specified in Example 5 and identified in Tables 3 or 4, as well as wild type, were expressed and purified using the above procedure.

Example 7

In Vitro Kinetic Assay of Mutant Rubiscos

Rubisco proteins purified using the method described in Example 6 were used to measure the Michaelis constants for $CO_2$ ($K_c$) and substrate saturated carboxylation rates ($V_c^{max}$) using $^{14}CO_2$-fixation assays at 25° C., pH 8 according to the method described in Andrews (1988), the entire contents of which is incorporated herein by reference.

The purified enzyme was pre-incubated at 25° C. for 30 min in buffer containing 20 mM $MgCl_2$ and 25 mM $NaHCO_3$, and $K_c$ measurements were performed in nitrogen sparged septum capped scintillation vials. The reactions were initiated by adding 10 μL of purified enzyme to 0.5 mL of $N_2$-equilibrated assay buffer (100 mM EPPS-NaOH, 20 mM MgCl$_2$, 0.8 mM ribulose-P$_2$, 0.1 mg/ml carbonic anhydrase) containing varying concentrations of NaH$^{14}$CO$_3$.

The Michaelis constants were determined by fitting the data to the Michaelis-Menten equation. Quantification of Rubisco content in the assays was measured using the [2-$^{14}$C] carboxyarabinitol-P$_2$ ($^{14}$2 CABP) binding assay described by Ruuska et al. (1998) and Whitney and Andrews (2001). The substrate saturated carboxylation turnover rate ($k^c_{cat}$) was calculated by dividing the extrapolated maximal carboxylase activity ($V_c^{max}$) by the concentration of Rubisco active sites in the assay. The purified Rubisco preparations were also used to measure the CO$_2$/O$_2$ specificity ($S_{c/o}$) at pH 8.3 as described in Kane et al. (1994).

A summary of the results obtained is presented in Table 5. For specificity, average results are given as % change compared with wild type: a positive value represents an improvement. For kinetics, the values and % change compared with wild type are given; a positive % change for the catalytic rate $k^c_{cat}$ and the catalytic efficiency $k^c_{cat}/K_c$ represents an improvement, while a negative % change for the Michaelis constant $K_c$ represents an improvement.

Of the eighteen mutants and two single (control) mutants for which specificity measurements were made, all showed specificity comparable with wild type, i.e. none was significantly impaired, while five mutants and the two controls showed improvements of 5% or better. Of interest, four of these include the mutations T23G and/or K81R. Also, of interest is that mutants with ACR variants (#1a and #1b for position 51, #5a and #5b for position 54, and #7a, #7b and #7d for positions 51 and 54) showed significant differences (in the order of 8% for the Mutant #5 and #7 variants) demonstrating the sensitivity of specificity to these changes which spatially are relatively far from the active site (see FIG. 14). The improvement in the $S_{C/O}$ value of 5.6% in Mutant #8 was noteworthy as the mutations were in a different part of the N-terminal domain (see FIG. 19) than most of the initial set of mutants predicted by the core method.

Of the 9 mutants for which $k^c_{cat}$ was assayed, most showed slightly to significantly lower (i.e. poorer) values compared with wild type with the exception, Mutant #4, which showed a significant improvement of 8%. The cor-

TABLE 5

Specificity and kinetic results for *Synechococcus* sp. PCC7942 mutant Rubiscos.

| | | | Kinetics | | |
|---|---|---|---|---|---|
| Mutant # (modified residue(s))[c] | SEQ ID[e] | $S_{c/o}$ Average[d] (% change wild type) | $k^c_{cat}$ (s$^{-1}$) (% change wild type) | $K_c$ (μM) (% change wild type) | $k^c_{cat}/K_c$ (s$^{-1}$mM$^{-1}$) (% change wild type) |
| Wild-Type | 22-24 | 41.6 ± 0.7 | 13.2 ± 0.2[a] | 203 ± 10[a] | 65[a] |
| | | | 13.0 ± 0.2[b] | 197 ± 10[b] | 66[b] |
| #1a (Y25W, D51I$^{Gp}$) | 25, 26 | (3.4%) | 11.5 ± 0.2[a] | 176 ± 6[a] | 65 |
| | | | (−13%) | (−13%) | (0%) |
| #1b (Y25W, D51V$^{Gm}$) | 27, 28 | (−1.1%) | | | |
| #4 (T23G, K81R) | 29, 30 | (10.0%) | 14.1 ± 0.2[b] | 198 ± 8[b] | 71 |
| | | | (8%) | (0%) | (8%) |
| #5a (G54A$^{Gp}$, C84A, I87V) | 31, 32 | (−6%) | 11.3 ± 0.3[a] | 182 ± 12[a] | 62 |
| | | | (−14%) | (−10%) | (4%) |
| #5b (G54S$^{Gm}$, C84A, I87V) | 33, 34 | (1.9%) | 10.6 ± 0.2[a] | 167 ± 8[a] | 63 |
| | | | (−20%) | (−18%) | (3%) |
| #6a (T23G, Y25W, D51I$^{Gp}$, K81R) | 35, 36 | (8.5%) | 12.2 ± 0.2[b] | 185 ± 9[b] | 66 |
| | | | (−6%) | (−6%) | (0%) |
| #7a (Y25W, D51I$^{Gp}$, G54A$^{Gp}$, C84A, I87V) | 37, 38 | (8.8%) | 12.4 ± 0.2[b] | 195 ± 11[b] | 64 |
| | | | (−5%) | (−1%) | (−3%) |
| #7b (Y25W, D51I$^{Gp}$, G54S$^{Gm}$, C84A, I87V) | 39, 40 | (1.4%) | n.m. | n.m. | n.m. |
| #7d (Y25W, D51V$^{Gm}$, G54A$^{Gp}$, C84A, I87V) | 41, 42 | (0.9%) | n.m. | n.m. | n.m. |
| #8 (V121I, M297G, V300T) | 43, 44 | (5.6%) | n.m. | n.m. | n.m. |
| #9 (L36I, I116L, F140L) | 45, 46 | (3.6%) | n.m. | n.m. | n.m. |
| #10 (L36I, I116L, V121I, F140L, M297G, V300T) | 47, 48 | (2.9%) | 10.8 ± 0.4[b] | 325 ± 27[b] | 33 |
| | | | (−17%) | (65%) | (−50%) |
| #12 (K18I, T23G) | 49, 50 | (1%) | n.m. | n.m. | n.m. |
| #14 (loop AKMGYW) | 51, 52 | (1.7%) | 7.1 ± 0.4[b] | 260 ± 36[b] | 27 |
| | | | (−45%) | (32%) | (−59%) |
| #17-1A (T23G, K18I, T68V, K81R) | 53, 54 | (−0.6%) | n.m. | n.m. | n.m. |
| #18-1A (T23G, K81R, P104E) | 55, 56 | (−0.5%) | n.m. | n.m. | n.m. |
| #19-1A (T23G, D19P, K81R) | 57, 58 | (−2.0%) | n.m. | n.m. | n.m. |
| #21-1A, B (T23G, K81R, V121I, M297G, V300T) | 59, 60 | (−0.9%) | n.m. | n.m. | n.m. |
| #22-1A (T23G) | 61, 62 | (5.0%) | n.m. | n.m. | n.m. |
| #23-1A (K81R) | 63, 64 | (7.0%) | n.m. | n.m. | n.m. |
| #24 (V121I, M297G) | 65, 66 | n.m. | n.m. | n.m. | n.m. |
| #25 (M297G) | 67, 68 | n.m. | n.m. | n.m. | n.m. |
| #26-1B (V121I) | 69, 70 | n.m. | n.m. | n.m. | n.m. |

[a,b]refers to replicate measurements on different Rubisco samples done on different days.
[c]where given, specifies mutations are in Subregions 1A, 1A, B or 1B.
[d]average of replicate measurements on different Rubisco samples done on different days.
[e]Sequence ID numbers correspond to those in the sequence file.
The numbers in the "SEQ ID" column correspond to the sequences on the computer-generated sequence listings.
n.m. represents not measured at time of filing.

responding 9 mutants assayed for $K_c$ exhibited a range of values, with 4 showing moderately improved $CO_2$ binding (#1a, #5a, #5b, #6a), 2 showing little change (#4, #7a) and 2 showing significant impairment (#10, #14). The overall catalytic efficiency values ($k^c{}_{cat}/K_c$) similarly show a range of small to significant improvement (#4, #5a, #5b), to little change (#1a, #6a, #7a) to significant impairment (#10, #12) when compared with wild type. It is notable that in tobacco (see Example 11), Mutant #23-1A showed a significantly poorer $k^c{}_{cat}$ value and also overall catalytic efficiency, whereas Mutant #4 showed significant improvements in all three kinetic measures.

From the results of the initial set of mutants predicted by the core method (#1-#14), the stand-out mutants in terms of overall performance were Mutants #4 and #6a, which showed improvements in specificity and kinetic efficiency of 10% and 8%, and 8.5% and 0%, respectively. The properties of the more complex mutant (#6a), which comprised the mutations in #4 and #1a, were overall inferior to Mutant #4 (the best mutant on the current list). This observation suggests that other mutations may be more advantageously grouped with those for Mutant #4 than those of Mutant #1a. As discussed in Example 4, this observation prompted the development of the concept of Sub-regions and the extended method, which led to the first predictions of Mutants #17-1A, #18-1A and #19-1A, as well as a more complex mutant including CRs from Sub-region 1B also (#21-1A,B). The specificity results for these extended-method predictions showed little change compared with wild type.

Example 8

Directed Evolution of *Synechococccus* Mutants in *E. coli*

The phylogenetic grafted mutants represent one "directed" strategy for exploring regions of sequence space not sampled naturally. However any increase in the activity of these mutants may be impaired due to some areas of "poor sequence fits", as they may not be optimized for the host Rubisco structure. Although the extended phylogenetic grafting method provides a rational in silico strategy which may be used for optimising "lead" mutants, including relieving steric conflicts by recruitment of SvRs and other naturally occurring variant residues which may be identified as complementary to mutations in the "leads", an alternative option to minimize the effects of these conflicts may be to use an experimental directed evolution method to optimize them, i.e. to use these partially optimized Rubiscos as starting points. These mutants also provide in themselves a novel starting point for directed evolution as they have different potential for exploring sequence space compared with wild type.

As detailed in Example 6, unlike all other Form I Rubiscos (i.e. hexadecameric) from eukaryotic organisms, Rubisco from *Synechococcus* PCC7942 can assemble correctly in *E. coli* and has been chosen for a mutant screening procedure. Using methods described in Examples 5-7, Candidate Mutant predictions (which may include groups of correlated mutations, and independent mutations in different structural regions surrounding the Target Residues) can be screened initially in *E. coli* to confirm they are active and to obtain in vitro kinetic constants for comparison against each other and wild type. Mutants with up to 10-12 mutations can be produced routinely using the current technology. As detailed in Examples 5-7, selected single mutants can be made to test the general hypothesis underlying the phylogenetic grafting method that single mutants are likely to be poorly active/inactive, and that at least two correlated mutations are necessary to produce an acceptably active enzyme.

A system suitable for directed evolution of Rubisco in *E. coli* has recently been reported (Mueller-Cajar et al., 2007). This uses an engineered *E. coli* strain, MM1, whose growth can be made dependent on functional expression of Rubisco, when co-expressed with phosphoribulokinase (PRK). Glycolysis in MM1 was blocked by deletion of the glyceraldehyde 3-phosphate dehydrogenase gene (gapA) and a metabolic bypass shunt comprising a *Synechococcus* PRK and *Rhodospirillum rubrum* Rubisco was introduced. As a result, MM1 is dependent on functional Rubisco expression to metabolize the product of PRK catalysis, ribulose-1,5-bisphosphate, that is toxic to *E. coli*.

This general method may be used to evaluate whether Rubiscos with significantly enhanced activity can be more efficiently evolved starting from inactivated forms of the most promising *Synechococcus* sp. PCC7942 grafted mutants detailed in Example 7 and Table 5. For this purpose, randomly mutagenised libraries (made using methods reported by Mueller-Cajar et al., 2007) of these inactivated genes may be transformed into MM1 cells grown under differing selective conditions (e.g. varying the growth $CO_2/O_2$ pressures, changing the extent of PRK production). Colonies expressing evolved Rubisco variants with improved fitness (i.e. those that survive the screen) may be isolated, sequenced and the kinetics of the purified mutated Rubiscos characterised as detailed in Example 7.

Example 9

Testing Biochemical and Physiological Competence of *Synechococcus* Mutants In Vivo The in vitro functional tests in Example 7 identified several *Synechococcus* mutants with improved Rubisco activity, and which also, necessarily, were, thus, correctly folded and assembled when expressed from the *E. coli* expression system and purified as described in Example 6. In the Rubisco re-engineering strategy, *Synechococcus* has been used as the most convenient initial host for experimental test of mutant predictions to identify "lead" candidates. Due to recent advances in engineering mutant Rubisco in a model plant, tobacco, using plastid transformation, as described in Example 10, in the work described here a Candidate Mutant (#4) identified as a promising *Synechococcus* mutant was tested directly in the test flowering plant (tobacco) without undertaking the intermediate step, shown in FIG. 1, of confirming that it can be acclimated back into its native host (*Synechococcus*) without detriment to its phenotype. This improved method allowed assessment of the assembly and kinetics of mutant Rubiscos in tobacco within 7-9 weeks which is faster than that required to obtain and grow cyanobacteria transformants Where the ultimate purpose of mutant development is for engineering improved Rubisco in plants, this strategy would be preferred. However, if the ultimate purpose is for engineering improved Rubisco in cyanobacteria, then it is preferred to perform this physiological-test step in *Synechococcus* to assess whether catalytically beneficial mutations might introduce incompatibility problems that perturb productive folding-assembly by cyanobacterial chaperone complexes or other interacting proteins such as those involved in carboxysome formation. A method for performing these tests in *Synechococcus* is described below.

In *Synechococcus* sp. PCC7942, the Rubisco genes (rbcLS and rbcSS) are coded by a single operon on the chromosome (of which there are typically 5 chromosome copies per cell) and, analogous to *E. coli*, this cyanobacterial strain is naturally competent and can be genetically transformed either by targeted modifications to its chromosome (e.g. gene deletion, gene substitution) by homologous recombination or by stable retainment of plasmid shuttle vectors within its cells.

*Synechococcus* PCC7942 mutant strains have been developed (see Emlyn-Jones et al., 2006 and Price et al., 1993 for examples). A *Synechococcus* PCC7942 mutant strain in which the chromosomal rbcLS-rbcSS operon is deleted (i.e. a 7942ΔrbcLS strain) may be used to facilitate the re-introduction of mutant Rubisco rbcLS-rbcSS genes. As *Synechococcus* sp. PCC7942 cannot grow heterotrophically (i.e. on an external carbon source) and requires a Rubisco for growth, 7942ΔrbcLS strains can be generated by: (1) introducing a second Rubisco gene (e.g. rbcM coding for the structurally different Form II Rubisco homodimer ($L_2$) from the bacterium *Rhodospirillum rubrum* or the native $L_8S_8$ PCC7942 Rubisco) on a plasmid shuttle vector into *Synechococcus* sp. PCC7942 then (2) homologously recombining in an antibiotic resistance gene $km^R$ to replace the rbcLS-rbcSS operon in each chromosome copy (i.e. so the mutation can be fully segregated). *Synechococcus* PCC7942 cells transformed with rbcM expressed on a shuttle vector can be subsequently transformed with another plasmid to homologously replace the chromosomal rbcLS-rbcSS coding region with a $km^R$ gene. Upon isolation of completely segregated ΔrbcLS-rbcSS::$km^R$ transformants (i.e. all the chromosomes have rbcLS-rbcSS replaced with $km^R$) the PCC7942ΔrbcLS cells may be used to homologously re-introduce the mutated rbcLS* and rbcSS genes and the cells cured of the shuttle vector.

Using established techniques (e.g. see Emlyn-Jones et al., 2006), the phenotype of the transformed cells may then be comprehensively characterised biochemically, for example, assessing whether the mutated Rubisco LSU subunits are readily folded and assembled properly, and physiologically, for example, assessing whether there are differences in photosynthetic capacity, inorganic carbon partitioning or growth rate.

Example 10

Generation of Rubisco Plastome Transformants in Tobacco

A strategy for re-engineering Rubisco which is applicable to higher plant Rubiscos is by plastome transformation using mutated rbcL* genes. The plastome of tobacco is readily transformable (Andrews and Whitney, 2003) and was used as a model to conduct proof-of-principle tests for the transformation of other plants.

The most promising *Synechococcus* Rubisco Mutant #4 was used as the initial test case. The component single mutants, T23G (Mutant #22-1A), and K81R (Mutant #23-1A), and the more complex mutant #6a (T23G, Y25W, E51I, K81R) were also tested. The nucleotide and protein SEQ ID NOS for tobacco Mutants #4, #22-1A, #23-1A and #6a are given in Table 6. As these residues are Candidate Residues (see Table 2) these same mutations were used in tobacco as in *Synechococcus*.

Transplastomic tobacco lines are available which allow more rapid screening of the kinetics of mutated tobacco Rubiscos than the traditional lengthy chloroplast transformation methods in which the native rbcL genes in the plastome are substituted with mutated versions (Andrews and Whitney, 2003 (supra)) using the biolistic transformation technique described in Svab and Maliga (1993). In a recent improvement to the method for transforming mutated or foreign rbcL genes back into the tobacco plastome the native rbcL gene was replaced with the rbcM gene from *Rhodospirillum rubrum* and the aadA selectable maker gene (coding for spectinomycin resistance) and then the aadA gene removed to produce marker-free (ΔaadA) tobacco-*rubrum* transplastomic lines. (Whitney and Sharwood, 2008, the entire contents of which are incorporated by reference) These lines were generated by biolistically transforming the plastome of wild-type tobacco (*Nicotiana tabacum* L. cv Petit Havana [N,N]) with plasmid rtrLA (Genbank accession number AY827488). The aadA gene in the transformants is flanked by 34-bp loxP sites that enable its excision by CRE-lox recombination. To excise aadA, leaves from a rtrLA-transformed line were biolistically bombarded with the CRE expressing plasmid pKO27 (Corneille et al., 2001). The bombarded leaves were dissected (~0.5 $cm^2$) and propagated in kanamycin-selective medium (agar-solidified Murashige-Skoog salts containing 3% (w/v) sucrose, 15 μg $ml^{-1}$ kanamycin and hormones (Svab and Maliga, 1993). The first plantlets to emerge from the bleached bombarded leaf sections were transferred to MS medium (selective medium without kanamycin or hormones) and loss of aadA confirmed by routine PCR analyses.

The ΔaadA tobacco-*rubrum* lines permit re-use of the aadA marker gene for subsequently transforming its plastome, such as re-transforming back in mutated tobacco rbcL* variants to replace rbcM. The transformation efficiency of replacing rbcM in the ΔaadA tobacco-*rubrum* with variant rbcL* genes is 3 to 10-fold higher than transforming wild-type tobacco, and is immune to unwanted recombination events that may occur when transforming rbcL* genes into wild-type tobacco plastomes. The method allowed the production of transformants containing only rbcL*-transformed plastome copies (i.e. homoplastic transformants) within 6 to 8 weeks as the plastome copies containing the rbcM gene were rapidly eliminated. As the *R. rubrum* Rubisco is a small homodimer of LSUs ($L_2$, ~100 kDa), rbcL*-transformed lines producing the larger form I $L_8S_8$ Rubiscos (~520 kDa) may be identified by separating the soluble leaf protein by non-denaturing polyacrylamide gel electrophoresis as described in Whitney and Sharwood (2007) and homoplasmicity measured by the absence of $L_2$ Rubisco.

This system is potentially adaptable to other plants where plastid transformation has been reported. The genetic transformation of plastids in a variety of different plants has been reported, for example in Koop et al. (1997), the entire contents of which is incorporated herein by reference.

A straightforward variation of the transformation system (Whitney and Sharwood, 2008) offers the potential to rapidly test the kinetics of predicted mutant Rubiscos of other flowering plants or crops of interest without performing a full plastid transformation in the plant of interest itself. Sharwood et al. (2008), the entire contents of which is incorporated herein by reference, have shown that the rbcL gene of another plant (sunflower) can be successfully transformed into the ΔaadA tobacco-*rubrum* line to produce active chimeric Rubisco consisting of sunflower LSUs and tobacco SSUs, which can be isolated and characterized kinetically. Its kinetic parameters mimic those of sunflower Rubisco. Use of this method would allow development and optimisation of Rubisco phenotype for a range of mutants of different plants of interest, using the convenient tobacco transformation model.

Mutations for Mutants #4, #22-1A, #23-1A and #6a were made to the wild-type tobacco (*Nicotiana tabacum*) plastome rbcL coding sequence using the QuickChange multi-mutagenesis kit (Stratagene) using appropriate primers, and introduced into the tobacco plastome transforming plasmid pLEV1 where selection of transformants is facilitated by the incorporation of a promoter-less aadA gene downstream of rbcL (Whitney et al., 1999). The pLEV1-derived transforming plasmids coding the mutagenized tobacco rbcL* copies with the nucleotide sequences coding for Mutants #4, #22-1A, #23-1A and #6a, as well as wild type, were biolistically transformed into a ΔaadA tobacco-*rubrum* line and spectinomoycin-resistant plantlets selected as described (Svab and Maliga, 1993). Transformants where the rbcM had been replaced with the rbcL* or rbcL genes were identified by the production of $L_8S_8$ Rubisco using non-denaturing polyacrylamide gel electrophoresis. A sample gel for transformants for wildtype, and Mutants #4 and #23-1A is shown in FIG. 24; comparable data (not shown) were obtained for Mutants #22-1A and #6a.

Example 11

Biochemical Characterization of Tobacco Rubisco Transformants

The following methods were used to extract and purify Rubisco expressed in homoplasmic transplastomic and wild-type tobacco cells to carry out kinetic analyses.

Radiolabeled $^{14}CO_2$ fixation assays were used to measure the substrate saturated turnover rate ($k_c^{cat}$) and Michaelis constant for $CO_2$ at 0% ($K_c^{0\%}$) or 21% $O_2$ ($K_c^{air}$) using soluble leaf protein extract. Leaf discs (~1 cm$^2$) were taken during the photoperiod and extracted on ice using glass homogenisors (Wheaton, USA) into 0.8 ml $CO_2$-free extraction buffer (50 mM Bicine-NaOH, pH8.0, 1 mM EDTA, 2 mM DTT, 1% (v/v) plant protease inhibitor cocktail (Sigma-Aldrich) and 1% (w/v) PVPP). The sample was centrifuged (36,000 g, 5 mM, 4° C.) and the soluble protein incubated (activated) with NaHCO$_3$ and MgCl$_2$ (15 mM each) for 15 min and used to measure Rubisco content in duplicate aliquots incubated with 40 μM of $^{14}$2-CABP and the amount of Rubisco-bound-$^{14}$2-CABP recovered by gel filtration (Ruuska et al., 1998), or used to measure $K_c^{0\%}$ and $K_c^{air}$ at 25° C., pH 8.0 using $^{14}CO_2$ fixation assays (Andrews 1988; Whitney and Sharwood, 2007). To confirm the samples used were homoplasmic (i.e. only contain plastome copies transformed with the rbcL* genes and none with rbcM) the protein was also separated on non-denaturing polyacrylamide gels (FIG. 24). As for the wild-type controls, only mutated $L_8S_8$ Rubisco and no $L_2$ Rubisco was expressed in the Mutant #4 and #23-1A transformants.

The kinetic assays were initiated by adding activated soluble protein extract into septum capped scintillation vials containing either $N_2$ (for $K_c^{0\%}$) or $CO_2$-free air (for $K_c^{air}$) equilibrated assay buffer (100 mM Bicine-NaOH, 15 mM MgCl$_2$, 0.6 mM ribulose-P$_2$, 0.1 mg·ml$^{-1}$ carbonic anhydrase) containing 0 to 90 μM $^{14}CO_2$. Ribulose-P$_2$ was synthesized according to (Kane et al., 1998). The assays were stopped after 1 min with 0.5 volumes of 25% (v/v) formic acid, the reactions dried at 80° C. and the residue dissolved in water, two volumes of scintillant were added, vortexed, and $^{14}C$ measured by scintillation counting. $K_c^{0\%}$ and $K_c^{air}$ were calculated from the Michaelis-Menten plot of carboxylation rate versus [$CO_2$].

Measurements of $k_c^{cat}$ were calculated using comparable $^{14}CO_2$ fixation assays containing 15 mM NaH$^{14}CO_3$ and dividing the substrate saturated carboxylation rate, $V_c^{max}$, by the concentration of Rubisco active sites measured by $^{14}$2-CABP binding (see above).

Specificity measurements were done using purified Rubisco. Soluble leaf protein was extracted as described above and 0.2 mL chromatographed through a Superdex 200HR 10/30 column equilibrated with specificity buffer (30 mM Triethanolamine pH 8.3, 30 mM Mg acetate) using an AKTA explorer system (APBiotech). The three peak fractions (0.3 ml) containing $L_8S_8$ Rubisco were pooled (~100-150 pmol L-subunit sites) and used to measure $CO_2/O_2$ specificity at 25° C. as described (Kane et al., 1994) after equilibrating with an atmosphere containing 500 ppm $CO_2$ in $O_2$ controlled using three Wösthoff precision gas-mixing pumps.

A summary of the results obtained is presented in Tables 6 and 7. For specificity, average results are given as % change compared with wild type: a positive value represents an improvement. For kinetics, the values and % change compared with wild type are given; a positive % change for the catalytic rate $k^c_{cat}$ and the catalytic efficiency $k^c_{cat}/K_c$ represents an improvement, while a negative % change for the Michaelis constant $K_c$ (in air or 0% $O_2$) represents an improvement.

TABLE 6

Specificity and kinetic results measured in air ($O_2$ 21%) for Tobacco mutant Rubiscos.

| | | | kinetics | | |
|---|---|---|---|---|---|
| Mutant # (modified residue(s)) | Seq ID[b] | $S_{c/o}$ Average[a] (% change from wildtype) | $k^c_{cat}(s^{-1})^a$ (% change from wildtype) | $K_c^{air}$ (μM) (% change from wildtype) | $k^c_{cat}/K_c^{air}$ ($s^{-1}$ mM$^{-1}$) (% change from wildtype) |
| wild-type | 71, 72 | 81.0 ± 1.6 | 3.2 ± 0.1 | 24.1 | 132 |
| #4 (T23G, K81R) | 73, 74 | 77.6 ± 2.8 (−4%) | 3.6 ± 0.1 (13%) | 20.4 (−15%) | 176 (33%) |
| #23-1A (K81R) | 75, 76 | 76.1 ± 3.4 (−6%) | 3.5 ± 0.1 (9%) | 23.8 (−1%) | 147 (11%) |
| #22-1A (T23G) | 77, 78 | 76.2 ± 1.0 (−6%) | 3.5 ± 0.1 (9%) | 20.5 (−15%) | 173 (31%) |
| #6a (T23G, Y25W, E51I, K81R) | 79, 80 | 66.4 ± 4.4 (−18%) | 3.5 ± 0.1 (9%) | 19.4 (−20%) | 179 (36%) |

[a]Average or calculated value from measurements made on 3 separate protein assays ± S.D.
[b]Sequence ID numbers correspond to those in the sequence listing; the first number is the nucleotide SEQ ID NO and the second number is the protein SEQ ID NO.

The results in Table 6 for measurements in air (21% $O_2$) show significant differences in specificity and kinetic parameters for the different mutants. Significant improvements over wild type are evident in both $k^c_{cat}$ and $K_c^{air}$ values for Mutant #4 (T23G, K81R) of 13% and −15%, respectively, producing an overall improvement in catalytic efficiency of 33%. These can be compared with $k^c_{cat}$ values of 9%, i.e. less improvement, and $K_c^{air}$ values of −1%, −15% and −20%, i.e. minimal (#23-1A) or similar improvement, for the single Mutants #23-1A (K81R) and #22-1A (T23G), and Mutant #6a (T23G, Y25W, E51I, K81R) which includes these two mutations. These translate into comparable improvement in catalytic efficiency of 31 and 36%, respectively, for #22-1A and #6a, but only 11% for #23-1A. The kinetic results (triplicate assays) were obtained using soluble leaf protein extracted from two or three different transformants for wildtype and mutants. The replicate isolated Rubiscos gave similar results, contributing to the small errors of the measurements.

The specificity results for Mutant #4 show a modest impairment (−4%) compared with wild type, while both the single mutants, #22-1A and #23-1A show slightly greater impairment (−6%). However, the specificity for Mutant #6a is greatly impaired (−18%. These values were obtained from triplicate measurements, as shown in Table 6, using different purified Rubiscos from two wildtype and two of each of the mutant transformants.

Consideration of the specificity and kinetic results together indicates that the improvement in carboxylation efficiency has been matched by a comparable improvement in oxygenation efficiency for Mutant #4, but much greater improvement for #6a. As an initial test of whether changes in oxygenation efficiency might be due to changes in $k^o_{cat}$ or $K_o$, $K_c^{0\%}$ was measured in 0% $O_2$. These results, given in Table 7, show that all the mutants have poorer $K_c^{0\%}$ values than wild type, 10, 30, 18 and 5%, respectively, for #4, #23-1A, #22-1A and #6a, but that the deterioration in the $K_o$ (i.e. $K_i(O_2)$) values are much greater—87%, 92%, 133% and 89% higher, respectively. The significantly higher $K_o$ values for the mutants compared with wild type indicate that the mutants are less inhibited by $O_2$. Values for $K_o$ were calculated according to Whitney et al. (1999). The improved oxygenation efficiency is explained by the values for $k^o_{cat}$ shown in Table 7, which show significant improvements of 201%, 173%, 234% and 241%, respectively for mutants #4, #23-1A, #22-1A and #6a compared with wildtype.

In summary, the results show that Mutant #4 retains its superior properties in tobacco, although they are expressed more as improvements in catalytic efficiency than as roughly equal improvements in specificity and efficiency, as is the case for the *Synechococcus* Mutant #4. Although Mutant #6a shows comparable catalytic efficiency to Mutant #4, it has significantly impaired specificity $S_{c/o}$.

Example 12

Simulation of Phenotype of Tobacco Rubisco Transformants

Results for *Synechococcus* and tobacco mutants in Tables 5 and 6 show a range of levels of improvements in key kinetic parameters ($S_{c/o}$, $k^c_{cat}$, $K_c$) compared with wildtype. These parameters are also expected to show different temperature dependence compared with wildtype. Thus, for each branch of photosynthetic organism the mutants show different profiles of improvements in the kinetic parameters, that is there is a range of percentage changes in the components of the parameter set $\{S_{c/o}, k^c_{cat}, K_c\}$ for a given mutant. This parameter set is termed Rubisco phenotype.

The rate of $CO_2$ assimilation in $C_3$ plants reflects Rubisco's kinetic properties and content in the plant (Farquhar et al., 1980; von Caemmerer, 2000). This correlation has been validated for mutant, foreign-transformant or differently expressed tobacco Rubiscos. Methods for simulating $CO_2$ assimilation under variable growth conditions, such as $CO_2$ concentration, water, nutrients, temperature and light intensity, have been used to predict photosynthetic performance in leaves using Rubisco kinetic data for a range of plants (von Caemmerer, 2000, the entire contents of which are incorporated herein by reference). An analogous study of performance within the leaf canopy of the whole plant has been reported (Zhu et al., 2004, the entire contents of which are incorporated herein by reference). By these means it is possible to predict how a plant with a given Rubisco and Rubisco phenotype, as determined by kinetic measurements in vitro, would perform under different sets of growth conditions in planta. There is also extensive experimental evidence that increases in leaf photosynthesis are translated into increases in biomass and crop yield. Together these studies have shown that increased efficiency of photosyn-

TABLE 7

Specificity and kinetic results measured in 0% $O_2$ for Tobacco mutant Rubiscos.

| | kinetics | | | | |
|---|---|---|---|---|---|
| Mutant # (modified residue(s)) | $k^c_{cat}$ (s$^{-1}$) (% change from wild type) | $K_c^{0\%}$ (µM) (% change from wild type) | $k^c_{cat}/K_c^{0\%}$ (s$^{-1}$ mM$^{-1}$) (% change from wild type) | $K_i(O_2)$ (µM) | $k^o_{cat}$(s$^{-1}$) (% change from wild type) |
| wild-type | 3.2 ± 0.1 [a] | 12.2 ± 0.4 [b] | 262 | 259 ± 23 [b] | 0.83 [d] |
| #4 (T23G, K81R) | 3.6 ± 0.1 [a] (13%) | 13.4 ± 0.5 [b] (10%) | 269 (3%) | 485 ± 56 [b] (87%) | 1.67 [d] (201%) |
| #23-1A (K81R) | 3.5 ± 0.1 [a] (9%) | 15.8 ± 0.4 [a] (30%) | 222 (−15%) | 497 ± 70 [a] (92%) | 1.44 [d] (173%) |
| #22-1A (T23G) | 3.5 ± 0.1 [a] (9%) | 14.4 ± 0.7 [c] (18%) | 243 (7%) | 603 ± 120 [c] (133%) | 1.94 [d] (234%) |
| #6a (T23G, Y25W, E51I, K81R) | 3.5 ± 0.1 [a] (9%) | 12.8 ± 0.5 [a] (5%) | 273 (4%) | 490 ± 68 [a] (89%) | 2.00 [d] (241%) |

[a] Average or calculated value from measurements made on 3 separate protein assays ± S.D.
[b] Calculated value from measurements made on 4 separate protein assays ± S.D.
[c] Calculated value from measurements made on 2 separate protein assays ± S.D.
[d] Calculated using the equation $S_{c/o} = (k^c_{cat}/K_c)/(k^o_{cat}/K_o)$.

thesis from improved Rubiscos benefits plant growth, improves water-use efficiency and increases the C/N ratio.

FIGS. 25 and 28 contain plots illustrating use of these models to predict plant phenotype, including examples of mutant tobacco Rubisco phenotype that have been produced by the inventors (Table 6) or within a similar range of improvements in *Synechococcus*, as in Table 5.

FIG. 25 provides a plot for wildtype tobacco growing under normal conditions. It shows that the carbon assimilation rate (A) is limited at lower leaf internal $CO_2$ concentrations ($C_i$) by Rubisco carboxylase activity (dependent on $k^c_{cat}$, $K_c$ and amount of enzyme) and at higher leaf internal $CO_2$ concentrations by electron-transport related factors (light, Rubisco specificity determining photorespiration, and RuBP regeneration rate). The region of the plot of interest is that spanning the range of $CO_2$ concentrations experienced in the chloroplast, i.e. from the atmospheric level of 380 μbar ($C_a$) downwards: this region is shown boxed. Under these normal growing conditions, the cross-over point (*) between Rubisco-limited and electron-transport limited growth is at a $C_i$ value of ~340 μbar; thus, under normal conditions, growth is Rubisco-limited. The leaf internal $CO_2$ concentrations of $C_i(1)$ and $C_i(2)$ at values of ~230 and 300 μbar correspond to stomatal conductances representing drought and average water-use conditions, respectively (as determined by von Caemmerer, 2000). It is clear that under drought, carbon assimilation is reduced by approximately 25% ($A_1$ compared with $A_2$)

FIG. 26 shows the predicted effect of variation in four growth conditions (water availability, nitrogen and light limitations, and temperature) for wildtype tobacco on the rate of $CO_2$ assimilation. Nitrogen limitation has been modelled as reduction of Rubisco content; as Rubisco constitutes 30-50% of chloroplast protein, nutrient limitation has a direct effect on photosynthetic capacity by limiting Rubisco biosynthesis. Again considering the positions of the plot with respect to the relevant range of $CO_2$ concentrations (shown boxed) and the cross-over points (*) between Rubisco-limited and electron-transport limited growth, it is apparent that A is Rubisco-limited under all conditions except low light (I=400 μmol quanta $m^{-2}$ $s^{-1}$; FIG. 26C) and high T (35° C.; FIG. 26D) where it is electron-transport limited. No cross-over points (*) are shown on the plots in FIG. 26B for 60% and 30% Rubisco content as they are beyond 500 μbar.

In FIG. 27, the key features of FIGS. 25 and 26 are combined in plots which show how hypothetical improvements in the key kinetic parameters ($S_{c/o}$, $k^c_{cat}$, $K_c$) compared with wildtype tobacco translate into enhanced carbon assimilation rates. These plots provide a picture of the general level of biomass increase which could be achieved for specific Rubisco mutant phenotypes under various limiting growth conditions; they thus provide guidance as to the most appropriate growth conditions for a particular mutant. Dotted lines represent the mutant predictions.

Plots in FIG. 27A for mutant tobacco with a hypothetical 25% improvement in $S_{c/o}$ (no change in $k^c_{cat}$, $K_c$) show greatest enhancements in A compared with wildtype at high T (9% at 35° C.) and low light (11% at I=400) under drought conditions ($C_i$=230 μbar), with slightly lower enhancements under average water-use (6% and 9%, respectively). These values should be compared with the small enhancements under normal T (25° C.) and light (I=1000) levels of 4% and 3% under drought and average water-use conditions, respectively.

Plots in FIG. 27B for mutant tobacco with a hypothetical 25% improvement in $k^c_{cat}$ (no change in $S_{c/o}$, $K_c$) show greatest enhancement in A compared with wildtype at normal and low T (18% at 25° C.; 14% at 15° C.) under drought, but with much lower values under average water-use conditions (5%, 2% for T=25, 15° C.). Consistent with A being Rubisco-limited within the relevant range of $C_i$ values (230-300 μbar) except for the mutant at 100% Rubisco content, the plots for effective N limitation (reduced Rubisco) show greatest enhancement at the lowest Rubisco contents (27% at content=30%; 23% at content=60%) over this $C_i$ range. However, interestingly, for normal (100%) Rubisco content where the cross-over point changes greatly for the mutant, there is a large variation in enhancements between drought and average water-use conditions of 18% and 5%, respectively. This mutant phenotype shows very large differences in enhancements under varying light conditions, particularly as a function of water availability. The latter dependence can be deduced from large shifts in cross-over points for the mutant at I=1000 and 1600 towards electron-transport limited carbon assimilation over the accessible $CO_2$ concentration range (shown boxed). Thus, the enhancements range from zero at low light (I=400) to 18% and 19%, respectively, under drought at I=1000 and 1600, but 6% and 12%, respectively, under average water usage.

Plots in FIG. 27C for mutant tobacco with a hypothetical 25% improvement in $K_c$ (no change in $S_{c/o}$, $k^c_{cat}$) show similar trends to those in FIG. 27B. In this case the change in $K_c$ again shifts the cross-over point (*) between Rubisco-limited and electron-transport limited growth towards the latter at normal and low T's and normal and high light, but the shift is not as great as for the $k^c_{cat}$ mutant. This results in only small dependencies of the enhancements on water availability for varying T, light and Rubisco content. Thus, at normal and low T the enhancements are 8% and 10% under drought and 8% and 7% under average water use, with little change (3%) at high T. Similarly, at normal and high light, enhancements are both 8% under drought and average water-use conditions, with only small changes (4-5%) at low light Enhancements under effective N limitation are also the same under drought and average water-use conditions, with values of 8%, 10% and 11% for 100%, 60% and 30% Rubisco content, respectively. Note that in this simulation, the $K_o$ value was not changed; this was done for mutant examples in FIG. 28.

In FIG. 28, the analyses are extended to model the change in carbon assimilation rates for tobacco mutants #4, #23-1A and #6a, using kinetic parameters from Tables 6 and 7.

The plots for mutant #4 in FIG. 28A show enhancements in A modelled with the kinetic profile of {$S_{c/o}$=−4%; $k^c_{cat}$=+13%; $K_c$=+10%; $K_O$=+87%). As for the models with $k^c_{cat}$=+25% and $K_c$=−25% in FIG. 27, the cross-over points (* and ♦, for wildtype and mutant respectively) between Rubisco-limited and electron-transport limited growth are shifted towards the latter for the mutants at normal and low T's and normal and high light, resulting in greater variation in levels of enhancements under given growth conditions. Thus, at normal and low T the enhancements are 15% and 11% under drought but 4% and 0% under average water-use conditions, with negligible change at high T. Similarly, at normal and high light, enhancements are 15 and 23%, respectively, under drought, but 4 and 10%, respectively, under average water-use conditions, with little change at low light. Large enhancements are also observed under effective N limitation, but with little dependence on water availability, i.e. 33% and 31% under drought and average water-use conditions, respectively, at a Rubisco content of 30% compared with 15% and 4% at normal Rubisco content, respectively. Overall, Mutant #4 is thus predicted to display strong enhancements under normal growth (T, I, N) conditions for varying water availability (15 to 4%), under drought conditions at low T (11%), under high light (23%), and under N depletion (33% at 30% Rubisco content).

The effectiveness of the double mutation in tobacco mutant #4 in enhancing carbon assimilation, may be seen from analogous modelling of the kinetic data (Tables 6 and 7) of mutant #23-1A, which contains one of its mutations (K81R). Mutant #23-1A has been modelled with the kinetic profile of {$S_{c/o}$=-6%; $k^c_{cat}$=+9%; $K_c$=+30%; $K_o$=+92%). Compared with the results in FIGS. 27B, 27C and 28A, the plots in FIG. 28B show the cross-over points (♦) for the mutant are still shifted to electron-transport limited growth but to a lesser extent. Consequently, the improvements are more modest. For example, 9 and 3% under drought and average water-use conditions, respectively, at normal T and light. The best performance is again under effective N limitation, with ~11% at 30-60% Rubisco content under both drought and and average water-use conditions.

The third set of predictions, shown in FIG. 28C, is for tobacco mutant #6a, which contains four mutations, including those in mutant #4. Mutant #6a has been modelled with the kinetic profile of {$S_{c/o}$=-18%; $k^c_{cat}$=+9%; $K_c$=+5%; $K_o$=+89%) from Tables 6 and 7. Compared with the results in FIG. 28A, the plots in FIG. 28C show that the cross-over points (♦) for the mutant are shifted more towards electron-transport limited growth, but the effects on improvements are more modest than for mutant #4. This is a consequence of the much poorer specificity. On the basis of kinetic parameters, mutant #6a is slightly more efficient than #4 (36% v. 33%) but shows different patterns of $k^c_{cat}$ (9 v. 13%, i.e. poorer) and $K_c$ (+5% v. +10%. i.e. better). Under normal conditions (T, I, N), the performance of mutant #6a is improved by 6% under drought but impaired by 3% under average water-use conditions. The best performance is under effective N limitation (30-60% Rubisco) with improvements of 20-27% under both drought and average water-use conditions.

In summary, this analysis demonstrates that particular improved mutant Rubisco phenotypes may be more suitable for particular growing conditions. The methods described herein provide the capability to produce mutant Rubiscos with kinetic profiles optimized for particular preferred plant growing conditions. It is expected that particular Rubisco phenotypes will show a range of benefits in the phenotype of the plant, such as faster growth rate and shorter time to flowering, lower requirements for water and/or nitrogen fertilizer, or ability to grow efficiently at higher temperatures. These are expected to translate into increased productivity of plant growth (and grain production) under growth conditions such as drought and/or heat stressed environments (hot arid climates), nutrient-poor soils, or low-light conditions with a short growing season (higher latitudes). Accordingly, the methods described in this example allow the prediction of the rate of $CO_2$ assimilation by a plant expressing a Rubisco, such as a mutant Rubisco produced by methods described herein, by modelling based on parameters for Rubisco functional properties obtained by in vitro measurements. The methods described in this example thus allow the prediction of plant performance under both optimal growth conditions and sub-optimal growth conditions, such as where illumination, water, or nitrogen are limiting, or where temperature is elevated.

Example 13

Experimental Characterization of Phenotype of Tobacco Rubisco Transformants

Homoplasmic transplastomic lines and wild-type tobacco controls are grown to maturity in soil in controlled environment growth chambers or glass houses and standard physiological tests are undertaken (as described in Whitney et al., 1999; Whitney and Andrews, 2001; and Whitney et al., 2001, the entire contents of which are incorporated herein by reference). Tests comprise an assessment of growth rate, biomass production, leaf index area, Rubisco mRNA and protein content, carbon to nitrogen rations of plant leaves, starch content, and photosynthetic performance.

These tests are performed under both optimum (high light, non limiting water and nutrients, temperature set at 25° C.) or resource-limiting conditions (e.g. reduced N, water or $CO_2$) or elevated temperatures. Tests under optimum conditions assess differences in various growth (e.g. exponential growth rate, biomass, leaf area index), biochemical (e.g. Rubisco mRNA and enzyme content, leaf C:N ratio, starch content) and metabolite (e.g. RuBP:PGA) indices. Tests under limiting conditions assess the performance of the mutants under growth conditions mimicking environmental stress, such as drought and/or heat stress (hot arid climates), nutrient-poor soils, or low-light conditions with a short growing season (higher latitudes), as detailed in Example 12. Gas-exchange measurements of photosynthetic performance at varying $CO_2$ and light levels are performed on the leaves of comparable fully expanded leaves from younger plants during their exponential growth phase (20-30 cm tall). The photosynthetic rates are quantified relative to Rubisco active-site content in the assayed leaves.

As demonstrated by the models in Example 12, and reported in the literature (Parry et al., 2005), improved photosynthesis may be obtained in different limiting growth conditions by different mutant Rubisco phenotypes.

REFERENCES

Altschul S F, Madden T L, Schaffer A A, Zhang J, Zhang Z, Miller W, Lipman D J. (1997) Gapped BLAST and PSI-BLAST: a new generation of protein database search programs. *Nucleic Acids Res.* 25, 3389-3402.

Andrews T J. (1988) Catalysis by cyanobacterial ribulosebisphosphate carboxylase large subunits in the complete absence of small subunits. *J. Biol. Chem.* 263, 12213-12220.

Andrews T J, Whitney S M. (2003) Manipulating ribulose bisphosphate carboxylase/oxygenase in the chloroplasts of higher plants. *Arch. Biochem. Biophys.* 414, 159-169.

Baker R T, Catanzariti A M, Karunasekara Y, Soboleva T A, Sharwood R, Whitney S, Board P G. (2005) Using deubiquitylating enzymes as research tools. *Methods Enzymol.* 398, 540-554.

Case D A, Darden T A, Cheatham III, T E, Simmerling C L, Wang J, Duke R E, Luo R, Merz K M, Pearlman D A, Crowley M, Walker R C, Zhang W, Wang B, Hayik S, Roitberg A, Seabra G, Wong K F, Paesani F, Wu X, Brozell S, Tsui V, Gohlke H, Yang L, Tan C, Mongan J, Hornak V, Cui G, Beroza P, Mathews D H, Schafmeister C, Ross W S, Kollman P A. (2006) *AMBER* 9, University of California, San Francisco. Ciniglia C, Yoon H S, Pollio A, Pinto G, Bhattacharya D. (2004) Hidden biodiversity of the extremophilic Cyanidiales red algae. *Mol. Ecol.* 13, 1827-1838.

Corneille S, Lutz K, Svab Z, Maliga P. (2001) Efficient elimination of selectable marker genes from the plastid genome by the CRE-lox site-specific recombination system. *Plant J.* 27, 171-178.

Cummins P L. (1996) Molecular Orbital Programs for Simulations (MOPS), Australian National University, Canberra.

Cummins P L, Gready J E. (1997) A coupled semiempirical molecular orbital and molecular mechanical model (QM/MM) for organic molecules in aqueous solution. *J. Comput. Chem.* 18, 1496-1512.

Cummins P L, Gready J E. (1998) A molecular dynamics and free energy perturbation (MD/FEP) study of the hydride-ion transfer step in dihydrofolate reductase using a combined quantum and molecular mechanical (QM/MM) model. *J. Comput. Chem.* 19, 977-988.

Cummins P L, Gready J E. (1999) Coupled semiempirical quantum mechanics and molecular mechanics model (QM/MM) calculations on the aqueous solvation energies of ionised molecules. *J. Comput. Chem.* 20, 1028-1038.

Cummins P L, Gready J E. (2003) Computational methods for the study of enzymic reaction mechanisms II: An overlapping mechanically embedded method for hybrid semiempirical-QM/MM calculations. *THEOCHEM* 632, 245-255.

Cummins P L, Gready J E. (2005) Computational methods for the study of enzymic reaction mechanisms III: a perturbation plus QM/MM approach for calculating relative free energies of protonation. *J. Comput. Chem.* 26, 561-568.

Cummins P L, Rostov I, Gready J E. (2007) Calculation of a complete enzymic reaction surface: reaction and activation free energies for hydride-ion transfer in dihydrofolate reductase. *J. Chem. Theor. Comput.* 3, 1203-1211.

Emlyn-Jones D, Woodger F J, Price G P, Whitney S M. (2006) RbcX can function as a rubisco chaperonin, but is non-essential in *Synechococcus* PCC7942. *Plant Cell Physiol.* 47, 1630-1640.

Evans J R, Austin R B. (1986) The specific activity of ribulose-1,5-bisphosphate carboxylase in relation to genotype in wheat. *Planta* 167, 344-350.

Farquhar G D, von Caemmerer S, Berry J A (1980) A biochemical model of photosynthetic $CO_2$ assimilation in leaves of $C_3$ species. *Planta* 149, 78-90.

Fersht A. (1998) Structure and mechanism in protein science: guide to enzyme catalysis and protein folding. W. H. Freeman & Co., 1998.

Frey P A, Hegeman A. (2007) Enzymatic reaction mechanisms. Oxford University Press USA, 2007.

Frisch M J, (80 co-authors) and Pople J A. (2004) *Gaussian* 03, Revision C.02, Gaussian Inc., Wallingford, C T.

Galmés J, Flexas J, Keys A J, Cifre J, Mitchell RAC, Madgwick P J, Haslam R P, Medrano H, Parry M A J. (2005) Rubisco specificity factor tends to be larger in plant species from drier habitats and in species with persistent leaves. *Plant Cell Environ.* 28, 571-579.

Gready J E, Rostov I, Cummins P L. (2006) Simulations of enzyme reaction mechanisms in active sites: accounting for an environment which is much more than a solvent perturbation. In "Modelling Molecular Structure and Reactivity in Biological Systems", K. J. Naidoo, M. Hann, J. Gao, M. Field and J, Brady, eds, Royal Society of Chemistry, London, pp. 101-118.

Hall T A. (1999) BioEdit: a user-friendly biological sequence alignment editor and analysis program for Windows 95/98/NT. *Nucl. Acids Symp. Ser.* 41, 95.

Kane H J, Viil J, Entsch B, Paul B K, Morell M K, Andrews T J. (1994) An improved method for measuring the $CO_2/O_2$ specificity of ribulosebisphosphate carboxylase-oxygenase. *Aust. J. Plant Physiol.* 21, 449-461.

Kane H J, Wilkin J M, Portis A R, Andrews T J. (1998) Potent inhibition of ribulosebisphosphate carboxylase by an oxidized impurity in ribulose-1,5-bisphosphate. *Plant Physiol.* 117, 1059-1069.

Kannappan B, Gready J E. (2008) Redefinition of Rubisco carboxylase reaction reveals origin of water for hydration and new roles for active-site residues. *J. Am. Chem. Soc.* 130, 15063-15080.

Koop H-U, Herz S, Golds T J, Nickelsen J. (2007) The genetic transformation of plastids. Topic in Current Genetics. DOI 10.1007/4735_2007_0225/Published online: 15 May 2007.

Mueller-Cajar O, Morell M, Whitney S M. (2007) Directed evolution of Rubisco in *Escherichia coli* reveals a specificity-determining hydrogen bond in the Form II enzyme. Biochemistry, in press, September 2007.

Parry M A, Andralojc P J, Mitchell R A, Madgwick P J, Keys A J. (2003) Manipulation of Rubisco: the amount, activity, function and regulation. *J. Exptl Bot.* 54, 1321-1333.

Parry M A J, Flexas J, Medrano H. (2005) Prospects for crop production under drought: research priorities and future directions. *Ann. Appl. Biol.* 147, 211-226.

Parry M A J, Madgwick P J, Carvalho J F C, Andralojc P J. (2007) Prospects from increasing photosynthesis by overcoming the limitations of Rubisco. *J. Ag. Sci.* 145, 31-43.

Price G D, Howitt S M, Harrison K, Badger M R. (1993) Analysis of a genomic DNA region from the cyanobacterium *Synechococcus* sp. strain PCC7942 involved in carboxysome assembly and function. *J. Bacteriol.* 175, 2871-2879.

Ruuska S, Andrews T J, Badger M R, Hudson G S, Laisk A, Price G D, von Caemmerer S. (1998). The interplay between limiting processes in C-3 photosynthesis studied by rapid-response gas exchange using transgenic tobacco impaired in photosynthesis. *Aust. J. Plant Physiol.* 25, 859-870.

Sharwood R E, von Caemmerer S, Maliga P, Whitney S M (2008) The catalytic properties of hybrid rubisco comprising tobacco small and sunflower large subunits mirror the kinetically equivalent source Rubiscos and can support tobacco growth. *Plant Physiol.* 146, 83-96.

Svab Z, Maliga P. (1993) High-frequency plastid transformation in tobacco by selection for a chimeric aadA gene. *Proc. Natl Acad. Sci. USA* 90, 913-917.

Spreitzer R J, Salvucci M E. (2002) Rubisco: structure, regulatory interactions, and possibilities for a better enzyme. *Annu. Rev. Plant. Biol.* 53, 449-475.

Thompson J D, Higgins D G, Gibson T J. (1994). CLUSTAL W: improving the sensitivity of progressive multiple sequence alignment through sequence weighting, position-specific gap penalties and weight matrix choice. *Nucleic Acids Res.* 22, 4673-4680.

von Caemmerer S. (2000) *Biochemical Models of Leaf Photosynthesis*, CSIRO Publishing, ISBN 0 643 06379 X.

Whitney S M, von Caemmerer S, Hudson G S, Andrews T J. (1999) Directed mutation of the Rubisco large subunit of tobacco influences photorespiration and growth. *Plant Physiol.* 121, 579-588.

Whitney S M, Andrews T J. (2001) Plastome-encoded bacterial ribulose-1,5-bisphosphate carboxylase/oxygenase (Rubisco) supports photosynthesis and growth in tobacco. *Proc. Natl Acad. Sci. USA* 98, 14738-14743.

Whitney S M, Baldet P, Hudson G S, Andrews T J. (2001). Form I Rubiscos from non-green algae are expressed abundantly but not assembled in tobacco chloroplasts. *Plant J.* 26, 535-547.

Whitney S M, Sharwood R E. (2007) Linked Rubisco subunits can assemble into functional oligomers without impeding catalytic performance. *J. Biol. Chem.* 282, 3809-3818.

Whitney S M, Sharwood R E. (2008) Construction of a tobacco master line to improve Rubisco engineering in chloroplasts. *J. Exp. Bot.* 59, 1909-1921.

Zhu X G, Portis A R, Long S P. (2004) Would transformation of $C_3$ crop plants with foreign Rubisco increase productivity? A computational analysis extrapolating from kinetic properties to canopy photosynthesis. *Plant, Cell Environ.* 27, 155-165.

The invention claimed is:

1. A mutant Rubisco large subunit polypeptide comprising one amino acid residue substitution or a combination of amino acid residue substitutions selected from the group consisting of (Y25W, D51I), (Y25W, D51V), (T23G, K81R), (G54A, C84A, I87V), (G54S, C84A, I87V), (T23G, Y25W, D51I, K81R), (T23G, Y25W, E51I, K81R), (Y25W, D51I, G54A, C84A, I87V), (Y25W, D51I, G54S, C84A, I87V), (Y25W, D51V, G54A, C84A, I87V), (V121I, M297G, V300T), (L36I, I116L, F140L), (L36I, I116L, V121I, F140L, M297G, V300T), (K18I, T23G), (K21A, L22K, (gap)M, T23G, Y25W), (T23G, K18I, T68V, K81R), (T23G, K81R, P104E), (T23G, D19P, K81R), (T23G, K81R, V121I, M297G, V300T), (T23G), (K81R), (V121I, M297G), (M297G), and (V121I).

2. The mutant Rubisco large subunit polypeptide according to claim 1, wherein the polypeptide comprises the sequence as set forth in any one of SEQ ID NOS: 26, 28, 30, 32, 34, 36, 38, 40, 42, 44, 46, 48, 50, 52, 54, 56, 58, 60, 62, 64, 66, 68, 70, 74, 76, 78, 80, or a functional equivalent thereof, wherein the functional equivalent comprises between 1 and 5 amino acid substitutions, amino acid deletions, or amino acid additions at the N-terminal region of the sequence, the C-terminal region of the sequence, or at each of both the N-terminal and C-terminal regions of the sequence, and wherein the functional equivalent has at least 90% of the activity of the Rubisco large subunit polypeptide without said amino acid substitutions, deletions, or additions.

3. A polynucleotide encoding the mutant Rubisco large subunit polypeptide according to claim 1.

4. The polynucleotide according to claim 3, wherein the encoded mutant Rubisco large subunit polypeptide comprises a sequence as set forth in any one of SEQ ID NOS: 26, 28, 30, 32, 34, 36, 38, 40, 42, 44, 46, 48, 50, 52, 54, 56, 58, 60, 62, 64, 66, 68, 70, 74, 76, 78, or 80.

5. The polynucleotide according to claim 3, wherein the polynucleotide comprises a sequence as set forth in any one of SEQ ID NOS: 25, 27, 29, 31, 33, 35, 37, 39, 41, 43, 45, 47, 49, 51, 53, 55, 57, 59, 61, 63, 65, 67, 69, 73, 75, 77, or 79.

6. A vector comprising the polynucleotide sequence according to claim 3.

7. A host cell transformed with the polynucleotide according to claim 3.

8. A photosynthetic organism transformed with the polynucleotide according to claim 3, or with a polynucleotide comprising a sequence as set forth in any one of SEQ ID NOS: 25, 27, 29, 31, 33, 35, 37, 39, 41, 43, 45, 47, 49, 51, 53, 55, 57, 59, 61, 63, 65, 67, 69, 73, 75, 77, or 79.

9. A photosynthetic organism transformed with the vector according to claim 6.

10. A polynucleotide encoding the mutant Rubisco large subunit polypeptide according to claim 2.

11. The polynucleotide according to claim 10, wherein the encoded mutant Rubisco large subunit polypeptide comprises a sequence as set forth in any one of SEQ ID NOS: 26, 28, 30, 32, 34, 36, 38, 40, 42, 44, 46, 48, 50, 52, 54, 56, 58, 60, 62, 64, 66, 68, 70, 74, 76, 78, or 80.

12. The polynucleotide according to claim 10, wherein the polynucleotide comprises a sequence as set forth in any one of SEQ ID NOS: 25, 27, 29, 31, 33, 35, 37, 39, 41, 43, 45, 47, 49, 51, 53, 55, 57, 59, 61, 63, 65, 67, 69, 73, 75, 77, or 79.

13. A vector comprising the polynucleotide sequence according to claim 10.

14. A host cell transformed with the polynucleotide according to claim 10.

15. A photosynthetic organism transformed with the polynucleotide according to claim 6, or with a polynucleotide comprising a sequence as set forth in any one of SEQ ID NOS: 25, 27, 29, 31, 33, 35, 37, 39, 41, 43, 45, 47, 49, 51, 53, 55, 57, 59, 61, 63, 65, 67, 69, 73, 75, 77, or 79.

16. A photosynthetic organism transformed with the vector according to claim 13.

* * * * *